United States Patent
Oikawa et al.

(10) Patent No.: US 12,319,683 B2
(45) Date of Patent: Jun. 3, 2025

(54) AZABENZIMIDAZOLE COMPOUNDS AND PHARMACEUTICAL

(71) Applicant: NIPPON SHINYAKU CO., LTD., Kyoto (JP)

(72) Inventors: Koya Oikawa, Muko (JP); Sho Hirai, Kyoto (JP); Kazuhiko Wakita, Muko (JP); Akiko Fujibayashi, Muko (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 951 days.

(21) Appl. No.: 17/053,380

(22) PCT Filed: May 7, 2019

(86) PCT No.: PCT/JP2019/018201
§ 371 (c)(1),
(2) Date: Nov. 6, 2020

(87) PCT Pub. No.: WO2019/216294
PCT Pub. Date: Nov. 14, 2019

(65) Prior Publication Data
US 2021/0371412 A1    Dec. 2, 2021

(30) Foreign Application Priority Data
May 8, 2018  (JP) ................ 2018-089867

(51) Int. Cl.
C07D 471/04    (2006.01)
A61P 13/10     (2006.01)
C07D 519/00    (2006.01)

(52) U.S. Cl.
CPC ............ C07D 471/04 (2013.01); A61P 13/10 (2018.01); C07D 519/00 (2013.01)

(58) Field of Classification Search
CPC ..... C07D 471/04; C07D 519/00; A61P 13/10; A61P 27/06; A61P 3/10; A61K 31/437; A61K 31/444; A61K 31/4545; A61K 31/551; A61K 31/497; A61K 31/496
See application file for complete search history.

(56) References Cited

U.S. PATENT DOCUMENTS

| | | | |
|---|---|---|---|
| 5,571,819 A | 11/1996 | Sabb et al. | |
| 6,017,927 A | 1/2000 | Takeuchi et al. | |
| RE49,111 E | 6/2022 | Takahashi et al. | |
| 2005/0203083 A1 | 9/2005 | Mammen et al. | |
| 2005/0203167 A1 | 9/2005 | Mammen et al. | |
| 2008/0015196 A1 | 1/2008 | Doller et al. | |
| 2008/0051404 A1 | 2/2008 | Claiborne et al. | |
| 2008/0275038 A1 | 11/2008 | Vidal Juan et al. | |
| 2009/0209540 A1 | 8/2009 | Kim et al. | |
| 2010/0292188 A1 | 11/2010 | Denonne et al. | |
| 2012/0128773 A1 | 5/2012 | Fischer et al. | |
| 2013/0150388 A1 | 6/2013 | McCarron et al. | |
| 2013/0217684 A1 | 8/2013 | Kim et al. |
| 2014/0135319 A1 | 5/2014 | Koppitz et al. |
| 2014/0187548 A1 | 7/2014 | Koppitz et al. |
| 2016/0002218 A1 | 1/2016 | Takahashi et al. |
| 2016/0222005 A1 | 8/2016 | Stupple et al. |
| 2017/0197955 A1 | 7/2017 | Takahashi et al. |
| 2017/0290824 A1 | 10/2017 | Takahashi et al. |
| 2018/0116965 A1 | 5/2018 | Suda et al. |
| 2020/0095261 A1 | 3/2020 | Gao et al. |
| 2021/0000831 A1 | 1/2021 | Segawa et al. |
| 2021/0371412 A1 | 12/2021 | Oikawa et al. |
| 2023/0000840 A1 | 1/2023 | Yoshinaga et al. |
| 2023/0002395 A1 | 1/2023 | Oikawa et al. |

FOREIGN PATENT DOCUMENTS

| CL | 2020002866 A1 | 2/2021 |
|---|---|---|
| CN | 103429591 A | 12/2013 |
| EA | 006437 B1 | 12/2005 |
| EP | 2 416 761 B1 | 2/2015 |
| EP | 3 590 931 A1 | 1/2020 |
| JP | 2009-510152 A | 3/2009 |
| JP | 2009-542802 A | 12/2009 |
| JP | 2011-510044 A | 3/2011 |
| JP | 2012-031152 A | 2/2012 |
| JP | 2013-237634 A | 11/2013 |
| JP | 2013-545776 A | 12/2013 |
| JP | 2013-545779 A | 12/2013 |
| JP | 2016-509048 A | 3/2016 |

(Continued)

OTHER PUBLICATIONS

Australian Government, IP Australia, "Examination Report No. 1", issued in Australian Application No. 2019265134, which is a counterpart to U.S. Appl. No. 17/053,380, on Sep. 28, 2023, 3 pages.
Astellas, "ASP8302 Non-Confidential Summary," Version Mar. 3, 2021, 19 pages.
Douglas A. Drossman et al., "Rome IV-Functional GI Disorders: Disorders of Gut-Brain Interaction," Gastroenterology, vol. 150, No. 6, pp. 1257-1261, 2016.
Douglas A. Drossman et al., "Rome III: New Standard for Functional Gastrointestinal Disorders," Journal of Gastrointestinal and Liver Diseases, vol. 15, No. 3, pp. 237-241, Sep. 2006.
The International Bureau of WIPO, "International Preliminary Report on Patentability," received for PCT Patent Application No. PCT/JP2020/042259, issued on May 17, 2022, 5 pages.
International Search Report received for PCT Patent Application No. PCT/JP2020/042259, mailed on Jan. 12, 2021, 2 pages.

(Continued)

*Primary Examiner* — Kortney L. Klinkel
*Assistant Examiner* — Padmaja S Rao

(57) ABSTRACT

The purpose of the present invention is to provide compounds having an M3 PAM action. Examples of the present invention include azabenzimidazole compounds represented, for example, by formula [I], and pharmacologically acceptable salts thereof. These compounds have M3 PAM activity. In addition, because these compounds have M3 PAM activity, these compounds are useful as agents for the prevention or treatment of voiding and/or storage disorders in underactive bladder, hypotonic bladder, acontractile bladder, detrusor underactivity, and neurogenic bladder.

22 Claims, No Drawings

(56) References Cited

FOREIGN PATENT DOCUMENTS

| | | |
|---|---|---|
| TW | 305842 B | 5/1997 |
| WO | 2001/042213 A1 | 6/2001 |
| WO | 2005/115399 A2 | 12/2005 |
| WO | 2007/025177 A2 | 3/2007 |
| WO | 2007/039297 A1 | 4/2007 |
| WO | 2008/007900 A1 | 1/2008 |
| WO | 2008/119713 A1 | 10/2008 |
| WO | 2009/092764 A1 | 7/2009 |
| WO | 2011/018894 A1 | 2/2011 |
| WO | 2012/032031 A1 | 3/2012 |
| WO | 2012/080230 A1 | 6/2012 |
| WO | 2012/080236 A1 | 6/2012 |
| WO | 2014/128465 A1 | 8/2014 |
| WO | 2014/133056 A1 | 9/2014 |
| WO | 2015/186821 A1 | 12/2015 |
| WO | 2016/031833 A1 | 3/2016 |
| WO | 2016/175230 A1 | 11/2016 |
| WO | 2018/118736 A1 | 6/2018 |
| WO | 2018/157857 A1 | 9/2018 |
| WO | 2019/124507 A1 | 6/2019 |
| WO | 2019/189766 A1 | 10/2019 |
| WO | 2019/215203 A1 | 11/2019 |
| WO | 2019/216294 A1 | 11/2019 |

OTHER PUBLICATIONS

"Rome IV: Functional Gastrointestinal Disorders," vol. 1, 4th Edition, 2016, pp. 2-5, 14-15, and 24-25, Rome Foundation, Inc.

Marta Tanasiewicz et al., "Xerostomia of Various Etiologies: A Review of the Literature," Advances in Clinical and Experimental Medicine, vol. 25, No. 1, pp. 199-206, 2016, Wroclaw Medical University.

Instituto Nacional de Propiedad Industrial (INAPI), "Notification of the Examiner's Report No. 2", issued in Chilean Patent Application No. 2020-002868, which is a counterpart to U.S. Appl. No. 17/053,380, on Oct. 3, 2022, 30 pages (15 pages of English translation of Notification of the Examiner's Report No. 2, and 15 pages of original Notification of the Examiner's Report No. 2).

Ministry of Law and Human Rights of the Republic of Indonesia, Directorate General of Intellectual Property, "Notification of result of first stage of substantive examination result", issued in Indonesian Patent Application No. P00202009247, which is a counterpart to U.S. Appl. No. 17/053,380, on Nov. 8, 2022, 6 pages (3 pages of English translation of Notification, and 3 pages of original Notification).

China National Intellectual Property Administration, "First Office Action", issued in Chinese Patent Application No. 201980046177.6, which is a counterpart to U.S. Appl. No. 17/053,380, on Nov. 22, 2022, 20 pages (12 pages of English translation of Office Action and 8 pages of original Office Action).

Ministry of Justice, Israel Patent Office, "Notice of Deficiencies", issued in Israeli Patent Application No. 278517, which is a counterpart to U.S. Appl. No. 17/053,380, on Nov. 16, 2022, 3 pages.

Taiwan Intellectual Property Office, "Office Action", issued in ROC (Taiwan) Patent Application No. 108115846, which is a counterpart to U.S. Appl. No. 17/053,380, on Jan. 9, 2023, 8 pages (3 pages of English translation of Office Action and 5 pages of original Office Action).

Saudi Authority for Intellectual Property, "Second Substantive Examination Report", issued in Saudi Arabian application No. 522432594, which is a counterpart to U.S. Appl. No. 17/775,345, on Nov. 1, 2023, 9 pages.

Republic of Colombia Superintendence of Industry and Commerce, "Office Action", issued in Colombian Patent Application No. NC2020/0013848, which is a counterpart to U.S. Appl. No. 17/053,380, on Nov. 23, 2022, 12 pages (6 pages of English translation of Office Action, and 6 pages of original Office Action).

European Patent Office, "Extended European Search Report", issued in European Patent Application No. 20 888 347.0, which is a counterpart to U.S. Appl. No. 17/775,345, on Oct. 16, 2023, 8 pages.

European Patent Office, "Extended European Search Report", issued in European Patent Application No. 20 886 259.9, which is a counterpart to U.S. Appl. No. 17/775,418, on Oct. 16, 2023, 6 pages.

Instituto Mexicano de la Propiedad Industrial (IMPI), "2nd Office Action", issued in Mexican Patent Application No. MX/a/2020/011855, which is a counterpart to U.S. Appl. No. 17/053,380, on Oct. 2, 2023, 8 pages (4 pages of English translation of Office Action, and 4 pages of original Office Action).

Rospatent Federal Service for Intellectual Property, "Official Action," issued in Russian Patent Application No. 2020139649, which is a counterpart to U.S. Appl. No. 17/053,380, on Nov. 2, 2022, 19 pages (10 pages of English translation of Official Action, and 9 pages of original Official Action).

Rospatent Federal Service for Intellectual Property, Federal Institute of Industrial Property (FIPS), "Search Report," Issued in Russian Patent Application No. 2020139649, which is a counterpart to U.S. Appl. No. 17/053,380, completed on Nov. 1, 2022, and received on Nov. 2, 2022, 5 pages (2 pages of English translation of Search Report, and 3 pages of original Search Report).

Mexican Patent Office (Instituto Mexicano de la Propiedad Industrial (IMPI)), "1st technical Office Action", issued in Mexican Patent Application No. MX/a/2020/011855, which is a counterpart to U.S. Appl. No. 17/053,380, on Apr. 12, 2023, 8 pages (4 pages of English translation of Office Action and 4 pages of original Office Action).

Rospatent Federal Service for Intellectual Property, "Official Action", issued in Eurasian application No. 202291442, which is a counterpart to U.S. Appl. No. 17/775,345, on May 19, 2023 , 4 pages (2 pages of English translation of Official Action and 2 pages of original Official Action).

Saudi Authority for Intellectual Property, "First Substantive Examination Report", issued in Saudi Arabian application No. 522432594, which is a counterpart to U.S. Appl. No. 17/775,345, on May 28, 2023, 8 pages (4 pages of English translation of Examination Report and 4 pages of original Examination Report).

Saudi Authority for Intellectual Property, "Second Substantive Examination Report", issued in Saudi Arabian application No. 520420487, which is a counterpart to U.S. Appl. No. 17/053,380, on May 25, 2023, 9 pages (4 pages of English translation of Examination Report and 5 pages of original Examination Report).

Banyu Pharm Co Ltd, "Novel, highly selective, muscarinic M3 receptor antagonists," Expert Opinion on Therapeutic Patents, vol. 11, No. 9, pp. 1475-1478, 2001.

Intellectual Property India, "Examination Report," issued in Indian Patent Application No. 202047052667, which is a counterpart to U.S. Appl. No. 17/053,380, mailed on May 23, 2022, 5 pages.

Naresh Kumar et al., "Synthesis and optimization of novel and selective muscarinic M3 receptor antagonists," Bioorganic & Medicinal Chemistry Letters, vol. 17, pp. 5256-5260, 2007, Elsevier Ltd.

Peter Norman, "Long-acting muscarinic M3 receptor antagonists," Expert Opinion on Therapeutic Patents, vol. 16, No. 9, pp. 1315-1320, 2006.

Paul Abrams et al., "Muscarinic receptors: their distribution and function in body systems, and the implications for treating overactive bladder," British Journal of Pharmacology, vol. 148, pp. 565-578 (2006).

Malcolm P. Caulfield and Nigel J. M. Birdsall, "International Union of Pharmacology. XVII. Classification of Muscarinic Acetylcholine Receptors," Pharmacological Reviews, vol. 50, No. 2, pp. 279-290 (1998), <online> https://www.researchgate.net/publication/13636638_International_Union_of_Pharmacology_XVII_Classification_of_muscarinic_acetylcholine_receptors, retrieved on Jan. 15, 2018.

Miles Congreve et al., "Applying Structure-Based Drug Design Approaches to Allosteric Modulators of GPCRs," Trends in Pharmacological Sciences, vol. 38, No. 9, pp. 837-847, Sep. 2017, doi: 10.1016/j.tips.2017.05.010, Elsevier Ltd.

Ciro Costagliola et al., "Pharmacotherapy of intraocular pressure: part I. Parasympathomimetic, sympathomimetic and sympatholytics," Expert Opinion on Pharmacotherapy, vol. 10, Issue 16, pp. 2663-2677 (2009).

International Search Report received for PCT Patent Application No. PCT/JP2019/018201, mailed on Jun. 11, 2019, 4 pages.

(56) References Cited

OTHER PUBLICATIONS

Andrew C. Kruse et al., "Structure and dynamics of the M3 muscarinic acetylcholine receptor," Nature, vol. 482, pp. 552-556, Feb. 23, 2012, Macmillan Publishers Limited.
Meredith Portalatin and Nathaniel Winstead, "Medical Management of Constipation," Clinics in Colon and Rectal Surgery, vol. 25, No. 1, pp. 12-19 (2012).
A. Abdel Raheem and Helmut Madersbacher, "Voiding dysfunction in women: How to manage it correctly," Arab Journal of Urology, vol. 11, pp. 319-330 (2013).
Kendrick Co Shih et al., "Systematic review of randomized controlled trials in the treatment of dry eye disease in Sjogren syndrome," Journal of Inflammation, vol. 14, No. 26, 11 pages, (2017) doi: 10.1186/s12950-017-0174-3.
The International Bureau of WIPO, "Written Opinion of the International Searching Authority," issued in International Application No. PCT/JP2019/018201, of which U.S. Appl. U.S. Appl. No. 17/053,380 is a U.S. national phase entry, mailed on Jun. 11, 2019, 6 pages.
The International Bureau of WIPO, "International Preliminary Report on Patentability," received for PCT Patent Application No. PCT/JP2020/042247, issued on May 17, 2022, 4 pages.
International Search Report received for PCT Patent Application No. PCT/JP2020/042247, mailed on Dec. 22, 2020, 2 pages.
European Patent Office, "Extended European Search Report," issued in European Patent Application No. 19 800 286.7, which is a counterpart to U.S. Appl. No. 17/053,380, on Jan. 10, 2022, 11 pages.
Naresh Kumar et al., "Synthesis and optimization of novel and selective muscarinic M3 receptor antagonists," Bioorganic & Medicinal Chemistry Letters, vol. 17, No. 18, pp. 5256-5260, 2007, Elsevier Ltd.
Peter Norman, "Long-acting muscarinic M3 receptor antagonists—Theravance: US20050203083, US20050203131, US20050203132, US20050203133, US20050203134, US20050203137, US20050203138, US20050203139, US20050203161 and US20050203167," Expert Opinion on Therapeutic Patents, vol. 16, No. 9, pp. 1321-1326, 2006.
Instituto Nacional de Propiedad Industrial (INAPI), "Examiner's Report," issued in Chilean Patent Application No. 202002868, which is a counterpart of U.S. Appl. No. 17/053,380, on Jan. 10, 2022, 33 pages (17 pages of English translation of Examiner's Report, and 16 pages of original Examiner's Report).
Saudi Authority for Intellectual Property, "Substantive Examination Report," issued in Saudi Arabian Patent Application No. 520420487, which is counterpart of U.S. Appl. No. 17/053,380, on Jan. 27, 2022, 11 pages (4 pages of English translation of Substantive Examination Report, and 7 pages of original Substantive Examination Report).
Taiwan Intellectual Property Office, "Decision of the Intellectual Property Office", issued in Taiwanese Patent Application No. 108115846, which is a counterpart to U.S. Appl. No. 17/053,380, on Dec. 5, 2023, 5 pages (2 pages of English translation of Office Action and 3 pages of original Office Action).
Ministry of Law and Human Rights of the Republic of Indonesia, Directorate General of Intellectual Property, "Notification of the first stage of substantive examination results", issued in Indonesian Patent Application No. P00202205790, which is a counterpart to U.S. Appl. No. 17/775,345, on Apr. 1, 2024, 6 pages (3 pages of English translation of Office Action, and 3 pages of original Office Action).
Rospatent Federal Service for Intellectual Property, "Official Action", issued in Russian Patent Application No. 2022115612, which is a counterpart to U.S. Appl. No. 17/775,418, on Mar. 27, 2024, 23 pages (11 pages of English translation of Office Action, and 12 pages of original Office Action).
Taiwan Intellectual Property Office, "Office Action of the Intellectual Property Office", issued in Taiwanese Patent Application No. 109139511, which is a counterpart to U.S. Appl. No. 17/775,345, on Mar. 28, 2024, 11 pages (5 pages of English translation of Office Action, and 6 pages of original Office Action).
Saudi Authority for Intellectual Property, "Notification of Application Rejection", issued in Saudi Arabian Application No. 522432594, which is a counterpart to U.S. Appl. No. 17/775,345, as received by Applicant on Jun. 10, 2024, 8 pages (4 pages of English translation of Notification, and 4 pages of original Notification).
Taiwan Intellectual Property Office, "Office Action of the Intellectual Property Office", issued in Taiwanese Patent Application No. 109139704, which is a counterpart to U.S. Appl. No. 17/775,418, on Jun. 4, 2024, 8 pages (3 pages of English translation of Office Action, and 5 pages of original Office Action).
Intellectual Property Office of Singapore, "Written Opinion," issued in Singaporean Patent Application No. 11202204908W, which is a counterpart to U.S. Appl. No. 17/775,345, on Mar. 12, 2024, 7 pages.
National Institute for the Defense of Competition and the Protection of Intellectual Property, "Patentability Examination", issued in Peruvian Patent Application No. 0001816-2020/DIN, which is a counterpart to U.S. Appl. No. 17/053,380, on Oct. 24, 2024, 17 pages (9 pages of English translation of Patentability Examination, and 8 pages of original Patentability Examination).
Egyptian Patent Office (EGPO), "Technical Report", issued in Egyptian Patent Application No. EG/P/2020/01740, which is a counterpart to U.S. Appl. No. 17/053,380, on Dec. 27, 2024, 12 pages (6 pages of English translation of Technical Report, and 6 pages of original Technical Report).
Intellectual Property Office of the Philippines, Bureau of Patents, "Substantive Examination Report", issued in Philippine Patent Application No. 1/2020/551873, which is a counterpart to U.S. Appl. No. 17/053,380, mailed on Feb. 3, 2025, 4 pages.
Taiwan Intellectual Property Office, "Decision of the Intellectual Property Office", issued in Taiwanese Patent Application No. 109139704, which is a counterpart to U.S. Appl. No. 17/775,418, on Feb. 10, 2025, 5 pages (2 pages of English translation of Office Action and 3 pages of original Office Action).
New Zealand Intellectual Property Office, "Patent examination report 1," issued in NZ Patent Application No. 788181, which is a counterpart of U.S. Appl. No. 17/775,345, on Feb. 19, 2025, 4 pages.
United States Patent and Trademark Office, "Non-Final Office Action," issued in U.S. Appl. No. 17/775,418 on Mar. 25, 2025, 317 pages.
Daniel G. Hackam and Donald A. Redelmeier, "Translation of Research Evidence From Animals to Humans," JAMA, vol. 296, No. 14, pp. 1731-1732 (Oct. 11, 2006).
V. Craig Jordan, "Tamoxifen: A Most Unlikely Pioneering Medicine," Nature Reviews—Drug Discovery, vol. 2, pp. 205-213 (Mar. 2003).
Sudha R. Vippagunta et al., "Crystalline solids," Advanced Drug Delivery Reviews, vol. 48, pp. 3-26 (2001).
United States Patent and Trademark Office, "Non-Final Office Action," issued in U.S. Appl. No. 17/775,345 on Apr. 7, 2025, 451 pages.
Qasim Aziz et al., "Esophageal Disorders," Gastroenterology, vol. 150, No. 6, pp. 1368-1379 (2016).
Bowel Interest Group, "Functional Constipation Webinar," from https://bowelinterestgroup.co.uk/resources/functional-constipation-webinar, recorded on Wednesday, Jul. 4, 2018.
M. Camilleri and V. Andresen, "Current and novel therapeutic options for irritable bowel syndrome management," Digestive and Liver Disease, vol. 41, pp. 854-862 (2009).
Jean Galmiche et al., "Functional Esophageal Disorders," Gastroenterology, vol. 130, No. 5, pp. 1459-1465 (2006).
Jitender Reddy Kubbi et al., "Xerostomia: An overview," Journal of Indian Academy of Oral Medicine and Radiology, vol. 27, No. 1, pp. 85-89 (2015).
Takeshi Nakamura et al., "M3 muscarinic acetylcholine receptor plays a critical role in parasympathetic control of salivation in mice," Journal of Physiology, vol. 558, No. 2, pp. 561-575 (2004).
Ministry of Justice, israel Patent Office, "Notice of Deficiencies", issued in Israeli Patent Application No. 292813, which is a counterpart to U.S. Appl. No. 17/775,345, on Mar. 20, 2025, 4 pages.

(56) References Cited

OTHER PUBLICATIONS

Ukrainian Intellectual Property Institute, "Official Action," issued in Ukrainian Patent Application No. a2022 01951, which is a counterpart to U.S. Appl. No. 17/775,345, on Mar. 26, 2025, 7 pages (3 pages of English translation of Official Action and 4 pages of original Official Action).

AZABENZIMIDAZOLE COMPOUNDS AND PHARMACEUTICAL

CROSS REFERENCE TO RELATED APPLICATIONS

This patent application is a U.S. national stage application under 35 U.S.C. § 371 of International Patent Application No. PCT/JP2019/018201 filed on May 7, 2019, which claims the benefit of foreign priority to Japanese Patent Application No. JP 2018-089867 filed on May 8, 2018. The International Application was published in Japanese on Nov. 14, 2019, as International Publication No. WO 2019/216294 A1 under PCT Article 21(2).

TECHNICAL FIELD

The present invention relates to a pharmaceutical composition containing a novel azabenzimidazole compound, or a pharmaceutically acceptable salt thereof, or a solvate thereof as an active ingredient.

BACKGROUND ART

Acetylcholine (ACh) is a neurotransmitter, which is released from the terminals of parasympathetic nerves and motor nerves and transmits nerve stimulation upon binding to the acetylcholine receptor (AChR). Acetylcholine receptors are classified into G protein-coupled muscarinic receptors and ion channel-type nicotine receptors. Muscarinic receptors are classified into five subtypes, M1 to M5. It has been reported that subtype M3 muscarinic receptors, which may be hereinafter referred to as "M3 receptors", are expressed mainly in bladder, gastrointestinal tract, pupil, salivary gland, lacrimal gland, etc., and involved in contraction of bladder, gastrointestinal tract and pupil, and secretion of saliva and tear (see Non-Patent Documents 1 and 2).

A compound having an action of enhancing M3 receptor signal is expected to be useful as a protective or therapeutic agent for bladder/urethral diseases, gastrointestinal diseases, oral diseases, ocular diseases, etc. (see Non-Patent Documents 3-6).

PRIOR ART DOCUMENTS

Non-Patent Documents

Non-Patent Document 1: Pharmacological Reviews, 1998, Vol. 50, No. 2, p. 279-290
Non-Patent Document 2: British Journal of Pharmacology, 2006, Vol. 148, no. 5, p. 565-578
Non-Patent Document 3: Arabian Journal of Urology, 2013, Vol. 11, No. 4, p. 319-330
Non-Patent Document 4: Clinics in Colon and Rectal Surgery, 2012, Vol. 25, p. 12-19
Non-Patent Document 5: Expert Opinion on Pharmacotherapy, 2009, Vol. 10, No. 16, p. 2663-2777
Non-Patent Document 6: Journal of Inflammation, 2017, Nov. 21, 14:26
Non-Patent Document 7: Trends in Pharmacological Sciences, 2017, Vol. 38, No. 9, p. 837-847
Non-Patent Document 8: Nature, 2012, Vol. 482, p. 552-556

SUMMARY OF INVENTION

Problem to be Solved by the Invention

Regarding G protein-coupled receptors, many structures of allosteric sites, which are different from orthosteric sites to which endogenous agonists bind, have been reported, and these allosteric sites are attracting attention in recent years (Non-patent Document 7). Some ligands to allosteric sites can alter the structure of a receptor so as to increase the affinity between an endogenous agonist and the receptor, whereby its signal in the presence of the endogenous agonist stimulation to the receptor can be enhanced. Such ligands that bind to an allosteric site and enhance the signal from a receptor caused by an endogenous agonist are herein referred to as Positive Allosteric Modulator (PAM). That is, a Positive Allosteric Modulator is a ligand that enhances the signal of an agonist by binding to an allosteric site, which is different from an orthosteric site to which the endogenous agonist binds.

For M3 receptor, allosteric sites, which are different from orthosteric sites to which endogenous agonists (acetylcholine and muscarin) bind, have been reported in recent years (see Non-Patent Document 8). M3 receptor PAM (hereinafter referred to as "M3 PAM") is considered to be able to enhance the signal dependent on endogenous agonist stimulation to the M3 receptor. Therefore, M3 PAM can enhance the signal level of M3 receptor under more physiological conditions, and is expected to be promising for the treatment of diseases involving M3 receptor.

The object of the present invention is to provide a compound having a M3 PAM activity.

Means to Solve the Problems

As a result of intensive studies, the inventors discovered that an azabenzimidazole compound represented by the formula [1] or a pharmaceutically acceptable salt thereof, or a solvate thereof, which may be herein referred to as "the present compound", has a M3 PAM activity.

That is, disclosed herein are the following (Item 1) to (Item 4).

(Item 1)

An azabenzimidazole compound of the formula [1]:

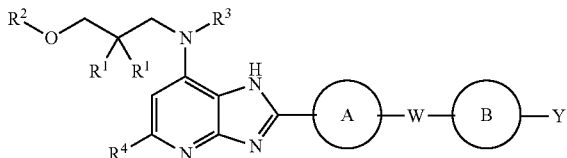

[1]

wherein:

$R^1$ is a hydrogen atom or alkyl, or two $R^1$ are taken together with adjacent carbon atom to form a 3- to 7-membered cycloalkyl or an oxygen-containing non-aromatic heterocycle;

$R^2$ is a hydrogen atom, alkyl, cycloalkyl, alkyl substituted with cycloalkyl, or alkoxyalkyl;

$R^3$ is a hydrogen atom, alkyl, or alkoxyalkyl;

$R^4$ is pyridyl optionally substituted with one or two groups selected from the group consisting of alkyl, trihaloalkyl, alkoxy, cyano and cycloalkyl, or phenyl optionally substituted with 1 to 3 groups selected from the group consisting of trihaloalkyl, halogen, alkoxy and cycloalkyl;

A is a group of the formula A-1, A-2, A-3, A-4, or A-5:

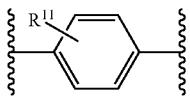
A-1

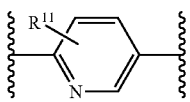
A-2

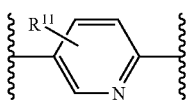
A-3

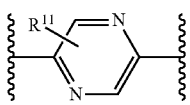
A-4

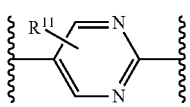
A-5 wherein the bond on the left side of each group is attached to the 2-position of the azabenzimidazole in the formula [1], and the bond on the right side is attached to W in the formula [1], and $R^{11}$ is a group selected from a hydrogen atom, halogen, alkyl, alkoxy or nitro;

W is a bond, or a group of the formula W-1, W-2, or W-3:

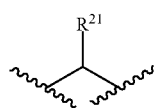
W-1

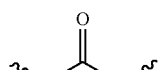
W-2

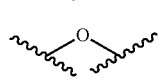
W-3 wherein $R^{21}$ is a hydrogen atom or alkyl;

B is a group of the formula B-1, B-2, B-3, or B-4:

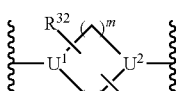
B-1

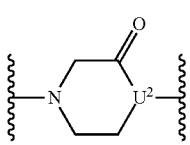
B-2

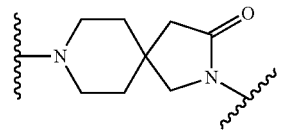
B-3

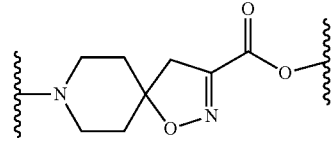
B-4 wherein the bond on the left side of each group is attached to W in the formula [1], the bond on the right side is attached to Y in the formula [1], $U^1$ is a nitrogen atom or $CR^{41}$, and $U^2$ is a nitrogen atom, or $CR^{42}$, and $R^{41}$ and $R^{42}$ are independently a hydrogen atom, alkyl, halogen or a hydroxyl group, m and n are independently 1, 2 or 3, and $R^{31}$ and $R^{32}$ are independently a hydrogen atom, alkyl, halogen or alkoxyalkyl, or $R^{31}$ and $R^{32}$ are taken together with adjacent carbon atom to form an alkylene bridge, provided that $R^{31}$ and $R^{32}$ substitute at any substitutable position other than $U^1$ and $U^2$;

Y is a hydrogen atom, or a group of any one the formula Y-1 to Y-4, Y-11 to Y-16:

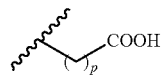
Y-1

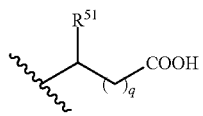
Y-2

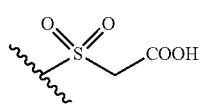
Y-3

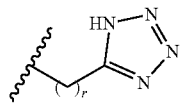
Y-4

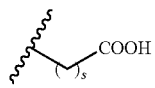
Y-11

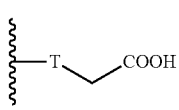
Y-12

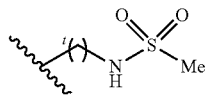
Y-13

-continued

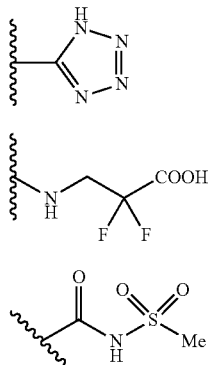

Y-14

Y-15

Y-16 wherein

R$^{51}$ is alkyl; p is 1, 2, or 3; q is 0, 1, or 2; r is 1, 2, or 3; T is O, S, SO$_2$, or NR$^{61}$ wherein R$^{61}$ is a hydrogen atom or alkyl; s is 0, 1, 2, or 3; and t is 0 or 1, with the proviso that
(a) when W is a bond,
 if B is B-1 or B-2 and U$^2$ is a nitrogen atom, then Y is Y-1, Y-2, Y-3, or Y-4,
 if B is B-1 or B-2 and U$^2$ is CR$^{42}$ wherein R$^{42}$ is as defined above, then U$^1$ is a nitrogen atom and Y is Y-11, Y-12, Y-13, Y-14, Y-15, or Y-16, and
 if B is B-3 or B-4, then Y is a hydrogen atom;
(b) when W is W-1,
 if B is B-1, U$^1$ is a nitrogen atom, and U$^2$ is a nitrogen atom, then Y is Y-1, Y-2, Y-3, or Y-4, and
 if B is B-1, U$^1$ is a nitrogen atom, and U$^2$ is CR$^{42}$ wherein R$^{42}$ is as defined above, then Y is Y-11, Y-12, Y-13, Y-14, Y-15, or Y-16;
(c) when W is W-2,
 if B is B-1 or B-2, U$^1$ is a nitrogen atom, and U$^2$ is a nitrogen atom, then Y is Y-1, Y-2, Y-3, or Y-4,
 if B is B-1 or B-2, U$^1$ is a nitrogen atom, and U$^2$ is CR$^{42}$ wherein R$^{42}$ is as defined above, then Y is Y-11, Y-12, Y-13, Y-14, Y-15, or Y-16, and
 if B is B-3 or B-4, then Y is a hydrogen atom; and
(d) when W is W-3,
 if B is B-1, U$^1$ is CR$^{41}$ wherein R$^{11}$ is as defined above, and U$^2$ is a nitrogen atom, then Y is Y-1, Y-2, Y-3, or Y-4,
or a pharmaceutically acceptable salt thereof, or a solvate thereof.

(Item 2)

A pharmaceutical composition comprising the azabenzimidazole compound according to Item 1 or a pharmaceutically acceptable salt thereof, or a solvate thereof, as an active ingredient.

(Item 3)

An M3 PAM comprising the azabenzimidazole compound according to Item 1 or Item 2 or a pharmaceutically acceptable salt thereof, or a solvate thereof, as an active ingredient.

(Item 4)

A prophylactic or therapeutic agent for voiding and/or storage disorders in bladder/urethral diseases, glaucoma or diabetes in which the M3 receptor is involved, comprising the azabenzimidazole compound according to any one of Items 1 to 3 or a pharmaceutically acceptable salt thereof, or a solvate thereof, as an active ingredient.

Effect of Invention

A compound having a M3 PAM activity is provided by the invention.

DESCRIPTION OF EMBODIMENTS

The definitions of the terms as used herein are as follows.

"Halogen" refers to a fluorine atom, a chlorine atom, a bromine atom, or an iodine atom.

"Alkyl" includes, for example, a straight or a branched alkyl having 1 to 10 carbon atoms, preferably 1 to 8 carbon atoms, more preferably 1 to 6 carbon atoms, specifically, methyl, ethyl, n-propyl, isopropyl, n-butyl, isobutyl, sec-butyl, tert-butyl, n-pentyl, sec-pentyl, 1-ethylpropyl, 1,2-dimethylpropyl, tert-pentyl, 2-methylbutyl, isopentyl, neopentyl, n-hexyl, sec-hexyl, 1-ethylbutyl, isohexyl, neohexyl, 1,1-dimethylbutyl, texyl, 2-ethylbutyl, 1,2,2-trimethylpropyl, 2,2-dimethylbutyl, n-heptyl, isoheptyl, n-octyl, isooctyl, and the like.

Example of the alkyl moiety of "alkoxyalkyl" and "alkyl substituted with cycloalkyl" includes the aforementioned "alkyl".

"Trihaloalkyl" refers to the above "alkyl" substituted with three of the above "halogen". Specific examples include trifluoromethyl, trichloromethyl, trifluoroethyl, and the like.

"Alkoxy" refers to a group in which the above "alkyl" is attached to an oxygen atom and includes a straight or a branched alkoxy having 1 to 8 carbon atoms, preferably 1 to 6 carbon atoms, specifically, methoxy, ethoxy, n-propoxy, isopropoxy, n-butoxy, isobutoxy, sec-butoxy, tert-butoxy, n-pentyloxy, n-hexyloxy, n-heptyloxy, and n-octyloxy, and the like.

Examples of the alkoxy moiety of "alkoxyalkyl" include the aforementioned "alkoxy".

"Alkylene" includes alkylene having a straight or a branched divalent hydrocarbon group having 1 to 6 carbon atoms. Specific examples include methylene, ethylene, and propylene.

"Cycloalkyl" includes a mono-, di- or tri-cyclic saturated hydrocarbon group having 3 to 10 carbon atoms. A monocyclic cycloalkyl having 3 to 6 carbon atoms is preferred. Specific examples include cyclopropyl, cyclobutyl, cyclopentyl, cyclohexyl, cycloheptyl, bicyclo[2.1.0]pentyl, bicyclo[2.2.1]heptyl, and bicyclo[2.2.2]octyl.

Examples of the cycloalkyl moiety of "alkyl substituted with cycloalkyl" include the aforementioned "cycloalkyl".

Examples of "oxygen-containing non-aromatic heterocycle" include a 3- to 8-membered non-aromatic heterocyclic group, more preferably 5- to 7-membered non-aromatic heterocyclic group, containing an oxygen atom and carbon atoms as ring-constituting atoms. Specific examples include oxolanyl (1-oxolanyl, 2-oxolanyl), oxanyl (1-oxanyl, 2-oxanyl, 3-oxanyl), oxepanyl (1-oxepanyl, 2-oxepanyl, 3-oxepanyl), and the like.

Each symbol in the formula [1] is described below.

In the formula [1], R$^1$ is a hydrogen atom or alkyl, or two R$^1$ are taken together with adjacent carbon atom to form a 3- to 7-membered cycloalkyl or an oxygen-containing non-aromatic heterocycle.

The "alkyl" for R$^1$ is preferably methyl, ethyl, n-propyl and n-butyl, more preferably methyl and ethyl.

The "cycloalkyl" for R$^1$ is preferably cyclopropyl, cyclobutyl, cyclopentyl, cyclohexyl and cycloheptyl, more preferably cyclobutyl, cyclopentyl and cyclohexyl.

The "oxygen-containing non-aromatic heterocycle" for $R^1$ is preferably 1-oxanyl, 2-oxanyl and 3-oxanyl, more preferably 3-oxanyl.

In the formula [1], $R^2$ is preferably a hydrogen atom, alkyl, cycloalkyl, alkyl substituted with cycloalkyl, or alkoxyalkyl.

The "alkyl" for $R^2$ is preferably methyl, ethyl, n-propyl, n-butyl and n-pentyl, more preferably methyl, ethyl, n-propyl and n-butyl.

The "cycloalkyl" for $R^2$ is preferably cyclopropyl or cyclobutyl.

The cycloalkyl of "alkyl substituted with cycloalkyl" for $R^2$ is preferably cyclobutyl or cyclopentyl, more preferably cyclobutyl.

The alkyl of "alkyl substituted with cycloalkyl" for $R^2$ is preferably methyl or ethyl, more preferably methyl.

The alkoxy of "alkoxyalkyl" for $R^2$ is preferably methoxy, ethoxy, n-propoxy and isopropoxy, more preferably methoxy and ethoxy.

The alkyl of "alkoxyalkyl" for $R^2$ is preferably methyl, ethyl and propyl, more preferably methyl and ethyl.

In the formula [1], $R^3$ is a hydrogen atom, alkyl, cycloalkyl, alkyl substituted with cycloalkyl, or alkoxyalkyl.

The "alkyl" for $R^3$ is preferably methyl, ethyl and n-propyl, more preferably methyl and ethyl.

The alkyl of "alkoxyalkyl" for $R^3$ is preferably methyl, ethyl and propyl, more preferably methyl and ethyl.

The alkoxy of "alkoxyalkyl" for $R^3$ is preferably methoxy and ethoxy, more preferably methoxy.

In the formula [1], $R^4$ is pyridyl optionally substituted with one or two groups selected from the group consisting of alkyl, trihaloalkyl, alkoxy, cyano and cycloalkyl, or phenyl optionally substituted with 1 to 3 groups selected from the group consisting of trihaloalkyl, halogen, alkoxy and cycloalkyl.

The "alkyl" in pyridyl optionally substituted with one or two alkyls according to $R^4$ is preferably methyl, ethyl or n-propyl.

The "trihaloalkyl" in pyridyl optionally substituted with one or two trihaloalkyl according to $R^4$ is preferably trifluoromethyl.

The "alkoxy" in pyridyl optionally substituted with one or two alkoxy according to $R^4$ is preferably methoxy, ethoxy, n-propoxy, or n-butoxy, more preferably ethoxy.

The "cycloalkyl" in pyridyl optionally substituted with one or two cycloalkyl according to $R^4$ is preferably cyclopropyl or cyclobutyl, more preferably cyclopropyl.

The "trihaloalkyl" in phenyl optionally substituted with 1 to 3 trihaloalkyl according to $R^4$ is preferably trifluoromethyl.

The "halogen" in phenyl optionally substituted with 1 to 3 halogens according to $R^4$ is preferably a chlorine atom, a bromine atom or a fluorine atom, more preferably a fluorine atom.

The "alkoxy" in phenyl optionally substituted with 1 to 3 alkoxy according to $R^4$ is preferably methoxy, ethoxy, n-propoxy, isopropoxy, n-butoxy, more preferably methoxy and ethoxy.

The "cycloalkyl" optionally substituted on phenyl according to $R^4$ is preferably cyclopropyl or cyclobutyl, more preferably cyclopropyl.

$R^4$ is preferably pyridyl substituted with one group selected from the group consisting of alkyl, trihaloalkyl, alkoxy, cyano and cycloalkyl, and trihaloalkyl.

In the formula [1], A is a group of the formula A-1, A-2, A-3, A-4, or A-5:

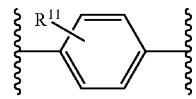

A-1

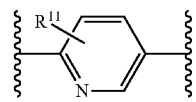

A-2

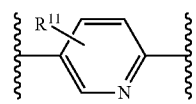

A-3

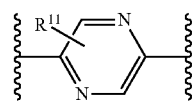

A-4

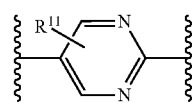

A-5

In the formula [1], $R^{11}$ is a group selected from a hydrogen atom, halogen, alkyl, alkoxy and nitro.

The "halogen" for $R^{11}$ is preferably a chlorine atom, a bromine atom and a fluorine atom, more preferably a chlorine atom and a fluorine atom.

The "alkyl" for $R^{11}$ is preferably methyl, ethyl and n-propyl, more preferably methyl and ethyl.

The "alkoxy" for $R^{11}$ is preferably methoxy and ethoxy, more preferably methoxy.

In the formula [1], A is preferably A-4.

In the formula [1], W is selected from a bond, or W-1, W-2 or W-3:

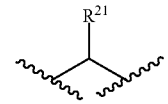

W-1

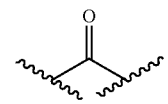

W-2

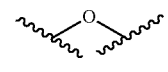

W-3

$R^{21}$ in W-1 is a group selected from a hydrogen atom or alkyl.

The "alkyl" for $R^{21}$ is preferably methyl or ethyl, more preferably methyl.

W in the formula [1] is preferably a bond.

B is selected from B-1, B-2, B-3 or B-4:

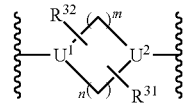

B-1

-continued

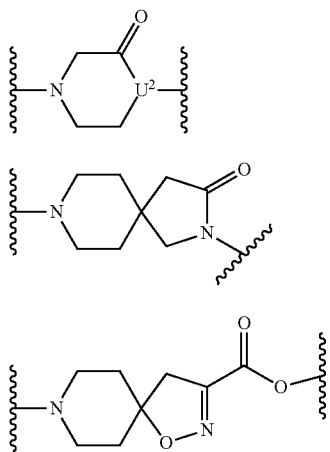

B-2

B-3

B-4 wherein the bond on the left side of each of B-1 to B-4 is attached to W in the formula [1], and the bond on the right side is attached to Y in the formula [1].

$U^1$ represents a nitrogen atom or $CR^{41}$, and $U^2$ represents a nitrogen atom or $CR^{42}$ $R^{41}$ and $R^{42}$ each independently represent a hydrogen atom, alkyl, halogen, or a hydroxyl group.

The "alkyl" according to $R^{41}$ and $R^{42}$ is preferably methyl and ethyl, more preferably methyl.

m and n are each 1, 2 or 3.

$R^{31}$ and $R^{32}$ are each independently a hydrogen atom, alkyl, halogen or alkoxyalkyl, or $R^{31}$ and $R^{32}$ may be taken together with adjacent carbon atoms to form an alkylene bridge.

$R^{31}$ and $R^{32}$ substitute at any substitutable position other than $U^1$ and $U^2$.

The "alkyl" for $R^{31}$ and $R^{32}$ is preferably methyl and ethyl, more preferably methyl.

The "halogen" for $R^{31}$ and $R^{32}$ is preferably a fluorine atom.

"Alkyl" of "alkoxyalkyl" for $R^{31}$ and $R^{32}$ is preferably methyl, ethyl or n-propyl, more preferably methyl or ethyl.

The alkoxy of "alkoxyalkyl" for $R^{31}$ and $R^{32}$ is preferably methoxy and ethoxy, more preferably methoxy.

The alkylene bridge formed by $R^{31}$ and $R^{32}$ is preferably a linear alkylene bridge having 1 to 3 carbon atoms, more preferably a methylene bridge or an ethylene bridge.

In the formula [1], B is preferably B-1, B-2, B-4, more preferably B-1, B-4, and even more preferably B-1.

Y is selected from a hydrogen atom or Y-1 to Y-4 or Y-11 to Y-16:

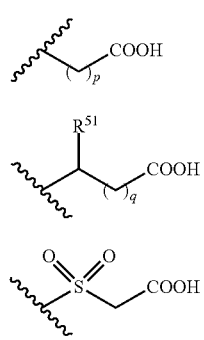

Y-1

Y-2

Y-3

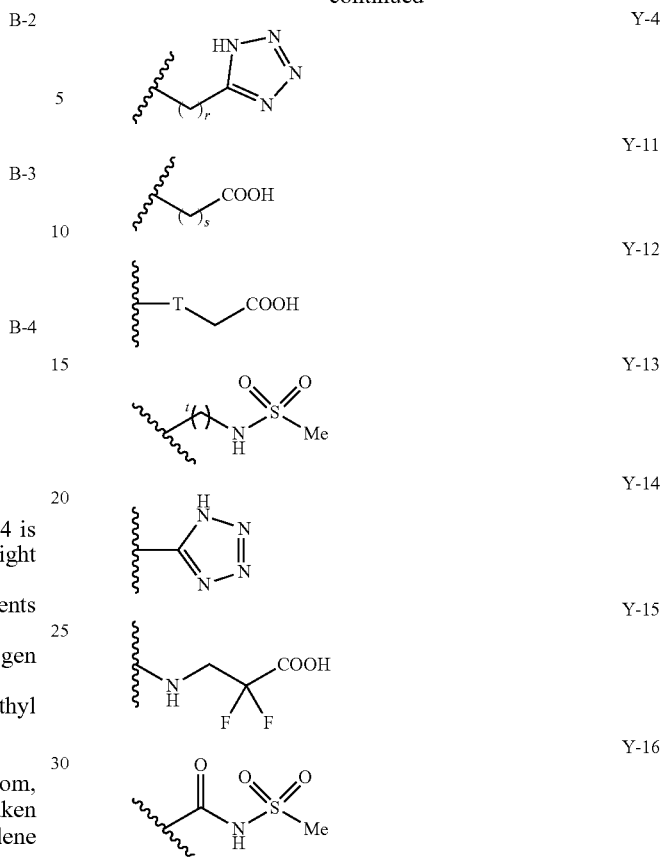

Y-4

Y-11

Y-12

Y-13

Y-14

Y-15

Y-16

$R^{51}$ is alkyl; p is 1, 2, or 3; q is 0, 1, or 2; r is 1, 2, or 3; T is O, S, $SO_2$, or $NR^{61}$ wherein $R^{61}$ is a hydrogen atom or alkyl; s is 0, 1, 2, or 3; and t is 0 or 1.

The "alkyl" for $R^{51}$ and $R^{61}$ is preferably methyl, ethyl and n-propyl, more preferably methyl and ethyl.

In the formula [1], Y is preferably Y-1, Y-2, Y-3, Y-11, Y-12, or Y-15.

The combination of W, B and Y in the formula [1] is preferably (a) When W is a bond,
   if B is B-1 or B-2 and $U^2$ is a nitrogen atom, then Y is Y-1, Y-2, Y-3, or Y-4, preferably Y-1, Y-2, or Y-3,
   if B is B-1 or B-2 and $U^2$ is $CR^{42}$ wherein $R^{42}$ is as defined above, then $U^1$ is a nitrogen atom and Y is Y-11, Y-12, Y-13, Y-14, Y-15, or Y-16, preferably Y-11, Y-12, or Y-15, and
   if B is B-3 or B-4, then Y is a hydrogen atom;

(b) when W is W-1,
   if B is B-1, $U^1$ is a nitrogen atom, and $U^2$ is a nitrogen atom, then Y is Y-1, Y-2, Y-3, or Y-4, preferably Y-1, Y-2, or Y-3, and
   if B is B-1, $U^1$ is a nitrogen atom, and $U^2$ is $CR^{42}$ wherein $R^{42}$ is as defined above, then Y is Y-11, Y-12, Y-13, Y-14, Y-15, or Y-16, preferably Y-11, Y-12, or Y-15;

(c) when W is W-2,
   if B is B-1 or B-2, $U^1$ is a nitrogen atom, and $U^2$ is a nitrogen atom, then Y is Y-1, Y-2, Y-3, or Y-4, preferably Y-1, Y-2, or Y-3,
   if B is B-1 or B-2, $U^1$ is a nitrogen atom, and $U^2$ is $CR^{42}$ wherein $R^{42}$ is as defined above, then Y is Y-11, Y-12, Y-13, Y-14, Y-15, or Y-16, preferably Y-11, Y-12, or Y-15, and if B is B-3 or B-4, then Y is a hydrogen atom; and (d) when W is W-3,
if B is B-1, $U^1$ is $CR^{41}$ wherein $R^{41}$ is as defined above, and $U^2$ is a nitrogen atom, then Y is Y-1, Y-2, Y-3, or Y-4, preferably Y-1, Y-2, or Y-3.

The compound of the invention can be, for example, prepared from a known compound or an easily synthesizable intermediate according to the following method. In the production of the compound of the invention, in the case where a starting material has a substituent which influences the reaction, the reaction is generally performed after protecting the starting material with a suitable protective group in advance by a known method. The protective group can be removed after the reaction by a known method.

The azabenzimidazole compound of the invention may be used as it is for pharmaceuticals, and can also be used in the form of a pharmaceutically acceptable salt, solvate or salt of the solvate thereof, according to a known method. Examples of pharmaceutically acceptable salts include salts with inorganic acids such as hydrochloric acid, hydrobromic acid, sulfuric acid, phosphoric acid, and organic acids such as acetic acid, malic acid, lactic acid, citric acid, tartaric acid, maleic acid, succinic acid, fumaric acid, p-toluenesulfonic acid, benzenesulfonic acid, methanesulfonic acid, salts with alkali metal such as lithium, potassium and sodium, salts with alkaline earth metal such as magnesium and calcium, and salts with organic base such as ammonium salts. These salts can be formed by methods well known in the art.

The solvates include hydrates as well as solvates with organic solvents. Examples of pharmaceutically acceptable solvates include alcoholates, such as ethanolate, and hydrates. The hydrate may include, for example, monohydrate and dihydrate. The solvate is formed by coordination with any type and number of solvents. The pharmaceutically acceptable salt may form a solvate.

For example, a hydrochloride salt of the azabenzimidazole compound of the invention can be prepared by dissolving the azabenzimidazole compound in a solution of hydrogen chloride in alcohol, a solution of hydrogen chloride in ethyl acetate, a solution of hydrogen chloride in 1,4-dioxane, a solution of hydrogen chloride in cyclopentyl methyl ether, or a solution of hydrogen chloride in diethyl ether.

Some of the compounds of the invention may have an asymmetric carbon, and the respective stereo isomers and mixtures thereof are all included in the present invention. The stereo isomers can be prepared, for example, by means of optical resolution from the racemate thereof according to a known method using an optically active acid (e.g., tartaric acid, dibenzoyltartaric acid, mandelic acid and 10-camphor sulfonic acid, etc.), utilizing its basicity, or by using an optically active compound prepared in advance as a starting material. In addition, the stereo isomers may be prepared by optical resolution using a chiral column or by asymmetric synthesis.

The formula [1] of the invention is not limited to a specific isomer, but includes all possible isomers and racemates. For example, as shown below, tautomers [1 Eq] and stereoisomers are also included.

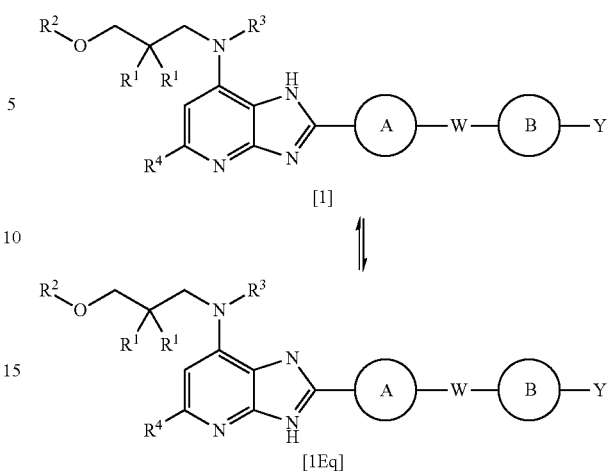

wherein the symbols are as defined above.

The Compound [1] of the invention and a salt thereof can be prepared from a known compound per se or an intermediate easily preparable from the known compound, according to the following method, the Examples described below or a known method.

If the solvents, reagents and starting materials used in each step of the following processes are commercially available, such commercially available products can be used as is. Also, the compounds obtained and the starting materials used in each step of the following processes may form a salt and can be converted by a well-known method into another type of salt or a free form. Alternatively, when the compound obtained or the starting material used in each step in the following processes is in a free form, it can be converted into a desired salt by a known method. Examples of such salts include those similar to the salts as described for the compound of the present invention.

In the production of the compound of the invention, when the starting material has a substituent capable of affecting the reaction, a protecting group may be introduced in these substituents by a known method in advance, and the target compound can be obtained by removing the protecting group after the reaction if necessary. Such protecting groups can be found, for example, in Wuts and Greene, "Greene's Protective Groups in Organic Synthesis", 4th edition, John Wiley & Sons Inc., 2006, or P. J. Kocienski, "Protecting Groups", 3rd edition, Thieme, 2005, and may be selected as appropriate according to the reaction conditions.

The compound obtained in each step of the following processes can be isolated or purified according to a conventional method such as solvent extraction, concentration, distillation, sublimation, recrystallization, reprecipitation, chromatography, and the like. Alternatively, the compound may be used in the next step as a reaction mixture or a crude product.

Unless otherwise specified, the reaction in each step of the following processes is conducted according to methods as described in, for example, "Comprehensive Organic Transformations: A Guide to Functional Group Preparations", 2nd Ed. by R. C. Larock, John Wiley & Sons, Inc., 1999; The Chemical Society of Japan, "Experimental Chemistry", 4th edition, Maruzen, 1992; L. Kuerti and B. Czako, "Strategic Applications of Named Reactions in Organic Synthesis", translated by Kiyoshi Tomioka, Kagaku-Dojin Publishing Company, Inc., 2006; G. S. Zweifel and M. H. Nantz, "Modern Organic Synthesis: An Introduction", translated by Tamejiro Hiyama, Kagaku-Dojin Publishing Company, Inc., 2009, or methods in a similar manner as described in the Examples, with modifications or combinations thereof as appropriate.

The Compound [1] of the invention comprises the following compounds [I], [II], [III] or [IV] depending on the type of W, and can be prepared by the methods described below, but the method for the production of these compounds and the starting materials are not limited to the following examples

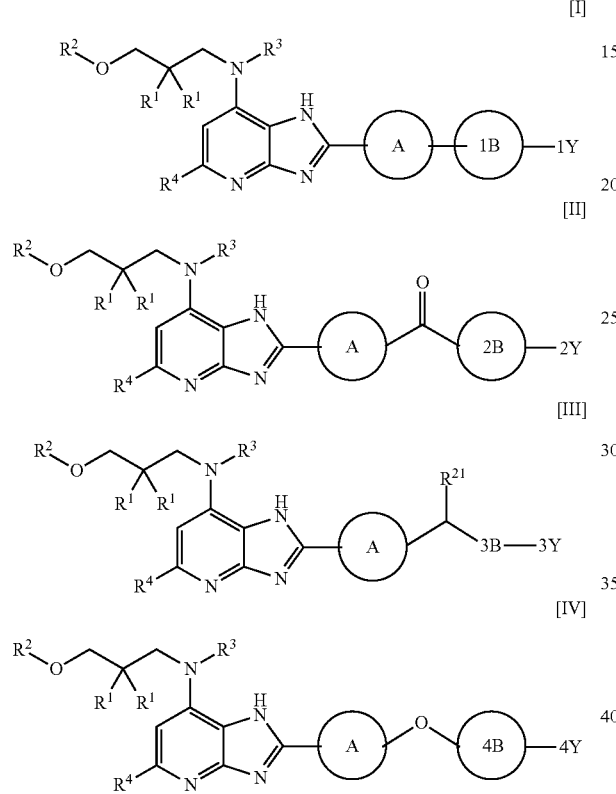

wherein $R^1$, $R^2$, $R^3$, $R^4$, $R^{21}$, A, B-1, B-2, B-3, B-4, $U^1$, $U^2$, $CR^{41}$, $CR^{42}$, Y-1, Y-2, Y-3, Y-4, Y-11, Y-12, Y-13, Y-14, Y-15 and Y-16 are as defined above.

In [I],
if 1B is B-1 or B-2, and $U^2$ is a nitrogen atom, then 1Y is Y-1, Y-2, Y-3, or Y-4,
if 1B is B-1 or B-2, and $U^2$ is $CR^{42}$, then $U^1$ is a nitrogen atom and 1Y is Y-11, Y-12, Y-13, Y-14, Y-15 or Y-16, and
if 1B is B-3 or B-4, then 1Y is a hydrogen atom.
In [II],
if 2B is B-1 or B-2, $U^1$ is a nitrogen atom, and $U^2$ is a nitrogen atom, then 2Y is Y-1, Y-2, Y-3, or Y-4,
if 2B is B-1 or B-2, $U^1$ is a nitrogen atom, and $U^2$ is $CR^{42}$, then 2Y is Y-11, Y-12, Y-13, Y-14, Y-15 or Y-16, and
if 2B is B-3 or B-4, then 2Y is a hydrogen atom.
In [III],
if 3B is B-1, $U^1$ is a nitrogen atom, and $U^2$ is a nitrogen atom, then 3Y is Y-1, Y-2, Y-3 or Y-4,
if 3B is B-1, $U^1$ is a nitrogen atom, and $U^2$ is $CR^{42}$, then 3Y is Y-11, Y-12, Y-13, Y-14, Y-15, or Y-16.
In [IV],
4B is B-1, $U^1$ is $CR^{41}$, $U^2$ is a nitrogen atom, and 4Y is Y-1, Y-2, Y-3, or Y-4.

Process 1: Production of Compound [Ia] Wherein W is a Bond (Part 1)

Compound [I] wherein 1B is B-1 or B-2, and 1Y is Y-1, Y-2, Y-3, Y-4, Y-11, Y-12, Y-14 or Y-15; or wherein 1B is B-4, and 1Y is a hydrogen atom, can be prepared according to the following scheme.

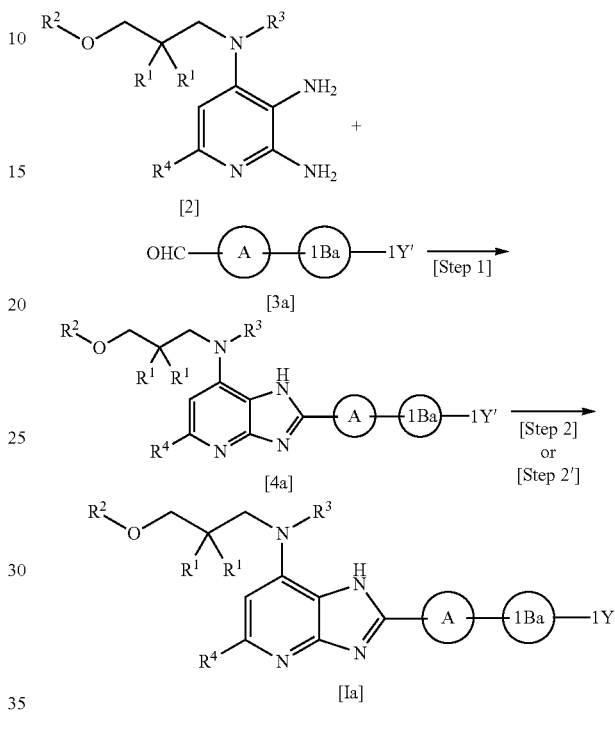

wherein $R^1$, $R^2$, $R^3$, $R^4$ and A are as defined above. 1Y' is (i) alkyl; (ii) a group of the formula Y'-1, Y'-2, Y'-3, Y'-11, Y'-12 or Y'-15 (shown below), which is an ester of Y-1, Y-2, Y-3, Y-11, Y-12 or Y-15, respectively; or (iii) a group of the formula Y'-4 or Y'-14 (shown below), which is a precursor of Y-4 or Y-14, respectively; provided that if 1Ba is B-1 or B-2, then 1Y' is Y'-1, Y'-2, Y'-3, Y'-11, Y'-12 or Y'-15, and if 1Ba is B-4, then 1Y' is alkyl.

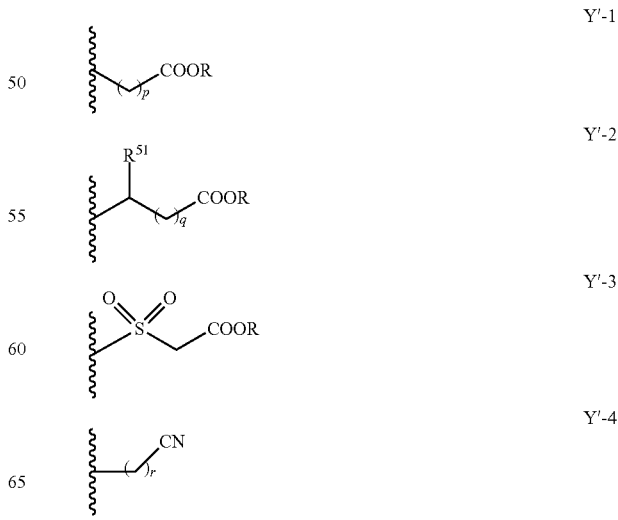

-continued

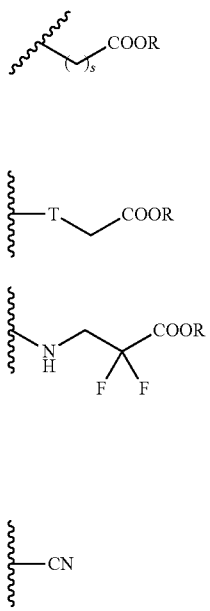

Y'-11

Y'-12

Y'-15

Y'-14 wherein p, q, r, s, T, $R^{51}$ and 1Ba are as defined above. R represents alkyl, for example, methyl or ethyl.

Step 1

This step affords Compound [4a] by cyclocondensation of Compound [2] with Compound [3a], which is commercially available or can be prepared according to a known method. The step can be carried out according to a method known per se.

The amount of Compound [3a] used in this step is preferably within the range of 0.5 to 2 molar equivalents to Compound [2].

This step is carried out in the presence of an oxidizing agent. Examples of the oxidizing agent include sodium dithionite and sodium pyrosulfite.

The oxidizing agent is preferably within the range of 1 to 5 molar equivalents to Compound [2].

The solvent used in this step is not limited so long as it does not participate in the reaction, and examples of such solvent include: hydrocarbons such as toluene and xylene; ethers such as 1,4-dioxane, tetrahydrofuran (hereinafter referred to as "THF"), ethylene glycol dimethyl ether (hereinafter referred to as "DME"); amides such as dimethylformamide (hereinafter referred to as "DMF"), dimethylacetamide (hereinafter referred to as "DMA"), N-methylpyrrolidone (hereinafter referred to as "NMP"); alcohols such as ethanol and propanol; dimethyl sulfoxide (hereinafter referred to as "DMSO"); acetonitrile; water; and a mixed solvent thereof.

The reaction temperature can vary depending on the starting materials and reagents to be used, and usually may be 20° C. to 200° C., preferably 50° C. to 180° C. Also, a microwave reaction apparatus may be used as necessary.

The reaction time can vary depending on the starting materials and the reaction temperature and is usually preferably within the range of 0.5 to 24 hours.

Step 2

This step is selected when 1Y' is an ester in Compound [4a] obtained in Step 1. Said ester moiety is hydrolyzed in a suitable solvent in the presence of a suitable acid or base to obtain Compound [Ia].

Examples of the acid used in this step include inorganic acids such as hydrochloric acid and sulfuric acid; organic acids such as trifluoroacetic acid (hereinafter referred to as "TFA"), methanesulfonic acid, and toluenesulfonic acid. Examples of the base include inorganic bases such as sodium hydroxide, potassium hydroxide and lithium hydroxide.

The amount of the acid or the base used in this step is preferably within the range of 1 to 10 molar equivalents to Compound [4a]. If necessary, an excess amount of the acid or the base may be used with respect to Compound [4a].

The solvent is not limited so long as it does not participate in the reaction, and examples of such solvent include: alcohols such as methanol, ethanol and 2-propanol; ethers such as THF, diethyl ether, 1,4-dioxane and DME; nitriles such as acetonitrile, propionitrile; ketones such as acetone; water; and a mixed solvent thereof.

The reaction temperature can vary depending on the starting materials and reagents to be used, and usually may be 20° C. to 200° C., preferably 20° C. to 100° C. Also, a microwave reaction apparatus may be used as necessary.

The reaction time can vary depending on the starting materials and the reaction temperature and is usually preferably within the range of 0.5 hours to 4 days.

Step 2'

This step is selected when 1Y' is a nitrile in Compound [4a] obtained in Step 1. Said nitrile moiety is reacted with an azide compound and an appropriate amine salt to obtain Compound [Ia] having a tetrazole group.

The amount of the azide compound and the amine salt used in this step is preferably within the range of 1 to 10 molar equivalents to Compound [4a].

Examples of the azide compound that can be used include sodium azide.

Examples of the amine salts that can be used include ammonium chloride and triethylamine hydrochloride.

The solvent is not limited so long as it does not participate in the reaction, and examples of such solvent include: hydrocarbons such as toluene and xylene; amides such as DMF, DMA, and NMP; DMSO; water; and a mixed solvent thereof.

The reaction temperature can vary depending on the starting materials and reagents to be used, and is usually preferably within the range of 80° C. to 200° C. Also, a microwave reaction apparatus may be used as necessary.

The reaction time can vary depending on the starting materials and the reaction temperature and is usually preferably within the range of 1 hour to 48 hours.

This step 2' can be applied to the synthesis of tetrazole compounds corresponding to compounds [II], [III] and [IV] described below.

Production of Compound [2]

A raw material, diamine Compound [2], can be prepared according to the following process.

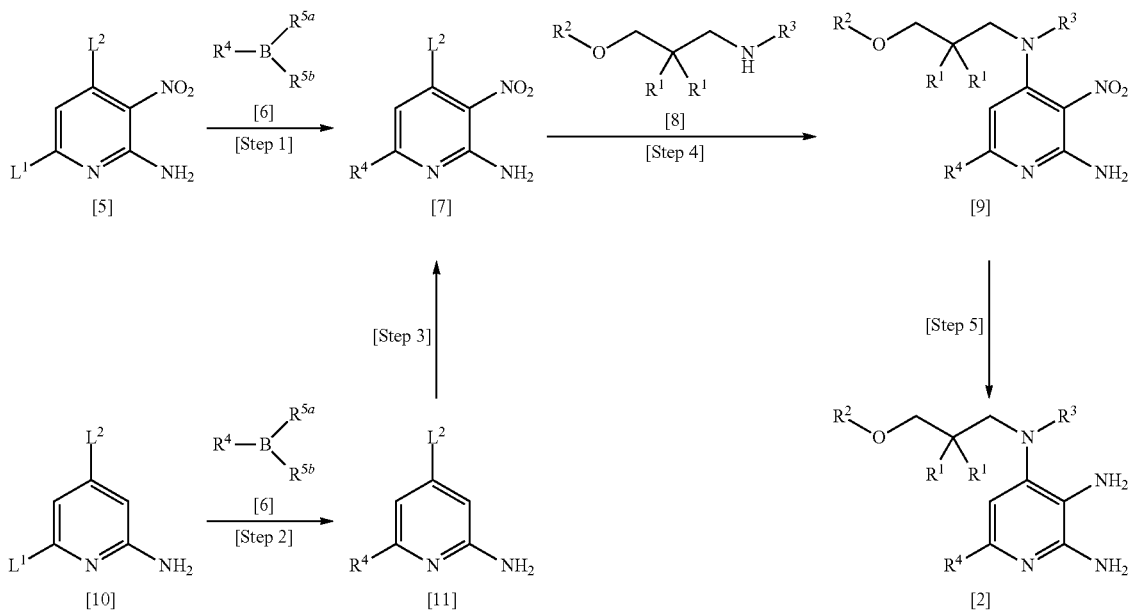

wherein $R^1$, $R^2$, $R^3$ and $R^4$ are as defined above. $R^{5a}$ and $R^{5b}$ each represent a hydroxy group, or $R^{5a}$ and $R^{5b}$ are combined together to be —O—C(CH$_3$)$_2$—C(CH$_3$)$_2$—O—, —O—(CH$_2$)$_3$—O—, or —O—CH$_2$—C(CH$_3$)$_2$—CH$_2$—O—, $L^1$ and $L^2$ are leaving groups, and examples of $L^1$ and $L^2$ include a chlorine atom and a bromine atom.

Step 1

This step is cross-coupling reaction of Compound [5] with a boron Compound [6], which is commercially available or can be prepared by a known method, in the presence of a palladium catalyst and a base to obtain Compound [7].

The amount of Compound [6] is preferably within the range of 1 to 3 molar equivalents to Compound [5].

Examples of the palladium catalyst include tris(dibenzylideneacetone)bispalladium chloroform adduct (hereinafter referred to as "Pd$_2$(dba)$_3$CHCl$_3$"), tris (dibenzylideneacetone)bispalladium (hereinafter referred to as "Pd$_2$(dba)$_3$"), tetrakistriphenylphosphine palladium (hereinafter referred to as "Pd(PPh$_3$)$_4$"), [1,1'-bis(diphenylphosphino) ferrocene]-dichloropalladium(II)·dichloromethane adduct (hereinafter referred to as "Pd(dppf)Cl$_2$·CH$_2$Cl$_2$"), bis(triphenylphosphine) palladium(II) dichloride (hereinafter referred to as "PdCl$_2$(PPh$_3$)$_2$"), [1,1'-bis(di-tert-butylphosphino)ferrocene] dichloropalladium(II) (hereinafter referred to as "Pd(dtbpf)Cl$_2$"), bis(tricyclohexylphosphine)palladium(II) dichloride (hereinafter referred to as "PdCl$_2$(PCy$_3$)$_2$"), and palladium(II) acetate (hereinafter referred to as "Pd (OAc)$_2$").

The amount of the palladium catalyst used is preferably within the range of, for example, 0.01 to 0.3 molar equivalents to Compound [5]

Examples of the base to be used include inorganic bases such as potassium carbonate, cesium carbonate, sodium carbonate, sodium bicarbonate, sodium acetate, potassium acetate, trisodium phosphate, and tripotassium phosphate.

The amount of the base to be used is preferably within the range of, for example, 1 to 4 molar equivalents to Compound [5].

In this step, an appropriate ligand may be used as necessary. Examples of such ligand include 1,1'-bis(diphenylphosphino)ferrocene (hereinafter referred to as "dppf"), 4,5-bis(diphenylphosphino)-9,9-dimethylxanthene (hereinafter referred to as "Xantphos"), 2-dicyclohexylphosphino-2',4',6'-triisopropylbiphenyl (hereinafter referred to as "XPhos"), 2,2'-bis(diphenylphosphino)-1,1'-binaphthyl (hereinafter referred to as "BINAP"), 2-dicyclohexylphosphino-2',6'-diisopropylbiphenyl (hereinafter referred to as "RuPhos"), triphenylphosphine (hereinafter referred to as "PPh$_3$"), and tricyclohexylphosphine (hereinafter referred to as "PCy$_3$")

The amount of the ligand to be used is preferably within the range of, for example, 1 to 5 molar equivalents to the palladium catalyst.

In this step, the solvent is not limited so long as it does not participate in the reaction, and examples of such solvent include: hydrocarbons such as toluene and xylene; ethers such as 1,4-dioxane, THF and DME; amides such as DMF, DMA, NMP; alcohols such as ethanol, 2-propanol and tert-butanol; water; or a mixed solvent thereof.

The reaction temperature can vary depending on the starting materials and reagents to be used, and is usually preferably within the range of 20° C. to 200° C. Also, a microwave reaction apparatus may be used as necessary.

The reaction time can vary depending on the starting materials and the reaction temperature and is usually preferably within the range of 0.1 to 24 hours.

Compound [7] can also be prepared via Step 2 and Step 3 described below.

Step 2

This step is cross-coupling reaction of Compound [10] with Compound [6] using a palladium catalyst and can be carried out under the same reaction conditions as described above in Step 1.

Step 3

This step is nitration of Compound [11] in the presence of an appropriate nitrating agent to obtain Compound [7]. This step can be carried out according to a method known as nitration reaction.

Examples of the nitrating agent to be used include nitric acid, fuming nitric acid, copper nitrate, sodium nitrate, and potassium nitrate.

The amount of the nitrating agent to be used is preferably within the range of 1 to 1.1 molar equivalents to Compound [11].

In this step, the solvent is selected depending on the type of reagents to be used, and examples include concentrated sulfuric acid and concentrated hydrochloric acid.

The reaction temperature can vary depending on the starting materials and reagents to be used, and is usually preferably within the range of 0° C. to 40° C., more preferably within the range of 5° C. to 15° C.

The reaction time can vary depending on the starting materials and reagents to be used, and is usually preferably within the range of 0.5 to 12 hours, more preferably within the range of 1 to 3 hours.

Step 4

This step affords aromatic amino Compound [9] by the reaction of Compound [7] with Compound [8], which is commercially available or can be prepared according to a known method.

Compound [7] may be used in the form of a salt with a suitable acid, such as hydrochloride, trifluoroacetate, and the like.

The amount of Compound [8] to be used is preferably within the range of 0.5 to 1.5 molar equivalents to Compound [7].

In this step, a base may be used as necessary. Examples of such base that may be used include triethylamine (hereinafter referred to as "TEA"), N,N-diisopropylethylamine (hereinafter referred to as "DIPEA"), 1,8-diazabicyclo [5.4.0]-7-undecene (hereinafter referred to as "DBU"), and inorganic bases such as potassium carbonate, cesium carbonate, and sodium carbonate.

The amount of the base is preferably within the range of 1 to 10 molar equivalents to Compound [7].

The solvent to be used is not limited so long as it does not participate in the reaction, and examples of such solvent include: hydrocarbons such as toluene and xylene; ethers such as 1,4-dioxane, THF and DME; amides such as DMF and DMA; nitriles such as acetonitrile and propionitrile; alcohols such as 2-propanol and tert-butanol; DMSO; water; and a mixed solvent thereof.

The reaction temperature can vary depending on the starting materials and reagents to be used, and is usually preferably within the range of 20° C. to 200° C. Also, a microwave reaction apparatus may be used as necessary.

The reaction time can vary depending on the starting materials and the reaction temperature to be used, and is usually preferably within the range of 0.5 to 24 hours.

If Compound [9] is prepared using Compound [5] as a starting material, the order of step 1 and step 4 can be switched to obtain Compound [9]. The reaction conditions in this case are the same as those described above in Step 1 and Step 4, respectively.

Step 5

This step is reduction of the nitro group in Compound [9] to obtain aromatic diamine Compound [2]. This step can be carried out according to a method known per se. This reduction reaction can be achieved, for example, by performing iron reduction using reduced iron and ammonium chloride in a suitable solvent, or by zinc reduction using zinc powder and ammonium chloride or acetic acid.

Examples of the reducing agent that can be used in the reduction reaction include reduced iron, zinc powder, and tin (II) chloride.

The amount of reducing agent used in this step is preferably within the range of 1 to 10 molar equivalents to Compound [9].

When using the above metal reagent in the reduction reaction, an acid is usually used. Examples of the acid to be used include hydrochloric acid, acetic acid, ammonium chloride, and the like.

The amount of acid used in this step is preferably within the range of 1 to 10 molar equivalents to Compound [9].

The solvent used in this step is not limited so long as it does not participate in the reaction, and examples of such solvent include: hydrocarbons such as toluene and 1,4-dioxane; ethers such as THF and DME; esters such as ethyl acetate; ketones such as acetone; nitriles such as acetonitrile; amides such as DMF; alcohols such as methanol, ethanol, 2-propanol, and tert-butanol; water; or a mixed solvent thereof.

The reaction temperature can vary depending on the starting materials and reagents to be used, and is usually preferably within the range of 0° C. to 200° C.

The reaction time can vary depending on the starting materials, reagents to be used and the reaction temperature, and is usually preferably within the range of 1 to 24 hours.

Production of Compound [8]

Compound [8], which is a raw material to obtain the above Compound [2], can be prepared, for example, according to the following process.

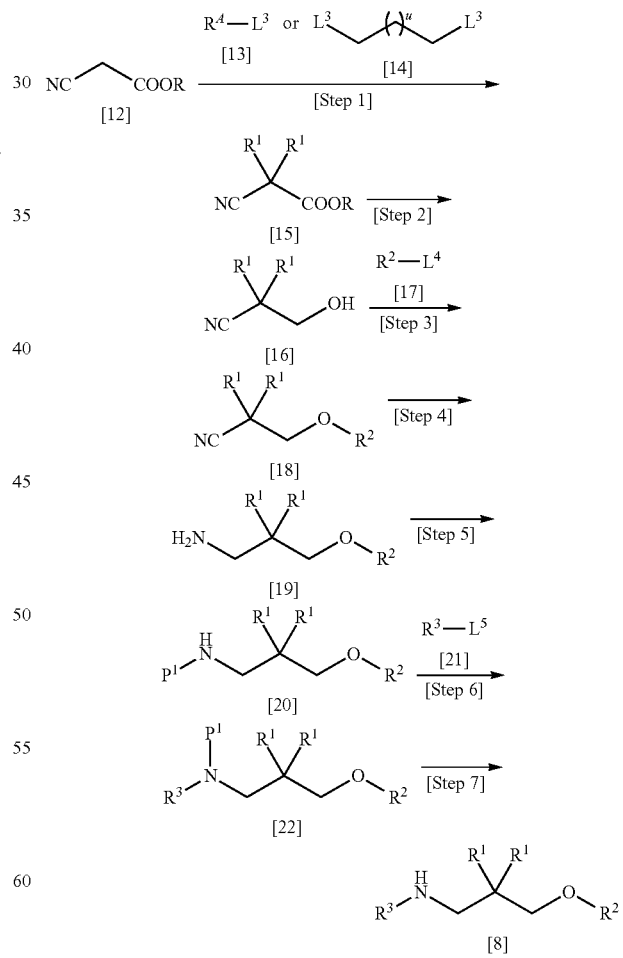

wherein $R^1$, $R^2$, and $R^3$ are as defined above. $R^4$ is alkyl as defined for $R^1$. R is alkyl and examples of R include methyl, ethyl, and the like. u is 0, 1, 2, 3, or 4. $L^3$, $L^4$, and $L^5$ represent a leaving group, and examples of $L^3$, $L^4$, and $L^5$ include bromine atom, chlorine atom, iodine atom, and the like. $P^1$ represents a protecting group, such as tert-butoxycarbonyl (hereinafter referred to as "Boc"), benzyloxycarbonyl (hereinafter referred to as "Cbz"), benzyl (hereinafter referred to as "Bn"), p-methoxybenzyl (hereinafter referred to as "PMB"), 2-nitrobenzenesulfonyl (hereinafter referred to as "Ns"), and 4-toluenesulfonyl (hereinafter referred to as "Ts"), and the like.

Step 1

This step affords Compound [15] from cyanoacetic acid ester [12] using alkylating agent [13] or [14] in the presence of a base. This step can be carried out according to a method known per se.

Examples of the alkylating agent to be used include methyl iodide, ethyl iodide, 1,3-dibromopropane, 1,4-dibromobutane and 1,5-dibromopentane.

The amount of the alkylating agent to be used is preferably within the range of 2 molar equivalents to 2.5 molar equivalents to Compound [12] when using the alkylating agent [13], and within the range of 1 to 1.3 molar equivalents to Compound [12] when using the alkylating agent [14].

Examples of the base to be used include sodium hydride, potassium hydride, potassium carbonate, sodium carbonate, cesium carbonate, sodium bicarbonate, sodium methoxide, sodium ethoxide, sodium tert-butoxide, potassium tert-butoxide, DBU, and the like.

The amount of base to be used is preferably within the range of 2 to 5 molar equivalents to Compound [12].

The reaction solvent is not limited so long as it does not participate in the reaction, and examples of such solvent include amides such as DMF and DMA, ethers such as THF, nitriles such as acetonitrile, DMSO, or a mixed solvent thereof.

The reaction temperature can vary depending on the starting materials and reagents to be used, and is usually preferably within the range of 20° C. to 150° C.

The reaction time can vary depending on the starting materials and the reaction temperature to be used, and is usually preferably within the range of 0.5 to 24 hours.

Step 2

This step affords Compound [16] by reducing the ester moiety of Compound [15] with a reducing agent.

Examples of the reducing agent to be used include lithium borohydride. Lithium borohydride can be prepared by mixing lithium chloride and sodium borohydride in the reaction system.

The amount of the reducing agent to be used is preferably within the range of 1 to 5 molar equivalents to Compound [15].

When lithium borohydride is prepared in the reaction system as described, the amounts of lithium chloride and sodium borohydride are preferably within the range of 1 to 5 molar equivalents to Compound [15].

The solvent used in this step is not limited so long as it does not participate in the reaction, and examples of such solvent include: alcohols such as methanol and ethanol; ethers such as THF, 1,4-dioxane and DME; halogenated hydrocarbons such as dichloromethane; water; or a mixed solvent thereof.

The reaction temperature can vary depending on the starting materials and reagents to be used, and is usually preferably within the range of −10° C. to 80° C.

The reaction time can vary depending on the starting materials and the reaction temperature to be used, and is usually preferably within the range of 0.1 to 24 hours.

Step 3

This step affords Compound [18] by alkylating the hydroxyl group of Compound [16] with alkylating agent [17] in the presence of a base. This step can be carried out according to a method known as an alkylation reaction.

Examples of the alkylating agent to be used include methyl iodide, ethyl iodide, 1-bromobutane, 1-iodobutane, 1-bromo-2-methoxyethane, and the like.

The amount of the alkylating agent to be used is preferably within the range of 1 to 1.5 molar equivalents to Compound [16].

Examples of the base to be used include sodium hydride, potassium hydride, potassium carbonate, sodium carbonate, cesium carbonate, sodium bicarbonate, sodium methoxide, sodium ethoxide, sodium tert-butoxide, potassium tert-butoxide, DBU, and the like.

The amount of base to be used is preferably within the range of 1 to 2 molar equivalents to Compound [16].

The solvent used in this step is not limited so long as it does not participate in the reaction, and examples of such solvent include: amides such as DMF and DMA; ethers such as THF; nitriles such as acetonitrile; DMSO; or a mixed solvent thereof.

The reaction temperature can vary depending on the starting materials and reagents to be used, and is usually preferably within the range of 0° C. to 150° C.

The reaction time can vary depending on the starting materials and the reaction temperature to be used, and is usually preferably within the range of 1 hour to 48 hours.

Step 4

This step affords amine Compound [19] by reducing the nitrile of Compound [18]. This step can be carried out according to a method known per se as a nitrile reduction reaction (for example, The Chemical Society of Japan, "Experimental Chemistry", 4th edition, Maruzen, 1992, Vol. 20, section of Organic Synthesis II Alcohol Amine, p. 280-282, and Vol. 26, section of Organic Synthesis VIII, p. 190-260; The Journal of Organic Chemistry, 1986, Vol. 51, Issue 21, p. 4000-4005; Tetrahedron, 2003, Vol. 59, Issue 29, p. 5417-5423, etc.).

Reduction of the nitrile may be conducted by hydrogenation using a catalyst such as platinum (IV) oxide, platinum, Raney nickel, platinum-carbon (hereinafter referred to as "Pt-C"), and palladium-carbon (hereinafter referred to as "Pd-C") or by reduction using lithium aluminum hydride, aluminum hydride, lithium borohydride, nickel borohydride, or the like.

Step 5

This step is a reaction for introducing a protecting group into the amino group of Compound [19]. This step can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005.

Step 6

This step affords Compound [22] by alkylating the amino group of Compound [20]. This step can be carried out as described above in Step 3.

Step 7

This step affords Compound [8] by deprotecting the protecting group from Compound [22]. This step can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005.

Production of Compound [3a]

Compound [3a], which is a raw material compound, can be prepared, for example, according to the following process.

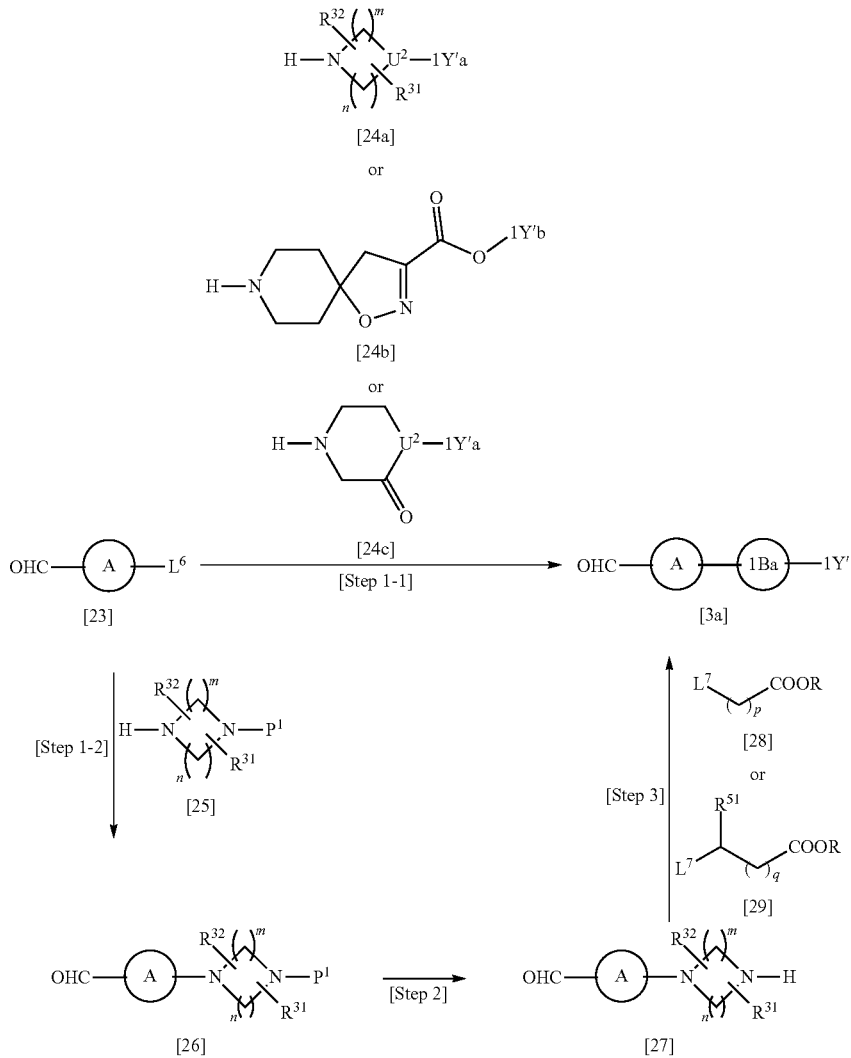

wherein A, $R^{31}$, $R^{32}$, $R^{51}$, m, n, p, q, 1Ba, $U^2$, and $P^1$ are as defined above. 1Y'a is Y'-1, Y'-2, Y'-3, Y'-4, Y'-11, Y'-12, Y'-14, or Y'-15, and 1Y'b is alkyl. R is alkyl such as methyl and ethyl. $L^6$ and $L^7$ are a leaving group. Examples of $L^6$ include fluorine atom and chlorine atom, and examples of $L^7$ include chlorine atom, bromine atom, and iodine atom.

Step 1-1

This step affords aromatic amino Compound [3a] by reacting Compound [23] with Compound [24a], [24b] or [24c], which is commercially available or can be prepared according to a known method.

Compound [24a], [24b] or [24c] may be used in the form of a salt with an appropriate acid such as hydrochloride, trifluoroacetate, and the like.

The amount of Compound [24a], [24b], or [24c] to be used is preferably within the range of 1 to 2 molar equivalents to Compound [23].

In this step, a base can be used as necessary. Examples of the base that can be used include organic bases such as TEA, DIPEA, and DBU, and inorganic bases such as sodium bicarbonate, potassium carbonate, cesium carbonate, sodium carbonate, potassium hydroxide, and potassium tert-butoxide.

The amount of the base to be used is preferably within the range of 1 to 10 molar equivalents to Compound [23].

The solvent used in this step is not limited so long as it does not participate in the reaction, and examples of such solvent include: hydrocarbons such as toluene and xylene; ethers such as 1,4-dioxane, THF and DME; amides such as DMF, DMA; nitriles such as acetonitrile and propionitrile; alcohols such as 2-propanol and tert-butanol; DMSO; water; and a mixed solvent thereof.

The reaction temperature can vary depending on the starting materials and reagents to be used, and usually can be within a range of 20° C. to 200° C. Also, one may use a microwave reaction apparatus as necessary.

The reaction time can vary depending on the starting materials and the reaction temperature to be used, and is usually preferably within the range of 0.5 to 24 hours.

Step 1-2

This step affords Compound [26] from Compound [23] and Compound [25], which is commercially available or known. This step can be carried out in a similar manner as described in Step 1-1 in the production of Compound [3a]

Step 2

This step affords Compound [27] by removing the protecting group $P^1$ of Compound [26], and the step can be carried out in a similar manner as described in Step 7 in the production of Compound [8].

Step 3

This step is alkylation of amine moiety of Compound [27] by the reaction with Compound [28] or Compound [29], which is commercially available or can be prepared according to a method known per se, to obtain Compound [3a].

The amount of Compound [28] or Compound [29] to be used is preferably within the range of 1 to 2 molar equivalents to Compound [27].

In this step, a base can be used as necessary. Examples of the base to be used include organic bases such as TEA and DIPEA, and inorganic bases such as potassium carbonate, cesium carbonate, and sodium bicarbonate.

The amount of the base is preferably within the range of 1 to 5 molar equivalents to Compound [27].

The solvent to be used is not limited so long as it does not participate in the reaction, and examples of such solvent include: hydrocarbons such as toluene and xylene; ethers such as 1,4-dioxane, THF and DME; amides such as DMF, DMA and NMP; halogenated hydrocarbons such as dichloromethane and chloroform; alcohols such as methanol and ethanol; nitriles such as acetonitrile and propionitrile; and a mixed solvent thereof.

The reaction temperature can vary depending on the starting materials and reagents to be used, and is usually preferably within the range of 0° C. to 150° C.

The reaction time can vary depending on the starting materials and the reaction temperature to be used, and is usually preferably within the range of 1 to 24 hours.

Production of Compound [Ib]

Compound [I], wherein 1B is B-1 or B-2 and 1Y is Y-13 or Y-16, or wherein 1B is B-3 and 1Y is hydrogen, can be prepared as follows.

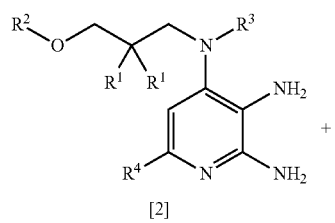

[2]

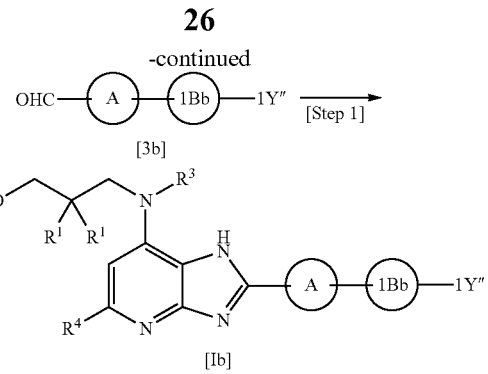

wherein A, $R^1$, $R^2$, $R^3$ and $R^4$ are as defined above. 1Y″ is Y-13 or Y-16, and 1Bb is B-1 or B-2.

Step 1

This step affords Compound [Ib] by reacting Compound [3b] with Compound [2]. This step can be carried out in a similar manner as described in step 1 of Process 1.

Production of Compound [3b]

Compound [3b] can be prepared as follows.

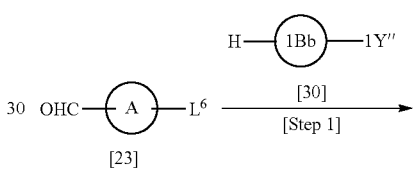

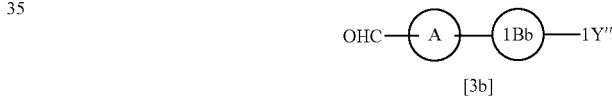

wherein A, 1Bb, Y″ and $L^6$ are as defined above.

Step 1

This step is an aromatic aminating reaction of Compound [23] with Compound [30], and the step can be carried out in a similar manner as described in Step 1-1 in the production of Compound [3a].

Production of Compounds [35] and [38]

Among compounds of formula [3a], Compound [35] having hydroxyl group as $R^{41}$ for $CR^{41}$ as defined above and Compound [38] having fluorine as $R^{41}$ for $CR^{41}$ as defined above can be prepared according to the following process.

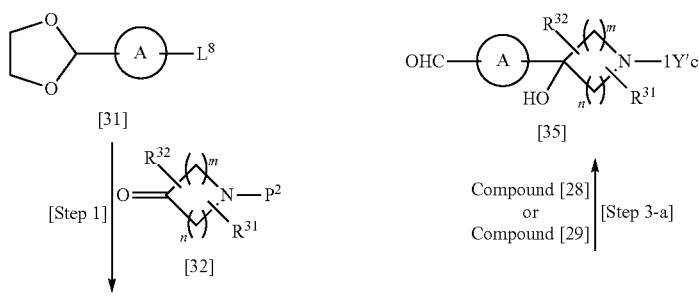

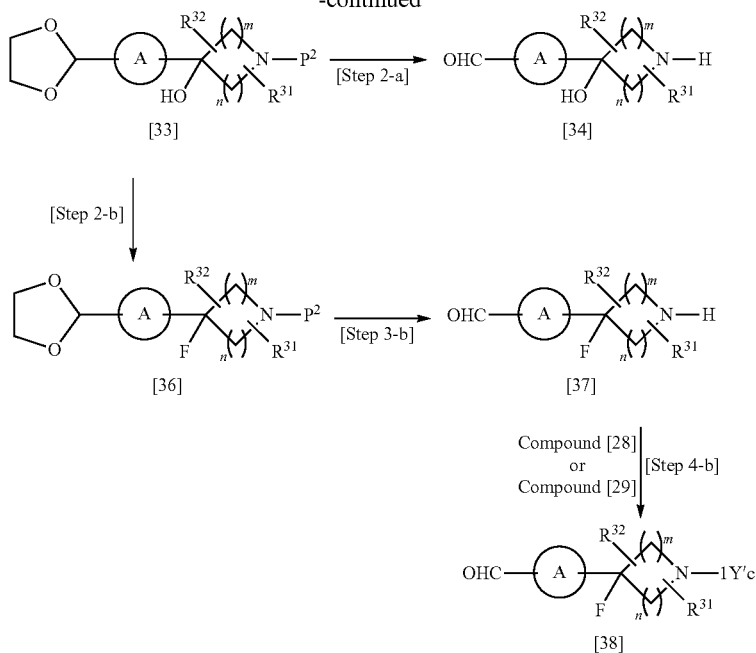

wherein A, $R^{31}$, $R^{32}$, m and n are as defied above. 1Y'c is Y'-1 or Y'-2. $L^8$ is a leaving group, and examples of $L^8$ include bromine atom and iodine atom. $P^2$ represents a protecting group, and examples of $P^2$ include Boc group and Cbz group.

Step 1

This step affords Compound [33] by reacting Compound [31] with Compound [32] in the presence of a base.

The reaction is usually carried out by reacting Compound [31] with a suitable base in a suitable solvent and then reacting with Compound [32].

The amount of Compound [32] to be used is preferably within the range of 0.5 to 2 molar equivalents to Compound [31].

Examples of the base to be used include organometallic reagents such as isopropylmagnesium chloride, isopropylmagnesium chloride/lithium chloride complex, n-butyllithium, lithium diisopropylamide, and the like.

The amount of the organometallic reagent to be used is preferably within the range of 1 to 2 molar equivalents to Compound [31].

The solvent to be used is not limited so long as it does not participate in the reaction, and examples of such solvent include: hydrocarbons such as n-hexane, toluene and xylene; ethers such as diethyl ether, 1,4-dioxane, THF and DME; and a mixed solvent thereof.

In this step, the reaction temperature can vary depending on the starting materials and reagents to be used, and is usually preferably within the range of −80° C. to 100° C.

The reaction time can vary depending on the starting materials and the reaction temperature to be used, and is usually preferably within the range of 1 to 24 hours.

Step 2-a

This step affords Compound [34] by deprotecting the acetal group and $P^2$ from Compound [33], and the step can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005, as described above.

Step 3-a

This step affords Compound [35] by amine alkylation reaction, and the step can be carried out in a similar manner as described in Step 3 in the Production of Compound [3a].

Step 2-b

This step affords Compound [36] by fluorinating the hydroxyl group of Compound [33] in the presence of a fluorinating reagent.

Examples of the fluorinating reagent to be used include electrophilic fluorinating reagents such as (diethylamino)sulfur trifluoride (hereinafter referred to as "DAST"), bis(2-methoxyethyl)aminosulfur trifluoride, and 4-tert-butyl-2,6-dimethylaminosulfur trifluoride.

The amount of the fluorinating reagent to be used is preferably within the range of 1 to 1.5 molar equivalents to Compound [33].

The solvent to be used is not limited so long as it does not participate in the reaction, and examples of such solvent include halogenated hydrocarbons such as dichloromethane.

In this step, the reaction temperature can vary depending on the starting materials and reagents to be used, and is usually preferably within the range of 0° C. to 100° C.

The reaction time can vary depending on the starting materials and the reaction temperature to be used, and is usually preferably within the range of 1 to 24 hours.

Step 3-b

This step affords Compound [37] by deprotecting the acetal group and $P^2$ from Compound [36], and the step can be carried out in a similar manner as described above in Step 2-a.

Step 4-b

This step affords Compound [38] by alkylation reaction of amine. This step can be carried out in a similar manner as described in Step 3 in the production of Compound [3a].

Compounds [35] and [38] can be reacted with Compound [2] according to Step 1 in Process 1 to lead to Compound [Ic], which is a compound corresponding to Compound [Ia].

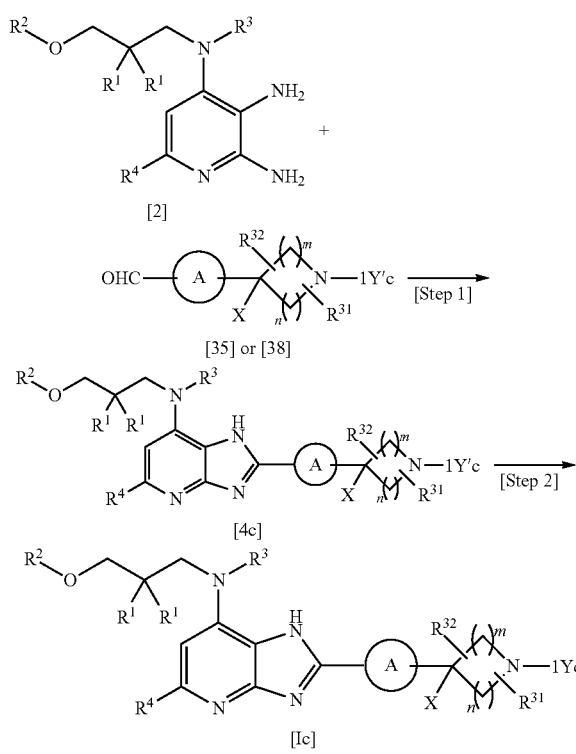

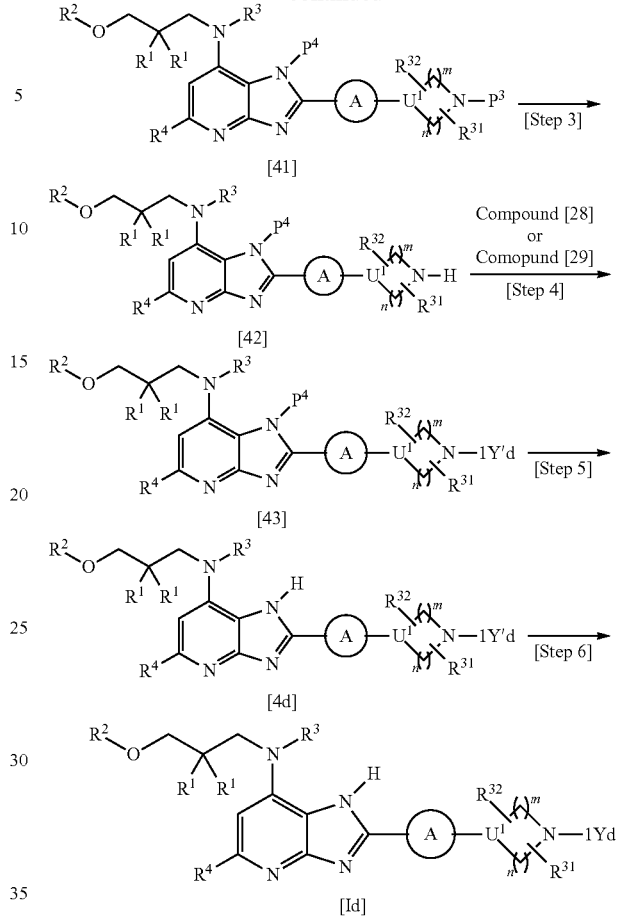

wherein A, $R^1$, $R^2$, $R^3$, $R^4$, $R^{31}$, $R^{32}$, m, n, 1Y'c, and 1Yc are as defined above. X represents a hydroxyl group or a fluorine atom.

Step 1

This step affords Compound [4c] by cyclocondensation of Compound [2] with Compound [35] or Compound [38], and the step can be carried out in a similar manner as described in Step 1 of Process 1.

Step 2

This step affords Compound [Ic] by hydrolyzing Compound [4c]. This step can be carried out in a similar manner as described in Step 2 of Process 1.

Process 2: Production of Compound [Id]

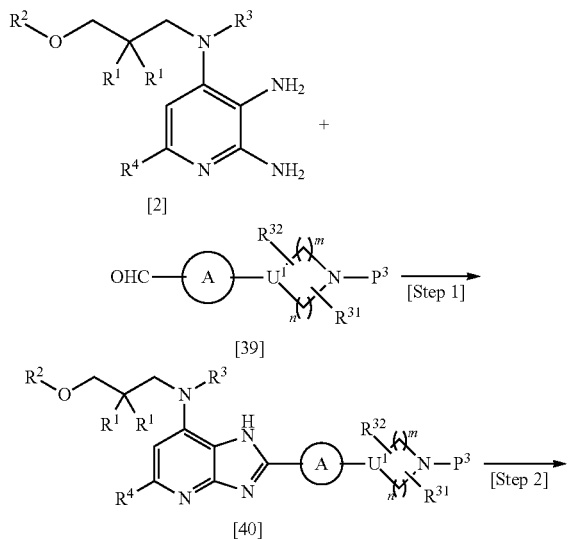

wherein $R^1$, $R^2$, $R^3$, $R^4$, $R^{31}$, $R^{32}$, $U^1$, m, n, A are as defined above. 1Yd is Y-1, Y-2, Y-3 or Y-4, and 1Y'd is Y'-1, Y'-2, Y'-3, or Y'-4. $P^3$ and $P^4$ are protecting groups. $P^3$ is a protecting group to be deprotected under basic conditions, such as trifluoroacetyl group, and $P^4$ is a protecting group not to be deprotected under basic conditions, such as 2-(trimethylsilyl)ethoxymethyl (SEM) group.

This process is an alternative to Process 1. That is, as described below, cyclocondensation of Compound [2] and Compound [39] is carried out to form Compound [40] having the basic structure of Compound [1], followed by introduction of Y substituent.

Step 1

This step affords Compound [40] by cyclocondensation of Compound [2] with Compound [39], and the step can be carried out according to Step 1 of Process 1.

Step 2

This step is to introduce a protecting group into the imidazole moiety of the azabenzimidazole in Compound [40], and the step can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005.

Depending on the conditions, such as protecting reagent and solvent to be used in this step, a compound in which the protecting group is introduced at the 1-position of azabenzoimidazole, a compound in which the protecting group is introduced at the 3-position of azabenzoimidazole, or a mixture thereof may be obtained, which can be used as it is in the next step.

The protecting group $P^4$ to be introduced and/or the reaction conditions in this step should be selected so that the protecting group is not deprotected under the conditions for deprotecting $P^3$ in the next step (third step). Examples of the combination of such $P^3$ and $P^4$ include: $P^4$ is 2-(trimethylsilyl)ethoxymethyl (SEM), and $P^3$ may be a trifluoroacetyl group or Bn.

Step 3

This step affords Compound [42] by deprotecting $P^3$ from Compound [41], and can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005.

Step 4

This step affords Compound [43] by alkylating the amine of Compound [42], and can be carried out in a similar manner as described in Step 3 of the production of Compound [3a].

Step 5

This step affords Compound [4d] by deprotecting $P^4$ from Compound [43], and can be carried out with reference to Wuts and Greene, "Greene's Protective Groups in Organic Synthesis", 4th edition, John Wiley & Sons Inc., 2006, or P. J. Kocienski, "Protecting Groups", 3rd edition, Thieme, 2005.

Step 6

This step affords Compound [Id] by hydrolyzing Compound [4d], and can be prepared in a similar manner as described in Step 2 of Process 1.

The Process 2 is also applicable to Compounds [II], [III] and [IV] described below.

Process 3: Production of Compound [IIa] (wherein W is W-2)

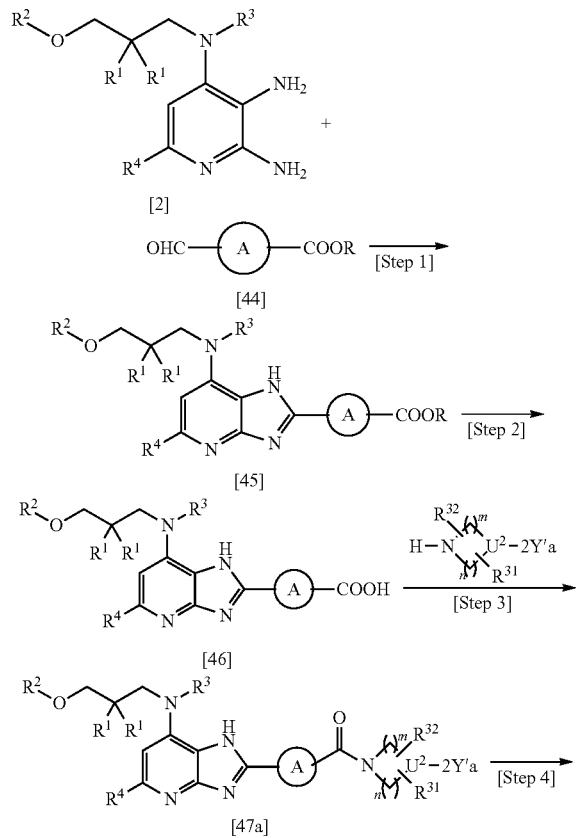

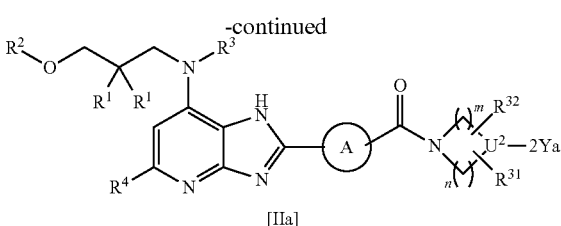

-continued

[IIa]

wherein $R^1$, $R^2$, $R^3$, $R^4$, R, A, $R^{31}$, $R^{32}$, m, n, and $U^2$ are as defined above. 2Ya is Y-1, Y-2, Y-3, Y-4, Y-11, Y-12, Y-14, or Y-15, and 2Y'a is Y'-1, Y'-2, Y'-3, Y'-4, Y'-11, Y'-12, Y'-14, or Y'-15.

This process is directed to the production of a compound of formula [IIa] among those of formula [1].

Step 1

This step affords Compound [45] by cyclocondensation of Compound [2] with Compound [44], which is commercially available or can be prepared according to a known method, and the step can be carried out in a similar manner as described in Step 1 of Process 1.

Step 2

This step affords Compound [46] by hydrolyzing Compound [45]. This step can be carried out in a similar manner as described in Step 2 of Process 1.

Step 3

This step affords Compound [47a] by condensing Compound [46] or a reactive derivative thereof and amine Compound [24a] in the presence of a condensing agent.

Examples of the reactive derivative of Compound [46] include those commonly used in amide condensation reactions, such as acid halides (e.g., acid chloride, acid bromide), mixed acid anhydrides, imidazolides, and active amides.

The amounts of the condensing agent and amine Compound [24a] to be used in this step are preferably within the range of 1 to 3 molar equivalents to Compound [46].

Examples of the condensing agent to be used in this step include 1,1'-carbonyldiimidazole (hereinafter referred to as "CDI"), 1-ethyl-3-(3-dimethylaminopropyl) carbodiimide (hereinafter referred to as "EDCI"), diisopropylcarbodiimide (hereinafter referred to as "DIC"), diethyl cyanophosphonate, O-(benzotriazol-1-yl)-N,N,N',N'-tetramethyluronium hexafluorophosphate (hereinafter referred to as "HBTU"), O-(7-azabenzotriazol-1-yl)-N,N,N',N'-tetramethyluronium hexafluorophosphate (hereinafter referred to as "HATU"), and the like.

In this step, a base can be used as necessary. Examples of the base that can be used include organic bases such as TEA, DIPEA, N,N-dimethylaniline, and DBU.

The amount of such base to be used is preferably within the range of 1 to 10 molar equivalents to Compound [46].

In this step, an additive, such as 1-hydroxybenzotriazole (hereinafter referred to as "HOBt"), N-hydroxysuccinimide, 1-hydroxy-7-azabenzotriazole (hereinafter referred to as "HOAt"), may be added, as necessary.

When the additive is used in this step, the amount of such additive is preferably within the range of 0.1 to 3 molar equivalents to Compound [46]

The solvent to be used is not limited so long as it does not participate in the reaction, and examples of such solvent include: hydrocarbons such as toluene and xylene; ethers such as 1,4-dioxane, THF and DME; amides such as DMF and DMA; halogenated hydrocarbons such as dichloromethane and chloroform; nitriles such as acetonitrile and propionitrile; and a mixed solvent thereof.

The reaction temperature can vary depending on the starting materials and reagents to be used, and is usually preferably within the range of −20° C. to 150° C. Also, a microwave reaction apparatus may be used as necessary.

The reaction time can vary depending on the starting materials and the reaction temperature to be used, and is usually preferably within the range of 0.1 to 72 hours.

Step 4

This step affords Compound [IIa] by hydrolyzing Compound [47a]. This step can be carried out in a similar manner as described in Step 2 of Process 1.

When 2Y'a is Y'-4 or Y'-14 (nitrile form) in Compound [47a], Compound [IIa] wherein 2Ya is Y-4 or Y-14 (tetrazole form), respectively, can be obtained in a similar manner as described in Step 2' of Process 1.

Also, Compound [24d] can be reacted with Compound [46] as follows, in a similar manner as described in Step 3 of Process 3, to afford Compound [IIb], which is a compound corresponding to Compound [Ib].

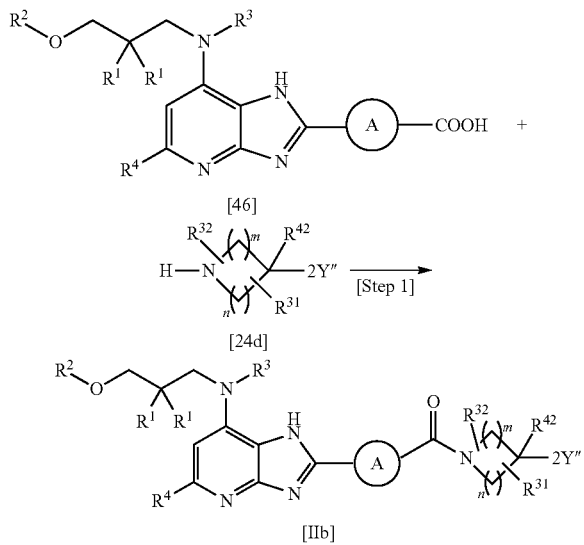

wherein $R^1$, $R^2$, $R^3$, $R^4$, R, $R^{31}$, $R^{32}$, $R^{42}$, A, m, and n are as defined above. 2Y'' is Y-13 or Y-16.

Process 4: Production of Compound [IIIa] (Wherein W is W-1 and $R^{21}$ is Alkyl)

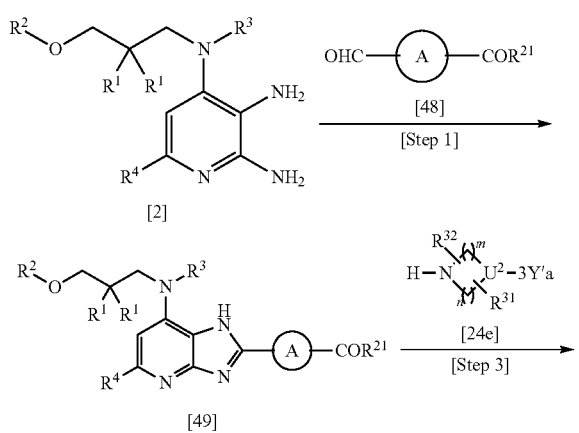

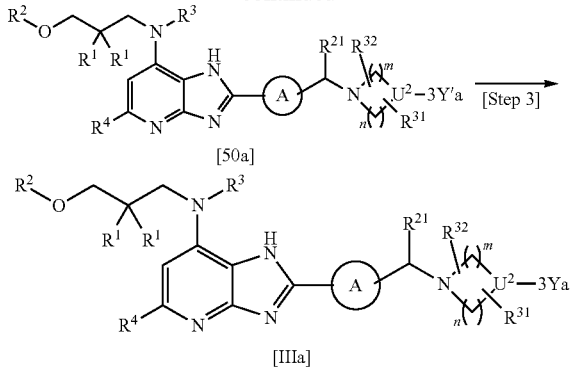

wherein $R^1$, $R^2$, $R^3$, $R^4$, $R^{31}$, $R^{32}$, $R^{21}$, A, $U^2$, m, and n are as defined above. 3Ya is Y-1, Y-2, Y-3, Y-4, Y-11, Y-12, Y-14, or Y-15, and 3Y'a is Y'-1, Y'-2, Y'-3, Y'-4, Y'-11, Y'-12, Y'-14, or Y'-15.

This process is directed to a production of a compound of formula [IIIa], which is a compound of formula [1] wherein $R^{21}$ is alkyl.

Step 1

This step affords Compound [49] by cyclocondensation of Compound [2] with Compound [48], which is commercially available or can be prepared according to a known method. This step can be carried out in a similar manner as described in Step 1 of Process 1.

Step 2

This step affords Compound [50a] by reductive amination reaction of Compound [49] with Compound [24e] and can be carried out according to a method known as reductive amination reaction. In this step, imine formation (first step) and reduction of the imine moiety (second step) can be carried out sequentially. Also, the first step and the second step may be carried out in one pot.

The first step affords an imine form by reacting Compound [49] with Compound [24e].

The amount of Compound [24e] to be used in the first step is preferably within the range of 1 to 2.5 molar equivalents to Compound [49].

In the first step, an acid or an appropriate Lewis acid may be used as necessary. Examples of the acid that can be used in the reaction include acetic acid, and examples of the Lewis acid that can be used include tetraisopropyl orthotitanate.

The amount of the acid, when using in the first step, is preferably within the range of 2 to 3 molar equivalents to Compound [49].

The amount of the Lewis acid, when using in the first step, is preferably within the range of 1.5 to 2 molar equivalents to Compound [49].

The solvent to be used in the first step is not limited so long as it does not participate in the reaction, and examples of such solvent include: hydrocarbons such as toluene and xylene; ethers such as 1,4-dioxane, THF and DME; halogenated hydrocarbons such as dichloromethane; and a mixed solvent thereof.

The reaction temperature in the first step can vary depending on the starting materials and reagents to be used, and is usually preferably within the range of 0° C. to 100° C.

The reaction time in the first step can vary depending on the starting materials and the reaction temperature to be used, and is usually preferably within the range of 0.1 to 48 hours.

The second step is a reaction with a reducing agent to obtain Compound [50a].

Examples of the reducing agent used in the second step include sodium triacetoxyborohydride, sodium cyanoborohydride, and the like.

The amount of the reducing agent to be used in the second step is preferably within the range of 1 to 2 molar equivalents to Compound [49].

The solvent to be used in the second step is not limited so long as it does not participate in the reaction, and examples of such solvent include: hydrocarbons such as toluene and xylene; ethers such as 1,4-dioxane, THF and DME; halogenated hydrocarbons such as dichloromethane; and a mixed solvent thereof.

The reaction temperature in the second step can vary depending on the starting materials and reagents to be used, and is usually preferably within the range of 0° C. to 100° C.

The reaction time in the second step can vary depending on the starting materials used and the reaction temperature, and is usually preferably within the range of 1 to 24 hours.

Step 3

This step affords Compound [IIIa] by hydrolyzing Compound [50a] This step can be carried out in a similar manner as described in Step 2 of Process 1.

When 3Y'a is Y'-4 or Y'-14 (nitrile form) in Compound [50a], Compound [IIIa] wherein 3Ya is Y-4 or Y-14 (tetrazole form), respectively, can be obtained in a similar manner as described in Step 2' of Process 1.

Also, Compound [46] can be reacted with Compound [24f] as follows, in a similar manner as described in Step 2 of Process 4, to afford Compound [IIIb], which is a compound corresponding to Compound [Ib].

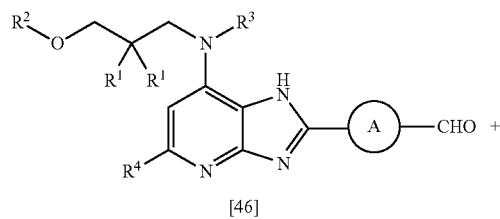

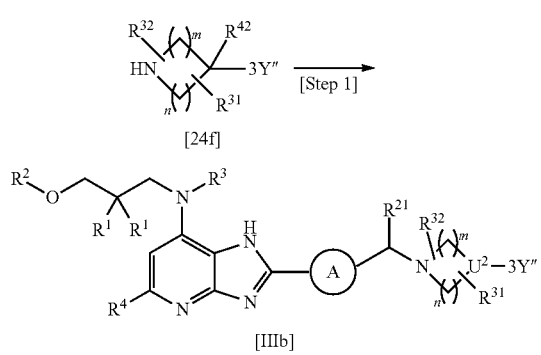

wherein $R^1$, $R^2$, $R^3$, $R^4$, $R^{31}$, $R^{32}$, $R^{42}$, A, m, and n are as defined above. 3Y'' is Y-13, or Y-16.

Process 5:

Production of Compound [IIIc] (Wherein W is W-1 and $R^{21}$ is a Hydrogen Atom).

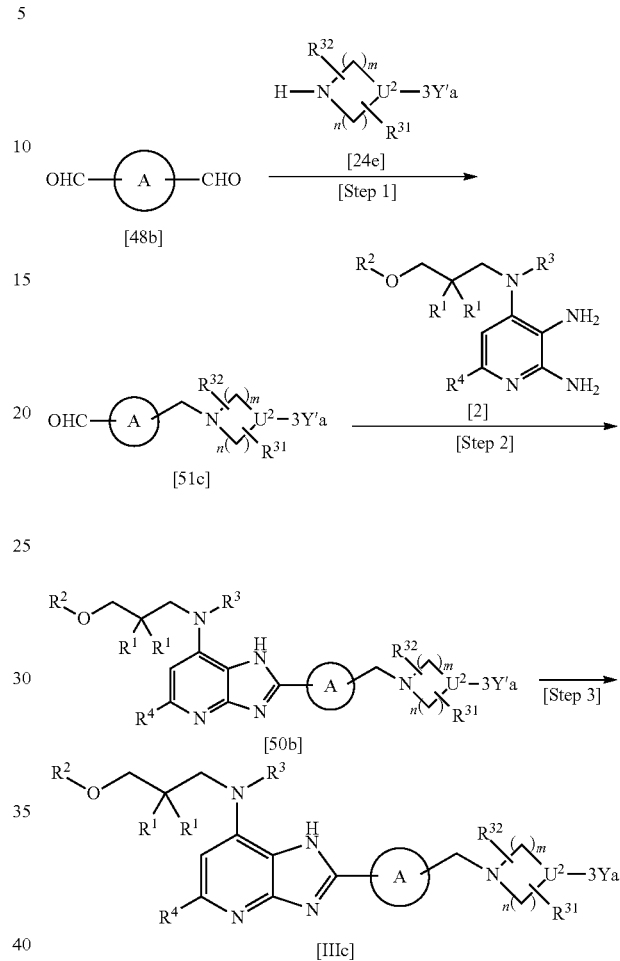

wherein $R^1$, $R^2$, $R^3$, $R^4$, $R^{31}$, $R^{32}$, $R^{21}$, A, $U^2$, 3Y', 3Y, m, and n are as defined above.

This process is directed to the production of a compound of formula [IIIc], which is a compound of formula [1] wherein $R^{21}$ is a hydrogen atom.

Step 1

This step affords Compound [51c] by reductive amination reaction of Compound [48b] with Compound [24e]. This step can be carried out in a similar manner as described in Step 2 of process 4.

Step 2

This step affords Compound [50b] by reacting Compound [51c] with Compound [2]. This step can be carried out in a similar manner as described in step 1 of process 4.

Step 3

This step affords Compound [IIIc] by hydrolyzing Compound [50b]. This step can be carried out in a similar manner as described in Step 2 of Process 1.

Also, Compound [48b] can be reacted with Compound [24f] as follows, in a similar manner as described in Step 1 of Process 1, to lead to Compound [IIId], which is a compound corresponding to Compound [Ib].

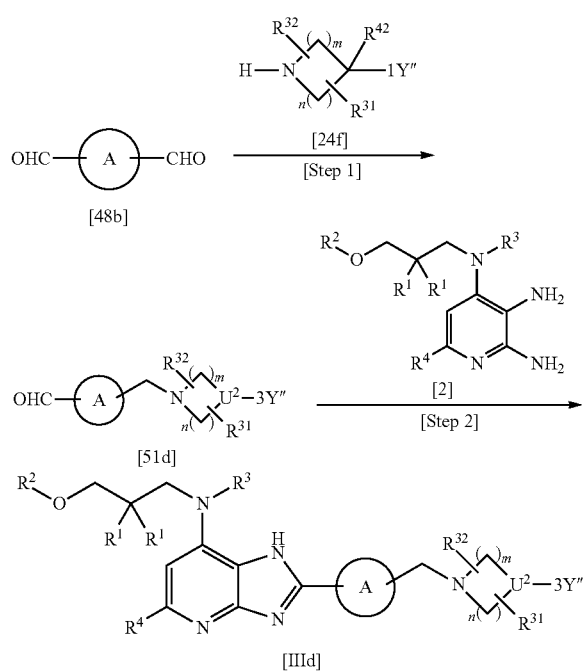

wherein $R^1$, $R^2$, $R^3$, $R^4$, $R^{31}$, $R^{32}$, $R^{42}$, A, 3Y″, m, and n are as defined above.

Process 6: Production of Compound [IV] (Wherein W is W-3)

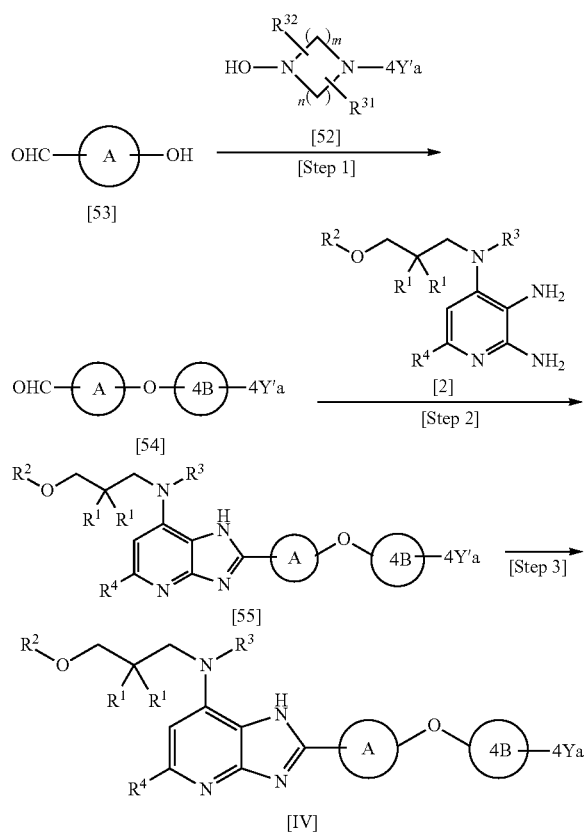

wherein $R^1$, $R^2$, $R^3$, $R^4$, $R^{31}$, $R^{32}$, A, 4B, m, and n are as defined above. 4Ya is Y-1, Y-2 or Y-3, and 4Y'a is Y'-1, Y'-2 or Y'-3.

Step 1

This step affords ether Compound [54] by Mitsunobu reaction between Compound [52] and Compound [53] and can be carried out according to a known method.

This step is usually carried out in an appropriate solvent in the presence of an azodicarboxylic acid ester reagent and a phosphine reagent.

The amount of Compound [53] to be used is preferably within the range of 0.5 to 1.5 molar equivalents to Compound [52].

Examples of the azodicarboxylate reagent to be used include diethyl azodicarboxylate (hereinafter referred to as "DEAD"), diisopropyl azodicarboxylate (hereinafter referred to as "DIAD"), and bis(2-methoxyethyl)azodicarboxylate (hereinafter referred to as "DMEAD"). Examples of the phosphine reagent to be used include triphenylphosphine and tributylphosphine.

The amount of the azodicarboxylic acid ester reagent to be used is preferably within the range of 1 to 2 molar equivalents to Compound [52].

The amount of the phosphine reagent to be used is preferably within the range of 1 to 2 molar equivalents to Compound [52].

The solvent to be used is not limited so long as it does not participate in the reaction, and examples of such solvent include: hydrocarbons such as toluene and xylene; ethers such as 1,4-dioxane, THF, and DME; or a mixed solvent thereof.

The reaction temperature in this step can vary depending on the starting materials and reagents to be used, and is usually preferably within the range of 0° C. to 100° C.

The reaction time can vary depending on the starting materials and the reaction temperature to be used, and is usually preferably within the range of 0.5 to 24 hours.

In this step, instead of Compound [52], Compound [52'] wherein 4Y'a of Compound [52] is a protecting group $P^1$ defined above may be used as a starting material. In that case, this step affords Compound [54'] wherein 4Y'a of Compound [54] is substituted with a protecting group $P^1$. Compound [54'] can be processed in a similar manner as described in Step 2 and Step 3 for the production of Compound [3a] to obtain Compound [54].

Step 2

This step affords Compound [55] by cyclocondensation of Compound [54] and Compound [2]. This step can be carried out in a similar manner as described in Step 1 of Process 1.

Step 3

This step affords Compound [IV] by hydrolyzing Compound [55], and the step can be carried out in a similar manner as described in Step 2 of Process 1.

Urinary storage and voiding are regulated by the action of the bladder and urethra. In urinary storage, urinary restraint is maintained by relaxation of bladder smooth muscle (detrusor) and contraction of urethral sphincter. On the other hand, voiding is caused by contraction of bladder smooth muscle and relaxation of urethral smooth muscle. During voiding, acetylcholine is released from the nerve endings of the pelvic nerve, which is the parasympathetic nerve that governs the bladder. The released acetylcholine binds to M3 receptor of the bladder smooth muscle, whereby the bladder smooth muscle contracts.

For example, if urine storage disorder occurs due to overactive bladder or the like, urine cannot be retained for urine storage. Further, if voiding dysfunction occurs due to, for example, underactive bladder, urine cannot be excreted sufficiently during micturition. Furthermore, residual urine after micturition may be found in voiding dysfunction. Increasing residual urine may lead to symptoms such as frequent urination. Thus, urinary storage and voiding dysfunction may develop together (see Current Urology Report, 2016, 17:17).

The compound of the invention can be used for the prevention or treatment of diseases involving M3 receptor, in particular, bladder/urethral diseases involving bladder contraction, digestive system diseases involving gastrointestinal contraction, oral diseases involving salivation, ocular diseases involving tear secretion and pupil contraction. The compound of the invention is particularly useful for the prevention or treatment of voiding and/or storage disorders in bladder/urethral diseases, glaucoma in ocular diseases, and diabetes. As used herein, diabetes refers to diabetes in which the insulin secretion ability involving M3 receptor is reduced (see Cell Metabolism, 2006, Vol. 3, p. 449-461).

Examples of voiding and/or storage disorders for which the prevention or treatment with the compounds of the invention are particularly useful include voiding and/or storage disorders in underactive bladder, hypotonic bladder, acontractile bladder, detrusor underactivity, neurogenic bladder, urethral relaxation failure, detrusor-external urethral sphincter dyssynergia, overactive bladder, frequent urination, nocturia, urinary incontinence, benign prostatic hyperplasia, interstitial cystitis, chronic prostatitis and urolithiasis.

The compound of the invention is particularly useful for the prevention or treatment of voiding and/or storage disorders in underactive bladder, hypotonic bladder, acontractile bladder, detrusor underactivity, benign prostatic hypertrophy and neurogenic bladder. For example, in underactive bladder, voiding dysfunction occurs due to decreased contractile force of the bladder detrusor during micturition, and the compound of the invention can improve the contractile force of the bladder detrusor during micturition to promote bladder emptying.

The compound of the present invention is particularly useful for the prevention or treatment of underactive bladder, hypotonic bladder, acontractile bladder and detrusor underactivity due to a specific cause. Specific causes include neurological diseases (multiple system atrophy, Parkinson's disease, multiple sclerosis, spinal cord injury, lumbar disc herniation, etc.), diabetes, pelvic surgery, prostate hypertrophy and aging.

Acetylcholine contracts the ciliary muscle via M3 receptor of the ciliary muscle of the eye. By the contraction of the ciliary muscle, Schlemm's canal opens, and aqueous humor outflows through the Schlemm's canal, thereby, intraocular pressure falls. Examples of glaucoma for which prevention or treatment with the compound of the present invention is particularly useful include primary open-angle glaucoma, normal-tension glaucoma, and primary closed-angle glaucoma.

When the compound of the present invention is administered as a pharmaceutical, the compound of the present invention is administered to a mammal including human as it is or as a pharmaceutical composition containing the compound in an amount, such as 0.001% to 99.5%, preferably 0.1% to 90%, in a pharmaceutically acceptable nontoxic and inert carrier.

The carrier may be one or more of solid, semi-solid or liquid diluents, fillers and other excipients. The pharmaceutical composition according to the present invention is preferably administered in a unit dosage form. The pharmaceutical composition can be administered via intra-tissue, oral, intravenous, topical (transdermal, eye drops, intraperitoneal, intrathoracic, etc.) or rectal route. Of course, the composition is administered in a dosage form suitable for the mode of administration.

The dose as a pharmaceutical is preferably adjusted taking into consideration the conditions such as age, weight, type and severity of disease of the patient, administration route, type of the compound of the invention, whether or not it is a salt, and the type of the salt. In general, the effective amount of the compound of the invention or a pharmaceutically acceptable salt thereof for adult, in the case of oral administration, is preferably within a range of 0.01 mg to 5 g/day, preferably 1 mg to 500 mg/day. In some cases, a smaller amount may be sufficient or a larger amount may be required. Usually, the dosage can be administered once a day or can be divided and administered several times a day, or in the case of intravenous administration, the dosage can be administered rapidly or sustainably within 24 hours.

One or more hydrogen, carbon and/or the other atoms in the compound of the invention may be replaced with an isotope thereof. Examples of such isotopes include $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, i.e., hydrogen, carbon, nitrogen, oxygen, phosphorus, sulfur, fluorine, iodine and chlorine. The compound substituted with such isotope may be useful as a pharmaceutical and includes all radiolabeled compounds of the compound of the invention.

The present invention is described in more detail with reference to, but is not limited to, the following Comparative Examples, Examples and Test Examples.

The following abbreviations are used in the following Examples, Reference Examples and Tables.

REx: Reference Example
PREx: Referenced Reference Example
Ex: Example No.
PEx: Referenced Example
TFA: Trifluoroacetic acid
Pt-C: Platinum-carbon
Pd-C: Palladium-carbon Pd$_2$(dba)$_3$·CHCl$_3$: Tris(dibenzylideneacetone)bispalladium·chloroform adduct
Pd$_2$(dba)$_3$: Tris(dibenzylideneacetone)bispalladium
Pd(dppf)Cl$_2$·CH$_2$Cl$_2$: [1,1-Bis(diphenylphosphino)ferrocene]-dichloropalladium(II)·dichloromethane adduct
Pd(OAc)$_2$: Palladium acetate(II)
dppf: 1,1'-Bis(diphenylphosphino)ferrocene
XPhos: 2-Dicyclohexylphosphino-2',4',6'-triisopropylbiphenyl
RuPhos: 2-Dicyclohexylphosphino-2',6'-diisopropylbiphenyl
PPh$_3$: Triphenylphosphine
Boc: Tert-butoxycarbonyl
Bn: Benzyl
Ts: 4-Toluenesulfonyl
SEM: 2-(Trimethylsilyl)ethoxymethyl
DAST: (Diethylamino)sulfur-trifluoride
HATU: O-(7-azabenzotriazol-1-yl)-N,N,N',N'-tetramethyluronium hexafluorophosphate
DEAD: Diethyl azodicarboxylate
DMF: Dimethylformamide
DMSO: Dimethylsulfoxide
DIPEA: N,N-diisopropylethylamine
TEA: Triethylamine
DBU: 1,8-Diazabicyclo[5.4.0]-7-undecene
CDCl$_3$: Deuterochloroform
DMSO-d6: Deuterodimethylsulfoxide
TLC: Thin layer chromatography MS: Mass spectrometry
LCMS: High performance liquid chromatography-Mass spectrometry
ESI: Electron Spray Ionization
M: Molar concentration (mol/L)
MS was performed using LCMS. ESI was used as a method for ionization. Observed values of the mass spectrometry are expressed as m/z.
The conditions for LCMS were as follows:
Instrument: ACQUITY UPLC MS/PDA system (Waters)
Mass spectrometry: Waters 3100 MS detector
Photodiode array detector: ACQUITY PDA detector (UV-detected wave length: 210-400 nm)
Column: Acquity BEH C18, 1.7 µm, 2.1×50 mm
Flow rate: 0.5 mL/min
Colum temperature: 40° C.
Solvent;
A: 0.1% formic acid/$H_2O$ (v/v; the same hereinafter)
B: 0.1% formic acid/acetonitrile $^1$H NMR spectrum was obtained using JNM-ECS400 Nuclear Magnetic Resonance Spectrometer (JEOL RESONANCE Ltd.). The observed peaks were shown as chemical shift values δ (ppm) (s=singlet, d=doublet, t=triplet, q=quartet, brs=broad singlet, m=multiplet, dd=double doublet, dt=double triplet).

In the experiment using microwave, Initiator 60 (Biotage) was used, which can achieve a temperature of 40-250° C. and a pressure of up to 20 bar.

The compounds described herein were named using naming software, ACD/NAME® (Advanced Chemistry Development Inc.) according to IUPAC nomenclature rules, or ChemBioDraw (version 14.0, Cambridge Soft), or named according to IUPAC nomenclature.

In a name of a compound, the descriptors "r" and "s" (lower case) refer to the stereochemistry of pseudoasymmetric carbon atom according to IUPAC rules.

Reference Example 1: N-{[1-(methoxymethyl)cyclopentyl]methyl}ethanamine hydrochloride

[Step 1] Preparation of tert-butyl {[1-(methoxymethyl)cyclopentyl]methyl}carbamate 1-(Methoxymethyl)cyclopentane-1-carbonitrile (33 g) was dissolved in ethanol (250 mL). After degassing, to the stirred solution was added hydrogen chloride (4 M in ethyl acetate, 65 mL) and platinum(IV) oxide (0.27 g) at room temperature under argon atmosphere. The reaction mixture was stirred at room temperature for 2 days under hydrogen atmosphere (0.45 MPa). After filtering insolubles off, the solvent was removed under reduced pressure. The residue was dissolved in methanol. To the stirred solution were added nickel(II) chloride hexahydrate (5.65 g) and di-tert-butyl dicarbonate (68 g) at room temperature. Sodium borohydride (63 g) was added portion-wise over 30 minutes to the stirred solution under ice-cooling, and then the reaction mixture was stirred at room temperature for 4 hours. Water was added to the reaction mixture, and insolubles were filtered off. The filtrate was concentrated under reduced pressure. The residue was diluted with water and saturated aq. sodium bicarbonate, and then extracted with ethyl acetate. The organic layer was washed with saturated saline, dried over anhydrous magnesium sulfate, and concentrated under reduced pressure. The residue was purified by silica gel column chromatography to afford the title compound (40 g).

[Step 2] Preparation of tert-butyl ethyl{[1-(methoxymethyl)cyclopentyl]methyl}carbamate Tert-butyl {[1-(methoxymethyl)cyclopentyl] methyl}carbamate (2.0 g) obtained in Step 1 was dissolved in DMF (20 mL). To the stirred solution was added 60% sodium hydride (0.99 g), and the reaction mixture was stirred at the same temperature for 10 minutes. Ethyl iodide (2.0 mL) was added thereto, and the reaction mixture was stirred at room temperature overnight. The reaction mixture was diluted with water, and extracted with ethyl acetate. The organic layer was washed with saturated saline, dried over anhydrous sodium sulfate, and concentrated under reduced pressure. The residue was purified by silica gel column chromatography to afford the title compound (2.1 g).

[Step 3] Preparation of N-{[1-(methoxymethyl)cyclopentyl]methyl}ethanamine hydrochloride A solution of tert-butyl ethyl{[1-(methoxymethyl)cyclopentyl]methyl}carbamate (2.09 g) obtained in Step 2 in ethyl acetate (8 mL) was stirred at room temperature, and hydrogen chloride (4 M in ethyl acetate, 5.8 mL) was added to the solution, and the reaction mixture was stirred at the same temperature for 4 hours. The reaction mixture was concentrated under reduced pressure. The residue was suspended in hexane (30 mL), and resulting precipitate was collected by filtration. The collected solid was washed with hexane and dried to afford the title compound (1.45 g).

Reference Example 2: 1-{1-[(2-Methoxyethoxy)methyl]cyclopentyl}-N-methylmethanamine hydrochloride

[Step 1] Preparation of 1-[(2-methoxyethoxy)methyl]cyclopentane-1-carbonitrile

To a stirred solution of 1-(hydroxymethyl)cyclopentane-1-carbonitrile (1.0 g) in DMF (40 mL) was added 60% sodium hydride (697 mg) at room temperature, and the reaction mixture was stirred at the same temperature for 30 minutes. 1-Bromo-2-methoxyethane (2.2 g) was added, and the reaction mixture was stirred at room temperature. After monitoring the consumption of the starting material on TLC, saturated aq. ammonium chloride and ethyl acetate were added to the reaction mixture, and then the mixture was extracted with ethyl acetate. The organic layer was washed with water and saturated saline, and then dried over anhydrous sodium sulfate. The solvent was removed under reduced pressure. The residue was purified by silica gel column chromatography to afford the title compound (1.3 g)

[Step 2] Preparation of 1-{1-[(2-methoxyethoxy)methyl]cyclopentyl}methanamine hydrochloride A solution of 1-[(2-methoxyethoxy)methyl]cyclopentane-1-carbonitrile obtained in Step 1 (1.3 g) in ethanol (24 mL) was degassed. To the stirred solution were added hydrogen chloride (4 M in ethyl acetate, 3.5 mL) and platinum(IV) oxide (32 mg) at room temperature under argon atmosphere, and the reaction mixture was stirred at room temperature for 2 days under hydrogen atmosphere (0.45 MPa). After filtering insolubles off, the solvent was removed under reduced pressure. The residue was dried to afford the title compound (1.4 g).

[Step 3] Preparation of tert-butyl ({1-[(2-methoxy-ethoxy)methyl]cyclopentyl}methyl)methylcarbamate To a stirred solution of 1-{1-[(2-methoxyethoxy)methyl]cyclopentyl}methanamine hydrochloride obtained in Step 2 (1.4 g) in dichloromethane (13 mL) were added triethylamine (1.9 mL) and di-tert-butyl dicarbonate (1.6 g) at room temperature, and the reaction mixture was stirred at the same temperature for 2 hours. The reaction mixture was concentrated under reduced pressure. The residue was diluted with water and ethyl acetate, and then extracted with ethyl acetate. The organic layer was washed with water and saturated saline, and then dried over anhydrous sodium sulfate. The solvent was removed under reduced pressure. The residue was dissolved in DMF (13 mL). To the stirred solution was added 60% sodium hydride (0.41 g) at room temperature, and the reaction mixture was stirred at the same temperature for 1 hour. The reaction mixture was cooled on ice, and methyl iodide (0.58 mL) was added dropwise. After the addition, the reaction mixture was warmed to room temperature and stirred overnight. Saturated aq. ammonium chloride was added, and the mixture was extracted with ethyl acetate. The organic layer was washed with saturated saline, dried over anhydrous sodium sulfate, and then concentrated under reduced pressure. The residue was purified by silica gel column chromatography to afford the title compound (1.87 g).

[Step 4] Preparation of 1-{1-[(2-methoxyethoxy)methyl] cyclopentyl}-N-methylmethanamine hydrochloride A solution of tert-butyl ({1-[(2-methoxyethoxy)methyl]cyclopentyl}methyl)methylcarbamate obtained in Step 3 (1.87 g) in ethyl acetate (6.2 mL) was stirred at room temperature. Hydrogen chloride (4 M solution in ethyl acetate, 7.8 mL) was added to the solution, and the reaction mixture was stirred at the same temperature for 2 hours. The reaction mixture was concentrated under reduced pressure to afford the title compound (1.45 g).

Reference Example 3: 1-[1-(Butoxymethyl)cyclopentyl]-N-methylmethanamine hydrochloride

[Step 1] Preparation of 1-(butoxymethyl)cyclopentane-1-carbonitrile

The title compound was obtained as described in Reference Example 2, Step 1, using 1-iodobutane instead of 1-bromo-2-methoxyethane.

[Step 2] Preparation of tert-butyl {[1-(butoxymethyl) cyclopentyl]methyl}carbamate To a stirred solution of 1-(butoxymethyl)cyclopentane-1-carbonitrile obtained in Step 1 (0.19 g) in methanol (2.6 mL) were added di-tert-butyl dicarbonate (0.46 g) and nickel(II) chloride hexahydrate (0.25 g) at room temperature. Sodium borohydride (0.28 g) was added portion-wise thereto under ice-cooling, and the reaction mixture was stirred at room temperature for 10 hours. The reaction mixture was diluted with saturated aq. sodium bicarbonate and ethyl acetate, and then the mixture was extracted with ethyl acetate. The organic layer was washed with saturated aq. sodium bicarbonate and saturated saline, dried over anhydrous sodium sulfate, and then concentrated under reduced pressure. The residue was purified by silica gel column chromatography to afford the title compound (0.24 g)

[Step 3] Preparation of tert-butyl {[1-(butoxymethyl) cyclopentyl]methyl}methylcarbamate Tert-butyl {[1-(butoxymethyl)cyclopentyl]methyl}carbamate obtained in Step 2 (0.24 g) was dissolved in DMF (1.7 mL). 60% sodium hydride (48 mg) was added to the stirred solution under ice-cooling, and the reaction mixture was stirred at room temperature for 1 hour. The reaction mixture was cooled on ice bath, and methyl iodide (0.078 mL) was added dropwise. After the addition, the reaction mixture was warmed to room temperature and stirred overnight. Water was added to the reaction mixture, and the mixture was extracted with ethyl acetate-hexane (1:1). The organic layer was washed with saturated saline, dried over anhydrous sodium sulfate, and then concentrated under reduced pressure. The residue was purified by silica gel column chromatography to afford the title compound (59 mg).

[Step 4] Preparation of 1-[1-(Butoxymethyl)cyclopentyl]-N-methylmethanamine hydrochloride The title compound (47 mg) was obtained as described in Reference Example 1, Step 3, using tert-butyl {[1-(butoxymethyl)cyclopentyl]methyl}methylcarbamate obtained in Step 3 instead of tert-butyl ethyl{[1-(methoxymethyl)cyclopentyl]methyl}carbamate.

Reference Example 4: 1-[1-(Ethoxymethyl)cyclopentyl]-N-methylmethanamine hydrochloride

[Step 1] Preparation of 1-(ethoxymethyl)cyclopentane-1-carbonitrile

The title compound was obtained as described in Reference Example 2, Step 1, using ethyl iodide instead of 1-bromo-2-methoxyethane.

[Step 2] Preparation of tert-butyl {[1-(ethoxymethyl) cyclopentyl]methyl}methylcarbamate Lithium aluminum hydride (11.4 g) was suspended in THF (800 mL), and a solution of 1-(ethoxymethyl)cyclopentane-1-carbonitrile (46.0 g) obtained in Step 1 in THF (200 mL) was added dropwise to the suspension under ice-cooling. After the addition, the reaction mixture was stirred at room temperature for 2 hours. The reaction mixture was cooled on ice bath, and water (11.4 mL), 15% aq. sodium hydroxide (11.4 mL) and water (34.2 mL) were added dropwise sequentially. After the addition, the reaction mixture was stirred at room temperature for 2 hours. Insolubles were filtered off through celite and washed with THF (220 mL) three times. The filtrate was stirred at room temperature, and triethylamine (46.0 mL) and di-tert-butyl dicarbonate (72.1 g) were added. The reaction mixture was stirred at the same temperature for 2 hours, and then concentrated under reduced pressure. The residue was diluted with water and extracted with ethyl acetate. The organic layer was washed with saturated saline, dried over anhydrous sodium sulfate, and then concentrated under reduced pressure. The residue was dissolved in DMF (600 mL). To the stirred solution was added 60% sodium hydride (14.4 g) under ice-cooling, and the reaction mixture was stirred for 1 hour at room temperature. The reaction mixture was cooled on ice bath, and methyl iodide (22.5 mL) was added dropwise. After the addition, the reaction mixture was stirred at room temperature for 15 hours. The reaction mixture was cooled on ice bath, diluted with water, and then extracted with ethyl acetate-hexane (1:2). The organic layer was washed with saturated saline, dried over anhydrous sodium sulfate, and then the solvent was removed under reduced pressure. The residue was purified by silica gel column chromatography to afford the title compound (71.2 g).

[Step 3] Preparation of 1-[1-(ethoxymethyl)cyclopentyl]-N-methylmethanamine hydrochloride The title compound (50.3 g) was obtained as described in Reference Example 1, Step 3, using tert-butyl {[1-(ethoxymethyl)cyclopentyl]methyl}methylcarbamate obtained in Step 2 instead of tert-butyl ethyl{[1-(methoxymethyl)cyclopentyl]methyl}carbamate.

Reference Example 5: 1-[1-(Methoxymethyl)cyclopentyl]-N-methylmethanamine hydrochloride

[Step 1] Preparation of tert-butyl {[1-(hydroxymethyl)cyclopentyl]methyl}carbamate To a stirred solution of [1-(aminomethyl)cyclopentyl]methanol (50.7 g) in THF (304 mL) was added triethylamine (60.2 mL) under ice-cooling. Di-tert-butyl dicarbonate (94.2 g) in THF (101 mL) was added dropwise to this solution. After the addition, the reaction mixture was stirred at room temperature overnight. The reaction mixture was diluted with water and ethyl acetate, and the mixture was extracted with ethyl acetate. The organic layer was washed with saturated saline, dried over anhydrous sodium sulfate, and then the solvent was removed under reduced pressure. The residue was extracted with ethyl acetate-hexane (1:9) (700 mL), and the extract was stirred at room temperature for 3 hours. Insolubles were collected by filtration, washed with hexane, and dried to afford the title compound (49.2 g). For the filtrate, the solvent was removed under reduced pressure, and the residue was purified by silica gel column chromatography to afford the title compound (15.9 g).

[Step 2] Preparation of tert-butyl {[1-(methoxymethyl)cyclopentyl]methyl}methylcarbamate To a stirred solution of tert-butyl {[1-(hydroxymethyl)cyclopentyl]methyl}carbamate (58 g) obtained in Step 1 in DMF (505 mL) was added methyl iodide (47 mL) at room temperature. 60% sodium hydride (30 g) was then added portion-wise under ice-cooling. After the reaction mixture was stirred for 30 minutes under ice-cooling, the mixture was warmed to room temperature and stirred overnight. Water (800 mL) was added dropwise to the reaction mixture under ice-cooling, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (68 g).

[Step 3] Preparation of 1-[1-(methoxymethyl)cyclopentyl]-N-methylmethanamine hydrochloride The title compound (52 g) was obtained as described in Reference Example 1, Step 3, using tert-butyl {[1-(methoxymethyl)cyclopentyl]methyl}methylcarbamate obtained in Step 2 instead of tert-butyl ethyl{[1-(methoxymethyl)cyclopentyl]methyl}carbamate.

Reference Example 6: 4-Chloro-6-[3-fluoro-5-(trifluoromethyl)phenyl]pyridin-2-amine To a mixture of [3-fluoro-5-(trifluoromethyl)phenyl]boronic acid (0.6 g), 4,6-dichloropyridin-2-amine (0.45 g), and potassium carbonate (1.2 g) were added 1,4-dioxane (9.6 mL) and water (2.4 mL). After degassing, to the stirred solution was added Pd(dppf)Cl$_2$'CH$_2$C12 (118 mg) at room temperature under argon atmosphere, and the reaction mixture was stirred at 80° C. for 3 hours. The reaction mixture was cooled to room temperature, diluted with water and ethyl acetate, and extracted with ethyl acetate. The organic layer was washed with water and saturated saline, dried over anhydrous magnesium sulfate, and then concentrated under reduced pressure. The residue was purified by silica gel column chromatography to afford the title compound (0.5 g).

Reference Example 7: 4-Chloro-6-[3-fluoro-5-(trifluoromethyl)phenyl]-3-nitropyridin-2-amine Under ice-cooling, concentrated sulfuric acid (2.5 mL) was added to 4-chloro-6-[3-fluoro-5-(trifluoromethyl)phenyl]pyridin-2-amine (0.5 g), and then potassium nitrate (165 mg) was added portion-wise. The reaction mixture was stirred for 15 minutes under ice-cooling and further stirred at room temperature for 4 hours. The reaction mixture was poured into ice-water. After the addition of 4 M aq. sodium hydroxide (25 mL), the mixture was extracted with ethyl acetate. The organic layer was washed with saturated saline, dried over anhydrous magnesium sulfate, and then concentrated under reduced pressure. The residue was purified by silica gel column chromatography to afford the title compound (0.35 g).

Reference Example 8: 6-Chloro-N$^4$-(3-methoxy-2,2-dimethylpropyl)-N$^4$-methyl-3-nitropyridin-2,4-diamine A mixture of 4,6-dichloro-3-nitropyridin-2-amine (6.3 g), 3-methoxy-N,2,2-trimethylpropan-1-amine hydrochloride (6.6 g), DIPEA (16 mL), and 2-propanol (100 mL) was stirred at 60° C. for 1 hour. The reaction mixture was cooled to room temperature. Water (50 mL) was added to the mixture, and resulting precipitate was collected by filtration. The collected precipitate was washed with 2-propanol and water sequentially and dried to afford the title compound (8.0 g)

Reference Example 9: 6'-Cyclopropyl-N$^4$-{[1-(methoxymethyl) cyclohexyl] methyl}-N$^4$-methyl-5-nitro-5'-(trifluoromethyl) [2,3'-bipyridine]-4,6-diamine A mixture of 6-chloro-N$^4$-{[1-(methoxymethyl) cyclohexyl]methyl}-N$^4$-methyl-3-nitropyridine-2,4-diamine (2.5 g), 2-cyclopropyl-5-(4,4,5,5-tetramethyl-1,3,2,-dioxaborolan-2-yl)-3-(trifluoromethyl)pyridine (2.7 g), potassium carbonate (3.0 g), 1,4-dioxane (29 mL) and water (11 mL) was degassed, and Pd(dppf)Cl$_2$·CH$_2$Cl$_2$ (0.24 g) was added to the mixture with stirring at room temperature under argon atmosphere. The reaction mixture was stirred at 95° C. for 2 hours. The reaction mixture was cooled to room temperature and diluted with water and ethyl acetate, and the mixture was extracted with ethyl acetate. The organic layer was washed with water and saturated saline, dried over anhydrous magnesium sulfate, and then concentrated under reduced pressure. The residue was purified by silica gel column chromatography to afford the title compound (3.5 g).

Reference Example 10: 2'-Ethoxy-$N^4$-{[1-(ethoxymethyl) cyclopentyl]methyl}-$N^4$-methyl-6'-(trifluoromethyl) [2,4'-bipyridine]-4,5,6-triamine A mixture of 6-chloro-$N^4$-{[1-(ethoxymethyl) cyclopentyl] methyl}-$N^4$-methyl-3-nitropyridine-2,4-diamine (0.70 g), 2-ethoxy-4-(4,4,5,5-tetramethyl-1,3,2,-dioxaborolan-2-yl)-6-(trifluoromethyl)pyridine (0.78 g), potassium carbonate (0.85 g), Pd(dppf)Cl$_2$·CH$_2$Cl$_2$ (67 mg), 1,4-dioxane (8.2 mL) and water (3.1 mL) was degassed and stirred at 90° C. for 2 hours. The reaction mixture was cooled to room temperature and diluted with water and ethyl acetate, and the mixture was extracted with ethyl acetate. The organic layer was washed with water and saturated saline, dried over anhydrous sodium sulfate, and then concentrated under reduced pressure. The residue was purified by silica gel column chromatography to afford 2'-ethoxy-$N^4$-{[1-(ethoxymethyl) cyclopentyl]methyl}-$N^4$-methyl-5-nitro-6'-(trifluoromethyl) [2,4'-bipyridine]-4,6-diamine. This compound was mixed with 2-propanol (6.8 mL), water (3.4 mL), ammonium chloride (0.33 g) and zinc powder (0.67 mg), and the mixture was stirred at room temperature for 1 hour. Insolubles were filtered off using celite, and the filtrate was concentrated under reduced pressure. The residue was purified by silica gel column chromatography to afford the title compound (0.83 g).

Reference Example 11: 6-[3-Fluoro-5-(trifluoromethyl)phenyl]-$N^4$-({1-[(2-methoxyethoxy)methyl] cyclopentyl}methyl)-$N^4$-methylpyridine-2,3,4-triamine To a stirred mixture of 4-chloro-6-[3-fluoro-5-(trifluoromethyl)phenyl]-3-nitropyridin-2-amine (100 mg), 1-{1-[(2-methoxyethoxy)methyl]cyclopentyl}-N-methylmethanamine hydrochloride (78 mg) and 2-propanol (1 mL) was added DIPEA (0.16 mL) at room temperature, and the mixture was stirred at 90° C. for 2 hours. Reduced iron (powder, 50 mg), ammonium chloride (48 mg) and water (0.5 mL) were added to the mixture, and the reaction mixture was stirred at the same temperature for 16 hours. The reaction mixture was cooled to room temperature and diluted with ethyl acetate. Insolubles were filtered off using celite, and the filtrate was extracted with ethyl acetate. The organic layer was washed with water and saturated saline, dried over anhydrous sodium sulfate, and then the solvent was removed under reduced pressure. The residue was purified by silica gel column chromatography to afford the title compound (126 mg).

Reference Example 12: 2'-Ethoxy-$N^4$-{[1-(methoxymethyl) cyclobutyl] methyl}-$N^4$-methyl-6'-(trifluoromethyl) [2,4'-bipyridine]-4,5,6-triamine To a mixture of 2'-ethoxy-$N^4$-{[1-(methoxymethyl) cyclobutyl]methyl}-$N^4$-methyl-5-nitro-6'-(trifluoromethyl) [2,4'-bipyridine]-4,6-diamine (684 mg), 2-propanol (7.5 mL) and water (2.5 mL) were added ammonium chloride (234 mg) and reduced iron (powder, 244 mg), and the reaction mixture was stirred at 90° C. overnight. The reaction mixture was cooled to room temperature and diluted with ethyl acetate and water. Insolubles were filtered off using celite, and the filtrate was extracted with ethyl acetate. The organic layer was washed with saturated saline, and dried over anhydrous sodium sulfate. The solvent was removed under reduced pressure. The residue was purified by silica gel column chromatography to afford the title compound (570 mg).

Reference Example 13: 6'-Cyclopropyl-$N^4$-{[1-(ethoxymethyl) cyclopentyl] methyl}-$N^4$-methyl-5'-(trifluoromethyl) [2,3'-bipyridine]-4,5,6-triamine To a stirred mixture of 6'-cyclopropyl-$N^4$-{[1-(ethoxymethyl) cyclopentyl] methyl}-$N^4$-methyl-5-nitro-5'-(trifluoromethyl) [2,3'-bipyridine]-4,6-diamine (5.8 g), ammonium chloride (1.9 g), 2-propanol (39 mL) and water (20 mL) was added zinc powder (3.9 g) at room temperature, and the reaction mixture was stirred at 50° C. for 4 hours. The reaction mixture was cooled to room temperature and then diluted with ethyl acetate. Insolubles were filtered off using celite. After concentrating the filtrate under reduced pressure, the residue was purified by silica gel column chromatography to afford the title compound (5.3 g).

Reference Example 14: Ethyl [4-(4-formylphenyl) piperazin-1-yl]acetate

To a stirred solution of ethyl (4-phenylpiperazin-1-yl) acetate (1.1 g) in DMF (10 mL) was added phosphorus oxychloride (1.3 mL) at room temperature, and the reaction mixture was stirred in oil bath at 100° C. for 1 hour. The reaction mixture was cooled to room temperature and diluted with water and ethyl acetate. Saturated aq. sodium bicarbonate was added thereto, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (1.1 g)

Reference Example 15: Ethyl 3-[(3R)-4-(4-formylphenyl)-3-methylpiperazin-1-yl] propanoate

[Step 1] Preparation of ethyl 3-[(3R)-3-methyl-4-phenylpiperazin-1-yl] propanoate To a stirred mixture of (2R)-2-methyl-1-phenylpiperazine dihydrochloride (1.5 g), sodium bicarbonate (1.8 g) and ethanol (30 mL) was added ethyl 3-bromopropanoate (0.92 mL) at room temperature, and the reaction mixture was stirred at 80° C. for 4 hours. The reaction mixture was cooled to room temperature and diluted with ethyl acetate. Insolubles were filtered off using celite, and the filtrate was concentrated under reduced pressure. The residue was purified by silica gel column chromatography to afford the title compound (1.52 g).

[Step 2] Preparation of ethyl 3-[(3R)-4-(4-formylphenyl)-3-methylpiperazin-1-yl] propanoate The title compound (1.35 g) was obtained as described in Reference Example 14, using ethyl 3-[(3R)-3-methyl-4-phenylpiperazin-1-yl]propanoate obtained in Step 1 instead of ethyl (4-phenylpiperazin-1-yl) acetate.

Reference Example 16: Ethyl {4-[(4-formylphenyl) methyl]piperazin-1-yl} acetate

To a stirred mixture of terephthalaldehyde (467 mg), ethyl (piperazin-1-yl) acetate (300 mg) and dichloromethane (10 mL) was added sodium triacetoxyborohydride (517 mg) under ice-cooling, and the mixture was stirred at room temperature overnight. The reaction mixture was diluted with water and ethyl acetate. Saturated aq. sodium bicarbonate was then added, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (236 mg).

Reference Example 17: Methyl {1-[(4-formylphenyl)methyl]piperidin-4-yl} acetate

A mixture of terephthalaldehyde (416 mg), methyl (piperidin-4-yl) acetate hydrochloride (300 mg), dichloromethane (10 mL) and DIPEA (0.268 mL) was stirred at room temperature for 1 hour. To the stirred solution was added sodium triacetoxyborohydride (460 mg) under ice-cooing, and the reaction mixture was stirred at room temperature overnight. The reaction mixture was diluted with water and ethyl acetate. Saturated aq. sodium bicarbonate was then added, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (196 mg).

Reference Example 18: Ethyl 3-[4-(5-formylpyridin-2-yl)-4-hydroxypiperidin-1-yl] propanoate

[Step 1] Preparation of tert-butyl 4-[5-(1,3-dioxoran-2-yl)pyridin-2-yl]-4-hydroxypiperidine-1-carboxylate To a stirred solution of 2-bromo-5-(1,3-dioxoran-2-yl) pyridine (1.0 g) in THF (15 mL) was added dropwise n-butyllithium (1.6 M in hexane, 3.0 mL) at −78° C. under argon atmosphere, and the reaction mixture was stirred at the same temperature for 30 minutes. A solution of tert-butyl 4-oxopiperidine-1-carboxylate (1.1 g) in THF (5 mL) was added dropwise, and the reaction mixture was stirred with warming to room temperature for 1 hour. The reaction mixture was diluted with water and saturated aq. ammonium chloride, and the mixture was extracted with ethyl acetate. The organic layer was washed with saturated saline and dried over anhydrous sodium sulfate, and then the solvent was removed under reduced pressure. The residue was purified by silica gel column chromatography to afford the title compound (0.77 g).

[Step 2] Preparation of ethyl 3-[4-(5-formylpyridin-2-yl)-4-hydroxypiperidin-1-yl]propanoate Tert-butyl 4-[5-(1,3-dioxoran-2-yl)pyridin-2-yl]-4-hydroxypiperidine-1-carboxylate (200 mg) obtained in Step 1 was mixed with THF (2 mL) and 4 M hydrochloric acid (2 mL), and the mixture was stirred at room temperature overnight and further stirred at 60° C. for 8 hours. After removing the solvent under reduced pressure, the residue was mixed with acetonitrile (4 mL) at room temperature. To the stirred mixture were added DIPEA (0.494 mL) and ethyl 3-bromopropanoate (0.146 mL), and the reaction mixture was stirred at 60° C. for 3 hours. The reaction mixture was cooled to room temperature and purified by silica gel column chromatography to afford the title compound (107 mg).

Reference Example 19: Tert-butyl 4-[6-(1,3-dioxoran-2-yl)pyridin-3-yl]-4-hydroxypiperidine-1-carboxylate To a stirred solution of 5-bromo-2-(1,3-dioxoran-2-yl) pyridine (1.0 g) in THF (15 mL) was added dropwise isopropylmagnesium chloride-lithium chloride complex (1 M in THF, 4.8 mL) at −45° C. under argon atmosphere. The reaction mixture was warmed to 0° C. and stirred for 30 minutes. The reaction mixture was cooled to −45° C., and tert-butyl 4-oxopiperidine-1-carboxylate (1.1 g) in THF (5 mL) was added thereto. The reaction mixture was stirred with warming to room temperature for 2 hours. The reaction mixture was diluted with water and ethyl acetate, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (1.3 g).

Reference Example 20: Ethyl [4-(6-formylpyridin-3-yl)-4-hydroxypiperidin-1-yl] acetate Tert-butyl 4-[6-(1,3-dioxoran-2-yl)pyridin-3-yl]-4-hydroxypiperidine-1-carboxylate (100 mg) was mixed with THF (1.5 mL) and 4 M hydrochloric acid (1.5 mL), and the mixture was stirred at room temperature for 3 hours. After removing the solvent under reduced pressure, the residue was mixed with dichloromethane (2 mL) at room temperature. To the stirred mixture were added DIPEA (0.30 mL) and bromoethyl acetate (0.038 mL), and the reaction mixture was stirred at room temperature for 6 hours. The reaction mixture was purified by silica gel column chromatography to afford the title compound (45 mg).

Reference Example 21: Tert-butyl 4-[6-(1,3-dioxoran-2-yl)pyridin-3-yl]-4-fluoropiperidin-1-carboxylate To a stirred solution of tert-butyl 4-[6-(1,3-dioxoran-2-yl)pyridin-3-yl]-4-hydroxypiperidin-1-carboxylate (200 mg) in dichloromethane (3 mL) was added DAST (0.0834 mL) dropwise in ice-water bath, and the reaction mixture was stirred at the same temperature for 1 hour. Saturated aq. sodium bicarbonate was added to the reaction mixture, and the mixture was diluted with water and ethyl acetate and then extracted with ethyl acetate. The organic layer was washed with saturated saline, dried over anhydrous sodium sulfate, and then the solvent was removed under reduced pressure. The residue was purified by silica gel column chromatography to afford the title compound (120 mg).

Reference Example 22: Ethyl 3-[4-fluoro-4-(6-formylpyridin-3-yl)piperidin-1-yl]propanoate The title compound (42 mg) was obtained as described in Reference Example 18, Step 2, using tert-butyl 4-[6-(1,3-dioxoran-2-yl)pyridin-3-yl]-4-fluoropiperidin-1-carboxylate instead of tert-butyl 4-[5-(1,3-dioxoran-2-yl)pyridin-2-yl]-4-hydroxypiperidin-1-carboxylate.

Reference Example 23: Ethyl 3-[(3R)-4-(5-formylpyrazin-2-yl)-3-methylpiperazin-1-yl]propanoate

[Step 1] Preparation of tert-butyl (3R)-4-(5-formylpyrazin-2-yl)-3-methylpiperazin-1-carboxylate A mixture of 5-chloropyrazine-2-carbaldehyde (350 mg), tert-butyl (3R)-3-methylpiperazine-1-carboxylate (541 mg), DIPEA (1.28 mL) and THF (4.9 mL) was stirred at 70° C. for 3 hours. The reaction mixture was cooled to room temperature, diluted with water and ethyl acetate, and then extracted with ethyl acetate. The organic layer was washed with saturated saline, dried over anhydrous magnesium sulfate, and then the solvent was removed under reduced pressure. The residue was purified by silica gel column chromatography to afford the title compound (755 mg).

[Step 2] Preparation of ethyl 3-[(3R)-4-(5-formylpyrazin-2-yl)-3-methylpiperazin-1-yl] propanoate Tert-butyl (3R)-4-(5-formylpyrazin-2-yl)-3-methylpiperazine-1-carboxylate (816 mg) was dissolved in ethyl acetate (5.3 mL). To the stirred solution was added hydrogen chloride (4 M in ethyl acetate, 5.3 mL) at room temperature, and the reaction mixture was stirred at the same temperature for 1 hour. After removing the solvent under reduced pressure, the residue was mixed with acetonitrile (5 mL). To the stirred mixture were added DIPEA (2.31 mL) and ethyl 3-bromopropanoate (0.442 mL) at room temperature, and the reaction mixture was stirred at 70° C. for 4 hours. The reaction mixture was cooled to room temperature and purified by silica gel column chromatography to afford the title compound (676 mg).

Reference Example 24: Ethyl [4-(4-formylphenyl)-4-hydroxypiperidin-1-yl] acetate

[Step 1] Preparation of tert-butyl 4-[4-(1,3-dioxoran-2-yl)phenyl]-4-hydroxypiperidine-1-carboxylate To a stirred solution of 2-(4-bromophenyl)-1,3-dioxorane (1.0 g) in THF (15 mL) was added dropwise n-butyllithium (1.6 M in hexane, 3.0 mL) at −78° C., and the reaction mixture was stirred at the same temperature for 30 minutes. Tert-butyl 4-oxopiperidine-1-carboxylate (1.1 g) in THF (5 mL) was added dropwise thereto, and the reaction mixture was stirred with warming to room temperature for 1 hour. The reaction mixture was diluted with water and extracted with ethyl acetate. The organic layer was washed with saturated saline, dried over anhydrous sodium sulfate, and then the solvent was removed under reduced pressure. The residue was purified by silica gel column chromatography to afford the title compound (1.5 g)

[Step 2] Preparation of ethyl [4-(4-formylphenyl)-4-hydroxypiperidin-1-yl] acetate Tert-butyl 4-[4-(1,3-dioxoran-2-yl)phenyl]-4-hydroxypiperidine-1-carboxylate (100 mg) obtained in Step 1 was mixed with 1,4-dioxane (2 mL) and hydrogen chloride (4 M solution in ethyl acetate, 2 mL), and the mixture was stirred at room temperature overnight. After removing the solvent under reduced pressure, the residue was mixed with dichloromethane (2 mL). To the stirred mixture were added DIPEA (0.297 mL) and bromoethyl acetate (0.038 mL) at room temperature, and the mixture was stirred at the same temperature for 6 hours. The reaction mixture was purified by silica gel column chromatography to afford the title compound (72 mg).

Reference Example 25: Ethyl [4-(4-formylphenoxy)piperidin-1-yl]acetate

To a mixture of ethyl (4-hydroxypiperidin-1-yl)acetate (100 mg), 4-hydroxybenzaldehyde (130 mg) and THF (2.67 mL) were added PPh₃ (210 mg) and DEAD (0.36 mL), and the reaction mixture was stirred at 50° C. for 4 hours overnight. The reaction mixture was diluted with ethyl acetate, and washed with saturated aq. sodium bicarbonate and saturated saline sequentially, and then the organic layer was dried over anhydrous magnesium sulfate. The solvent was removed under reduced pressure, and the residue was purified by silica gel column chromatography to afford the title compound (246 mg).

Reference Example 26: Ethyl 3-[4-(4-formylphenoxy)piperidin-1-yl]propanoate

To a stirred mixture of 4-[(piperidin-4-yl)oxy]benzaldehyde hydrochloride (200 mg) and acetonitrile (2.1 mL) were added DIPEA (0.716 mL) and ethyl 3-bromopropanoate (0.137 mL) at room temperature, and the reaction mixture was stirred at 70° C. for 3 hours. The reaction mixture was cooled to room temperature. The solvent was removed under reduced pressure, and the residue was purified by silica gel column chromatography to afford the title compound (158 mg).

Reference Example 27: Ethyl [4-(3-chloro-4-formylphenoxy)piperidin-1-yl] acetate

[Step 1] Preparation of tert-butyl 4-(3-chloro-4-formylphenoxy)piperidine-1-carboxylate To a stirred mixture of tert-butyl 4-hydroxypiperidine-1-carboxylate (200 mg), 2-chloro-4-hydroxybenzaldehyde (171 mg) and THF (5 mL) was added PPh₃ (391 mg) at room temperature. DEAD (0.68 mL) was added under ice-cooling, and the reaction mixture was stirred with warming to room temperature for 3 hours. The reaction mixture was diluted with ethyl acetate, and washed with saturated aq. sodium bicarbonate and saturated saline sequentially, and then the organic layer was dried over anhydrous magnesium sulfate. The solvent was removed under reduced pressure, and the residue was purified by silica gel column chromatography to afford the title compound (105 mg).

[Step 2] 2-chloro-4-[(piperidin-4-yl)oxy]benzaldehyde hydrochloride

To a stirred solution of tert-butyl 4-(3-chloro-4-formylphenoxy)piperidine-1-carboxylate (105 mg) obtained in Step 1 in ethyl acetate (1.5 mL) was added hydrogen chloride (4 M in ethyl acetate, 0.231 mL) at room temperature, and the reaction mixture was stirred at the same temperature for 2 hours. Methanol (0.77 mL) was added thereto, and the mixture was stirred at room temperature for 2 hours and further at 40° C. for 2 hours. The reaction mixture was cooled to room temperature. Hydrogen chloride (4 M in ethyl acetate, 0.231 mL) was then added, and the reaction mixture was stirred at the same temperature overnight. The reaction mixture was concentrated under reduced pressure and dried to afford the title compound (85 mg).

[Step 3] Preparation of ethyl [4-(3-chloro-4-formylphenoxy)piperidin-1-yl]acetate To a stirred mixture of 2-chloro-4-[(piperidin-4-yl)oxy]benzaldehyde hydrochloride (85 mg) obtained in Step 2 and acetonitrile (2 mL) were added DIPEA (0.27 mL) and bromoethyl acetate (0.045 mL), and the reaction mixture was stirred at the same temperature for 6 hours. The reaction mixture was purified by silica gel column chromatography to afford the title compound (77 mg).

Reference Example 28: Ethyl 3-[(1R,3s,5S)-3-(4-formylphenoxy)-8-azabicyclo[3.2.1]octan-8-yl]propanoate

[Step 1] Preparation of tert-butyl (1R,3r,5S)-3-hydroxy-8-azabicyclo[3.2.1]octan-8-carboxylate To a stirred mixture of (1R,3r,5S)-8-azabicyclo[3.2.1]octan-3-ol (1.0 g), dichloromethane (30 mL) and triethylamine (2.2 mL) was added di-tert-butyl dicarbonate (2.1 g) under ice-cooling, and the reaction mixture was stirred at room temperature for 2.5 hours. The reaction mixture was diluted with chloroform. The organic layer was washed with saturated aq. citric acid and dried over anhydrous magnesium sulfate. The solvent was removed under reduced pressure. Hexane was added to the residue, and the resulting precipitate was collected by filtration, washed with hexane and dried to afford the title compound (1.6 g).

[Step 2] Preparation of tert-butyl (1R,3s,5S)-3-(4-formylphenoxy)-8-azabicyclo[3.2.1]octane-8-carboxylate The title compound was obtained as described in Reference Example 27, Step 1, using tert-butyl (1R,3r,5S)-3-hydroxy-8-azabicyclo[3.2.1]octane-8-carboxylate obtained in Step 1 instead of tert-butyl 4-hydroxypiperidine-1-carboxylate.

[Step 3] Preparation of ethyl 3-[(1R,3s,5S)-3-(4-formylphenoxy)-8-azabicyclo[3.2.1]octan-8-yl]propanoate To a stirred mixture of tert-butyl (1R,3s,5S)-3-(4-formylphenoxy)-8-azabicyclo[3.2.1]octane-8-carboxylate (0.774 g) obtained in Step 2 and methanol (5 mL) was added hydrogen chloride (4 M in ethyl acetate, 2.92 mL) at room temperature, and the reaction mixture was stirred at the same temperature. After monitoring the completion of the reaction by TLC, the reaction mixture was concentrated under reduced pressure. The residue was diluted with acetonitrile (3 mL). To the stirred solution were added DIPEA (1.05 mL) and ethyl 3-bromopropanoate (0.186 mL) at room temperature, and the reaction mixture was stirred at 70° C. overnight. The reaction mixture was cooled to room temperature and concentrated under reduced pressure. The residue was purified by silica gel column chromatography to afford the title compound (0.353 g) Reference Example 29: Ethyl {[(1R,3r,5S)-8-(5-formylpyrazin-2-yl)-8-azabicyclo[3.2.1]octan-3-yl]oxy}acetate

[Step 1] Preparation of tert-butyl (1R,3r,5S)-3-(2-ethoxy-2-oxoethoxy)-8-azabicyclo[3.2.1]octane-8-carboxylate To a solution of tert-butyl (1R,3r,5S)-3-hydroxy-8-azabicyclo[3.2.1]octane-8-carboxylate (790 mg) in dichloromethane (8.7 mL) were added rhodium(II) acetate dimer (23 mg) and diazoethyl acetate (1.46 mL), and the reaction mixture was stirred at room temperature for 2 hours. Diazoethyl acetate (0.731 mL) was added thereto, and the reaction mixture was stirred at room temperature for 1 hour. Water was added to the reaction mixture, and the mixture was extracted with dichloromethane. The organic layer was washed with water and saturated saline sequentially, dried over anhydrous magnesium sulfate, and then the solvent was removed under reduced pressure. The residue was purified by silica gel column chromatography to afford the title compound (1.08 g).

[Step 2] Preparation of ethyl {[(1R,3r,5S)-8-azabicyclo[3.2.1]octan-3-yl]oxy}acetate hydrochloride Tert-butyl (1R,3r,5S)-3-(2-ethoxy-2-oxoethoxy)-8-azabicyclo[3.2.1]octane-8-carboxylate (1.08 g) obtained in Step 1 was mixed with ethanol (5 mL). Hydrogen chloride (4 M in ethyl acetate, 2.6 mL) was added to the solution, and the reaction mixture was stirred at 80° C. for 1 hour. The reaction mixture was cooled to room temperature, and hexane was added thereto. The resulting solid was collected by filtration, washed with hexane and then dried to afford the title compound (0.567 g).

[Step 3] Preparation of ethyl {[(1R,3r,5S)-8-(5-formylpyrazin-2-yl)-8-azabicyclo[3.2.1]octan-3-yl]oxy}acetate A mixture of ethyl {[(1R,3r,5S)-8-azabicyclo[3.2.1]octan-3-yl]oxy}acetate hydrochloride (0.281 g) obtained in Step 2, 5-chloropyrazine-2-carbaldehyde (0.150 g), DIPEA (0.728 mL) and THF (2.1 mL) was stirred at 70° C. for 5 hours. The reaction mixture was cooled to room temperature. Saturated aq. ammonium chloride was added, and the mixture was extracted with ethyl acetate. The organic layer was washed with water and saturated saline, and dried over anhydrous sodium sulfate, and then the solvent was removed under reduced pressure. The residue was purified by silica gel column chromatography to afford the title compound (0.258 g).

Reference Example 30: Ethyl {[(1R,3s,5S)-8-(5-formylpyrazin-2-yl)-8-azabicyclo[3.2.1]octan-3-yl]oxy}acetate

[Step 1] Preparation of tert-butyl (1R,3s,5S)-3-[(4-nitrobenzoyl)oxy]-8-azabicyclo[3.2.1]octane-8-carboxylate To a solution of tert-butyl (1R,3r,5S)-3-hydroxy-8-azabicyclo[3.2.1]octane-8-carboxylate (0.790 g) in THF (10 mL) were added 4-nitrobenzoic acid (0.871 g) and PPh$_3$ (1.37 g), and DEAD (40% in toluene, 2.05 mL) was further added dropwise under ice-cooling. The reaction mixture was stirred at room temperature overnight. Then the reaction mixture was diluted with ethyl acetate, washed with saturated aq. sodium bicarbonate and saturated saline sequentially, and then the organic layer was dried over anhydrous magnesium sulfate. The solvent was removed under reduced pressure, and the residue was purified by silica gel column chromatography to afford the title compound (1.05 g).

[Step 2] Preparation of tert-butyl (1R,3s,5S)-3-hydroxy-8-azabicyclo[3.2.1]octane-8-carboxylate To a mixture of tert-butyl (1R,3s,5S)-3-[(4-nitrobenzoyl)oxy]-8-azabicyclo[3.2.1]octane-8-carboxylate (1.05 g) obtained in Step 1, THF (6 mL) and water (2 mL) was added lithium hydroxide monohydrate (0.176 g), and the mixture was stirred at room temperature for 1 hour. The reaction mixture was diluted with ethyl acetate, washed with saturated aq. sodium bicarbonate, and then dried over anhydrous magnesium sulfate. The solvent was removed under reduced pressure to afford the title compound (0.660 g).

[Step 3] Preparation of tert-butyl (1R,3s,5S)-3-(2-ethoxy-2-oxoethoxy)-8-azabicyclo[3.2.1]octan-8-carboxylate The title compound was obtained as described in Reference Example 29, Step 1, using tert-butyl (1R,3s, 5S)-3-hydroxy-8-azabicyclo[3.2.1]octane-8-carboxylate obtained in Step 2 instead of tert-butyl (1R,3r,5S)-3-hydroxy-8-azabicyclo[3.2.1]octane-8-carboxylate.

[Step 4] Preparation of ethyl {[(1R,3s,5S)-8-azabicyclo[3.2.1]octan-3-yl]oxy}acetate hydrochloride The title compound was obtained as described in Reference Example 29, Step 2, using tert-butyl (1R,3s,5S)-3-(2-ethoxy-2-oxoethoxy)-8-azabicyclo[3.2.1]octane-8-carboxylate obtained in Step 3 instead of tert-butyl (1R,3r,5S)-3-(2-ethoxy-2-oxoethoxy)-8-azabicyclo[3.2.1]octane-8-carboxylate.

[Step 5] Preparation of ethyl {[(1R,3s,5S)-8-(5-formylpyrazin-2-yl)-8-azabicyclo[3.2.1]octan-3-yl]oxy}acetate The title compound was obtained as described in Reference Example 29, Step 3, using ethyl {[(1R,3s,5S)-8-azabicyclo[3.2.1]octan-3-yl]oxy}acetate hydrochloride obtained in Step 4 instead of ethyl {[(1R,3r,5S)-8-azabicyclo[3.2.1]octan-3-yl]oxy} acetate hydrochloride.

Reference Example 31: Ethyl 3-[4-(5-formylpyrazin-2-yl)-2,2-dimethylpiperazin-1-yl]propanoate

[Step 1] Preparation of tert-butyl 4-(3-ethoxy-3-oxopropyl)-3,3-dimethylpiperazin-1-carboxylate A mixture of tert-butyl 3,3-dimethylpiperazin-1-carboxylate (500 mg), ethanol (1.17 mL) and ethyl acrylate (0.684 mL) was stirred at 90° C. overnight. The reaction mixture was cooled to room temperature and then concentrated under reduced pressure. The residue was purified by silica gel column chromatography to afford the title compound (650 mg).

[Step 2] Preparation of ethyl 3-(2,2-dimethylpiperazin-1-yl)propanoate dihydrochloride The title compound was obtained as described in Reference Example 29, Step 2, using tert-butyl 4-(3-ethoxy-3-oxopropyl)-3,3-dimethylpiperazine-1-carboxylate obtained in Step 1 instead of tert-butyl (1R,3r,5S)-3-(2-ethoxy-2-oxoethoxy)-8-azabicyclo[3.2.1]octan-8-carboxylate.

[Step 3] Preparation of ethyl 3-[4-(5-formylpyrazin-2-yl)-2,2-dimethylpiperazin-1-yl]propanoate The title compound (564 mg) was obtained as described in Reference Example 29, Step 3, using ethyl 3-(2,2-dimethylpiperazin-1-yl)propanoate dihydrochloride obtained in Step 2 instead of ethyl {[(1R,3r,5S)-8-azabicyclo[3.2.1]octan-3-yl]oxy}acetate hydrochloride.

Reference Example 32: Ethyl 3-[4-(6-formylpyridin-3-yl)piperazin-1-yl]propanoate

[Step 1] Preparation of ethyl 3-{4-[6-(1,3-dioxoran-2-yl)pyridin-3-yl]piperazin-1-yl}propanoate A mixture of 5-bromo-2-(1,3-dioxoran-2-yl)pyridine (1 g), ethyl 3-(piperazin-1-yl)propanoate (1.62 g), Pd$_2$(dba)$_3$ (0.199 g), XPhos (0.414 g), cesium carbonate (4.25 g) and 1,4-dioxane (20 mL) was degassed and stirred at 100° C. overnight under argon atmosphere. The reaction mixture was cooled to room temperature and diluted with ethyl acetate. Insolubles were filtered off using celite, and the filtrate was concentrated under reduced pressure. The residue was purified by silica gel column chromatography to afford the title compound (1.53 g).

[Step 2] Preparation of ethyl 3-[4-(6-formylpyridin-3-yl)piperazin-1-yl]propanoate A mixture of ethyl 3-{4-[6-(1,3-dioxoran-2-yl)pyridin-3-yl]piperazin-1-yl}propanoate (1.20 g) obtained in Step 1, p-toluenesulfonic acid (1.36 g), acetone (15 mL) and water (5 mL) was stirred at 60° C. for 3 hours. The reaction mixture was cooled to room temperature and diluted with water and ethyl acetate. Saturated aq. sodium bicarbonate was added, and the mixture was extracted with ethyl acetate. The organic layer was washed with saturated saline, dried over anhydrous sodium sulfate, and then the solvent was removed under reduced pressure. The residue was purified by silica gel column chromatography to afford the title compound (0.734 g).

Reference Example 33: Ethyl 3-[(3R)-4-(5-formylpyridin-2-yl)-3-methylpiperazin-1-yl]propanoate

[Step 1] Preparation of tert-butyl (3R)-4-[5-(1,3-dioxoran-2-yl)pyridin-2-yl]-3-methylpiperazin-1-carboxylate A mixture of 2-bromo-5-(1,3-dioxoran-2-yl)pyridine (100 mg), tert-butyl (3R)-3-methylpiperazine-1-carboxylate (95.8 mg), RuPhos (40.6 mg), Pd(OAc)$_2$ (9.76 mg), sodium tert-butoxide (62.7 mg) and 1,4-dioxane (2.2 mL) was degassed and stirred at 120° C. for 2 hours under argon atmosphere. The reaction mixture was cooled to room temperature, diluted with ethyl acetate, washed with water and saturated saline, and then dried over anhydrous sodium sulfate. The solvent was removed under reduced pressure, and the residue was purified by silica gel column chromatography to afford the title compound (72.6 mg).

[Step 2] Preparation of ethyl 3-[(3R)-4-(5-formylpyridin-2-yl)-3-methylpiperazin-1-yl]propanoate Tert-butyl (3R)-4-[5-(1,3-dioxoran-2-yl)pyridin-2-yl]-3-methylpiperazin-1-carboxylate (72 mg) obtained in Step 1 was mixed with acetone (1 mL) and 4 M hydrochloric acid (1 mL), and the mixture was stirred at 60° C. for 3 hours. The reaction mixture was cooled to room temperature, and the solvent was removed under reduced pressure. The residue was diluted with acetonitrile (1 mL). To the stirred solution were added DIPEA (0.18 mL) and ethyl 3-bromopropanoate (0.053 mL) at room temperature, and the reaction mixture was stirred at 60° C. for 3 hours. The reaction mixture was cooled to room temperature and concentrated under reduced pressure. The residue was purified by silica gel column chromatography to afford the title compound (42 mg).

Reference Example 34: Ethyl 1-(5-formylpyrazin-2-yl)piperidin-4-carboxylate

A mixture of 5-chloropyrazine-2-carbaldehyde (0.49 g), ethyl piperidine-4-carboxylate (0.54 g), DMSO (10 mL) and sodium bicarbonate (1.4 g) was stirred at 70° C. for 17 hours. The reaction mixture was cooled to room temperature and then ice-cooled. The mixture was diluted with water, 2 M hydrochloric acid (6 mL) and ethyl acetate, and then extracted with ethyl acetate. The organic layer was washed with saturated saline and dried over anhydrous magnesium sulfate, and then the solvent was removed under reduced pressure. The residue was purified by silica gel column chromatography to afford the title compound (0.79 g).

Reference Example 35: Ethyl 2,2-difluoro-3-{[1-(5-formylpyrazin-2-yl)piperidin-4-yl]amino}propanoate

[Step 1] Preparation of tert-butyl 4-[(3-ethoxy-2,2-difluoro-3-oxopropyl)amino]piperidine-1-carboxylate A mixture of tert-butyl 4-oxopiperidine-1-carboxylate (210 mg), ethyl 3-amino-2,2-difluoropropanoate hydrochloride (100 mg), dichloromethane (3 mL), and acetic acid (0.091 mL) was stirred at room temperature. Sodium triacetoxyborohydride (224 mg) was added thereto, and the mixture was stirred at the same temperature for three days. The reaction mixture was diluted with water, and saturated aq. sodium bicarbonate was added to the mixture. The organic layer was separated, and the aqueous layer was extracted with dichloromethane. The organic layers were combined, washed with saturated saline and dried over anhydrous magnesium sulfate. The solvent was removed under reduced pressure. The residue was purified by silica gel column chromatography to afford the title compound (176 mg).

[Step 2] Preparation of ethyl 2,2-difluoro-3-[(piperidin-4-yl)amino]propanoate dihydrochloride The title compound was obtained as described in Reference Example 29, Step 2, using tert-butyl 4-[(3-ethoxy-2,2-difluoro-3-oxopropyl)amino]piperidin-1-carboxylate obtained in Step 1 instead of tert-butyl (1R,3r,5S)-3-(2-ethoxy-2-oxoethoxy)-8-azabicyclo[3.2.1]octan-8-carboxylate.

[Step 3] Preparation of ethyl 2,2-difluoro-3-{[1-(5-formylpyrazin-2-yl)piperidin-4-yl]amino}propanoate The title compound (91 mg) was obtained as described in Reference Example 29, Step 3, using ethyl 2,2-difluoro-3-[(piperidin-4-yl)amino]propanoate dihydrochloride obtained in Step 2 instead of ethyl {[(1R,3r,5S)-8-azabicyclo[3.2.1]octan-3-yl]oxy} acetate hydrochloride.

Reference Example 36: Ethyl N-[(3S,4R)-3-fluoro-1-(5-formylpyrazin-2-yl)piperidin-4-yl]glycinate

[Step 1] Preparation of tert-butyl(3S,4R)-4-[(2-ethoxy-2-oxoethyl)amino]-3-fluoropiperidine-1-carboxylate To a solution of tert-butyl(3S,4R)-4-amino-3-fluoropiperidine-1-carboxylate (500 mg) in acetonitrile (2.86 mL) were added ethyl bromoacetate (0.253 mL) and DIPEA (0.792 mL), and the reaction mixture was stirred at room temperature overnight. After concentrating the reaction mixture under reduced pressure, the residue was purified by silica gel column chromatography to afford the title compound (588 mg).

[Step 2] Preparation of ethyl N-[(3S,4R)-3-fluoropiperidin-4-yl]glycinate dihydrochloride The title compound was obtained as described in Reference Example 29, Step 2, using tert-butyl(3S,4R)-4-[(2-ethoxy-2-oxoethyl)amino]-3-fluoropiperidine-1-carboxylate obtained in Step 1 instead of tert-butyl (1R,3r,5S)-3-(2-ethoxy-2-oxoethoxy)-8-azabicyclo[3.2.1]octan-8-carboxylate.

[Step 3] Preparation of ethyl N-[(3S,4R)-3-fluoro-1-(5-formylpyrazin-2-yl)piperidin-4-yl]glycinate The title compound (113 mg) was obtained as described in Reference Example 29, Step 3, using ethyl N-[(3S,4R)-3-fluoropiperidin-4-yl]glycinate dihydrochloride obtained in Step 2 instead of ethyl {[(1R,3r,5S)-8-azabicyclo[3.2.1]octan-3-yl]oxy}acetate hydrochloride.

Reference Example 37: Ethyl N-[(3S,4R)-3-fluoro-1-(5-formylpyrazin-2-yl)piperidin-4-yl]-N-methylglycinate A mixture of ethyl N-[(3S,4R)-3-fluoro-1-(5-formylpyrazin-2-yl)piperidin-4-yl]glycinate (84 mg), DMF (1.4 mL), potassium carbonate (112 mg) and methyl iodide (0.025 mL) was stirred at room temperature overnight. Additional methyl iodide (0.025 mL) was added thereto, and the reaction mixture was stirred overnight. The reaction mixture was diluted with water and extracted with ethyl acetate. The organic layer was washed with water and brine, and then dried over anhydrous magnesium sulfate. The solvent was removed under reduced pressure. The residue was purified by silica gel column chromatography to afford the title compound (27 mg).

Reference Example 38: Ethyl 3-[4-(3-fluoro-5-formylpyridin-2-yl)piperazine-1-yl]propanoate

[Step 1] Preparation of tert-butyl 4-(3-fluoro-5-formylpyridin-2-yl)piperazine-1-carboxylate A solution of tert-butyl 4-(5-bromo-3-fluoropyridin-2-yl)piperazine-1-carboxylate (500 mg) in THF (10 mL) was degassed. Under argon atmosphere, to the stirred solution was added isopropylmagnesium chloride-lithium chloride complex (1 M in THF, 1.67 mL) at 0° C., and the reaction mixture was stirred at room temperature for 3 hours. Additional isopropylmagnesium chloride-lithium chloride complex (1 M in THF, 0.42 mL) was added, and the reaction mixture was stirred at room temperature for 1 hour. To the stirred solution was added DMF (0.216 mL) dropwise under ice-cooling, and the reaction mixture was stirred at room temperature for 2 hours. The reaction mixture was diluted with water and ethyl acetate. The mixture was neutralized by adding dilute hydrochloric acid and extracted with ethyl acetate. The organic layer was washed with brine and dried over anhydrous sodium sulfate. The solvent was removed under reduced pressure. The residue was purified by silica gel column chromatography to afford the title compound (269 mg).

[Step 2] Preparation of ethyl 3-[4-(3-fluoro-5-formylpyridin-2-yl)piperazin-1-yl]propanoate A mixture of tert-butyl 4-(3-fluoro-5-formylpyridin-2-yl)piperazine-1-carboxylate (180 mg) obtained in Step 1, ethyl acetate (2 mL) and hydrogen chloride (4 M in ethyl acetate, 2 mL) was stirred at room temperature for 2 hours. After concentrating the reaction mixture under reduced pressure, the residue was diluted with acetonitrile (3 mL). To the stirred solution were added DIPEA (0.50 mL) and ethyl 3-bromopropanoate (0.11 mL) at room temperature, and the reaction mixture was stirred at 70° C. for 4 hours. The reaction mixture was cooled to room temperature and concentrated under reduced pressure. The residue was purified by silica gel column chromatography to afford the title compound (131 mg).

Reference Example 39: Ethyl [4-(3-fluoro-5-formylpyridin-2-yl)piperazin-1-yl] acetate The title compound (65 mg) was obtained as described in Reference Example 38, Step 2, using ethyl bromoacetate instead of ethyl 3-bromopropanoate.

Reference Example 40: Ethyl 3-[4-(5-formylpyrazin-2-yl)piperazin-1-yl]propanoate A mixture of ethyl 3-(piperazin-1-yl)propanoate (0.142 mL), 5-chloropyrazine-2-carbaldehyde (100 mg), potassium carbonate (485 mg) and DMSO (3.5 mL) was stirred at 90° C. for 2 hours. The reaction mixture was cooled to room temperature, diluted with saturated aq. ammonium chloride, and then extracted with ethyl acetate. The organic layer was washed with water and brine, and then dried over anhydrous magnesium sulfate. The solvent was removed under reduced pressure. The residue was purified by silica gel column chromatography to afford the title compound (138 mg).

Reference Example 41: Ethyl {[1-(5-formylpyrazin-2-yl)piperidin-4-yl]oxy} acetate A mixture of 5-chloropyrazine-2-carbaldehyde (0.55 g), ethyl [(piperidin-4-yl)oxy] acetate hydrochloride (0.92 g), THF (7.7 mL) and DIPEA (2.7 mL) was stirred at 70° C. for 4 hours. The reaction mixture was cooled to room temperature, diluted with saturated aq. ammonium chloride, and then extracted with ethyl acetate. The organic layer was washed with water and brine, and then dried over anhydrous sodium sulfate. The solvent was removed under reduced pressure. The residue was purified by silica gel column chromatography to afford the title compound (1.0 g).

Reference Example 42: [4-(5-Formylpyrazin-2-yl)piperazin-1-yl]acetonitrile

A mixture of 5-chloropyrazine-2-carbaldehyde (0.10 g), (piperazin-1-yl)acetonitrile dihydrochloride (0.14 g), acetonitrile (1.6 mL) and DIPEA (0.39 mL) was stirred at 150° C. for 1 hour in a microwave reactor. The reaction mixture was cooled to room temperature, diluted with water and ethyl acetate, and extracted with ethyl acetate. The organic layer was concentrated under reduced pressure, and the residue was purified by silica gel column chromatography to afford the title compound (91 mg).

Reference Example 43: Ethyl 1-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylate A mixture of 2'-ethoxy-$N^4$-(3-methoxy-2,2-dimethylpropyl)-$N^4$-methyl-6'-(trifluoromethyl) [2,4'-bipyridine]-4,5,6-triamine (50 mg), ethyl 1-(5-formylpyrazin-2-yl)piperidine-4-carboxylate (32 mg), sodium dithionite (51 mg) and DMF (1 mL) was stirred at 100° C. for 8 hours. The reaction mixture was cooled to room temperature and concentrated under reduced pressure. The residue was purified by silica gel column chromatography to afford the title compound (75 mg).

Reference Example 44: Ethyl 1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylate A mixture of 2'-ethoxy-$N^4$-{[1-(methoxymethyl)cyclopentyl]methyl}-$N^4$-methyl-6'-(trifluoromethyl) [2,4'-bipyridine]-4,5,6-triamine (50 mg), ethyl 1-(5-formylpyrazin-2-yl)piperidine-4-carboxylate (31 mg), sodium dithionite (48 mg) and DMF (1 mL) was stirred at 100° C. for 8 hours. The reaction mixture was cooled to room temperature and concentrated under reduced pressure. The residue was purified by silica gel column chromatography to afford the title compound (75 mg).

Reference Example 45: Ethyl 1-(5-{5-[6-cyclopropyl-5-(trifluoromethyl)pyridin-3-yl]-7-[{[1-(ethoxymethyl) cyclopentyl]methyl}(methyl) amino]-1H-imidazo[4,5-b]pyridin-2-yl}pyrazin-2-yl) piperidine-4-carboxylate A mixture of 6'-cyclopropyl-$N^4$-{[1-(ethoxymethyl) cyclopentyl] methyl}-$N^4$-methyl-5'-(trifluoromethyl) [2,3'-bipyridine]-4,5,6-triamine (50 mg), ethyl 1-(5-formylpyrazin-2-yl)piperidine-4-carboxylate (30 mg), sodium dithionite (23 mg) and DMF (0.72 mL) was stirred at 100° C. for 8 hours. The reaction mixture was cooled to room temperature and purified by silica gel column chromatography to afford the title compound (76 mg).

Reference Example 46: Ethyl {[1-(5-{5-[2-cyclopropyl-6-(trifluoromethyl)pyridin-4-yl]-7-[{[1-(methoxymethyl)cyclopentyl]methyl}(methyl) amino]-1H-imidazo[4,5-b]pyridin-2-yl}pyrazin-2-yl) piperidin-4-yl]oxy} acetate A mixture of 2'-cyclopropyl-$N^4$-{[1-(methoxymethyl)cyclopentyl]methyl}-$N^4$-methyl-6'-(trifluoromethyl) [2,4'-bipyridine]-4,5,6-triamine (115 mg), ethyl {[1-(5-formylpyrazin-2-yl)piperidin-4-yl]oxy} acetate (79 mg), sodium dithionite (112 mg) and DMF (2.6 mL) was stirred at 100° C. for 5 hours. The reaction mixture was cooled to room temperature, diluted with water and saturated aq. ammonium chloride, and then extracted with ethyl acetate-hexane. The organic layer was washed with brine, and the solvent was removed under reduced pressure. The residue was purified by silica gel column chromatography to afford the title compound (142 mg).

Reference Example 47: Ethyl 3-[4-(5-{5-[2-fluoro-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl] propanoate A mixture of 2'-fluoro-$N^4$-{[1-(methoxymethyl)cyclopentyl]methyl}-$N^4$-methyl-5'-(trifluoromethyl) [2,3'-bipyridine]-4,5,6-triamine (30 mg), ethyl 3-[4-(5-formylpyrazin-2-yl)piperazin-1-yl]propanoate (21 mg), sodium dithionite (30 mg) and DMF (1 mL) was stirred at 100° C. for 3 hours. The reaction mixture was cooled to room temperature, diluted with water and ethyl acetate, and then extracted with ethyl acetate. Saturated aq. sodium bicarbonate was added to the aqueous layer, and the aqueous layer was extracted with ethyl acetate. The organic layers were combined, dried over anhydrous sodium sulfate, and then the solvent was removed under reduced pressure. The residue was purified by silica gel column chromatography to afford the title compound (17 mg).

Reference Example 48: Ethyl 3-[4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperazin-1-yl]propanoate A mixture of 6'-cyclopropyl-$N^4$-{[1-(methoxymethyl)cyclohexyl] methyl}-$N^4$-methyl-5'-(trifluoromethyl) [2,3'-bipyridine]-4,5,6-triamine (1.12 g), ethyl 3-[4-(5-formylpyrazin-2-yl)piperazin-1-yl]propanoate (0.742 g), sodium dithionite (1.05 g) and DMF (24 mL) was stirred at 110° C. for 4 hours. The reaction mixture was cooled to room temperature. Sodium dithionite (1.05 g) was added thereto, and the reaction mixture was stirred at 100° C. for 3 hours. The reaction mixture was cooled to room temperature, diluted with water and saturated aq. sodium bicarbonate, and then extracted with ethyl acetate. The organic layer was washed with water and brine, and then dried over anhydrous magnesium sulfate. The solvent was removed under reduced pressure. The residue was purified by silica gel column chromatography to afford the title compound (1.24 g).

Reference Example 49: Ethyl 3-[(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate A mixture of 6'-cyclopropyl-$N^4$-{[1-(methoxymethyl)cyclohexyl] methyl}-$N^4$-methyl-5'-(trifluoromethyl) [2,3'-bipyridine]-4,5,6-triamine (1.8 g), ethyl 3-[(3R)-4-(5-formylpyrazin-2-yl)-3-methylpiperazin-1-yl]propanoate (1.3 g), sodium dithionite (1.4 g) and DMF (3.9 mL) was stirred at 100° C. for 6 hours. The reaction mixture was cooled to room temperature, diluted with water, and then extracted with ethyl acetate. The organic layer was dried over anhydrous sodium sulfate, and the solvent was removed under reduced pressure. The residue was purified by silica gel column chromatography to afford the title compound (1.6 g).

Reference Example 50: Ethyl 3-[(2S)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl] propanoate A mixture of 6'-cyclopropyl-$N^4$-{[1-(methoxymethyl)cyclohexyl] methyl}-$N^4$-methyl-5'-(trifluoromethyl) [2,3'-bipyridine]-4,5,6-triamine (38 mg), ethyl 3-[(2S)-4-(5-formylpyrazin-2-yl)-2-(methoxymethyl)piperazin-1-yl]propanoate (29 mg), sodium dithionite (36 mg) and DMA (0.82 mL) was stirred at 110° C. for 11 hours. The reaction mixture was cooled to room temperature, diluted with water, and then extracted with dichloromethane. The organic layer was concentrated under reduced pressure, and the residue was purified by silica gel column chromatography to afford the title compound (48 mg).

Reference Example 51: Ethyl 1-(5-{5-[2-ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylate A mixture of 2'-ethoxy-$N^4$-{[1-(methoxymethyl) cyclopentyl]methyl}-6'-(trifluoromethyl) [2,4'-bipyridine]-4,5,6-triamine (35 mg), ethyl 1-(5-formylpyrazin-2-yl)piperidine-4-carboxylate (23 mg), sodium dithionite (28 mg) and DMF (1 mL) was stirred at 100° C. for 3 hours. The reaction mixture was cooled to room temperature and purified by silica gel column chromatography to afford the title compound (46 mg).

Reference Example 52: Ethyl [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl] acetate A mixture of 6'-cyclopropyl-$N^4$-{[1-(methoxymethyl)cyclopentyl]methyl}-$N^4$-methyl-5'-(trifluoromethyl) [2,3'-bipyridine]-4,5,6-triamine (35.6 mg), ethyl [4-(3-fluoro-4-formylphenoxy)piperidin-1-yl] acetate (25.7 mg), sodium dithionite (34.5 mg) and DMF (0.79 mL) was stirred at 110° C. overnight. The reaction mixture was cooled to room temperature and purified by silica gel column chromatography to afford the title compound (40.7 mg).

Reference Example 53: Ethyl 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylate A mixture of 2'-ethoxy-$N^4$-{[1-(methoxymethyl)cyclobutyl]methyl}-$N^4$-methyl-6'-(trifluoromethyl) [2,4'-bipyridine]-4,5,6-triamine (2.30 g), ethyl 1-(5-formylpyrazin-2-yl)piperidine-4-carboxylate (1.45 g), sodium dithionite (2.30 g) and DMF (26 mL) was stirred at 110° C. for 4.5 hours. The reaction mixture was cooled to room temperature and concentrated under reduced pressure. The residue was purified by silica gel column chromatography to afford the title compound (3.06 g) Reference Example 54: Ethyl 3-[4- fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidin-1-yl] propanoate A mixture of 6-[3-fluoro-5-(trifluoromethyl)phenyl]-$N^4$-{[1-(methoxymethyl)cyclobutyl]methyl}-$N^4$-methylpyridine-2,3,4-triamine (50 mg), ethyl 3-[4-fluoro-4-(6-formylpyridin-3-yl)piperidin-1-yl]propanoate (41 mg), sodium dithionite (42 mg) and DMF (1 mL) was stirred at 100° C. for 7 hours. The reaction mixture was cooled to room temperature and purified by silica gel column chromatography to afford the title compound (38 mg).

Reference Example 55: Ethyl 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl] propanoate A mixture of 6'-ethoxy-$N^4$-{[1-(methoxymethyl)cyclobutyl]methyl}-$N^4$-methyl-5'-(trifluoromethyl) [2,3'-bipyridine]-4,5,6-triamine (61 mg), ethyl 3-[4-(5-formylpyrazin-2-yl)piperazin-1-yl]propanoate (45 mg), sodium dithionite (34 mg) and DMF (1.4 mL) was stirred at 110° C. for 3 hours. The reaction mixture was cooled to room temperature and purified by silica gel column chromatography to afford the title compound (41 mg).

Reference Example 56: Ethyl 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propanoate A mixture of 6'-cyclopropyl-$N^4$-{[1-(ethoxymethyl)cyclopentyl]methyl}-$N^4$-methyl-5'-(trifluoromethyl) [2,3'-bipyridine]-4,5,6-triamine (1.5 g), ethyl 3-[(3R)-4-(5-formylpyrazin-2-yl)-3-methylpiperazin-1-yl]propanoate (1.1 g), sodium dithionite (1.1 g) and DMF (15 mL) was stirred at 100° C. for 3 hours. The reaction mixture was cooled to room temperature, diluted with water and ethyl acetate, and then extracted with ethyl acetate. The organic layer was washed with brine and dried over anhydrous sodium sulfate. The solvent was removed under reduced pressure. The residue was purified by silica gel column chromatography to afford the title compound (1.9 g).

Reference Example 57: Ethyl {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate A mixture of 2'-ethoxy-$N^4$-{[1-(methoxymethyl)cyclopentyl]methyl}-$N^4$-methyl-6'-(trifluoromethyl) [2,4'-bipyridine]-4,5,6-triamine (50 mg), ethyl {[(1R,3r,5S)-8-(5-formylpyrazin-2-yl)-8-azabicyclo[3.2.1]octan-3-yl]oxy} acetate (37 mg), sodium dithionite (48 mg) and DMF (0.5 mL) was stirred at 100° C. for 10 hours. The reaction mixture was cooled to room temperature and concentrated under reduced pressure. The residue was purified by silica gel column chromatography to afford the title compound (85 mg).

Reference Example 58: Ethyl 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate A mixture of 2'-cyclopropyl-$N^4$-{[1-(methoxymethyl)cyclohexyl]methyl}-$N^4$-methyl-6'-(trifluoromethyl) [2,4'-bipyridine]-4,5,6-triamine (50 mg), ethyl 3-[(3R)-4-(5-formylpyrazin-2-yl)-3-methylpiperazin-1-yl]propanoate (36 mg), sodium dithionite (47 mg) and DMF (0.5 mL) was stirred at 100° C. for 8 hours. The reaction mixture was cooled to room temperature and concentrated under reduced pressure. The residue was purified by silica gel column chromatography to afford the title compound (76 mg).

Reference Example 59: Ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl] acetate A mixture of 6-[3-fluoro-5-(trifluoromethyl)phenyl]-$N^4$-{[1-(methoxymethyl)cyclobutyl]methyl}-$N^4$-methylpyridine-2,3,4-triamine (30 mg), ethyl [4-(4-formylphenoxy)piperidin-1-yl] acetate (89 mg), sodium dithionite (32 mg) and DMF (2 mL) was stirred at 100° C. for 3 hours. The reaction mixture was cooled to room temperature and concentrated under reduced pressure. The residue was purified by silica gel column chromatography to afford the title compound (38 mg).

Reference Example 60: Ethyl 1-(4-{5-[3-fluoro-5-(trifluoromethyl)phenyl]-7-[(3-methoxy-2,2-dimethylpropyl)(methyl)amino]-1H-imidazo[4,5-b]pyridin-2-yl}phenyl)piperidine-4-carboxylate A mixture of 6-[3-fluoro-5-(trifluoromethyl)phenyl]-$N^4$-(3-methoxy-2,2-dimethylpropyl)-$N^4$-methylpyridine-2,3,4-triamine (95 mg), ethyl 1-(4-formylphenyl)piperidine-4-carboxylate (68 mg), sodium metabisulfite (59 mg) and acetonitrile (2.4 mL) was stirred at 180° C. for 1.5 hours, using microwave reactor. The reaction mixture was cooled to room temperature and diluted with water and ethyl acetate. The organic layer was washed with brine. The solvent was removed under reduced pressure, and the residue was purified by silica gel column chromatography to afford the title compound (150 mg).

Reference Example 61: 1-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carbonitrile A mixture of 6-[3-fluoro-5-(trifluoromethyl)phenyl]-$N^4$-{[1-(methoxymethyl)cyclobutyl]methyl}-$N^4$-methylpyridine-2,3,4-triamine (182 mg), 1-(5-formylpyrazin-2-yl)piperidine-4-carbonitrile (95 mg), sodium dithionite (192 mg) and DMF (4.4 mL) was stirred at 90° C. for 23 hours. The reaction mixture was cooled to room temperature and diluted with water and ethyl acetate. The organic layer was washed with brine and dried over anhydrous magnesium sulfate, and then the solvent was removed under reduced pressure. The residue was purified by silica gel column chromatography to afford the title compound (247 mg).

Reference Example 181: Ethyl 8-(4-{7-[{[1-(methoxymethyl)cyclobutyl]methyl}(methyl)amino]-5-[3-(trifluoromethyl)phenyl]-1H-imidazo[4,5-b]pyridin-2-yl}phenyl)-1-oxa-2,8-diazaspiro[4.5]deca-2-ene-3-carboxylate A mixture of $N^4$-{[1-(methoxymethyl)cyclobutyl]methyl}-$N^4$-methyl-6-[3-(trifluoromethyl)phenyl]pyridine-2,3,4-triamine (70 mg), ethyl 8-(4-formylphenyl)-1-oxa-2,8-diazaspiro[4.5]deca-2-ene-3-carboxylate (59 mg), sodium dithionite (77 mg) and DMF (2.1 mL) was stirred at 90° C. overnight. The reaction mixture was cooled to room temperature, diluted with water, and stirred for 15 minutes. The resulting precipitate was collected by filtration and washed with water to afford the crude product. The crude product was purified by silica gel column chromatography to afford the title compound (123 mg).

Example 1: 1-(5-{5-[2-Ethoxy-6-(trifluoromethyl) pyridin-4-yl]-7-[(3-methoxy-2,2-dimethylpropyl) (methyl)amino]-1H-imidazo[4,5-b]pyridin-2-yl}pyrazin-2-yl)piperidine-4-carboxylic acid To a solution of ethyl 1-(5-{5-[2-ethoxy-6-(trifluoromethyl)pyridin-4-yl]-7-[(3-methoxy-2,2-dimethylpropyl) (methyl)amino]-1H-imidazo[4,5-b]pyridin-2-yl}pyrazin-2-yl)piperidine-4-carboxylate (75 mg) in ethanol (1 mL) was added 1 M aq. sodium hydroxide (0.56 mL), and the reaction mixture was stirred at 50° C. for 2 hours. The reaction mixture was cooled to room temperature, diluted with water, and neutralized with 1 M hydrochloric acid. The resulting precipitate was collected by filtration and dried to afford the title compound (62 mg).

Example 2: 1-(5-{5-[2-Ethoxy-6-(trifluoromethyl) pyridin-4-yl]-7-[{[1-(methoxymethyl) cyclopentyl] methyl}(methyl)amino]-1H-imidazo[4,5-b]pyridin-2-yl}pyrazin-2-yl)piperidine-4-carboxylic acid To a solution of ethyl 1-(5-{5-[2-ethoxy-6-(trifluoromethyl)pyridin-4-yl]-7-[{[1-(methoxymethyl)cyclopentyl] methyl}(methyl)amino]-1H-imidazo[4,5-b]pyridin-2-yl}pyrazin-2-yl)piperidine-4-carboxylate (75 mg) in ethanol (1 mL) was added 1 M aq. sodium hydroxide (0.54 mL), and the reaction mixture was stirred at 50° C. for 2 hours. The reaction mixture was cooled to room temperature, diluted with water, and neutralized with 1 M hydrochloric acid. The resulting precipitate was collected by filtration and dried to afford the title compound (63 mg).

Example 3 1-(5-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)piperidine-4-carboxylic acid To a mixture of ethyl 1-(5-{5-[6-cyclopropyl-5-(trifluoromethyl)pyridin-3-yl]-7-[{[1-(ethoxymethyl) cyclopentyl] methyl}(methyl)amino]-1H-imidazo[4,5-b]pyridin-2-yl}pyrazin-2-yl)piperidine-4-carboxylate (76 mg), ethanol (0.54 mL), THF (0.54 mL) and water (0.18 mL) was added lithium hydroxide monohydrate (23 mg), and the reaction mixture was stirred at room temperature for 2 hours. The solvent was removed under reduced pressure, diluted with water, and then neutralized with 6 M hydrochloric acid. The resulting precipitate was collected by filtration to afford the title compound (40 mg).

Example 4: {[1-(5-{5-[2-Cyclopropyl-6-(trifluoromethyl)pyridin-4-yl]-7-[{[1-(methoxymethyl)cyclopentyl]methyl}(methyl)amino]-1H-imidazo[4,5-b] pyridin-2-yl}pyrazin-2-yl)piperidin-4-yl]oxy}acetic acid To a mixture of ethyl {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy} acetate (141 mg), THF (0.78 mL), methanol (0.78 mL), and water (0.78 mL) was added lithium hydroxide monohydrate (32.8 mg), and the reaction mixture was stirred at room temperature for 30 minutes and further stirred at 50° C. overnight. The reaction mixture was cooled to room temperature and concentrated under reduced pressure. The residue was diluted with water and neutralized by adding 2 M hydrochloric acid with stirring at room temperature. The resulting precipitate was collected by filtration, washed with water, and dried to afford the title compound (133 mg).

Example 5: 3-[4-(5-{5-[2-Ethoxy-5-(trifluoromethyl)pyridin-3-yl]-7-[{[1-(methoxymethyl) cyclopentyl]methyl}(methyl)amino]-1H-imidazo[4,5-b] pyridin-2-yl}pyrazin-2-yl)piperazin-1-yl]propanoic acid To a stirred mixture of ethyl 3-[4-(5-{5-[2-fluoro-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate (17.6 mg), ethanol (0.5 mL), water (0.25 mL), and THF (0.25 mL) was added lithium hydroxide monohydrate (5.1 mg) at room temperature. The reaction mixture was stirred at room temperature overnight and further stirred at 70° C. for 5 hours. The reaction mixture was cooled to room temperature. The solvent was removed under reduced pressure, and the residue was diluted with water and neutralized by adding 2 M hydrochloric acid with stirring at room temperature. The resulting precipitate was collected by filtration, washed with water, and then dried to afford the title compound (13.9 mg).

Example 6: 3-[4-(5-{5-[6-Cyclopropyl-5-(trifluoromethyl)pyridin-3-yl]-7-[{[1-(methoxymethyl)cyclohexyl]methyl}(methyl)amino]-1H-imidazo[4,5-b] pyridin-2-yl}pyrazin-2-yl)piperazin-1-yl]propanoic acid To a stirred mixture of ethyl 3-[4-(5-{5-[6-cyclopropyl-5-(trifluoromethyl)pyridin-3-yl]-7-[{[1-(methoxymethyl) cyclohexyl]methyl}(methyl)amino]-1H-imidazo[4,5-b] pyridin-2-yl}pyrazin-2-yl)piperazin-1-yl]propanoate (1.24 g), THF (8.4 mL), methanol (8.4 mL), and water (8.4 mL) was added lithium hydroxide monohydrate (0.285 g), and the reaction mixture was stirred at 50° C. overnight. The reaction mixture was cooled to room temperature and concentrated under reduced pressure. The residue was diluted with water, and neutralized by adding 2 M hydrochloric acid (3.4 mL) with stirring at room temperature. The resulting precipitate was collected by filtration, washed with water, and then dried to afford the title compound (1.14 g).

Example 7: 3-[(3R)-4-(5-{5-[6-Cyclopropyl-5-(trifluoromethyl)pyridin-3-yl]-7-[{[1-(methoxymethyl) cyclohexyl]methyl}(methyl)amino]-1H-imidazo[4,5-b]pyridin-2-yl}pyrazin-2-yl)-3-methylpiperazin-1-yl]propanoic acid A mixture of ethyl 3-[(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate (1.6 g), ethanol (11 mL), and 4 M aq. sodium hydroxide (2.7 mL) was stirred at 50° C. for 1 hour. The reaction mixture was cooled to room temperature and concentrated under reduced pressure. The residue was diluted with water and neutralized by adding 6 M hydrochloric acid. The resulting precipitate was collected by filtration, washed with water, and then dried to afford the title compound (1.44 g).

Example 8: 3-[(2S)-4-(5-{5-[6-Cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propanoic acid To a stirred mixture of ethyl 3-[(2S)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propanoate (96.7 mg), THF (0.74 mL), methanol (0.74 mL) and water (0.74 mL) was added lithium hydroxide monohydrate (21.8 mg) at room temperature, and the reaction mixture was stirred at the same temperature for 2 hours. The reaction mixture was concentrated under reduced pressure. The residue was diluted with water and neutralized with 2 M hydrochloric acid. The resulting precipitate was collected by filtration, washed with water, and then dried to afford the title compound (76.3 mg).

Example 9: 1-(5-{5-[2-Ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylic acid To a stirred mixture of ethyl 1-(5-{5-[2-ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylate (45 mg), ethanol (0.5 mL) and water (0.5 mL) was added 4 M aq. sodium hydroxide (0.082 mL) with stirring at room temperature. The reaction mixture was stirred at 50° C. for 1 hour. The reaction mixture was cooled to room temperature, diluted with water, and then neutralized with 6 M hydrochloric acid. The resulting precipitate was collected by filtration, washed with water, and then dried to afford the title compound (38 mg).

Example 10: [4-(4-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl]acetic acid To a stirred mixture of ethyl [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl] acetate (39.5 mg) in ethanol (1.1 mL) was added 2 M aq. sodium hydroxide (0.134 mL) with stirring at room temperature. The reaction mixture was stirred at the same temperature for 4 hours. The reaction mixture was diluted with water and neutralized with 2 M hydrochloric acid. The resulting precipitate was collected by filtration, washed with water, and then dried to afford the title compound (35.6 mg).

Example 11: 1-(5-{5-[2-Ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid dihydrochloride

[Step 1] Preparation of 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid A mixture of ethyl 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylate (285 mg), ethanol (8 mL) and 1 M aq. sodium hydroxide (2.1 mL) was stirred at 50° C. for 1 hour. The reaction mixture was cooled to room temperature, and the solvent was concentrated under reduced pressure. The residue was diluted with water and neutralized with 1 M hydrochloric acid. The resulting precipitate was collected by filtration and dried to afford the title compound (245 mg).

[Step 2] Preparation of 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid dihydrochloride 1-(5-{5-[2-Ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid (245 mg) obtained in Step 1 was diluted with ethyl acetate (8 mL). To the stirred solution was added hydrogen chloride (4 M in ethyl acetate, 0.47 mL) at room temperature, and the reaction mixture was stirred at the same temperature for 1 hour. The solvent was removed under reduced pressure, and the residue was diluted with diethyl ether. The insolubles were collected by filtration, washed with diethyl ether, and then dried to afford the title compound (244 mg).

Example 12: 3-[4-Fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidin-1-yl]propanoic acid trihydrochloride A mixture of ethyl 3-[4-fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidin-1-yl]propanoate (37 mg) and 2 M hydrochloric acid (1 mL) was stirred at 60° C. for 3 hours. The solvent was removed under reduced pressure. The residue was diluted with ethyl acetate and stirred at room temperature. The insolubles were collected by filtration and dried to afford the title compound (32 mg).

Example 13: 3-[4-(5-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid dihydrochloride

[Step 1] Preparation of 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid To a stirred mixture of ethyl 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoate (41 mg), THF (0.38 mL), water (0.38 mL) and ethanol (0.38 mL) was added lithium hydroxide monohydrate (9.7 mg) with stirring at room temperature, and the reaction mixture was stirred at the same temperature for 2 hours. The reaction mixture was neutralized by adding 6 M hydrochloric acid. The resulting precipitate was collected by filtration and washed with water to afford the title compound (38 mg).

[Step 2] Preparation of 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid dihydrochloride To a stirred mixture of 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid (36 mg) obtained in Step 1 and ethyl acetate (0.52 mL) was added hydrogen chloride (4 M in ethyl acetate, 0.066 mL) with stirring at room temperature, and the reaction mixture was stirred at the same temperature for 2 hours. The resulting precipitate was collected by filtration and washed with ethyl acetate to afford the title compound (38 mg).

Example 14: Sodium 3-[(3R)-4-(5-{5-[6-cyclopropyl-5-(trifluoromethyl)pyridin-3-yl]-7-[{[1-(ethoxymethyl) cyclopentyl]methyl}(methyl)amino]-1H-imidazo[4,5-b]pyridin-2-yl}pyrazin-2-yl)-3-methylpiperazin-1-yl]propanoate

[Step 1] Preparation of 3-[(3R)-4-(5-{5-[6-cyclopropyl-5-(trifluoromethyl)pyridin-3-yl]-7-[{[1-(ethoxymethyl) cyclopentyl]methyl}(methyl)amino]-1H-imidazo[4,5-b]pyridin-2-yl}pyrazin-2-yl)-3-methylpiperazin-1-yl]propanoic acid To a stirred mixture of ethyl 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propanoate (1.82 g), ethanol (9 mL) and water (9 mL) was added 4 M aq. sodium hydroxide (3 mL) with stirring at room temperature, and the reaction mixture was stirred at 50° C. for 1 hour. The reaction mixture was diluted with water and neutralized with 6 M hydrochloric acid. The reaction mixture was stirred at room temperature overnight. The resulting precipitate was collected by filtration, washed with water, and then dried to afford the title compound (1.73 g).

[Step 2] Preparation of sodium 3-[(3R)-4-(5-{5-[6-cyclopropyl-5-(trifluoromethyl)pyridin-3-yl]-7-[{[1-(ethoxymethyl) cyclopentyl]methyl}(methyl)amino]-1H-imidazo[4,5-b]pyridin-2-yl}pyrazin-2-yl)-3-methylpiperazin-1-yl]propanoate To a stirred mixture of 3-[(3R)-4-(5-{5-[6-cyclopropyl-5-(trifluoromethyl)pyridin-3-yl]-7-[{[1-(ethoxymethyl) cyclopentyl]methyl}(methyl)amino]-1H-imidazo[4,5-b]pyridin-2-yl}pyrazin-2-yl)-3-methylpiperazin-1-yl]propanoic acid (1.20 g) obtained in Step 1 and methanol (30 mL) was added sodium methoxide (0.5 M in methanol, 3.32 mL) with stirring at room temperature, and the reaction mixture was stirred at the same temperature for 1 hour. The solvent was removed under reduced pressure. The residue was diluted with diethyl ether (20 mL) and stirred at room temperature for 3 hours. Hexane (20 mL) was added thereto, and the mixture was stirred at room temperature for 1 hour. The insolubles were collected by filtration, washed with diethyl ether-hexane (1:1), and then dried to afford the title compound (1.16 g)

Example 15: Sodium {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate

[Step 1] Preparation of {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid To a stirred solution of ethyl {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate (85 mg) in ethanol (1 mL) was added 1 M aq. sodium hydroxide (0.53 mL) with stirring at room temperature, and the reaction mixture was stirred at the same temperature for 1 hour. The reaction mixture was neutralized by adding 2 M hydrochloric acid. After the solvent was removed under reduced pressure, the residue was diluted with water. The resulting precipitate was collected by filtration, washed with water and hexane-ethyl acetate (7:3) sequentially, and dried to afford the title compound (59 mg).

[Step 2] Preparation of sodium {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate To a stirred mixture of {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid (58 mg) obtained in Step 1 and methanol (1 mL) was added sodium methoxide (0.5 M in methanol, 0.16 mL) with stirring at room temperature, and the reaction mixture was stirred at the same temperature for 1 hour. The solvent was removed under reduced pressure. The residue was diluted with diethyl ether-hexane (1:1) and stirred at room temperature for 1 hour. The insolubles were collected by filtration, washed with diethyl ether-hexane (1:1), and then dried to afford the title compound (56 mg).

Example 16: Sodium 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate

[Step 1] Preparation of 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoic acid To a stirred solution of ethyl 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate (76 mg) in ethanol (1 mL) was added 1 M aq. sodium hydroxide (0.50 mL) with stirring at room temperature, and the reaction mixture was stirred at the same temperature for 1 hour. The reaction mixture was neutralized by adding 2 M hydrochloric acid and concentrated under reduced pressure. The residue was diluted with water. The resulting precipitate was collected by filtration, washed with water, and then dried to afford the title compound (68 mg).

[Step 2] Preparation of sodium 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate To a stirred mixture of 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoic acid (68 mg) obtained in Step 1 and methanol (1 mL) was added sodium methoxide (0.5 M in methanol, 0.19 mL) with stirring at room temperature, and the reaction mixture was stirred at the same temperature for 1 hour. The solvent was removed under reduced pressure. The residue was diluted with diethyl ether-hexane (1:1) and stirred at room temperature for 1 hour. The insolubles were collected by filtration, washed with diethyl ether-hexane (1:1), and then dried to afford the title compound (63 mg).

Example 17: Sodium [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetate

[Step 1] Preparation of [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetic acid To a stirred mixture of ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl] acetate (38 mg) in ethanol (1 mL) was added 1 M aq. sodium hydroxide (0.28 mL) with stirring at room temperature, and the reaction mixture was stirred at the same temperature for 1 hour. The reaction mixture was neutralized by adding 2 M hydrochloric acid and diluted with water. The resulting precipitate was collected by filtration, washed with water, and then dried to afford the title compound (32 mg).

[Step 2] Preparation of sodium [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetic acid To a stirred mixture of 4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetic acid (32 mg) obtained in Step 1 and methanol (2 mL) was added sodium methoxide (0.5 M in methanol, 0.098 mL) with stirring at room temperature, and the reaction mixture was stirred at the same temperature for 1 hour. The solution was removed under reduced pressure. The residue was diluted with diethyl ether-hexane (1:1) and stirred at room temperature for 1 hour. The insolubles were collected by filtration and washed with diethyl ether-hexane (1:1), and then dried to afford the title compound (23 mg).

Example 18: 1-(4-{5-[6-Ethoxy-5-(trifluoromethyl)pyridin-3-yl]-7-[{[1-(methoxymethyl) cyclobutyl]methyl}(methyl)amino]-1H-imidazo[4,5-b]pyridin-2-yl}phenyl)piperidine-4-carboxylic acid

[Step 1] Preparation of ethyl 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylate A mixture of 6'-ethoxy-N$^4$-{[1-(methoxymethyl)cyclobutyl]methyl}-N$^4$-methyl-5'-(trifluoromethyl) [2,3'-bipyridine]-4,5,6-triamine (50 mg), ethyl 1-(4-formylphenyl)piperidine-4-carboxylate (33 mg), sodium dithionite (40 mg) and DMF (1 mL) was stirred at 100° C. for 7 hour. The reaction mixture was cooled to room temperature, and then purified by silica gel column chromatography to afford the title compound (57 mg).

[Step 2] Preparation of 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylic acid To a stirred mixture of ethyl 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylate (58 mg) obtained in Step 1, THF (0.5 mL) and water (0.5 mL) was added 4 M aq. sodium hydroxide (0.11 mL) with stirring at room temperature, and the reaction mixture was stirred at 50° C. for 2 hours. Ethanol (0.5 mL) was added thereto, and the reaction mixture was stirred at 50° C. for 2 hours. The reaction mixture was cooled to room temperature, diluted with water and then neutralized by adding 1 M hydrochloric acid. The resulting precipitate was collected by filtration, washed with water, and then dried to afford the title compound (52 mg).

Example 19: [4-(6-{5-[3-Fluoro-5-(trifluoromethyl)
phenyl]-7-[{[1-(methoxymethyl)cyclobutyl]methyl}
(methyl)amino]-1H-imidazo[4,5-b]pyridin-2-
yl}pyridin-3-yl)-4-hydroxypiperidin-1-yl]acetic acid
trihydrochloride

[Step 1] Preparation of ethyl [4-(6-{5-[3-fluoro-5-
(trifluoromethyl)phenyl]-7-[{[1-(methoxymethyl)
cyclobutyl]methyl}(methyl)amino]-1H-imidazo[4,5-
b]pyridin-2-yl}pyridin-3-yl)-4-hydroxypiperidin-1-
yl] acetate A mixture of 6-[3-fluoro-5-(trifluoromethyl)phenyl]-$N^4$-
{[1-(methoxymethyl)cyclobutyl]methyl}-$N^4$-methylpyri-
dine-2,3,4-triamine (50 mg), ethyl [4-(6-formylpyridin-3-
yl)-4-hydroxypiperidin-1-yl]acetate (39 mg), sodium
dithionite (42 mg) and DMF (1 mL) was stirred at 100° C.
for 7 hours. The reaction mixture was cooled to room
temperature, and then purified by silica gel column chro-
matography to afford the title compound (52 mg).

[Step 2] Preparation of [4-(6-{5-[3-fluoro-5-(trifluo-
romethyl)phenyl]-7-[{[1-(methoxymethyl)cy-
clobutyl]methyl}(methyl)amino]-1H-imidazo[4,5-b]
pyridin-2-yl}pyridin-3-yl)-4-hydroxypiperidin-1-yl]
acetic acid To a stirred mixture of ethyl [4-(6-{5-[3-fluoro-5-(trifluo-
romethyl)phenyl]-7-[{[1-(methoxymethyl)cyclobutyl]
methyl}(methyl)amino]-1H-imidazo[4,5-b]pyridin-2-
yl}pyridin-3-yl)-4-hydroxypiperidin-1-yl] acetate (52 mg)
obtained in Step 1, THF (0.5 mL) and water (0.5 mL) was
added 4 M aq. sodium hydroxide (0.095 mL) with stirring at
room temperature, and the reaction mixture was stirred at
50° C. for 1 hour. The reaction mixture was cooled to room
temperature, diluted with water, and then neutralized by
adding 1 M hydrochloric acid. The resulting precipitate was
collected by filtration, washed with water, and then dried to
afford the title compound (39 mg).

[Step 3] Preparation of [4-(6-{5-[3-fluoro-5-(trifluo-
romethyl)phenyl]-7-[{[1-(methoxymethyl)cy-
clobutyl]methyl}(methyl)amino]-1H-imidazo[4,5-b]
pyridin-2-yl}pyridin-3-yl)-4-hydroxypiperidin-1-yl]
acetic acid trihydrochloride To a stirred mixture of [4-(6-{5-[3-fluorom-
ethyl)phenyl]-7-[{[1-(methoxymethyl)cyclobutyl]methyl}
(methyl)amino]-1H-imidazo[4,5-b]pyridin-2-yl}pyridin-3-
yl)-4-hydroxypiperidin-1-yl]acetic acid (38 mg) obtained in
Step 2 and ethyl acetate (1 mL) was added hydrogen
chloride (4 M in ethyl acetate, 0.072 mL) with stirring at
room temperature, and the reaction mixture was stirred at the
same temperature for 1 hour. The reaction mixture was
diluted with ethyl acetate. The insolubles were collected by
filtration, washed with ethyl acetate, and then dried to afford
the title compound (41 mg).

Example 20: Sodium 3-[(3R)-4-(5-{5-[6-Cyclopro-
pyl-5-(trifluoromethyl)pyridin-3-yl]-7-[{[1-
(methoxymethyl)cyclopentyl]methyl}(methyl)
amino]-1H-imidazo[4,5-b]pyridin-2-yl}pyrazin-2-
yl)-3-methylpiperazin-1-yl]propanoate

[Step 1] Preparation of ethyl 3-[(3R)-4-(5-{5-[6-
cyclopropyl-5-(trifluoromethyl)pyridin-3-yl]-7-[{[1-
(methoxymethyl)cyclopentyl]methyl}(methyl)
amino]-1H-imidazo[4,5-b]pyridin-2-yl}pyrazin-2-
yl)-3-methylpiperazin-1-yl]propanoate A mixture of 6'-cyclopropyl-$N^4$-{[1-(methoxymethyl)cy-
clopentyl]methyl}-$N^4$-methyl-5'-(trifluoromethyl) [2,3'-bi-
pyridine]-4,5,6-triamine (50 mg), ethyl 3-[(3R)-4-(5-form-
ylpyrazin-2-yl)-3-methylpiperazin-1-yl]propanoate (38
mg), sodium dithionite (39 mg) and DMF (0.5 mL) was
stirred at 110° C. for 3 hours. The reaction mixture was
cooled to room temperature, and then purified by silica gel
column chromatography to afford the title compound (75
mg).

[Step 2] Preparation of 3-[(3R)-4-(5-{5-[6-cyclo-
propyl-5-(trifluoromethyl)pyridin-3-yl]-7-[{[1-
(methoxymethyl)cyclopentyl]methyl}(methyl)
amino]-1H-imidazo[4,5-b]pyridin-2-yl}pyrazin-2-
yl)-3-methylpiperazin-1-yl]propanoic acid To a stirred mixture of ethyl 3-[(3R)-4-(5-{5-[6-cyclopro-
pyl-5-(trifluoromethyl)pyridin-3-yl]-7-[{[1-(methoxym-
ethyl)cyclopentyl]methyl}(methyl)amino]-1H-imidazo[4,5-
b]pyridin-2-yl}pyrazin-2-yl)-3-methylpiperazin-1-yl]
propanoate (75 mg) obtained in Step 1, THF (0.5 mL) and
water (0.5 mL) was added 4 M aq. sodium hydroxide (0.127
mL) with stirring at room temperature, and the reaction
mixture was stirred at 50° C. for 1 hour. The reaction
mixture was cooled to room temperature, diluted with water,
and then neutralized by adding 1 M hydrochloric acid. The
resulting precipitate was collected by filtration, washed with
water, and then dried to afford the title compound (66 mg).

[Step 3] Preparation of sodium 3-[(3R)-4-(5-{5-[6-
cyclopropyl-5-(trifluoromethyl)pyridin-3-yl]-7-[{[1-
(methoxymethyl)cyclopentyl]methyl}(methyl)
amino]-1H-imidazo[4,5-b]pyridin-2-yl}pyrazin-2-
yl)-3-methylpiperazin-1-yl]propanoate To a stirred mixture of 3-[(3R)-4-(5-{5-[6-cyclopropyl-5-
(trifluoromethyl)pyridin-3-yl]-7-[{[1-(methoxymethyl)cy-
clopentyl]methyl}(methyl)amino]-1H-imidazo[4,5-b]pyri-
din-2-yl}pyrazin-2-yl)-3-methylpiperazin-1-yl]propanoic
acid (65 mg) obtained in Step 2 and methanol (2 mL) was
added sodium methoxide (0.5 M in methanol, 0.184 mL)
with stirring at room temperature, and the reaction mixture
was stirred at the same temperature for 30 minutes. The
solvent was removed under reduced pressure. The residue
was diluted with diethyl ether-hexane (1:1) and stirred at
room temperature for 1 hour. The insolubles were collected
by filtration, washed with diethyl ether-hexane (1:1), and
then dried to afford the title compound (65 mg).

Example 21: 1-(4-{5-[3-Fluoro-5-(trifluoromethyl)
phenyl]-7-[(3-methoxy-2,2-dimethylpropyl)(methyl)
amino]-1H-imidazo[4,5-b]pyridin-2-yl}phenyl)pip-
eridine-4-carboxylic acid To a stirred mixture of ethyl 1-(4-{5-[3-fluoro-5-(trifluo-
romethyl)phenyl]-7-[(3-methoxy-2,2-dimethylpropyl)
(methyl)amino]-1H-imidazo[4,5-b]pyridin-2-yl}phenyl)pi-
peridine-4-carboxylate (131 mg), THF (2.4 mL) and water
(0.82 mL) was added 4 M aq. sodium hydroxide (0.255 mL)
with stirring at room temperature, and the reaction mixture
was stirred at 70° C. for 1 hour. The reaction mixture was
cooled to room temperature, diluted with water, and then
neutralized by adding 6 M hydrochloric acid. The resulting
precipitate was collected by filtration to afford the title
compound (122 mg).

Example 22: Sodium [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetate

[Step 1] Preparation of ethyl [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl] acetate A mixture of 6'-cyclopropyl-$N^4$-{[1-(methoxymethyl)cyclopentyl]methyl}-$N^4$-methyl-5'-(trifluoromethyl) [2,3'-bipyridine]-4,5,6-triamine (50 mg), ethyl [4-(3-fluoro-5-formylpyridin-2-yl)piperazin-1-yl] acetate (33 mg), sodium dithionite (39 mg) and DMF (0.5 mL) was stirred 110° C. for 3 hours. The reaction mixture was cooled to room temperature, and then purified by silica gel column chromatography to afford the title compound (68 mg).

[Step 2] Preparation of [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetic acid To a stirred mixture of ethyl [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl] acetate (67 mg) obtained in Step 1, THF (0.5 mL) and water (0.5 mL) was added 4 M aq. sodium hydroxide (0.116 mL) with stirring at room temperature, and the reaction mixture was stirred at 50° C. for 1 hour. The reaction mixture was cooled to room temperature, diluted with water, and then neutralized by adding 1 M hydrochloric acid. The resulting precipitate was collected by filtration, washed with water, and then dried to afford the title compound (59 mg).

[Step 3] Preparation of sodium [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetate To a stirred mixture of [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetic acid (59 mg) obtained in Step 2 and methanol (2 mL) was added sodium methoxide (0.5 M in methanol, 0.169 mL) with stirring at room temperature, and the reaction mixture was stirred at the same temperature for 30 minutes. The solvent was removed under reduced pressure. The residue was diluted with diethyl ether-hexane (1:1) and stirred at room temperature for 1 hour. The insolubles were collected by filtration, diluted with diethyl ether-hexane (1:1), and then dried to afford the title compound (56 mg).

Example 23: 5-[3-Fluoro-5-(trifluoromethyl)phenyl]-N-{[1-(methoxymethyl)cyclobutyl]methyl}-N-methyl-2-{5-[4-(1H-tetrazol-5-yl)piperidin-1-yl]pyrazin-2-yl}-1H-imidazo[4,5-b]pyridine-7-amine To a stirred solution of 1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carbonitrile (50 mg) in DMF (1 mL) were added ammonium chloride (13.2 mg) and sodium azide (16 mg) sequentially with stirring under ice-cooling, and the reaction mixture was stirred at 100° C. for 3 days. The reaction mixture was cooled to room temperature, diluted with water and ethyl acetate, and then extracted with ethyl acetate. The organic layer was concentrated under reduced pressure, and the residue was purified by silica gel column chromatography to afford the title compound (7.4 mg).

Example 24: 8-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-2,8-diazaspiro[4.5]decan-3-one A mixture of 6-[3-fluoro-5-(trifluoromethyl)phenyl]-$N^4$-{[1-(methoxymethyl) cyclobutyl]methyl}-$N^4$-methylpyridine-2,3,4-triamine (25 mg), 4-(3-oxo-2,8-diazaspiro[4.5]decan-8-yl)benzaldehyde (17 mg), sodium metabisulfite (16 mg) and acetonitrile (0.6 mL) was stirred at 180° C. for 1 hour, using a microwave reactor. The reaction mixture was cooled to room temperature, diluted with water and ethyl acetate, and extracted with ethyl acetate. The organic layer was concentrated under reduced pressure, and the residue was purified by silica gel column chromatography to afford the title compound (16 mg).

Example 25: 1-(5-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-N-(methansulfonyl)piperidine-4-carboxamide A mixture of 6'-cyclopropyl-$N^4$-{[1-(ethoxymethyl)cyclopentyl] methyl}-$N^4$-methyl-5'-(trifluoromethyl) [2,3'-bipyridine]-4,5,6-triamine (42 mg), 1-(5-formylpyrazin-2-yl)-N-(methansulfonyl)piperidine-4-carboxamide (30 mg), sodium dithionite (39 mg) and DMF (0.9 mL) was stirred at 110° C. for 5 hours. The reaction mixture was cooled to room temperature and diluted with water. The resulting solids were collected by filtration and washed with water. The solids were diluted with diethyl ether-hexane (1:1, 2 mL) and stirred at room temperature overnight. The insolubles were collected by filtration, washed with diethyl ether-hexane (1:1), and then dried to afford the title compound (57 mg).

Example 26: [4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]acetic acid

[Step 1] Preparation of 2,2,2-trifluoro-1-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]ethan-1-one A mixture of 6-[3-fluoro-5-(trifluoromethyl)phenyl]-$N^4$-{[1-(methoxymethyl) cyclobutyl]methyl}-$N^4$-methylpyridine-2,3,4-triamine (300 mg), 4-[1-(trifluoroacetyl)piperidin-4-yl]benzaldehyde (228 mg), sodium dithionite (253 mg) and DMF (3.5 mL) was stirred at 100° C. for 7 hours. The reaction mixture was cooled to room temperature, diluted with water and ethyl acetate, and then extracted with ethyl acetate. The organic layer was washed with water and brine, dried over anhydrous magnesium sulfate, and then concentrated under reduced pressure. The residue was purified by silica gel column chromatography to afford the title compound (442 mg).

[Step 2] Preparation of 2,2,2-trifluoro-1-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperidin-1-yl}ethan-1-one and its isomer 2,2,2-trifluoro-1-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperidin-1-yl}ethan-1-one To a stirred solution of 2,2,2-trifluoro-1-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]ethan-1-one (430 mg) obtained in Step 1 in dichloromethane (5 mL) were added DIPEA (0.16 mL) and 2-(chloromethoxy)ethyltrimethylsilane (0.13 mL) with stirring under ice-cooling, and the reaction mixture was stirred at room temperature for 2 hours. The reaction mixture was concentrated under reduced pressure, and the residue was purified by silica gel column chromatography to afford the title compound (484 mg).

[Step 3] Preparation of 5-[3-fluoro-5-(trifluoromethyl)phenyl]-N-{[1-(methoxymethyl)cyclobutyl]methyl}-N-methyl-2-[4-(piperidin-4-yl)phenyl]-3-{[2-(trimethylsilyl)ethoxy]methyl}-3H-imidazo[4,5-b]pyridine-7-amine and its isomer 5-[3-fluoro-5-(trifluoromethyl)phenyl]-N-{[1-(methoxymethyl)cyclobutyl]methyl}-N-methyl-2-[4-(piperidin-4-yl)phenyl]-1-{[2-(trimethylsilyl)ethoxy]methyl}-1H-imidazo[4,5-b]pyridine-7-amine To a mixture of 2,2,2-trifluoro-1-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperidin-1-yl}ethan-1-one and its isomer 2,2,2-trifluoro-1-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperidin-1-yl}ethan-1-one (480 mg) obtained in Step 2, and potassium carbonate (410 mg) were added methanol (4.5 mL) and water (0.5 mL), and the reaction mixture was stirred at 70° C. for 2 hours. The reaction mixture was cooled to room temperature, diluted with water and ethyl acetate, and then extracted with ethyl acetate. The organic layer was washed with water and brine, dried over anhydrous sodium sulfate, and then concentrated under reduced pressure. The residue was purified by silica gel column chromatography to afford the title compound (391 mg).

[Step 4] Preparation of ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl] acetate To a stirred mixture of 5-[3-fluoro-5-(trifluoromethyl)phenyl]-N-{[1-(methoxymethyl)cyclobutyl]methyl}-N-methyl-2-[4-(piperidin-4-yl)phenyl]-3-{[2-(trimethylsilyl)ethoxy]methyl}-3H-imidazo[4,5-b]pyridine-7-amine and its isomer 5-[3-fluoro-5-(trifluoromethyl)phenyl]-N-{[1-(methoxymethyl)cyclobutyl]methyl}-N-methyl-2-[4-(piperidin-4-yl)phenyl]-1-{[2-(trimethylsilyl)ethoxy]methyl}-1H-imidazo[4,5-b]pyridine-7-amine (70 mg) obtained in Step 3 and ethanol (1 mL) were added sodium bicarbonate (11 mg) and ethyl bromoacetate (0.012 mL) with stirring at room temperature, and the reaction mixture was stirred at 80° C. for 2 hours. The reaction mixture was cooled to room temperature. Concentrated sulfuric acid (0.026 mL) was added thereto, and the reaction mixture was stirred at 80° C. for 1 hour. The reaction mixture was cooled to room temperature and then purified by silica gel column chromatography to afford the title compound (58 mg).

[Step 5] Preparation of [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]acetic acid To a mixture of ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl] acetate (55 mg) obtained in Step 4, ethanol (0.5 mL) and water (0.5 mL) was added 4 M aq. sodium hydroxide (0.1 mL), and the reaction mixture was stirred at 50° C. for 1 hour. The reaction mixture was cooled to room temperature and diluted with water, and 1 M hydrochloric acid was added. The resulting precipitate was collected by filtration, washed with water, and then dried to afford the title compound (45 mg).

Example 27: 2-[4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propanoic acid dihydrochloride

[Step 1] Preparation of 2,2,2-trifluoro-1-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]ethan-1-one The title compound was obtained as described in Example 26, Step 1, using 4-[4-(trifluoroacetyl)piperazin-1-yl]benzaldehyde instead of 4-[1-(trifluoroacetyl)piperidin-4-yl]benzaldehyde.

[Step 2] Preparation of 2,2,2-trifluoro-1-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperazin-1-yl}ethan-1-one and its isomer 2,2,2-trifluoro-1-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperazin-1-yl}ethan-1-one The title compound was obtained as described in Example 26, Step 2, using 2,2,2-trifluoro-1-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]ethan-1-one obtained in Step 1 instead of 2,2,2-trifluoro-1-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]ethan-1-one.

[Step 3] Preparation of 5-[3-fluoro-5-(trifluoromethyl)phenyl]-N-{[1-(methoxymethyl)cyclobutyl]methyl}-N-methyl-2-[4-(piperazin-1-yl)phenyl]-3-{[2-(trimethylsilyl)ethoxy]methyl}-3H-imidazo[4,5-b]pyridine-7-amine and its isomer 5-[3-fluoro-5-(trifluoromethyl)phenyl]-N-{[1-(methoxymethyl)cyclobutyl]methyl}-N-methyl-2-[4-(piperazin-1-yl)phenyl]-1-{[2-(trimethylsilyl)ethoxy]methyl}-1H-imidazo[4,5-b]pyridine-7-amine The title compound was obtained in Example 26, Step 3, using 2,2,2-trifluoro-1-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperazin-1-yl}ethan-1-one and its isomer, 2,2,2-trifluoro-1-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperazin-1-yl}ethan-1-one obtained in Step 2 instead of 2,2,2-trifluoro-1-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperidin-1-yl}ethan-1-one and its isomer 2,2,2-trifluoro-1-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperidin-1-yl}ethan-1-one.

[Step 4] Preparation of ethyl 2-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperazin-1-yl}propanoate and its isomer ethyl 2-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperazin-1-yl}propanoate To a stirred mixture of 5-[3-fluoro-5-(trifluoromethyl)phenyl]-N-{[1-(methoxymethyl)cyclobutyl]methyl}-N-methyl-2-[4-(piperazin-1-yl)phenyl]-3-{[2-(trimethylsilyl)ethoxy]methyl}-3H-imidazo[4,5-b]pyridine-7-amine and its isomer 5-[3-fluoro-5-(trifluoromethyl)phenyl]-N-{[1-(methoxymethyl)cyclobutyl]methyl}-N-methyl-2-[4-(piperazin-1-yl)phenyl]-1-{[2-(trimethylsilyl)ethoxy]methyl}-1H-imidazo[4,5-b]pyridine-7-amine (95 mg) obtained in Step 3 and NMP (1 mL) were added potassium carbonate (48 mg) and ethyl 2-bromopropionate (0.035 mL) with stirring at room temperature, and the reaction mixture was stirred at 100° C. for 4 hours. The reaction mixture was cooled to room temperature, and then purified by silica gel column chromatography to afford the title compound (67 mg).

[Step 5] Preparation of ethyl 2-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propanoate To a stirred solution of ethyl 2-{4-[4-(5-[3-fluoro-5-(trifluoromethyl)phenyl]-7-[{[1-(methoxymethyl)cyclobutyl]methyl}(methyl)amino]-3-{[2-(trimethylsilyl)ethoxy]methyl}-3H-imidazo[4,5-b]pyridin-2-yl)phenyl]piperazin-1-yl}propanoate and its isomer ethyl 2-{4-[4-(5-[3-fluoro-5-(trifluoromethyl)phenyl]-7-[{[1-(methoxymethyl)cyclobutyl]methyl}(methyl)amino]-1-{[2-(trimethylsilyl)ethoxy]methyl}-1H-imidazo[4,5-b]pyridin-2-yl)phenyl]piperazin-1-yl}propanoate (65 mg) obtained in Step 4 in dichloromethane (0.5 mL) was added TFA (0.5 mL) with stirring at room temperature, and the reaction mixture was stirred for 2 hours. The reaction mixture was purified by silica gel column chromatography to afford the title compound (47 mg).

[Step 6] Preparation of 2-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propanoic acid dihydrochloride To a mixture of ethyl 2-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propanoate (40 mg) obtained in Step 5, ethanol (0.5 mL) and water (0.5 mL) was added 4 M aq. sodium hydroxide (0.15 mL), and the reaction mixture was stirred with heating at 70° C. for 1 hour. The reaction mixture was cooled to room temperature and diluted with water, and 1 M hydrochloric acid was added. The resulting precipitate was collected by filtration to afford the solids. To the stirred mixture of the solids and ethyl acetate (1 mL) was added hydrogen chloride (4 M in ethyl acetate, 0.052 mL) with stirring at room temperature, and the reaction mixture was stirred for 1 hour. The resulting precipitates were collected by filtration, washed with ethyl acetate, and then dried to afford the title compound (25 mg).

Example 28: 1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperidine-4-carboxylic acid

[Step 1] Preparation of methyl 4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoate A mixture of 6-[3-fluoro-5-(trifluoromethyl)phenyl]-N⁴-{[1-(methoxymethyl) cyclobutyl]methyl}-N⁴-methylpyridine-2,3,4-triamine (200 mg), 4-formylbenzoate (84 mg), sodium dithionite (211 mg) and DMF (2 mL) was stirred at 100° C. for 2 hours. The reaction mixture was cooled to room temperature and concentrated under reduced pressure. The residue was purified by silica gel column chromatography to afford the title compound (193 mg).

[Step 2] Preparation of 4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoic acid To a mixture of methyl 4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoate (193 mg) obtained in Step 1 and ethanol (2.5 mL) was added 1 M aq. sodium hydroxide (1.7 mL), and the reaction mixture was stirred at room temperature for 1 hour. The reaction mixture was diluted with water, and 1 M hydrochloric acid (1.7 mL) was added. The resulting precipitate was collected by filtration, washed with water, and then dried to afford the title compound (182 mg).

[Step 3] Preparation of ethyl 1-(4-{5-[3-fluoro-5-(trifluoromethyl)phenyl]-7-[{[1-(methoxymethyl) cyclobutyl]methyl}(methyl)amino]-1H-imidazo[4,5-b]pyridin-2-yl}benzoyl)piperidine-4-carboxylate To a mixture of 4-{5-[3-fluoro-5-(trifluoromethyl)phenyl]-7-[{[1-(methoxymethyl) cyclobutyl]methyl}(methyl)amino]-1H-imidazo[4,5-b]pyridin-2-yl}benzoic acid (40 mg) obtained in Step 2 and DMF (1 mL) were added DIPEA (0.038 mL), HATU (34 mg) and ethyl piperidine-4-carboxylate (0.014 mL), and the reaction mixture was stirred overnight at room temperature. The reaction mixture was purified by silica gel column chromatography to afford the title compound (25 mg).

[Step 4] Preparation of 1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperidine-4-carboxylic acid The title compound (19 mg) was obtained as described in Example 26, Step 5, using ethyl 1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperidine-4-carboxylate obtained in Step 3 instead of ethyl [4-(4-{5-[3-fluoro-5-(trifluoromethyl)phenyl]-7-[{[1-(methoxymethyl) cyclobutyl]methyl}(methyl)amino]-1H-imidazo[4,5-b]pyridin-2-yl}phenyl)piperidin-1-yl] acetate.

Example 29: {4-[1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethyl]piperazin-1-yl}acetic acid trihydrochloride

[Step 1] Preparation of 1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethan-1-one The title compound was obtained as described in Example 26, Step 1, using 1-formyl-4-acetybenzene instead of 4-[1-(trifluoroacetyl)piperidin-4-yl]benzaldehyde.

[Step 2] Preparation of ethyl {4-[1-(4-{5-[3-fluoro-5-(trifluoromethyl)phenyl]-7-[{[1-(methoxymethyl) cyclobutyl]methyl}(methyl)amino]-1H-imidazo[4,5-b]pyridin-2-yl}phenyl)ethyl]piperazin-1-yl} acetate 1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethan-1-one (50 mg) obtained in Step 1, 1-piperazine ethyl acetate (32 mg), tetraisopropyl orthotitanate (0.055 mL), acetic acid (0.016 mL) and dichloromethane (1 mL) were mixed, and the mixture was stirred at room temperature overnight. Sodium triacetoxyborohydride (39 mg) was added thereto, and the reaction mixture was stirred at the same temperature overnight. The reaction mixture was purified by silica gel column chromatography to afford the title compound (38 mg).

[Step 3] Preparation of {4-[1-(4-{5-[3-fluoro-5-(trifluoromethyl)phenyl]-7-[{[1-(methoxymethyl) cyclobutyl]methyl}(methyl)amino]-1H-imidazo[4,5-b]pyridin-2-yl}phenyl)ethyl]piperazin-1-yl}acetic acid trihydrochloride To a mixture of ethyl {4-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethyl]piperazin-1-yl} acetate (36 mg) obtained in Step 2, THF (0.5 mL) and water (0.5 mL) was added 4 M aq. sodium hydroxide (0.065 mL), and the reaction mixture was stirred at 50° C. for 1 hour. The reaction mixture was cooled to room temperature and diluted with water, and then 1 M hydrochloric acid was added. The resulting precipitate was collected by filtration to afford the solids. To a stirred mixture of the solids and ethyl acetate (1 mL) was added hydrogen chloride (4 M in ethyl acetate, 0.056 mL) with stirring at room temperature, and the reaction mixture was stirred for 1 hour. The resulting precipitate was collected by filtration, washed with ethyl acetate, and then dried to afford the title compound (28 mg).

Example 89: 3-[4-(5-{5-[6-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid dihydrochloride

[Step 1] Preparation of 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl] propanoic acid To a stirred mixture of ethyl 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate (49 mg), THF (0.45 mL), water (0.45 mL) and ethanol (0.45 mL) was added lithium hydroxide monohydrate (11 mg) with stirring at room temperature, and the reaction mixture was stirred at room temperature for 2 hours. The reaction mixture was neutralized by adding 6 M hydrochloric acid and diluted with water. The resulting solids were collected by filtration, washed with hexane-ethyl acetate (1:1) to afford the title compound (21 mg).

[Step 2] Preparation of 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl] propanoic acid dihydrochloride To a stirred mixture of 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid (21 mg) obtained in Step 1 and ethyl acetate (0.3 mL) was added hydrogen chloride (4 M in ethyl acetate, 0.038 mL) with stirring at room temperature, and the reaction mixture was stirred at the same temperature for 2 hours. The reaction mixture was concentrated under reduced pressure to afford the title compound (23 mg).

Example 109: Sodium 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate

[Step 1] Preparation of 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoic acid To a stirred mixture of ethyl 3-[(2S)-4-(5-{5-[4-fluoro-3-(trifluoromethyl)phenyl]-7-[{(1-(methoxymethyl)cyclobutyl]methyl}(methyl)amino]-1H-imidazo[4,5-b]pyridin-2-yl}pyrazin-2-yl)-2-methylpiperazin-1-yl]propanoate (59 mg), THF (0.85 mL), methanol (0.85 mL) and water (0.85 mL) was added lithium hydroxide monohydrate (14 mg) with stirring at room temperature, and the reaction mixture was stirred at the same temperature overnight. The reaction mixture was concentrated under reduced pressure. The residue was diluted with water and neutralized with 2 M hydrochloric acid. The resulting precipitate was collected by filtration, diluted with water, and then dried to afford the title compound (54 mg).

[Step 2] Preparation of sodium 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate To a stirred mixture of 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoic acid (51 mg) obtained in Step 1 and methanol (1.5 mL) was added sodium methoxide (0.5 M in methanol, 0.15 mL) with stirring at room temperature, and the reaction mixture was stirred at the same temperature for 10 minutes. The reaction mixture was concentrated under reduced pressure. To the residue was added diethyl ether-hexane (1:1), and the mixture was stirred at room temperature for 2 hours. The solvent was removed. The insolubles were washed with diethyl ether-hexane (1:1), and then dried to afford the title compound (52 mg).

Compounds of Reference Examples and Examples are further provided below in Tables 1 to 109. In the tables, PREx means the Reference Example No. where the compound was prepared according to the method as described in said Reference Example using a corresponding starting material. For example, the compound of the following Reference Example with the indication of PREx No. as 1 was prepared using the method as described in Reference Example 1. Also, in the tables, PEx means the Example No. where the compound was prepared according to the method as described in said Example using a corresponding starting material. For example, the compound of the following Example with the indication of PEx No. as 1 was prepared using the method as described in Example 1. Further, in the tables, Chemical Name refers to the name of the Reference Example (REx) or the Example (Ex). In addition, Data means the instrumental analytical data, such as mass spectrometric data (m/z values), $^1$H NMR data (δ (ppm) of peaks), and elemental analytical data (composition (%) of C, H and N).

TABLE 1

| REx | PREx | Chemical Name | Data |
|---|---|---|---|
| 1 | 1 | N-{[1-(methoxymethyl)cyclopentyl]methyl}ethanamine hydrochloride | $^1$H-NMR (400 MHz, DMSO-d$_6$) δ: 8.14 (brs, 2H), 3.27 (s, 3H), 3.23 (s, 2H), 2.96-2.90 (m, 2H), 2.88-2.84 (m, 2H), 1.60-1.53 (m, 4H), 1.48-1.43 (m, 4H), 1.20 (t, 3H) |
| 2 | 2 | 1-{1-[(2-Methoxyethoxy)methyl]cyclopentyl}-N-methylmethanamine hydrochloride | $^1$H-NMR (400 MHz, CDCl$_3$) δ: 3.65-3.63 (m, 2H), 3.55-3.53 (m, 2H), 3.49 (s, 2H), 3.41 (s, 3H), 3.00 (dd, 2H), 2.70 (t, 3H), 1.77-1.57 (m, 8H) |
| 3 | 3 | 1-[1-(Butoxymethyl)cyclopentyl]-N-methylmethanamine hydrochloride | $^1$H-NMR (400 MHz, CDCl$_3$) δ: 3.52-3.49 (m, 2H), 3.44-3.41 (m, 2H), 3.04 (s, 1H), 2.90 (s, 1H), 2.75 (brs, 3H), 1.81-1.28 (m, 12H), 0.96-0.88 (m, 3H) |
| 4 | 4 | 1-[1-(Ethoxymethyl)cyclopentyl]-N-methylmethanamine hydrochloride | $^1$H-NMR (400 MHz, CDCl$_3$) δ: 3.58 (dd, 2H), 3.44 (s, 2H), 3.02 (t, 2H), 2.74 (t, 3H), 1.76-1.58 (m, 8H), 1.21 (t, 3H) |
| 5 | 5 | 1-[1-(methoxymethyl)cyclopentyl]-N-methylmethanamine hydrochloride | $^1$H-NMR (400 MHz, CDCl$_3$) δ: 3.42 (s, 3H), 3.41 (s, 2H), 3.02-2.99 (m, 2H), 2.75 (t, 3H), 2.17-2.12 (m, 2H), 1.75-1.56 (m, 6H) |

TABLE 2

| REx | PREx | Chemical Name | Data |
|---|---|---|---|
| 6 | 6 | 4-Chloro-6-[3-fluoro-5-(trifluoromethyl)phenyl]pyridin-2-amine | MS (ESI+) m/z: 291.0 (M + H)+ |
| 7 | 7 | 4-Chloro-6-[3-fluoro-5-(trifluoromethyl)phenyl]-3-nitropyridin-2-amine | MS (ESI+) m/z: 235.9 (M + H)+ |
| 8 | 8 | 6-Chloro-N$^4$-(3-methoxy-2,2-dimethylpropyl)-N$^4$-methyl-3-nitropyridin-2,4-diamine | MS (ESI+) m/z: 303.6 (M + H)+ |
| 9 | 9 | 6'-Cyclopropyl-N$^4$-{[1-(methoxymethyl)cyclohexyl]methyl}-N$^4$-methyl-5-nitro-5'-(trifluoromethyl)[2,3'-bipyridin]-4,6-diamine | MS (ESI+) m/z: 494.4 (M + H)+ |
| 10 | 10 | 2'-Ethoxy-N$^4$-{[1-(ethoxymethyl)cyclopentyl]methyl}-N$^4$-methyl-6'-(trifluoromethyl)[2,4'-bipyridin]-4,5,6-triamine | MS (ESI+) m/z: 468.4 (M + H)+ |
| 11 | 11 | 6-[3-Fluoro-5-(trifluoromethyl)phenyl]-N$^4$-({1-[(2-methoxyethoxy)methyl]cyclopentyl}methyl)-N$^4$-methylpyridin-2,3,4-triamine | MS (ESI+) m/z: 471.7 (M + H)+ |

TABLE 3

| REx | PREx | Chemical Name | Data |
|---|---|---|---|
| 12 | 12 | 2'-Ethoxy-N$^4$-{[1-(methoxymethyl)cyclobutyl]methyl}-N$^4$-methyl-6'-(trifluoromethyl)[2,4'-bipyridin]-4,5,6-triamine | MS (ESI+) m/z: 440.2 (M + H)+ |
| 13 | 13 | 6'-Cyclopropyl-N$^4$-{[1-(ethoxymethyl)cyclopentyl]methyl}-N$^4$-methyl-5'-(trifluoromethyl)[2,3'-bipyridin]-4,5,6-triamine | MS (ESI+) m/z: 464.3 (M + H)+ |
| 14 | 14 | Ethyl [4-(4-formylphenyl)piperazin-1-yl]acetate | MS (ESI+) m/z: 277.1 (M + H)+ |
| 15 | 15 | Ethyl 3-[(3R)-4-(4-formylphenyl)-3-methylpiperazin-1-yl]propanoate | MS (ESI+) m/z: 305.1 (M + H)+ |
| 16 | 16 | Ethyl {4-[(4-formylphenyl)methyl]piperazin-1-yl}acetate | MS (ESI+) m/z: 291.1 (M + H)+ |
| 17 | 17 | Methyl {1-[(4-formylphenyl)methyl]piperidin-4-yl}acetate | MS (ESI+) m/z: 276.1 (M + H)+ |
| 18 | 18 | Ethyl 3-[4-(5-formylpyridin-2-yl)-4-hydroxypiperidin-1-yl]propanoate | MS (ESI+) m/z: 307.1 (M + H)+ |
| 19 | 19 | Tert-butyl 4-[6-(1,3-dioxolan-2-yl)pyridin-3-yl]-4-hydroxypiperidine-1-carboxylate | MS (ESI+) m/z: 351.6 (M + H)+ |

TABLE 4

| REx | PREx | Chemical Name | Data |
|---|---|---|---|
| 20 | 20 | Ethyl [4-(6-formylpyridin-3-yl)-4-hydroxypiperidin-1-yl]acetate | $^1$H-NMR (400 MHz, CDCl$_3$) δ: 10.08 (s, 1H), 8.96 (d, 1H), 8.02 (dd, 1H), 7.96 (d, 1H), 4.22 (q, 2H), 3.75 (s, 1H), 3.31 (s, 1H), 2.93-2.90 (m, 2H), 2.70 (dt, 2H), 2.29 (dt, 2H), 1.80-1.77 (m, 2H), 1.30 (t, 2H) |
| 21 | 21 | Tert-butyl 4-[6-(1,3-dioxolan-2-yl)pyridin-3-yl]-4-fluoropiperidine-1-carboxylate | MS (ESI+) m/z: 353.3 (M + H) + |
| 22 | 22 | Ethyl 3-[4-fluoro-4-(6-formylpyridin-3-yl)piperidin-1-yl]propanoate | MS (ESI+) m/z: 309.1 (M + H) + |
| 23 | 23 | Ethyl 3-[(3R)-4-(5-formylpyrazin-2-yl)-3-methylpiperazin-1-yl]propanoate | MS (ESI+) m/z: 307.1 (M + H) + |
| 24 | 24 | Ethyl [4-(4-formylphenyl)-4-hydroxypiperidin-1-yl]acetate | MS (ESI+) m/z: 292.1 (M + H) + |

TABLE 5

| REx | PREx | Chemical Name | Data |
|---|---|---|---|
| 25 | 25 | Ethyl [4-(4-formylphenoxy)piperidin-1-yl]acetate | MS (ESI+) m/z: 292.3 (M + H)+ |
| 26 | 26 | Ethyl 3-[4-(4-formylphenoxy)piperidin-1-yl]propanoate | MS (ESI+) m/z: 306.2 (M + H)+ |
| 27 | 27 | Ethyl [4-(3-chloro-4-formylphenoxy)piperidin-1-yl]acetate | MS (ESI+) m/z: 326.1 (M + H)+ |
| 28 | 28 | Ethyl 3-[(1R,3s,5S)-3-(4-formylphenoxy)-8-azabicyclo[3.2.1]octan-8-yl]propanoate | MS (ESI+) m/z: 332.2 (M + H)+ |
| 29 | 29 | Ethyl {[(1R,3r,5S)-8-(5-formylpyrazin-2-yl)-8-azabicyclo[3.2.1]octan-3-yl]oxy}acetate | MS (ESI+) m/z: 320.1 (M + H)+ |
| 30 | 30 | Ethyl {[(1R,3s,5S)-8-(5-formylpyrazin-2-yl)-8-azabicyclo[3.2.1]octan-3-yl]oxy}acetate | MS (ESI+) m/z: 320.6 (M + H)+ |
| 31 | 31 | Ethyl 3-[4-(5-formylpyrazin-2-yl)-2,2-dimethylpiperazin-1-yl]propanoate | MS (ESI+) m/z: 321.6 (M + H)+ |

TABLE 6

| REx | PREx | Chemical Name | Data |
|---|---|---|---|
| 32 | 32 | Ethyl 3-[4-(6-formylpyridin-3-yl)piperazin-1-yl]propanoate | MS (ESI+) m/z: 292.5 (M + H)+ |
| 33 | 33 | Ethyl 3-[(3R)-4-(5-formylpyridin-2-yl)-3-methylpiperazin-1-yl]propanoate | MS (ESI+) m/z: 306.3 (M + H)+ |
| 34 | 34 | Ethyl 1-(5-formylpyrazin-2-yl)piperidine-4-carboxylate | MS (ESI+) m/z: 264.2 (M + H)+ |
| 35 | 35 | Ethyl 2,2-difuloro-3-{[1-(5-formylpyrazin-2-yl)piperidin-4-yl]amino}propanoate | MS (ESI+) m/z: 343.6 (M + H)+ |
| 36 | 36 | Ethyl N-[(3S,4R)-3-fluoro-1-(5-formylpyrazin-2-yl)piperidin-4-yl]glycinate | MS (ESI+) m/z: 311.2 (M + H)+ |
| 37 | 37 | Ethyl N-[(3S,4R)-3-fluoro-1-(5-formylpyrazin-2-yl)piperidin-4-yl]-N-methylglycinate | MS (ESI+) m/z: 325.6 (M + H)+ |
| 38 | 38 | Ethyl 3-[4-(3-fluoro-5-formylpyridin-2-yl)piperazin-1-yl]propanoate | MS (ESI+) m/z: 310.1 (M + H)+ |

TABLE 7

| REx | PREx | Chemical Name | Data |
|---|---|---|---|
| 39 | 38 | Ethyl [4-(3-fluoro-5-formylpyridin-2-yl)piperazin-1-yl]acetate | MS (ESI+) m/z: 296.1 (M + H)+ |
| 40 | 40 | Ethyl 3-[4-(5-formylpyrazin-2-yl)piperazin-1-yl]propanoate | MS (ESI+) m/z: 293.5 (M + H)+ |
| 41 | 41 | Ethyl {[1-(5-formylpyrazin-2-yl)piperidin-4-yl]oxy}acetate | MS (ESI+) m/z: 294.1 (M + H)+ |
| 42 | 42 | [4-(5-Formylpyrazin-2-yl)piperazin-1-yl]acetonitrile | MS (ESI+) m/z: 232.5 (M + H)+ |
| 43 | 43 | Ethyl 1-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylate | MS (ESI+) m/z: 671.9 (M + H)+ |
| 44 | 44 | Ethyl 1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 697.9 (M + H)+ |

TABLE 8

| REx | PREx | Chemical Name | Data |
|---|---|---|---|
| 45 | 45 | Ethyl 1-(5-{5-[6-cyclopropyl-5-(trifluoromethyl)pyridin-3-yl]-7-[{[1-(ethoxymethyl)cyclo-pentyl]methyl}(methyl)amino]-1H-imidazo[4,5-b]pyridin-2-yl}pyrazin-2-yl)piperidine-4-carboxylate | MS (ESI+) m/z: 708.0 (M + H) + |
| 46 | 46 | Ethyl {1-(5-{5-[2-cyclopropyl-6-(trifluoromethyl)pyridin-4-yl]-7-[{[1-(methoxymethyl)cyclo-pentyl]methyl}(methyl)amino]-1H-imidazo[4,5-b]pyridin-2-yl}pyrazin-2-yl)piperidin-4-yl]oxy}acetate | MS (ESI+) m/z: 724.4 (M + H) + |
| 47 | 47 | Ethyl 3-[4-(5-{5-[2-fluoro-5-(trifluoromethyl)pyridin-3-yl]-7-[{[1-(methoxymethyl)cyclo-pentyl]methyl}(methyl)amino]-1H-imidazo[4,5-b]pyridin-2-yl}pyrazin-2-yl)piperazin-1-yl]propanoate | MS (ESI+) m/z: 700.4 (M + H) + |
| 48 | 48 | Ethyl 3-[4-(5-{5-[6-cyclopropyl-5-(trifluoromethyl)pyridin-3-yl]-7-[{[1-(methoxymethyl)cyclo-hexyl]methyl}(methyl)amino]-1H-imidazo[4,5-b]pyridin-2-yl}pyrazin-2-yl)piperazin-1-yl]propanoate | MS (ESI+) m/z: 736.6 (M + H) + |

TABLE 9

| REx | PREx | Chemical Name | Data |
|---|---|---|---|
| 49 | 49 | Ethyl 3-[(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate | MS (ESI+) m/z: 750.8 (M + H)+ |
| 50 | 50 | Ethyl 3-[(2S)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propanoate | MS (ESI+) m/z: 780.5 (M + H)+ |
| 51 | 51 | Ethyl 1-(5-{5-[2-ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylate | MS (ESI+) m/z: 683.7 (M + H)+ |
| 52 | 52 | Ethyl [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl]acetate | MS (ESI+) m/z: 740.2 (M + H)+ |

TABLE 10

| REx | PREx | Chemical Name | Data |
|---|---|---|---|
| 53 | 53 | Ethyl 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylate | MS (ESI+) m/z: 683.9 (M + H)+ |
| 54 | 54 | Ethyl 3-[4-fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidin-1-yl]propanoate | MS (ESI+) m/z: 701.3 (M + H)+ |
| 55 | 55 | Ethyl 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoate | MS (ESI+) m/z: 712.5 (M + H)+ |
| 56 | 56 | Ethyl 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propanoate | MS (ESI+) m/z: 751.0 (M + H)+ |

TABLE 11

| REx | PREx | Chemical Name | Data |
|---|---|---|---|
| 57 | 57 | Ethyl {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate | MS (ESI+) m/z: 754.0 (M + H)+ |
| 58 | 58 | Ethyl 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate | MS (ESI+) m/z: 751.0 (M + H)+ |
| 59 | 59 | Ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetate | MS (ESI+) m/z: 684.6 (M + H)+ |
| 60 | 60 | Ethyl 1-(4-{5-[3-fluoro-5-(trifluoromethyl)phenyl]-7-[(3-methoxy-2,2-dimethylpropyl)(methyl)amino]-1H-imidazo[4,5-b]pyridin-2-yl}phenyl)piperidine-4-carboxylate | MS (ESI+) m/z: 642.8 (M + H)+ |

TABLE 12

| REx | PREx | Chemical Name | Data |
|---|---|---|---|
| 61 | 61 | 1-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carbonitrile | MS (ESI+) m/z: 609.9 (M + H)+ |
| 62 | 5 | 1-[1-(methoxymethyl)cyclohexyl]-N-methylmethanamine hydrochloride | $^1$H-NMR (400 MHz, CDCl$_3$) δ: 9.16 (brs, 2H), 3.49 (s, 2H), 3.41 (s, 3H), 2.94 (s, 2H), 2.74 (s, 3H), 1.62-1.39 (m, 10H) |
| 63 | 8 | 6-Chloro-N$^4$-{[1-(methoxymethyl)cyclobutyl]methyl}-N$^4$-methyl-3-nitropyridin-2,4-diamine | MS (ESI+) m/z: 315.5 (M + H)+ |
| 64 | 8 | 6-Chloro-N$^4$-{[1-(methoxymethyl)cyclopentyl]methyl}-N$^4$-methyl-3-nitropyridin-2,4-diamine | MS (ESI+) m/z: 329.1 (M + H)+ |
| 65 | 8 | 6-Chloro-N$^4$-{[1-(methoxymethyl)cyclohexyl]methyl}-N$^4$-methyl-3-nitropyridin-2,4-diamine | MS (ESI+) m/z: 343.5 (M + H)+ |
| 66 | 8 | 6-Chloro-N$^4$-{[1-(ethoxymethyl)cyclopentyl]methyl}-N$^4$-methyl-3-nitropyridin-2,4-diamine | MS (ESI+) m/z: 343.2 (M + H)+ |

TABLE 13

| REx | PREx | Chemical Name | Data |
|---|---|---|---|
| 67 | 8 | 6-Chloro-N$^4$-ethyl-N$^4$-{[1-(methoxymethyl)cyclopentyl]methyl}-3-nitropyridin-2,4-diamine | MS (ESI+) m/z: 343.6 (M + H)+ |
| 68 | 8 | 6-Chloro-N$^4$-{[1-(ethoxymethyl)cyclopentyl]methyl}-N$^4$-ethyl-3-nitropyridin-2,4-diamine | MS (ESI+) m/z: 357.2 (M + H)+ |
| 69 | 8 | 6-Chloro-N$^4$-{[1-(methoxymethyl)cyclopentyl]methyl}-3-nitropyridin-2,4-diamine | MS (ESI+) m/z: 315.4 (M + H)+ |
| 70 | 9 | N$^4$-{[1-(methoxymethyl)cyclobutyl]methyl}-N$^4$-methyl-3-nitro-6-[3-(trifluoromethyl)phenyl]pyridin-2,4-diamine | MS (ESI+) m/z: 425.6 (M + H)+ |
| 71 | 9 | 6-[3-Fluoro-5-(trifluoromethyl)phenyl]-N$^4$-{[1-(methoxymethyl)cyclobutyl]methyl}-N$^4$-methyl-3-nitropyridin-2,4-diamine | MS (ESI+) m/z: 443.6 (M + H)+ |
| 72 | 9 | 6-[4-Fluoro-3-(trifluoromethyl)phenyl]-N$^4$-(3-methoxy-2,2-dimethylpropyl)-N$^4$-methyl-3-nitropyridin-2,4-diamine | MS (ESI+) m/z: 431.7 (M + H)+ |
| 73 | 9 | 6-[4-Fluoro-3-(trifluoromethyl)phenyl]-N$^4$-{[1-(methoxymethyl)cyclobutyl]methyl}-N$^4$-methyl-3-nitropyridin-2,4-diamine | MS (ESI+) m/z: 443.1 (M + H)+ |

TABLE 14

| REx | PREx | Chemical Name | Data |
|---|---|---|---|
| 74 | 9 | 6-[4-Fluoro-3-(trifluoromethyl)phenyl]-N$^4$-{[1-(methoxymethyl)cyclopentyl]methyl}-N$^4$-methyl-3-nitropyridin-2,4-diamine | MS (ESI+) m/z: 457.7 (M + H)+ |
| 75 | 9 | 6-[3,5-Bis(trifluoromethyl)phenyl]-N$^4$-{[1-(methoxymethyl)cyclopentyl]methyl}-N$^4$-methyl-3-nitropyridin-2,4-diamine | MS (ESI+) m/z: 507.7 (M + H)+ |
| 76 | 9 | 6-[3-Ethoxy-5-(trifluoromethyl)phenyl]-N$^4$-{[1-(methoxymethyl)cyclopentyl]methyl}-N$^4$-methyl-3-nitropyridin-2,4-diamine | MS (ESI+) m/z: 483.8 (M + H)+ |
| 77 | 9 | 6-[4-Cyclopropyl-3-(trifluoromethyl)phenyl]-N$^4$-{[1-(methoxymethyl)cyclopentyl]methyl}-N$^4$-methyl-3-nitropyridin-2,4-diamine | MS (ESI+) m/z: 479.3 (M + H)+ |
| 78 | 9 | N$^4$-{[1-(methoxymethyl)cyclobutyl]methyl}-N$^4$-methyl-5-nitro-5'-(trifluoromethyl)[2,3'-bipyridin]-4,6-diamine | MS (ESI+) m/z: 426.4 (M + H)+ |
| 79 | 9 | 2'-Fluoro-N$^4$-{[1-(methoxymethyl)cyclobutyl]methyl}-N$^4$-methyl-5-nitro-5'-(trifluoromethyl)[2,3'-bipyridin]-4,6-diamine | MS (ESI+) m/z: 444.6 (M + H)+ |

TABLE 15

| REx | PREx | Chemical Name | Data |
|---|---|---|---|
| 80 | 9 | 2'-Fluoro-N$^4$-{[1-(methoxymethyl)cyclopentyl]methyl}-N$^4$-methyl-5-nitro-5'-(trifluoromethyl)[2,3'-bipyridin]-4,6-diamine | MS (ESI+) m/z: 458.2 (M + H)+ |
| 81 | 9 | 6-Amino-4-[{[1-(methoxymethyl)cyclopentyl]methyl}(methyl)amino]-5-nitro-5'-(trifluoromethyl)[2,3'-bipyridin]-6'-carbonitrile | MS (ESI+) m/z: 465.3 (M + H)+ |
| 82 | 9 | 6'-Ethoxy-N$^4$-(3-methoxy-2,2-dimethylpropyl)-N$^4$-methyl-5-nitro-5'-(trifluoromethyl)[2,3'-bipyridin]-4,6-diamine | MS (ESI+) m/z: 458.6 (M + H)+ |
| 83 | 9 | 6'-Ethoxy-N$^4$-{[1-(methoxymethyl)cyclobutyl]methyl}-N$^4$-methyl-5-nitro-5'-(trifluoromethyl)[2,3'-bipyridin]-4,6-diamine | MS (ESI+) m/z: 470.2 (M + H)+ |
| 84 | 9 | 6'-Ethoxy-N$^4$-{[1-(methoxymethyl)cyclopentyl]methyl}-N$^4$-methyl-5-nitro-5'-(trifluoromethyl)[2,3'-bipyridin]-4,6-diamine | MS (ESI+) m/z: 484.1 (M + H)+ |
| 85 | 9 | 6'-Ethoxy-N$^4$-{[1-(methoxymethyl)cyclohexyl]methyl}-N$^4$-methyl-5-nitro-5'-(trifluoromethyl)[2,3'-bipyridin]-4,6-diamine | MS (ESI+) m/z: 498.7 (M + H)+ |
| 86 | 9 | 2'-Ethoxy-N$^4$-(3-methoxy-2,2-dimethylpropyl)-N$^4$-methyl-5-nitro-6'-(trifluoromethyl)[2,4'-bipyridin]-4,6-diamine | MS (ESI+) m/z: 458.7 (M + H)+ |

TABLE 16

| REx | PREx | Chemical Name | Data |
|---|---|---|---|
| 87 | 9 | 2'-Ethoxy-$N^4$-{[1-(methoxymethyl)cyclobutyl]methyl}-$N^4$-methyl-5-nitro-6'-(trifluoromethyl)[2,4'-bipyridin]-4,6-diamine | MS (ESI+) m/z: 470.2 (M + H)+ |
| 88 | 9 | 2'-Ethoxy-$N^4$-{[1-(methoxymethyl)cyclopentyl]methyl}-$N^4$-methyl-5-nitro-6'-(trifluoromethyl)[2,4'-bipyridin]-4,6-diamine | MS (ESI+) m/z: 484.7 (M + H)+ |
| 89 | 9 | 2'-Ethoxy-$N^4$-{[1-(methoxymethyl)cyclohexyl]methyl}-$N^4$-methyl-5-nitro-6'-(trifluoromethyl)[2,4'-bipyridin]-4,6-diamine | MS (ESI+) m/z: 498.7 (M + H)+ |
| 90 | 9 | 6'-Cyclopropyl-$N^4$-(3-methoxy-2,2-dimethylpropyl)-$N^4$-methyl-5-nitro-5'-(trifluoromethyl)[2,3'-bipyridin]-4,6-diamine | MS (ESI+) m/z: 454.7 (M + H)+ |
| 91 | 9 | 6'-Cyclopropyl-$N^4$-{[1-(methoxymethyl)cyclobutyl]methyl}-$N^4$-methyl-5-nitro-5'-(trifluoromethyl)[2,3'-bipyridin]-4,6-diamine | MS (ESI+) m/z: 466.7 (M + H)+ |
| 92 | 9 | 6'-Cyclopropyl-$N^4$-{[1-(methoxymethyl)cyclopentyl]methyl}-$N^4$-methyl-5-nitro-5'-(trifluoromethyl)[2,3'-bipyridin]-4,6-diamine | MS (ESI+) m/z: 480.6 (M + H)+ |

TABLE 17

| REx | PREx | Chemical Name | Data |
|---|---|---|---|
| 93 | 9 | 6'-Cyclopropyl-$N^4$-{[1-(ethoxymethyl)cyclopentyl]methyl}-$N^4$-methyl-5-nitro-5'-(trifluoromethyl)[2,3'-bipyridin]-4,6-diamine | MS (ESI+) m/z: 494.3 (M + H)+ |
| 94 | 9 | 6'-Cyclopropyl-$N^4$-ethyl-$N^4$-{[1-(methoxymethyl)cyclopentyl]methyl}-5-nitro-5'-(trifluoromethyl)[2,3'-bipyridin]-4,6-diamine | MS (ESI+) m/z: 494.4 (M + H)+ |
| 95 | 9 | 5'-Cyclopropyl-$N^4$-{[1-(methoxymethyl)cyclobutyl]methyl}-$N^4$-methyl-5-nitro-6'-(trifluoromethyl)[2,3'-bipyridin]-4,6-diamine | $^1$H-NMR (400 MHz, CDCl$_3$) δ: 8.89 (s, 1H), 7.95 (d, 1H), 6.90 (s, 1H), 6.17 (brs, 2H), 3.58 (s, 2H), 3.40 (s, 2H), 3.21 (s, 3H), 2.93 (s, 3H), 2.31-2.24 (m, 1H), 2.03-1.82 (m, 6H), 1.17-1.12 (m, 2H), 0.90-0.86 (m, 2H) |
| 96 | 9 | 5'-Cyclopropyl-$N^4$-{[1-(methoxymethyl)cyclopentyl]methyl}-$N^4$-methyl-5-nitro-6'-(trifluoromethyl)[2,3'-bipyridin]-4,6-diamine | MS (ESI+) m/z: 480.2 (M + H)+ |

TABLE 18

| REx | PREx | Chemical Name | Data |
|---|---|---|---|
| 97 | 9 | 5'-Cyclopropyl-$N^4$-{[1-(methoxymethyl)cyclohexyl]methyl}-N4-methyl-5-nitro-6'-(trifluoromethyl)[2,3'-bipyridin]-4,6-diamine | MS (ESI+) m/z: 494.2 (M + H)+ |
| 98 | 9 | $N^4$-{[1-(methoxymethyl)cyclopentyl]methyl}-$N^4$-methyl-5-nitro-5',6'-bis(trifluoromethyl)[2,3'-bipyridin]-4,6-diamine | MS (ESI+) m/z: 508.2 (M + H)+ |
| 99 | 9 | 2'-Cyclopropyl-$N^4$-(3-methoxy-2,2-dimethylpropyl)-$N^4$-methyl-5-nitro-6'-(trifluoromethyl)[2,4'-bipyridin]-4,6-diamine | MS (ESI+) m/z: 454.7 (M + H)+ |
| 100 | 9 | 2'-Cyclopropyl-$N^4$-{[1-(methoxymethyl)cyclobutyl]methyl}-$N^4$-methyl-5-nitro-6'-(trifluoromethyl)[2,4'-bipyridin]-4,6-diamine | MS (ESI+) m/z: 466.7 (M + H)+ |
| 101 | 9 | 2'-Cyclopropyl-$N^4$-{[1-(methoxymethyl)cyclopentyl]methyl}-$N^4$-methyl-5-nitro-6'-(trifluoromethyl)[2,4'-bipyridin]-4,6-diamine | MS (ESI+) m/z: 480.6 (M + H)+ |
| 102 | 9 | $N^4$-{[1-(methoxymethyl)cyclobutyl]methyl}-6-[4-methoxy-3-(trifluoromethyl)phenyl]-$N^4$-methyl-3-nitropyridin-2,4-diamine | MS (ESI+) m/z: 455.6 (M + H)+ |
| 103 | 9 | $N^4$-{[1-(methoxymethyl)cyclobutyl]methyl}-$N^4$-methyl-5-nitro-6'-propyl-5'-(trifluoromethyl)[2,3'-bipyridin]-4,6-diamine | MS (ESI+) m/z: 468.7 (M + H)+ |

TABLE 19

| REx | PREx | Chemical Name | Data |
|---|---|---|---|
| 104 | 9 | 2'-Ethoxy-$N^4$-{[1-(methoxymethyl)cyclopentyl]methyl}-5-nitro-6'-(trifluoromethyl)[2,4'-bipyridin]-4,6-diamine | MS (ESI+) m/z: 470.6 (M + H)+ |
| 105 | 12 | $N^4$-{[1-(methoxymethyl)cyclobutyl]methyl}-$N^4$-methyl-6-[3-(trifluoromethyl)phenyl]pyridin-2,3,4-triamine | MS (ESI+) m/z: 395.7 (M + H)+ |
| 106 | 11 | 6-[3-Fluoro-5-(trifluoromethyl)phenyl]-$N^4$-(3-methoxy-2,2-dimethylpropyl)-$N^4$-methylpyridin-2,3,4-triamine | MS (ESI+) m/z: 401.7 (M + H)+ |
| 107 | 13 | 6-[3-Fluoro-5-(trifluoromethyl)phenyl]-$N^4$-{[1-(methoxymethyl)cyclobutyl]methyl}-$N^4$-methylpyridin-2,3,4-triamine | MS (ESI+) m/z: 413.6 (M + H)+ |
| 108 | 11 | 6-[3-Fluoro-5-(trifluoromethyl)phenyl]-$N^4$-{[1-(methoxymethyl)cyclopentyl]methyl}-$N^4$-methylpyridin-2,3,4-triamine | MS (ESI+) m/z: 427.3 (M + H)+ |
| 109 | 11 | 6-[3-Fluoro-5-(trifluoromethyl)phenyl]-$N^4$-{[1-(methoxymethyl)cyclohexyl]methyl}-$N^4$-methylpyridin-2,3,4-triamine | MS (ESI+) m/z: 441.4 (M + H)+ |
| 110 | 11 | $N^4$-{[1-(Ethoxymethyl)cyclopentyl]methyl}-6-[3-fluoro-5-(trifluoromethyl)phenyl]-$N^4$-methylpyridin-2,3,4-triamine | MS (ESI+) m/z: 441.7 (M + H)+ |

TABLE 20

| REx | PREx | Chemical Name | Data |
|---|---|---|---|
| 111 | 11 | $N^4$-{[1-(Butoxymethyl)cyclopentyl]methyl}-6-[3-fluoro-5-(trifluoromethyl)phenyl]-$N^4$-methylpyridin-2,3,4-triamine | MS (ESI+) m/z: 469.5 (M + H)+ |

TABLE 20-continued

| REx | PREx | Chemical Name | Data |
|---|---|---|---|
| 112 | 12 | 6-[4-Fluoro-3-(trifluoromethyl)phenyl]-$N^4$-(3-methoxy-2,2-dimethylpropyl)-$N^4$-methylpyridin-2,3,4-triamine | MS (ESI+) m/z: 401.2 (M + H)+ |
| 113 | 12 | 6-[4-Fluoro-3-(trifluoromethyl)phenyl]-$N^4$-{[1-(methoxymethyl)cyclobutyl]methyl}-$N^4$-methylpyridin-2,3,4-triamine | MS (ESI+) m/z: 413.7 (M + H)+ |
| 114 | 12 | 6-[4-Fluoro-3-(trifluoromethyl)phenyl]-$N^4$-{[1-(methoxymethyl)cyclopentyl]methyl}-$N^4$-methylpyridin-2,3,4-triamine | MS (ESI+) m/z: 427.7 (M + H)+ |
| 115 | 12 | 6-[3,5-Bis(trifluoromethyl)phenyl]-$N^4$-{[1-(methoxymethyl)cyclopentyl]methyl}-$N^4$-methylpyridin-2,3,4-triamine | MS (ESI+) m/z: 477.7 (M + H)+ |
| 116 | 12 | 6-[3-Ethoxy-5-(trifluoromethyl)phenyl]-$N^4$-{[1-(methoxymethyl)cyclopentyl]methyl}-$N^4$-methylpyridin-2,3,4-triamine | MS (ESI+) m/z: 453.3 (M + H)+ |
| 117 | 12 | 6-[4-Cyclopropyl-3-(trifluoromethyl)phenyl]-$N^4$-{[1-(methoxymethyl)cyclopentyl]methyl}-$N^4$-methylpyridin-2,3,4-triamine | MS (ESI+) m/z: 449.7 (M + H)+ |

TABLE 21

| REx | PREx | Chemical Name | Data |
|---|---|---|---|
| 118 | 12 | $N^4$-{[1-(methoxymethyl)cyclobutyl]methyl}-$N^4$-methyl-5'-(trifluoromethyl)[2,3'-bipyridin]-4,5,6-triamine | MS (ESI+) m/z: 396.6 (M + H)+ |
| 119 | 12 | 2'-Fluoro-$N^4$-{[1-(methoxymethyl)cyclobutyl]methyl}-$N^4$-methyl-5'-(trifluoromethyl)[2,3'-bipyridin]-4,5,6-triamine | MS (ESI+) m/z: 414.2 (M + H)+ |
| 120 | 12 | 2'-Fluoro-$N^4$-{[1-(methoxymethyl)cyclopentyl]methyl}-$N^4$-methyl-5'-(trifluoromethyl)[2,3'-bipyridin]-4,5,6-triamine | MS (ESI+) m/z: 428.2 (M + H)+ |
| 121 | 12 | 5,6-Diamino-4-[{[1-(methoxymethyl)cyclopentyl]methyl}(methyl)amino]-5'-(trifluoromethyl)[2,3'-bipyridin]-6'-carbonitrile | MS (ESI+) m/z: 435.3 (M + H)+ |
| 122 | 13 | 6'-Ethoxy-$N^4$-(3-methoxy-2,2-dimethylpropyl)-$N^4$-methyl-5'-(trifluoromethyl)[2,3'-bipyridin]-4,5,6-triamine | MS (ESI+) m/z: 428.7 (M + H)+ |
| 123 | 13 | 6'-Ethoxy-$N^4$-{[1-(methoxymethyl)cyclobutyl]methyl}-$N^4$-methyl-5'-(trifluoromethyl)[2,3'-bipyridin]-4,5,6-triamine | MS (ESI+) m/z: 440.6 (M + H)+ |
| 124 | 13 | 6'-Ethoxy-$N^4$-{[1-(methoxymethyl)cyclopentyl]methyl}-$N^4$-methyl-5'-(trifluoromethyl)[2,3'-bipyridin]-4,5,6-triamine | MS (ESI+) m/z: 454.7 (M + H)+ |

TABLE 22

| REx | PREx | Chemical Name | Data |
|---|---|---|---|
| 125 | 12 | 6'-Ethoxy-$N^4$-{[1-(methoxymethyl)cyclohexyl]methyl}-$N^4$-methyl-5'-(trifluoromethyl)[2,3'-bipyridin]-4,5,6-triamine | $^1$H-NMR (400 MHz, CDCl$_3$) δ: 8.74 (d, 1H), 8.38 (d, 1H), 7.05 (s, 1H), 4.51 (q, 2H), 4.23 (brs, 2H), 3.72 (brs, 2H), 3.14 (s, 2H), 3.12 (s, 3H), 3.08 (s, 2H), 2.72 (s, 3H), 1.46-1.24 (m, 13H) |
| 126 | 13 | 2'-Ethoxy-$N^4$-(3-methoxy-2,2-dimethylpropyl)-$N^4$-methyl-6'-(trifluoromethyl)[2,4'-bipyridin]-4,5,6-triamine | MS (ESI+) m/z: 428.4 (M + H)+ |
| 127 | 13 | 2'-Ethoxy-$N^4$-{[1-(methoxymethyl)cyclopentyl]methyl}-$N^4$-methyl-6'-(trifluoromethyl)[2,4'-bipyridin]-4,5,6-triamine | MS (ESI+) m/z: 454.4 (M + H)+ |
| 128 | 12 | 2'-Ethoxy-$N^4$-{[1-(methoxymethyl)cyclohexyl]methyl}-$N^4$-methyl-6'-(trifluoromethyl)[2,4'-bipyridin]-4,5,6-triamine | MS (ESI+) m/z: 468.7 (M + H)+ |

TABLE 23

| REx | PREx | Chemical Name | Data |
|---|---|---|---|
| 129 | 12 | 6'-Cyclopropyl-$N^4$-(3-methoxy-2,2-dimethylpropyl)-$N^4$-methyl-5'-(trifluoromethyl)[2,3'-bipyridin]-4,5,6-triamine | MS (ESI+) m/z: 424.3 (M + H)+ |
| 130 | 12 | 6'-Cyclopropyl-$N^4$-{[1-(methoxymethyl)cyclobutyl]methyl}-$N^4$-methyl-5'-(trifluoromethyl)[2,3'-bipyridin]-4,5,6-triamine | MS (ESI+) m/z: 436.3 (M + H)+ |
| 131 | 13 | 6'-Cyclopropyl-$N^4$-{[1-(methoxymethyl)cyclopentyl]methyl}-$N^4$-methyl-5'-(trifluoromethyl)[2,3'-bipyridin]-4,5,6-triamine | MS (ESI+) m/z: 450.6 (M + H)+ |
| 132 | 13 | 6'-Cyclopropyl-$N^4$-{[1-(methoxymethyl)cyclohexyl]methyl}-$N^4$-methyl-5'-(trifluoromethyl)[2,3'-bipyridin]-4,5,6-triamine | MS (ESI+) m/z: 464.5 (M + H)+ |
| 133 | 12 | 6'-Cyclopropyl-$N^4$-ethyl-$N^4$-{[1-(methoxymethyl)cyclopentyl]methyl}-5'-(trifluoromethyl)[2,3'-bipyridin]-4,5,6-triamine | MS (ESI+) m/z: 464.7 (M + H)+ |
| 134 | 10 | 6'-Cyclopropyl-$N^4$-{[1-(ethoxymethyl)cyclopentyl]methyl}-$N^4$-ethyl-5'-(trifluoromethyl)[2,3'-bipyridin]-4,5,6-triamine | MS (ESI+) m/z: 478.6 (M + H)+ |
| 135 | 12 | 5'-Cyclopropyl-$N^4$-{[1-(methoxymethyl)cyclobutyl]methyl}-$N^4$-methyl-6'-(trifluoromethyl)[2,3'-bipyridin]-4,5,6-triamine | MS (ESI+) m/z: 436.6 (M + H)+ |

TABLE 24

| REx | PREx | Chemical Name | Data |
|---|---|---|---|
| 136 | 12 | 5'-Cyclopropyl-$N^4$-{[1-(methoxymethyl)cyclopentyl]methyl}-$N^4$-methyl-6'-(trifluoromethyl)[2,3'-bipyridin]-4,5,6-triamine | MS (ESI+) m/z: 450.3 (M+H)+ |
| 137 | 12 | 5'-Cyclopropyl-$N^4$-{[1-(methoxymethyl)cyclohexyl]methyl}-$N^4$-methyl-6'-(trifluoromethyl)[2,3'-bipyridin]-4,5,6-triamine | MS (ESI+) m/z: 464.3 (M+H)+ |
| 138 | 12 | $N^4$-{[1-(methoxymethyl)cyclopentyl]methyl}-$N^4$-methyl-5',6'-bis(trifluoromethyl)[2,3'-bipyridin]-4,5,6-triamine | MS (ESI+) m/z: 478.2 (M+H)+ |

TABLE 24-continued

| REx | PREx | Chemical Name | Data |
|---|---|---|---|
| 139 | 12 | 2'-Cyclopropyl-N$^4$-(3-methoxy-2,2-dimethylpropyl)-N$^4$-methyl-6'-(trifluoromethyl)[2,4'-bipyridin]-4,5,6-triamine | MS (ESI+) m/z: 424.7 (M+H)+ |
| 140 | 12 | 2'-Cyclopropyl-N$^4$-{[1-(methoxymethyl)cyclobutyl]methyl}-N$^4$-methyl-6'-(trifluoromethyl)[2,4'-bipyridin]-4,5,6-triamine | MS (ESI+) m/z: 436.7 (M+H)+ |
| 141 | 13 | 2'-Cyclopropyl-N$^4$-{[1-(methoxymethyl)cyclopentyl]methyl}-N$^4$-methyl-6'-(trifluoromethyl)[2,4'-bipyridin]-4,5,6-triamine | MS (ESI+) m/z: 450.6 (M+H)+ |
| 142 | 10 | 2'-Cyclopropyl-N$^4$-{[1-(methoxymethyl)cyclohexyl]methyl}-N$^4$-methyl-6'-(trifluoromethyl)[2,4'-bipyridin]-4,5,6-triamine | MS (ESI+) m/z: 464.8 (M+H)+ |

TABLE 25

| REx | PREx | Chemical Name | Data |
|---|---|---|---|
| 143 | 13 | N$^4$-{[1-(methoxymethyl)cyclobutyl]methyl}-6-[4-methoxy-3-(trifluoromethyl)phenyl]-N$^4$-methylpyridin-2,3,4-triamine | MS (ESI+) m/z: 425.6 (M + H)+ |
| 144 | 13 | N$^4$-{[1-(methoxymethyl)cyclobutyl]methyl}-N$^4$-methyl-6'-propyl-5'-(trifluoromethyl)[2,3'-bipyridin]-4,5,6-triamine | MS (ESI+) m/z: 438.7 (M + H)+ |
| 145 | 13 | 2'-Ethoxy-N$^4$-{[1-(methoxymethyl)cyclopentyl]methyl}-6'-(trifluoromethyl)[2,4'-bipyridin]-4,5,6-triamine | MS (ESI+) m/z: 440.6 (M + H)+ |
| 146 | 14 | Ethyl 3-[4-(4-formylphenyl)piperazin-1-yl]propanoate | MS (ESI+) m/z: 291.1 (M + H)+ |
| 147 | 40 | Ethyl 8-(4-formylphenyl)-1-oxa-2,8-diazaspiro[4.5]deca-2-ene-3-carboxylate | MS (ESI+) m/z: 317.1 (M + H)+ |
| 148 | 34 | 4-(3-Oxo-2,8-diazaspiro[4.5]decan-8-yl)benzaldehyde | MS (ESI+) m/z: 259.1 (M + H)+ |
| 149 | 40 | Methyl N-[1-(4-formylphenyl)piperidin-4-yl]-N-methylglycinate | MS (ESI+) m/z: 293.2 (M + H)+ |

TABLE 26

| REx | PREx | Chemical Name | Data |
|---|---|---|---|
| 150 | 40 | Ethyl N-[1-(4-formylphenyl)piperidin-4-yl]glycinate | MS (ESI+) m/z: 291.6 (M + H)+ |
| 151 | 40 | Methyl {[1-(4-formylphenyl)piperidin-4-yl]oxy}acetate | MS (ESI+) m/z: 278.2 (M + H)+ |
| 152 | 40 | Ethyl 1-(3-fluoro-4-formylphenyl)piperidine-4-carboxylate | MS (ESI+) m/z: 280.6 (M + H)+ |
| 153 | 40 | Ethyl 1-(4-formyl-3-methylphenyl)piperidine-4-carboxylate | MS (ESI+) m/z: 276.5 (M + H)+ |
| 154 | 27 | Ethyl [4-(3-fluoro-4-formylphenoxy)piperidin-1-yl]acetate | MS (ESI+) m/z: 310.2 (M + H)+ |
| 155 | 41 | Methyl {[1-(5-formylpyrazin-2-yl)piperidin-4-yl]oxy}acetate | MS (ESI+) m/z: 280.1 (M + H)+ |
| 156 | 41 | Ethyl 3-[(2S)-4-(5-formylpyrazin-2-yl)-2-(methoxymethyl)piperazin-1-yl]propanoate | MS (ESI+) m/z: 337.2 (M + H)+ |
| 157 | 40 | Ethyl [4-(5-formylpyrazin-2-yl)piperazin-1-yl]acetate | MS (ESI+) m/z: 279.3 (M + H)+ |
| 158 | 40 | Ethyl 4-fluoro-1-(5-formylpyrazin-2-yl)piperidine-4-carboxylate | MS (ESI+) m/z: 282.1 (M + H)+ |
| 159 | 40 | Methyl 3-[4-(5-formylpyrazin-2-yl)-2-oxopiperazin-1-yl]propanoate | MS (ESI+) m/z: 293.2 (M + H)+ |
| 160 | 40 | Ethyl [4-(5-formylpyrazin-2-yl)-1,4-diazepan-1-yl]acetate | MS (ESI+) m/z: 293.1 (M + H)+ |

TABLE 27

| REx | PREx | Chemical Name | Data |
|---|---|---|---|
| 161 | 41 | Ethyl 3-[(2S)-4-(5-formylpyrazin-2-yl)-2-methylpiperazin-1-yl]propanoate | MS (ESI+) m/z: 307.6 (M + H)+ |
| 162 | 42 | 1-(5-Formylpyrazin-2-yl)piperidine-4-carbonitrile | MS (ESI+) m/z: 217.4 (M + H)+ |
| 163 | 40 | Methyl 4-[4-(5-formylpyrazin-2-yl)piperazin-1-yl]butanoate | MS (ESI+) m/z: 293.2 (M + H)+ |
| 164 | 40 | Ethyl N-[1-(5-formylpyrazin-2-yl)piperidin-4-yl]glycinate | MS (ESI+) m/z: 293.1 (M + H)+ |
| 165 | 23 | Ethyl 3-[(3S)-4-(5-formylpyrazin-2-yl)-3-methylpiperazin-1-yl]propanoate | MS (ESI+) m/z: 307.6 (M + H)+ |
| 166 | 41 | N-{2-[4-(5-Formylpyrazin-2-yl)piperazin-1-yl]ethyl}methanesulfonamide | MS (ESI+) m/z: 314.6 (M + H)+ |
| 167 | 41 | Ethyl 3-[4-(5-formylpyrazin-2-yl)piperazin-1-yl]butanoate | MS (ESI+) m/z: 307.2 (M + H)+ |
| 168 | 42 | 3-[4-(5-Formylpyrazin-2-yl)piperazin-1-yl]propanenitrile | MS (ESI+) m/z: 246.5 (M + H)+ |
| 169 | 23 | Ethyl [(3R)-4-(5-formylpyrazin-2-yl)-3-methylpiperazin-1-yl]acetate | MS (ESI+) m/z: 293.1 (M + H)+ |
| 170 | 31 | Ethyl 3-[(2R,6S)-4-(5-formylpyrazin-2-yl)-2,6-dimethylpiperazin-1-yl]propanoate | MS (ESI+) m/z: 321.7 (M + H)+ |

TABLE 28

| REx | PREx | Chemical Name | Data |
|---|---|---|---|
| 171 | 41 | Ethyl 3-[(2R)-4-(5-formylpyrazin-2-yl)-2-methylpiperazin-1-yl]propanoate | MS (ESI+) m/z: 307.8 (M + H)+ |
| 172 | 41 | Methyl [4-(5-formylpyrazin-2-yl)piperazine-1-sufonyl]acetate | MS (ESI+) m/z: 329.1 (M + H)+ |
| 173 | 41 | Ethyl {[1-(5-formylpyrazin-2-yl)-3,3-dimethylpiperidin-4-yl]oxy}acetate | MS (ESI+) m/z: 322.1 (M + H)+ |
| 174 | 41 | Ethyl {[1-(5-formylpyrazin-2-yl)-4-methylpiperidin-4-yl]oxy}acetate | MS (ESI+) m/z: 308.6 (M + H)+ |

TABLE 28-continued

| REx | PREx | Chemical Name | Data |
|---|---|---|---|
| 175 | 41 | Ethyl {[1-(5-formylpyrazin-2-yl)piperidin-4-yl]sulfanyl+56 acetate | MS (ESI+) m/z: 310.2 (M + H)+ |
| 176 | 34 | 1-(5-Formylpyrazin-2-yl)-N-(methansulfonyl)piperidine-4-carboxamide | MS (ESI+) m/z: 313.1 (M + H)+ |
| 177 | 32 | Ethyl [4-(6-formylpyridin-3-yl)-1,4-diazepan-1-yl]acetate | MS (ESI+) m/z: 292.6 (M + H)+ |
| 178 | 38 | Ethyl 3-[(3R)-4-(3-fluoro-5-formylpyridin-2-yl)-3-methylpiperazin-1-yl]propanoate | MS (ESI+) m/z: 324.6 (M + H)+ |
| 179 | 41 | Methyl 1-(5-formylpyrazin-2-yl)-4-hydroxypiperidine-4-carboxylate | MS (ESI+) m/z: 266.4 (M + H)+ |

TABLE 29

| REx | PREx | Chemical Name | Data |
|---|---|---|---|
| 180 | 49 | Methyl 4-hydroxy-1-(5-{7-[{[1-(methoxymethyl)cyclobutyl]methyl}(methyl)amino]-5-[3-(trifluoromethyl)phenyl]-1H-imidazo[4,5-b]pyridin-2-yl}pyrazin-2-yl)piperidine-4-carboxylate | MS (ESI+) m/z: 640.9 (M + H)+ |
| 181 | 181 | Ethyl 8-(4-{7-[{[1-(methoxymethyl)cyclobutyl]methyl}(methyl)amino]-5-[3-(trifluoromethyl)phenyl]-1H-imidazo[4,5-b]pyridin-2-yl}phenyl)-1-oxa-2,8-diazaspiro[4.5]dec-2-ene-3-carboxylate | MS (ESI+) m/z: 691.4 (M + H)+ |
| 182 | 45 | Ethyl 1-(5-{7-[{[1-(methoxymethyl)cyclobutyl]methyl}(methyl)amino]-5-[4-methoxy-3-(trifluoromethyl)phenyl]-1H-imidazo[4,5-b]pyridin-2-yl}pyrazin-2-yl)piperidine-4-carboxylate | MS (ESI+) m/z: 668.7 (M + H)+ |
| 183 | 46 | Ethyl 8-(4-{7-[{[1-(methoxymethyl)cyclobutyl]methyl}(methyl)amino]-5-[5-(trifluoromethyl)pyridin-3-yl]-1H-imidazo[4,5-b]pyridin-2-yl}phenyl)-1-oxa-2,8-diazaspiro[4.5]dec-2-ene-3-carboxylate | MS (ESI+) m/z: 692.4 (M + H)+ |

TABLE 30

| REx | PREx | Chemical Name | Data |
|---|---|---|---|
| 184 | 181 | Methyl 1-(4-{7-[{[1-(methoxymethyl)cyclobutyl]methyl}(methyl)amino]-5-[3-(trifluoromethyl)phenyl]-1H-imidazo[4,5-b]pyridin-2-yl}phenyl)pyrrolidine-3-carboxylate | MS (ESI+) m/z: 608.3 (M + H)+ |
| 185 | 45 | Ethyl {4-[(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)methyl]piperazin-1-yl}acetate | MS (ESI+) m/z: 683.8 (M + H)+ |
| 186 | 181 | Ethyl 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]propanoate | MS (ESI+) m/z: 685.3 (M + H)+ |
| 187 | 181 | Ethyl [4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]acetate | MS (ESI+) m/z: 671.3 (M + H)+ |

TABLE 31

| REx | PREx | Chemical Name | Data |
|---|---|---|---|
| 188 | 181 | Ethyl 4-fluoro-1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carboxylate | MS (ESI+) m/z: 674.8 (M + H)+ |
| 189 | 45 | Ethyl [4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperazin-1-yl]acetate | MS (ESI+) m/z: 670.3 (M + H)+ |
| 190 | 181 | Methyl N-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]-N-methylglycinate | MS (ESI+) m/z: 683.9 (M + H)+ |
| 191 | 181 | Ethyl [4-(4-{7-[{[1-(methoxymethyl)cyclobutyl]methyl}(methyl)amino]-5-[5-(trifluoromethyl)pyridin-3-yl]-1H-imidazo[4,5-b]pyridin-2-yl}phenyl)piperazin-1-yl]acetate | MS (ESI+) m/z: 652.8 (M + H)+ |

TABLE 32

| REx | PREx | Chemical Name | Data |
|---|---|---|---|
| 192 | 46 | Ethyl 1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylate | MS (ESI+) m/z: 883.9 (M + H)+ |
| 193 | 45 | Ethyl [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-4-hydroxypiperidin-1-yl]acetate | MS (ESI+) m/z: 684.3 (M + H)+ |
| 194 | 181 | Methyl 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-oxopiperazin-1-yl]propanoate | MS (ESI+) m/z: 685.8 (M + H)+ |
| 195 | 181 | Ethyl 3-[4-(5-{5-[2-fluoro-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoate | MS (ESI+) m/z: 686.3 (M + H)+ |

TABLE 33

| REx | PREx | Chemical Name | Data |
|---|---|---|---|
| 196 | 181 | Ethyl [4-(5-{5-[3-fluoro-5-(trifluoromethyl)phenyl]-7- | MS (ESI+) m/z: 685.9 (M + H) + |

TABLE 33-continued

| REx | PREx | Chemical Name | Data |
|---|---|---|---|
| 197 | 181 | Ethyl 3-[(2S)-4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate | MS (ESI+) m/z: 700.0 (M + H) + |
| 198 | 181 | Methyl 4-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoate | MS (ESI+) m/z: 685.6 (M + H) + |
| 199 | 181 | Ethyl N-[1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidin-4-yl]glycinate | MS (ESI+) m/z: 685.9 (M + H) + |
| 200 | 181 | Methyl {[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]oxy}acetate | MS (ESI+) m/z: 670.9 (M + H) + |

TABLE 34

| REx | PREx | Chemical Name | Data |
|---|---|---|---|
| 201 | 181 | Methyl {[1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidin-4-yl]oxy}acetate | MS (ESI+) m/z: 699.9 (M + H) + |
| 202 | 181 | Ethyl N-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]glycinate | MS (ESI+) m/z: 683.9 (M + H) + |
| 203 | 181 | Ethyl [4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)-1,4-diazepan-1-yl]acetate | MS (ESI+) m/z: 684.5 (M + H) + |
| 204 | 181 | Ethyl [4-(5-{5-[3-fluoro-5-(trifluoromethyl)phenyl]-7-[(3-methoxy-2,2-dimethylpropyl)(methyl)amino]-1H-imidazo[4,5-b]pyridin-2-yl}pyrazin-2-yl)-1,4-diazepan-1-yl]acetate | MS (ESI+) m/z: 673.9 (M + H) + |
| 205 | 181 | Ethyl [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-1,4-diazepan-1-yl]acetate | MS (ESI+) m/z: 723.0 (M + H) + |

TABLE 35

| REx | PREx | Chemical Name | Data |
|---|---|---|---|
| 206 | 181 | Ethyl 3-[(2S)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate | MS (ESI+) m/z: 727.0 (M + H) + |
| 207 | 45 | Ethyl 3-[4-(5-{7-[{[1-(ethoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propanoate | MS (ESI+) m/z: 713.5 (M + H) + |
| 208 | 45 | Ethyl 3-[4-(5-{5-[3-fluoro-5-(trifluoromethyl)phenyl]-7-[({1-[(2-methoxyethoxy)methyl]cyclopentyl}methyl)(methyl)amino]-1H-imidazo[4,5-b]pyridin-2-yl}pyrazin-2-yl)piperazin-1-yl]propanoate | MS (ESI+) m/z: 743.5 (M + H) + |
| 209 | 181 | Methyl {[1-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 709.4 (M + H) + |

TABLE 36

| REx | PREx | Chemical Name | Data |
|---|---|---|---|
| 210 | 181 | Ethyl 3-[(2S)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 736.9 (M + H) + |
| 211 | 49 | Ethyl 1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 693.9 (M + H) + |

TABLE 36-continued

| REx | PREx | Chemical Name | Data |
|---|---|---|---|
| 212 | 181 | Ethyl 1-(4-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperidine-4-carboxylate | MS (ESI+) m/z: 665.9 (M + H) + |
| 213 | 181 | Ethyl 1-(4-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 692.0 (M + H) + |

TABLE 37

| REx | PREx | Chemical Name | Data |
|---|---|---|---|
| 214 | 181 | Ethyl 1-(4-{5-[5,6-bis(trifluoromethyl)pyridin-3-yl]7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 719.9 (M + H) + |
| 215 | 43 | Ethyl 1-(4-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 696.0 (M + H) + |
| 216 | 43 | Ethyl 1-(4-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}phenyl)piperidine-4-carboxylate | MS (ESI+) m/z: 667.9 (M + H) + |
| 217 | 43 | Ethyl 1-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 692.0 (M + H) + |
| 218 | 46 | Ethyl 1-(4-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenyl)piperidine-4-carboxylate | MS (ESI+) m/z: 714.0 (M + H) + |

TABLE 38

| REx | PREx | Chemical Name | Data |
|---|---|---|---|
| 219 | 43 | Ethyl 1-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylate | MS (ESI+) m/z: 679.9 (M + H) + |
| 220 | 43 | Ethyl 1-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 698.0 (M + H) + |
| 221 | 43 | Ethyl 1-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidine-4-carboxylate | MS (ESI+) m/z: 671.9 (M + H) + |
| 222 | 43 | Ethyl 1-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylate | MS (ESI+) m/z: 667.9 (M + H) + |
| 223 | 43 | Ethyl 1-(5-{5-[3-ethoxy-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 696.9 (M + H) + |

TABLE 39

| REx | PREx | Chemical Name | Data |
|---|---|---|---|
| 224 | 46 | Ethyl 1-(4-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}-3-fluorophenyl)piperidine-4-carboxylate | MS (ESI+) m/z: 713.9 (M + H) + |
| 225 | 43 | Ethyl 1-(5-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidine-4-carboxylate | MS (ESI+) m/z: 711.9 (M + H) + |
| 226 | 43 | Ethyl 1-(4-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylate | MS (ESI+) m/z: 709.8 (M + H) + |
| 227 | 43 | Ethyl 1-(5-{5-[5-cyclopropyl-6-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylate | MS (ESI+) m/z: 679.8 (M + H) + |

TABLE 40

| REx | PREx | Chemical Name | Data |
|---|---|---|---|
| 228 | 43 | Ethyl 1-(5-{5-[6-cyclopropyl-5-(trifluoromethyl)pyridin-3-yl]7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 693.8 (M + H) + |
| 229 | 43 | Ethyl 1-(5-{5-[5-cyclopropyl-6-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylate | MS (ESI+) m/z: 707.9 (M + H) + |
| 230 | 43 | Ethyl 1-(5-{5-[6-ethoxy-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylate | MS (ESI+) m/z: 711.9 (M + H) + |
| 231 | 43 | Ethyl 1-(4-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}phenyl)piperidine-4-carboxylate | MS (ESI+) m/z: 705.9 (M + H) + |

TABLE 41

| REx | PREx | Chemical Name | Data |
|---|---|---|---|
| 232 | 45 | Ethyl 1-(4-{7-[{[1-(ethoxymethyl)cyclopentyl]methyl}(methyl)amino]-5-[2-ethoxy-6-(trifluoromethyl)pyridin-4-yl]-1H-imidazo[4,5-b]pyridin-2-yl}phenyl)piperidine-4-carboxylate | MS (ESI+) m/z: 709.6 (M + H) + |
| 233 | 45 | Ethyl 1-(5-{5-[6-cyclopropyl-5-(trifluoromethyl)pyridin-3-yl]-7-[{[1-(ethoxymethyl)cyclopentyl]methyl}(ethyl)amino]-1H-imidazo[4,5-b]pyridin-2-yl}pyrazin-2-yl)piperidine-4-carboxylate | MS (ESI+) m/z: 721.8 (M + H) + |
| 234 | 46 | Ethyl 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-fluorophenyl)piperidine-4-carboxylate | MS (ESI+) m/z: 699.8 (M + H) + |
| 235 | 46 | Ethyl 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-methylphenyl)piperidine-4-carboxylate | MS (ESI+) m/z: 695.8 (M + H) + |

TABLE 42

| REx | PREx | Chemical Name | Data |
|---|---|---|---|
| 236 | 50 | Ethyl 3-[(2S)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-2-(methoxymethyl)piperazin-1-yl]propanoate | MS (ESI+) m/z: 780.8 (M + H) + |
| 237 | 49 | Ethyl 1-(5-{7-[{[1-(methoxymethyl)cyclobutyl]methyl}(methyl)amino]-5-[6-propyl-5-(trifluoromethyl)pyridin-3-yl]-1H-imidazo[4,5-b]pyridin-2-yl}pyrazin-2-yl)piperidine-4-carboxylate | MS (ESI+) m/z: 681.9 (M + H) + |
| 238 | 45 | Ethyl 3-[4-(5-{5-[3-fluoro-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propanoate | MS (ESI+) m/z: 699.9 (M + H) + |
| 239 | 45 | Ethyl 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate | MS (ESI+) m/z: 727.0 (M + H) + |

TABLE 43

| REx | PREx | Chemical Name | Data |
|---|---|---|---|
| 240 | 49 | Ethyl 3-[4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propanoate | MS (ESI+) m/z: 699.4 (M + H) + |
| 241 | 181 | Ethyl 3-[4-(5-{6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propanoate | MS (ESI+) m/z: 696.9 (M + H) + |
| 242 | 181 | Ethyl 3-[4-(4-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propanoate | MS (ESI+) m/z: 695.0 (M + H) + |

TABLE 43-continued

| REx | PREx | Chemical Name | Data |
|---|---|---|---|
| 243 | 181 | Ethyl 3-[(2S)-4-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate | MS (ESI+) m/z: 711.0 (M + H) + |

TABLE 44

| REx | PREx | Chemical Name | Data |
|---|---|---|---|
| 244 | 181 | Methyl {[1-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidin-4-yl]oxy}acetate | MS (ESI+) m/z: 683.9 (M + H) + |
| 245 | 45 | Methyl {[1-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 713.4 (M + H) + |
| 246 | 49 | Ethyl 3-[4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate | MS (ESI+) m/z; 750.9 (M + H) + |
| 247 | 49 | Ethyl 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate | MS (ESI+) m/z; 723.0 (M + H) + |

TABLE 45

| REx | PREx | Chemical Name | Data |
|---|---|---|---|
| 248 | 46 | Ethyl 3-[4-(4-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}phenyl)piperazin-1-yl]propanoate | MS (ESI+) m/z: 697.4 (M + H) + |
| 249 | 49 | Ethyl 3-[4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propanoate | MS (ESI+) m/z: 700.9 (M + H) + |
| 250 | 46 | Ethyl 3-[(2S)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate | MS (ESI+) m/z: 715.0 (M + H) + |
| 251 | 181 | Ethyl 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoate | MS (ESI+) m/z: 699.9 (M + H) + |

TABLE 46

| REx | PREx | Chemical Name | Data |
|---|---|---|---|
| 252 | 181 | Ethyl 3-[4-(4-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperazin-1-yl]propanoate | MS (ESI+) m/z: 721.0 (M + H)+ |
| 253 | 181 | Ethyl 3-[4-(4-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}phenyl)piperazin-1-yl]propanoate | MS (ESI+) m/z: 749.0 (M + H)+ |
| 254 | 181 | Ethyl 3-[(2S)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 737.0 (M + H)+ |
| 255 | 181 | Ethyl 3-[(2S)-4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 764.9 (M + H)+ |

TABLE 47

| REx | PREx | Chemical Name | Data |
|---|---|---|---|
| 256 | 181 | Methyl [1-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 737.9 (M + H) + |
| 257 | 46 | Ethyl 3-[4-(4-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propanoate | MS (ESI+) m/z: 699.0 (M + H) + |

TABLE 47-continued

| REx | PREx | Chemical Name | Data |
|---|---|---|---|
| 258 | 46 | Ethyl 3-[(2S)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate | MS (ESI+) m/z: 688.0 (M + H) + |
| 259 | 46 | Ethyl 3-[(2S)-4-(5-{5-[4-fluoro-3-(trifluoromethyl)phenyl]-7-[{(1-(methoxy-methyl)cyclo-butyl]methyl}(methyl)amino]-1H-imidazo[4,5-b]pyridin-2-yl}pyrazin-2-yl)-2-methylpiperazin-1-yl]propanoate | MS (ESI+) m/z: 699.9 (M + H) + |

TABLE 48

| REx | PREx | Chemical Name | Data |
|---|---|---|---|
| 260 | 46 | Methyl {[1-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 686.9 (M+H)+ |
| 261 | 181 | Ethyl 3-[(3R)-4-(5-{5-[5,6-bis(trifluoromethyl)pyridin-3-yl]-7-[([1-(methoxymethyl)cyclopentyl]methyl}(methyl)amino]-1H-imidazo[4,5-b]pyridin-2-yl}pyrazin-2-yl)-3-methylpiperazin-1-yl]propanoate | MS (ESI+) m/z: 764.9 (M+H)+ |
| 262 | 48 | Ethyl 2,2-difluoro-3-{(1-(5-{5-[3-fluoro-5-(trlfluoromethyl)phenyl]-7-[{[1-(methoxymethyl)cyclobutyl]methyl}(methyl)amino]-1H-imidazo[4,5-b]pyridin-2-yl}pyrazin-2-yl)piperidin-4-yl]amino)propanoate | MS (ESI+) m/z: 735.9 (M+H)+ |
| 263 | 181 | Ethyl N-[(3S,4R)-1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-fluoropiperidin-4-yl]glycinate | MS (ESI+) m/z: 741.0 (M+H)+ |

TABLE 49

| REx | PREx | Chemical Name | Data |
|---|---|---|---|
| 264 | 43 | Ethyl 3-[4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperazin-1-yl]butanoate | MS (ESI+) m/z: 723.0 (M + H)+ |

TABLE 49-continued

| REx | PREx | Chemical Name | Data |
|---|---|---|---|
| 265 | 46 | Ethyl 3-[(3R)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate | MS (ESI+) m/z: 726.4 (M + H)+ |
| 266 | 46 | Methyl {[1-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidin-4-yl]oxy}acetate | MS (ESI+) m/z: 687.9 (M + H)+ |
| 267 | 46 | Ethyl 3-[(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate | MS (ESI+) m/z: 713.9 (M + H)+ |

TABLE 50

| REx | PREx | Chemical Name | Data |
|---|---|---|---|
| 268 | 43 | Ethyl N-[(3S,4R)-1-(5-{5-[2-cyclopropyl-6-(trifluoromethyl)pyridin-4-yl]-7-[{[1-(methoxy-methyl)cyclo-pentyl]methyl}(methyl)amino]-1H-imidazo[4,5-b]pyridin-2-yl}pyrazin-2-yl)-3-fluoropiperidin-4-yl]-N-methylglycinate | MS (ESI+) m/z: 755.0 (M + H) + |
| 269 | 45 | Ethyl 3-[4-(5-{7-[{[1-(butoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propanoate | MS (ESI+) m/z: 742.0 (M + H) + |
| 270 | 43 | Ethyl 3-[(2R,6S)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2,6-dimethylpiperazin-1-yl]propanoate | MS (ESI+) m/z: 729.0 (M + H) + |
| 271 | 43 | Ethyl 3-[(2R,6S)-4-(5-{5-[3,5-bis(trifluoromethyl)phenyl]-7-[1[1-(methoxymethyl)cyclopentyl]methyl}(methyl)amino]-1H-imidazo[4,5-b]pyridin-2-yl}pyrazin-2-yl)-2,6-dimethylpiperazin-1-yl]propanoate | MS (ESI+) m/z: 778.0 (M + H) + |

TABLE 51

| REx | PREx | Chemical Name | Data |
|---|---|---|---|
| 272 | 43 | Methyl{[1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 714.0 (M + H)+ |
| 273 | 43 | Ethyl 3-[(2R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 737.0 (M + H)+ |
| 274 | 46 | Ethyl 3-[(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate | MS (ESI+) m/z: 687.9 (M + H)+ |
| 275 | 43 | Ethyl{[1-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidin-4-yl]oxy}acetate | MS (ESI+) m/z: 710.0 (M + H)+ |

TABLE 52

| REx | PREx | Chemical Name | Data |
|---|---|---|---|
| 276 | 45 | Ethyl 3-[(3R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate | MS (ESI+) m/z: 727.0 (M + H) + |
| 277 | 45 | Ethyl 3-[(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate | MS (ESI+) m/z: 715.0 (M + H) + |
| 278 | 45 | Ethyl 3-[(3R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate | MS (ESI+) m/z: 723.0 (M + H) + |
| 279 | 45 | Ethyl 3-[(3R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate | MS (ESI+) m/z: 711.0 (M + H) + |

TABLE 53

| REx | PREx | Chemical Name | Data |
|---|---|---|---|
| 280 | 45 | Ethyl 3-[(2R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate | MS (ESI+) m/z: 727.0 (M + H)+ |
| 281 | 45 | Ethyl 3-[(2R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate | MS (ESI+) m/z: 723.0 (M + H)+ |
| 282 | 45 | Ethyl 3-[(2R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate | MS (ESI+) m/z: 715.0 (M + H)+ |
| 283 | 45 | Ethyl 3-[(2R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate | MS (ESI+) m/z: 711.0 (M + H)+ |

TABLE 54

| REx | PREx | Chemical Name | Data |
|---|---|---|---|
| 284 | 46 | Ethyl[(3R)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate | MS (ESI+) m/z: 700.0 (M + H)+ |
| 285 | 43 | Ethyl 3-[(2R,6S)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2,6-dimethylpiperazin-1-yl]propanoate | MS (ESI+) m/z: 741.0 (M + H)+ |
| 286 | 43 | Ethyl {[(1R,3r,5S)-8-(5-{5-[6-ethoxy-5-(trifluoromethyl)pyridin-3-yl]-7-[{[1-(methoxymethyl)cyclobutyl]methyl}(methyl)amino]-1H- | MS (ESI+) m/z: 739.7 (M + H)+ |

TABLE 54-continued

| REx | PREx | Chemical Name | Data |
|---|---|---|---|
|  |  | imidazo[4,5-b]pyridin-2-yl}pyrazin-2-yl)-8-azabicyclo[3.2.1]octan-3-yl]oxy}acetate |  |
| 287 | 43 | Ethyl {[(1R,3r,5S)-8-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate | MS (ESI+) m/z: 749.4 (M + H)+ |

TABLE 55

| REx | PREx | Chemical Name | Data |
|---|---|---|---|
| 288 | 45 | Methyl [4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazine-1-sulfonyl]acetate | MS (ESI+) m/z: 758.4 (M + H)+ |
| 289 | 46 | Ethyl [(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate | MS (ESI+) m/z: 701.0 (M + H)+ |
| 290 | 46 | Ethyl [(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate | MS (ESI+) m/z: 674.0 (M + H)+ |
| 291 | 46 | Ethyl [(3R)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetate | MS (ESI+) m/z: 685.9 (M + H)+ |

TABLE 56

| REx | PREx | Chemical Name | Data |
|---|---|---|---|
| 292 | 46 | Ethyl [(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetate | MS (ESI+) m/z: 700.0 (M + H)+ |
| 293 | 45 | Ethyl 3-[(2R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 737.0 (M + H) + |
| 294 | 43 | Ethyl 3-[(2R,6S)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,6-dimethylpiperazin-1-yl]propanoate | MS (ESI+) m/z: 755.1 (M + H) + |
| 295 | 43 | Ethyl {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3,3-dimethylpiperidin-4-yl]oxy}acetate | MS (ESI+) m/z: 752.0 (M + H) + |

TABLE 57

| REx | PREx | Chemical Name | Data |
|---|---|---|---|
| 296 | 45 | Ethyl 1-(4-{5-[6-cyano-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 676.4 (M + H)+ |
| 297 | 46 | Ethyl 3-[(2R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 741.0 (M + H)+ |
| 298 | 46 | Ethyl [(3R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetate | MS (ESI+) m/z: 727.0 (M + H)+ |
| 299 | 43 | Ethyl {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidin-4-yl]oxy}acetate | MS (ESI+) m/z: 738.0 (M + H)+ |

TABLE 58

| REx | PREx | Chemical Name | Data |
|---|---|---|---|
| 300 | 43 | Ethyl {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-4-methylpiperidin-4-yl]oxy}acetate | MS (ESI+) m/z: 738.0 (M + H)+ |
| 301 | 43 | Ethyl {[(1R,3r,5S)-8-(5-{5-[2-cyclopropyl-6-(trifluoromethyl)pyridin-4- | MS (ESI+) m/z: 764.0 (M + H)+ |

TABLE 58-continued

| REx | PREx | Chemical Name | Data |
|---|---|---|---|
| | | yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxy}acetate | |
| 302 | 43 | Ethyl{[1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-4-methylpiperidin-4-yl]oxy}acetate | MS (ESI+) m/z: 728.0 (M + H)+ |
| 303 | 43 | Ethyl 1-(4-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylate | MS (ESI+) m/z: 706.0 (M + H)+ |

TABLE 59

| REx | PREx | Chemical Name | Data |
|---|---|---|---|
| 304 | 45 | Ethyl 3-[(3R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate | MS (ESI+) m/z: 741.0 (M + H)+ |
| 305 | 45 | Ethyl 3-[(2R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate | MS (ESI+) m/z: 741.0 (M + H)+ |
| 306 | 43 | Ethyl 3-[4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperazin-1-yl]propanoate | MS (ESI+) m/z: 737.0 (M + H)+ |
| 307 | 46 | Ethyl 1-(5-{5-[4-cyclopropyl-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-carboxylate | MS (ESI+) m/z: 692.9 (M + H)+ |

TABLE 60

| REx | PREx | Chemical Name | Data |
|---|---|---|---|
| 308 | 46 | Ethyl 1-(4-{5-[4-cyclopropyl-3-(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylate | MS (ESI+) m/z: 690.9 (M + H) + |
| 309 | 43 | Ethyl {[1-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate | MS (ESI+) m/z: 723.9 (M + H) + |
| 310 | 43 | Ethyl 3-[(3R)-4-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate | MS (ESI+) m/z: 736.9 (M + H) + |
| 311 | 43 | Ethyl {[(1R,3s,5S)-8-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxy}acetate | MS (ESI+) m/z: 763.9 (M + H) + |

TABLE 61

| REx | PREx | Chemical Name | Data |
|---|---|---|---|
| 312 | 43 | Ethyl 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propanoate | MS (ESI+) m/z: 750.9 (M + H) + |
| 313 | 49 | Ethyl 3-[(3R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyridin-2-yl)-3-methylpiperazin-1-yl]propanoate | MS (ESI+) m/z: 735.9 (M + H) + |
| 314 | 46 | Ethyl [(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetate | MS (ESI+) m/z: 736.3 (M + H) + |
| 315 | 46 | Ethyl [(3R)-4-(5-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetate | MS (ESI+) m/z: 740.9 (M + H) + |

TABLE 62

| REx | PREx | Chemical Name | Data |
|---|---|---|---|
| 316 | 43 | Ethyl 3-[4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propanoate | MS (ESI+) m/z: 754.9 (M + H)+ |
| 317 | 43 | Ethyl 3-[(2R,6S)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-2,6-dimethylpiperazin-1-yl]propanoate | MS (ESI+) m/z: 764.9 (M + H)+ |
| 318 | 43 | Ethyl {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3,3-dimethylpiperidin-4-yl]oxy}acetate | MS (ESI+) m/z: 765.9 (M + H)+ |
| 319 | 43 | Ethyl 3-[(3R)-4-(5-{5-[6-cyclopropyl-5-(trifluoromethyl)pyridin-3-yl]-7-(ethyl{[1-(methoxymethyl)cyclopentyl]methyl}amino)-1H-imidazo[4,5-b]pyridin-2-yl}pyrazin-2-yl)-3-methylpiperazin-1-yl]propanoate | MS (ESI+) m/z: 750.9 (M + H)+ |

TABLE 63

| REx | PREx | Chemical Name | Data |
|---|---|---|---|
| 320 | 43 | Ethyl {[(1R,3s,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate | MS (ESI+) m/z: 753.5 (M + H) + |
| 321 | 43 | Ethyl 1-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylate | MS (ESI+) m/z: 707.9 (M + H) + |
| 322 | 43 | Ethyl {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]sulfanyl}acetate | MS (ESI+) m/z: 739.8 (M + H) + |

TABLE 63-continued

| REx | PREx | Chemical Name | Data |
|---|---|---|---|
| 323 | 43 | Ethyl {[1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidin-4-yl]sulfanyl}acetate | MS (ESI+) m/z: 729.8 (M + H) + |

TABLE 64

| REx | PREx | Chemical Name | Data |
|---|---|---|---|
| 324 | 43 | Ethyl [4-(4-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}phenoxy)piperidin-1-yl]acetate | MS (ESI+) m/z: 711.8 (M + H) + |
| 325 | 43 | Ethyl [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]acetate | MS (ESI+) m/z: 721.8 (M + H) + |
| 326 | 43 | Ethyl 3-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]propanoate | MS (ESI+) m/z: 698.6 (M + H) + |
| 327 | 43 | Ethyl [4-(3-chloro-4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]acetate | MS (ESI+) m/z: 755.5 (M + H) + |

TABLE 65

| REx | PREx | Chemical Name | Data |
|---|---|---|---|
| 328 | 43 | Ethyl 3-[4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]propanoate | MS (ESI+) m/z: 735.5 (M + H)+ |
| 329 | 43 | Ethyl 3-[(1R,3s,5S)-3-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)-8-azabicyclo[3.2.1]octan-8-yl]propanoate | MS (ESI+) m/z: 761.5 (M + H)+ |
| 330 | 61 | [4-(5-{5-[3-Fluoro-5-(trifluoromethyl)phenyl]-7-[{[1-(methoxymethyl)cyclobutyl]methyl}(methyl)amino]-1H- | MS (ESI+) m/z: 624.9 (M + H)+ |

TABLE 65-continued

| REx | PREx | Chemical Name | Data |
|---|---|---|---|
|  |  | imidazo[4,5-b]pyridin-2-yl}pyrazin-2-yl)piperazin-1-yl]acetonitrile |  |
| 331 | 61 | 3-[4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]propanenitrile | MS (ESI+) m/z: 638.9 (M + H)+ |

TABLE 66

| Ex | PEx | Chemical Name |
|---|---|---|
| 1 | 1 | 1-(5-{5-[2-Ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylic acid |
| 2 | 2 | 1-(5-{5-[2-Ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid |
| 3 | 3 | 1-(5-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)piperidine-4-carboxylic acid |
| 4 | 4 | {[1-(5-{5-[2-Cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetic acid |
| 5 | 5 | 3-[4-(5-{5-[2-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid |
| 6 | 6 | 3-[4-(5-{5-[6-Cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperazin-1-yl]propanoic acid |
| 7 | 7 | 3-[(3R)-4-(5-{5-[6-Cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoic acid |

TABLE 67

| Ex | PEx | Chemical Name |
|---|---|---|
| 8 | 8 | 3-[(2S)-4-(5-{5-[6-Cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propanoic acid |
| 9 | 9 | 1-(5-{5-[2-Ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylic acid |
| 10 | 10 | [4-(4-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl]acetic acid |
| 11 | 11 | 1-(5-{5-[2-Ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid dihydrochloride |

TABLE 67-continued

| Ex | PEx | Chemical Name |
|---|---|---|
| 12 | 12 | 3-[4-Fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidin-1-yl]propanoic acid trihydrochloride |
| 13 | 13 | 3-[4-(5-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid dihydrochloride |

TABLE 68

| Ex | PEx | Chemical Name |
|---|---|---|
| 14 | 14 | Sodium 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propanoate |
| 15 | 15 | Sodium {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate |
| 16 | 16 | Sodium 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoate |
| 17 | 17 | Sodium [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetate |
| 18 | 18 | 1-(4-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylic acid |
| 19 | 19 | [4-(6-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)-4-hydroxypiperidin-1-yl]acetic acid trihydrochloride |

TABLE 69

| Ex | PEx | Chemical Name |
|---|---|---|
| 20 | 20 | 3-[(3R)-4-(5-{5-[6-Cyclopropyl-5-(trifluoromethyl)pyridin-3-yl]-7-[{[1-(methoxymethyl)cyclopentyl[methyl](methyl)amino]-1H-imidazo[4,5-b]pyridin-2-yl}pyrazin-2-yl)-3-methylpiperazin-1-yl]propanoate |
| 21 | 21 | 1-(4-{5-[3-Fluoro-5-(trifluoromethyl)phenyl]-7-[(3-methoxy-2,2-dimethylpropyl)(methyl)amino]-1H-imidazo[4,5-b]pyridin-2-yl}phenyl)piperidine-4-carboxylic acid |
| 22 | 22 | Sodium [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetate |
| 23 | 23 | 5-[3-Fluoro-5-(trifluoromethyl)phenyl]-N-{[1-(methoxymethyl)cyclobutyl]methyl}-N-methyl-2-{5-[4-(1H-tetrazol-5-yl)piperazin-1-yl]pyrazin-2-yl}-1H-imidazo[4,5-b]pyridin-7-amine |
| 24 | 24 | 8-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-2,8-diazaspiro[4.5]decan-3-one |

TABLE 69-continued

| Ex | PEx | Chemical Name |
|----|-----|---------------|
| 25 | 25 | 1-(5-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-N-(methansulfonyl)piperidine-4-carboxamide |
| 26 | 26 | [4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]acetic acid |

TABLE 70

| Ex | PEx | Chemical Name |
|----|-----|---------------|
| 27 | 27 | 2-[4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propanoic acid dihydrochloride |
| 28 | 28 | 1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperidine-4-carboxylic acid |
| 29 | 29 | {4-[1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethyl]piperazin-1-yl}acetic acid trihydrochloride |
| 30 | 9 | 4-Hydroxy-1-(5-{7-[{[1-(methoxymethyl)cyclobutyl]methyl}(methyl)amino]-5-[3-(trifluoromethyl)phenyl]-1H-imidazo[4,5-b]pyridin-2-yl}pyrazin-2-yl)piperidine-4-carboxylic acid |
| 31 | 7 | 8-(4-{7-[{[1-(Methoxymethyl)cyclobutyl]methyl}(methyl)amino]-5-[3-(trifluoromethyl)phenyl]-1H-imidazo[4,5-b]pyridin-2-yl}phenyl)-1-oxa-2,8-diazaspiro[4.5]dec-2-ene-3-carboxylic acid |
| 32 | 4 | 1-(5-{7-[{[1-(Methoxymethyl)cyclobutyl]methyl}(methyl)amino]-5-[4-methoxy-3-(trifluoromethyl)phenyl]-1H-imidazo[4,5-b]pyridin-2-yl}pyrazin-2-yl)piperidine-4-carboxylic acid |
| 33 | 7 | 8-(4-{7-[{[1-(Methoxymethyl)cyclobutyl]methyl}(methyl)amino]-5-[5-(trifluoromethyl)pyridin-3-yl]-1H-imidazo[4,5-b]pyridin-2-yl}phenyl)-1-oxa-2,8-diazaspiro[4.5]dec-2-ene-3-carboxylic acid |

TABLE 71

| Ex | PEx | Chemical Name |
|----|-----|---------------|
| 34 | 1 | 1-(4-{7-[{[1-(Methoxymethyl)cyclobutyl]methyl}(methyl)amino]-5-[3-(trifluoromethyl)phenyl]-1H-imidazo[4,5-b]pyridin-2-yl}phenyl)pyrrolidine-3-carboxylic acid |
| 35 | 9 | {4-[(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)methyl]piperazin-1-yl}acetic acid |
| 36 | 10 | 3-[4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid |
| 37 | 10 | [4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]acetic acid |
| 38 | 10 | 4-Fluoro-1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carboxylic acid |
| 39 | 9 | [4-(6-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperazin-1-yl]acetic acid |
| 40 | 10 | N-[1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]-N-methylglycine |

TABLE 72

| Ex | PEx | Chemical Name |
|----|-----|---------------|
| 41 | 8 | [4-(4-{7-[{[1-(Methoxymethyl)cyclobutyl]methyl}(methyl)amino]-5-[5-(trifluoromethyl)pyridin-3-yl]-1H-imidazo[4,5-b]pyridin-2-yl}phenyl)piperazin-1-yl]acetic acid |
| 42 | 1 | 1-(5-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid |
| 43 | 21 | [4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-4-hydroxypiperidin-1-yl]acetic acid |
| 44 | 7 | 3-[4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-oxopiperazin-1-yl]propanoic acid |
| 45 | 7 | 3-[4-(5-{5-[2-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoic acid |
| 46 | 10 | [4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-1,4-diazepan-1-yl]acetic acid |
| 47 | 10 | 3-[(2S)-4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoic acid |

TABLE 73

| Ex | PEx | Chemical Name |
|----|-----|---------------|
| 48 | 10 | 4-[4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoic acid |
| 49 | 10 | N-[1-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidin-4-yl]glycine |
| 50 | 10 | {[1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]oxy}acetic acid |
| 51 | 10 | {[1-(5-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidin-4-yl]oxy}acetic acid |
| 52 | 10 | N-[1-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-4-yl]glycine |
| 53 | 10 | [4-(6-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)-1,4-diazepan-1-yl]acetic acid |
| 54 | 10 | [4-(5-{5-[3-Fluoro-5-(trifluoromethyl)phenyl]-7-[(3-methoxy-2,2-dimethylpropyl)(methyl)amino]-1H- |

TABLE 73-continued

| Ex | PEx | Chemical Name |
|---|---|---|
|  |  | imidazo[4,5-b]pyridin-2-yl}pyrazin-2-yl)-1,4-diazepan-1-yl]acetic acid |

TABLE 74

| Ex | PEx | Chemical Name |
|---|---|---|
| 55 | 10 | [4-(5-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-1,4-diazepan-1-yl]acetic acid |
| 56 | 10 | 3-[(2S)-4-(5-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoic acid |
| 57 | 9 | 3-[4-(5-{7-[{[1-(Ethoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propanoic acid |
| 58 | 9 | 3-[4-(5-{5-[3-Fluoro-5-(trifluoromethyl)phenyl]-7-[({1-[(2-methoxyethoxy)methyl]cyclopentyl}methyl)(methyl)amino]-1H-imidazo[4,5-b]pyridin-2-yl}pyrazin-2-yl)piperazin-1-yl]propanoic acid |
| 59 | 10 | {[1-(5-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetic acid |
| 60 | 10 | 3-[(2S)-4-(5-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoic acid |
| 61 | 1 | 1-(5-{5-[2-Cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid |

TABLE 75

| Ex | PEx | Chemical Name |
|---|---|---|
| 62 | 10 | 1-(4-{5-[6-Cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperidine-4-carboxylic acid |
| 63 | 10 | 1-(4-{5-[2-Cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperidine-4-carboxylic acid |
| 64 | 10 | 1-(4-{5-[5,6-Bis(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid |
| 65 | 1 | 1-(4-{5-[6-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid |
| 66 | 1 | 1-(4-{5-[2-Cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}phenyl)piperidine-4-carboxylic acid |

TABLE 75-continued

| Ex | PEx | Chemical Name |
|---|---|---|
| 67 | 1 | 1-(4-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid |
| 68 | 4 | 1-(4-{5-[6-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenyl)piperidine-4-carboxylic acid |

TABLE 76

| Ex | PEx | Chemical Name |
|---|---|---|
| 69 | 1 | 1-(5-{5-[2-Cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid |
| 70 | 1 | 1-(5-{5-[6-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid |
| 71 | 1 | 1-(5-{5-[6-Ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidine-4-carboxylic acid |
| 72 | 1 | 1-(5-{5-[2-Cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylic acid |
| 73 | 1 | 1-(5-{5-[3-Ethoxy-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-carboxylic acid |
| 74 | 4 | 1-(4-{5-[2-Ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}-3-fluorophenyl)piperidine-4-carboxylic acid |
| 75 | 1 | 1-(5-{5-[2-Ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid |

TABLE 77

| Ex | PEx | Chemical Name |
|---|---|---|
| 76 | 1 | 1-(4-{5-[2-Ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylic acid |
| 77 | 1 | 1-(5-{5-[5-Cyclopropyl-6-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid |
| 78 | 1 | 1-(5-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid |
| 79 | 1 | 1-(5-{5-[5-Cyclopropyl-6-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid |
| 80 | 1 | 1-(5-{5-[6-Ethoxy-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid |

TABLE 77-continued

| Ex | PEx | Chemical Name |
|---|---|---|
| 81 | 10 | 1-(4-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}phenyl)piperidine-4-carboxylic acid |
| 82 | 7 | 1-(4-{7-[{[1-(Ethoxymethyl)cyclopentyl]methyl}(methyl)amino]-5-[2-ethoxy-6-(trifluoromethyl)pyridin-4-yl]-1H-imidazo[4,5-b]pyridin-2-yl}phenyl)piperidine-4-carboxylic acid |

TABLE 78

| Ex | PEx | Chemical Name |
|---|---|---|
| 83 | 7 | 1-(5-{5-[6-Cyclopropyl-5-(trifluoromethyl)pyridin-3-yl]-7-[{[1-(ethoxymethyl)cyclopentyl]methyl}(ethyl)amino]-1H-imidazo[4,5-b]pyridin-2-yl}pyrazin-2-yl)piperidine-4-carboxylic acid |
| 84 | 4 | 1-(4-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-fluorophenyl)piperidine-4-carboxylic acid |
| 85 | 10 | 1-(4-{5-[6-Ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-methylphenyl)piperidine-4-carboxylic acid |
| 86 | 8 | 3-[(2S)-4-(5-{5-[6-Cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-2-(methoxymethyl)piperazin-1-yl]propanoic acid |
| 87 | 1 | 1-(5-{7-[{[1-(methoxymethyl)cyclobutyl]methyl}(methyl)amino]-5-[6-propyl-5-(trifluoromethyl)pyridin-3-yl]-1H-imidazo[4,5-b]pyridin-2-yl}pyrazin-2-yl)piperidine-4-carboxylic acid |
| 88 | 11 | 3-[4-(5-{5-[3-Fluoro-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid trihydrochloride |
| 89 | 89 | 3-[4-(5-{5-[6-Ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid dihydrochloride |

TABLE 79

| Ex | PEx | Chemical Name |
|---|---|---|
| 90 | 89 | 3-[4-(5-{5-[4-Fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid trihydrochloride |
| 91 | 15 | Sodium 3-[4-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propanoate |
| 92 | 17 | Sodium 3-[4-(4-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propanoate |
| 93 | 17 | Sodium 3-[(2S)-4-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate |
| 94 | 17 | Sodium {[1-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidin-4-yl]oxy}acetate |
| 95 | 14 | Sodium {[1-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate |
| 96 | 14 | Sodium 3-[4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate |

TABLE 80

| Ex | PEx | Chemical Name |
|---|---|---|
| 97 | 14 | Sodium 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoate |
| 98 | 89 | 3-[4-(4-{5-[4-Fluoro-3-(trifluoromethyl)phenyl]-7-[{[1-(methoxymethyl)cyclopentyl]methyl}(methyl)amino]-1H-imidazo[4,5-b]pyridin-2-yl}phenyl)piperazin-1-yl]propanoic acid dihydrochloride |
| 99 | 15 | Sodium 3-[4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propanoate |
| 100 | 15 | Sodium 3-[(2S)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate |
| 101 | 17 | Sodium 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoate |
| 102 | 17 | Sodium 3-[4-(4-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperazin-1-yl]propanoate |
| 103 | 17 | Sodium 3-[4-(4-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}phenyl)piperazin-1-yl]propanoate |

TABLE 81

| Ex | PEx | Chemical Name |
|---|---|---|
| 104 | 17 | Sodium 3-[(2S)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 105 | 17 | Sodium 3-[(2S)-4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 106 | 17 | Sodium [1-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate |
| 107 | 15 | Sodium 3-[4-(4-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propanoate |

TABLE 81-continued

| Ex | PEx | Chemical Name |
|---|---|---|
| 108 | 15 | Sodium 3-[(2S)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate |
| 109 | 109 | Sodium 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate |

TABLE 82

| Ex | PEx | Chemical Name |
|---|---|---|
| 110 | 15 | Sodium {[1-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate |
| 111 | 15 | Sodium 3-[(3R)-4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate |
| 112 | 17 | Sodium 2,2-difuloro-3-{[1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidin-4-yl]amino}propanoate |
| 113 | 17 | Sodium {[(3S,4R)-1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-fluoropiperidin-4-yl]amino}acetate |
| 114 | 15 | Sodium 3-[4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperazin-1-yl]butanoate |
| 115 | 15 | Sodium 3-[(3R)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate |

TABLE 83

| Ex | PEx | Chemical Name |
|---|---|---|
| 116 | 15 | Sodium {[1-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidin-4-yl]oxy}acetate |
| 117 | 15 | Sodium 3-[(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate |
| 118 | 17 | Sodium {[(3S,4R)-1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-fluoropiperidin-4-yl]methyl}amino}acetate |
| 119 | 109 | Sodium 3-[4-(5-{7-[{[1-(butoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propanoate |
| 120 | 15 | Sodium 3-[(2R,6S)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2,6-dimethylpiperazin-1-yl]propanoate |

TABLE 83-continued

| Ex | PEx | Chemical Name |
|---|---|---|
| 121 | 17 | Sodium 3-[(2R,6S)-4-(5-{5-[3,5-bis(trifluoromethyl)phenyl]-7-[{[1-(methoxymethyl)cyclopentyl]methyl}(methyl)amino]-1H-imidazo[4,5-b]pyridin-2-yl}pyrazin-2-yl)-2,6-dimethylpiperazin-1-yl]propanoate |

TABLE 84

| Ex | PEx | Chemical Name |
|---|---|---|
| 122 | 17 | Sodium {[1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]oxy}acetate |
| 123 | 15 | Sodium 3-[(2R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 124 | 15 | Sodium 3-[(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate |
| 125 | 17 | Sodium {[1-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidin-4-yl]oxy}acetate |
| 126 | 14 | Sodium 3-[(3R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate |
| 127 | 14 | Sodium 3-[(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate |

TABLE 85

| Ex | PEx | Chemical Name |
|---|---|---|
| 128 | 14 | Sodium 3-[(3R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate |
| 129 | 14 | Sodium 3-[(3R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propanoate |
| 130 | 14 | Sodium 3-[(2R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate |
| 131 | 14 | Sodium 3-[(2R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate |
| 132 | 14 | Sodium 3-[(2R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate |

TABLE 85-continued

| Ex | PEx | Chemical Name |
|---|---|---|
| 133 | 14 | Sodium 3-[(2R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propanoate |

TABLE 86

| Ex | PEx | Chemical Name |
|---|---|---|
| 134 | 15 | Sodium [(3R)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate |
| 135 | 15 | Sodium 3-[(2R,6S)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2,6-dimethylpiperazin-1-yl]propanoate |
| 136 | 15 | Sodium {[(1R,3r,5S)-8-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-8-azabicyclo[3.2.1]octan-3-yl]oxy}acetate |
| 137 | 15 | Sodium {[(1R,3r,5S)-8-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate |
| 138 | 109 | Sodium [4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazine-1-sulfonyl]acetate |
| 139 | 15 | Sodium [(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate |

TABLE 87

| Ex | PEx | Chemical Name |
|---|---|---|
| 140 | 15 | Sodium [(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]acetate |
| 141 | 15 | Sodium [(3R)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetate |
| 142 | 15 | Sodium [(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetate |
| 143 | 14 | Sodium 3-[(2R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 144 | 15 | Sodium 3-[(2R,6S)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,6-dimethylpiperazin-1-yl]propanoate |

TABLE 87-continued

| Ex | PEx | Chemical Name |
|---|---|---|
| 145 | 15 | Sodium {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3,3-dimethylpiperidin-4-yl]oxy}acetate |

TABLE 88

| Ex | PEx | Chemical Name |
|---|---|---|
| 146 | 109 | Sodium 1-(4-{5-[6-cyano-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylate |
| 147 | 15 | Sodium 3-[(2R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 148 | 15 | Sodium [(3R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetate |
| 149 | 15 | Sodium {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidin-4-yl]oxy}acetate |
| 150 | 15 | Sodium {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-4-methylpiperidin-4-yl]oxy}acetate |
| 151 | 15 | Sodium {[(1R,3r,5S)-8-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxy}acetate |

TABLE 89

| Ex | PEx | Chemical Name |
|---|---|---|
| 152 | 15 | Sodium {[1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-4-methylpiperidin-4-yl]oxy}acetate |
| 153 | 15 | Sodium 1-(4-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylate |
| 154 | 14 | Sodium 3-[(3R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate |
| 155 | 14 | Sodium 3-[(2R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propanoate |
| 156 | 15 | Sodium 3-[4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperazin-1-yl]propanoate |
| 157 | 15 | Sodium 1-(5-{5-[4-cyclopropyl-3-(trifluoromethyl)phenyl]-7-[{[1-(methoxymethyl)cyclopentyl]methyl}(methyl)amino]-1H- |

TABLE 89-continued

| Ex | PEx | Chemical Name |
|---|---|---|
|  |  | imidazo[4,5-b]pyridin-2-yl}pyrazin-2-yl)piperidine-4-carboxylate |

TABLE 90

| Ex | PEx | Chemical Name |
|---|---|---|
| 158 | 15 | Sodium 1-(4-{5-[4-cyclopropyl-3-(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylate |
| 159 | 15 | Sodium {[1-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidin-4-yl]oxyacetate |
| 160 | 15 | Sodium 3-[(3R)-4-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoate |
| 161 | 15 | Sodium {[(1R,3s,5S)-8-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxyacetate |
| 162 | 15 | Sodium 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propanoate |
| 163 | 109 | Sodium 3-[(3R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyridin-2-yl)-3-methylpiperazin-1-yl]propanoate |

TABLE 91

| Ex | PEx | Chemical Name |
|---|---|---|
| 164 | 15 | Sodium [(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl+56pyrazin-2-yl)-3-methylpiperazin-1-yl]acetate |
| 165 | 15 | Sodium [(3R)-4-(5-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetate |
| 166 | 15 | Sodium 3-[4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propanoate |
| 167 | 15 | Sodium 3-[(2R,6S)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-2,6-dimethylpiperazin-1-yl]propanoate |
| 168 | 15 | Sodium {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3,3-dimethylpiperidin-4-yl]oxylacetate |
| 169 | 17 | Sodium 3-[(3R)-4-(5-{5-[6-cyclopropyl-5-(trifluoromethyl)pyridin-3-yl]-7-(ethyl{[1-(methoxymethyl)cyclopentyl]methyl}amino)-1H-imidazo[4,5-b]pyridin-2-yl}pyrazin-2-yl)-3-methylpiperazin-1-yl]propanoate |

TABLE 92

| Ex | PEx | Chemical Name |
|---|---|---|
| 170 | 17 | Sodium {[(1R,3s,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetate |
| 171 | 10 | Sodium 1-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid |
| 172 | 17 | Sodium {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidin-4-yl]sulfanyl}acetate |
| 173 | 17 | Sodium {[1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidin-4-yl]sulfanyl}acetate |
| 174 | 17 | Sodium [4-(4-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}phenoxy)piperidin-1-yl]acetate |
| 175 | 17 | Sodium [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]acetate |
| 176 | 17 | Sodium 3-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]propanoate |

TABLE 93

| Ex | PEx | Chemical Name |
|---|---|---|
| 177 | 17 | Sodium [4-(3-chloro-4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]acetate |
| 178 | 17 | Sodium 3-[4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidin-1-yl]propanoate |
| 179 | 17 | Sodium 3-[(1R,3s,5S)-3-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)-8-azabicyclo[3.2.1]octan-8-yl]propanoate |
| 180 | 18 | [4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]acetic acid |
| 181 | 18 | 1-(4-{5-[6-Cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylic acid |
| 182 | 18 | 1-(4-{5-[3,5-Bis(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylic acid |
| 183 | 18 | 1-(4-{5-[2-Ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperidine-4-carboxylic acid |

TABLE 94

| Ex | PEx | Chemical Name |
|---|---|---|
| 184 | 18 | 1-(4-{5-[2-Cyclopropyl-6-(trifluoromethyl)pyridin-4-yl]-7-[(3-methoxy-2,2-dimethylpropyl)(methyl)amino]-1H-imidazo[4,5-b]pyridin-2-yl}phenyl)piperidine-4-carboxylic acid |
| 185 | 18 | 1-(4-{5-[2-Ethoxy-6-(trifluoromethyl)pyridin-4-yl]-7-[(3-methoxy-2,2-dimethylpropyl)(methyl)amino]-1H-imidazo[4,5-b]pyridin-2-yl}phenyl)piperidine-4-carboxylic acid |
| 186 | 19 | {1-[(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}phenyl)methyl]piperidin-4-yl}acetic acid dihydrochloride |
| 187 | 19 | 3-[4-(5-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}pyridin-2-yl)-4-hydroxypiperidin-1-yl]propanoic acid trihydrochloride |
| 188 | 19 | 3-[4-(5-{5-[3-Fluoro-5-(trifluoromethyl)phenyl]-7-[(3-methoxy-2,2-dimethylpropyl)(methyl)amino]-1H-imidazo[4,5-b]pyridin-2-yl}pyrazin-2-yl)piperazin-1-yl]propanoic acid trihydrochloride |
| 189 | 19 | 3-[4-(6-{5-[3-Fluoro-5-(trifluoromethyl)phenyl]-7-[{[1-(methoxymethyl)cyclohexyl]methyl}(methyl)amino]-1H-imidazo[4,5-b]pyridin-2-yl}pyridin-3-yl)piperazin-1-yl]propanoic acid trihydrochloride |
| 190 | 19 | 3-[4-(5-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propanoic acid trihydrochloride |

TABLE 95

| Ex | PEx | Chemical Name |
|---|---|---|
| 191 | 19 | 3-[4-(4-{5-[6-Cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperazin-1-yl]propanoic acid dihydrochloride |
| 192 | 19 | 3-[4-(4-{5-[6-Ethoxy-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperazin-1-yl]propanoic acid dihydrochloride |
| 193 | 19 | 3-[4-(4-{5-[6-Cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperazin-1-yl]propanoic acid dihydrochloride |
| 194 | 20 | Sodium 3-[4-(5-{5-[3,5-bis(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propanoate |
| 195 | 20 | Sodium 3-[4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propanoate |
| 196 | 20 | Sodium 3-[(2S)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propanoate |
| 197 | 20 | Sodium 3-[(3S)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propanoate |

TABLE 96

| Ex | PEx | Chemical Name |
|---|---|---|
| 198 | 20 | Sodium [(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetate |
| 199 | 20 | Sodium [(3R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetate |
| 200 | 20 | Sodium [(3R)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetate |
| 201 | 20 | Sodium 3-[4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]propanoate |
| 202 | 20 | Sodium [(3R)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetate |
| 203 | 20 | Sodium [(3R)-4-(5-{5-[6-cyclopropyl-5-(trifluoromethyl)pyridin-3-yl]-7-[}[1-(ethoxymethyl)cyclopentyl]methyl}(methyl)amino]-1H-imidazo[4,5-b]pyridin-2-yl}pyrazin-2-yl)-3-methylpiperazin-1-yl]acetate |

TABLE 97

| Ex | PEx | Chemical Name |
|---|---|---|
| 204 | 20 | Sodium 1-(4-{5-[4-ethoxy-3-(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylate |
| 205 | 20 | Sodium 1-(4-{5-[5-cyclopropyl-6-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperidine-4-carboxylate |
| 206 | 20 | Sodium 3-[(3R)-4-(4-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)-3-methylpiperazin-1-yl]propanoate |
| 207 | 20 | Sodium 3-[(3R)-4-(4-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)-3-methylpiperazin-1-yl]propanoate |
| 208 | 20 | Sodium 3-[(3R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)-3-methylpiperazin-1-yl]propanoate |
| 209 | 23 | 5-[3-Fluoro-5-(trifluoromethyl)phenyl]-N-{[1-(methoxymethyl)cyclobutyl]methyl}-N-methyl-2-(5-{4-[(1H-tetrazol-5-yl)methyl]piperazin-1-yl}pyrazin-2-yl)-1H-imidazo[4,5-b]pyridin-7-amine |

TABLE 98

| Ex | PEx | Chemical Name |
|---|---|---|
| 210 | 23 | 5-[3-Fluoro-5-(trifluoromethyl)phenyl]-N-}[1-(methoxymethyl)cyclobutyl]methyl}-N-methyl-2-(5-{4-[2-(1H-tetrazol-5-yl)ethyl]piperazin-1-yl}pyrazin-2-yl)-1H-imidazo[4,5-b]pyridin-7-amine |

TABLE 98-continued

| Ex | PEx | Chemical Name |
|---|---|---|
| 211 | 24 | N-{2-[4-(5-{5-[6-Cyclopropyl-5-(trifluoromethyl)pyridin-3-yl]-7-[}[1-(methoxymethyl)cyclopentyl]methyl}(methyl)amino]-1H-imidazo[4,5-b]pyridin-2-yl}pyrazin-2-yl)piperazin-1-yl]ethyl]methansulfonamide |
| 212 | 26 | 3-[4-(4-{5-[3-Fluoro-5-(trifluoromethyl)phenyl]-7-[}[1-(methoxymethyl)cyclobutyl]methyl}(methyl)amino]-1H-imidazo[4,5-b]pyridin-2-yl}phenyl)piperidin-1-yl]propanoic acid |
| 213 | 28 | [4-(4-{5-[3-Fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperazin-1-yl]acetic acid |

TABLE 99

| Ex | Data |
|---|---|
| 1 | MS (ESI+) m/z: 643.9 (M + H)+ |
| 2 | MS (ESI+) m/z: 669.9 (M + H)+ |
| 3 | MS (ESI+) m/z: 679.4 (M + H)+ |
| 4 | MS (ESI+) m/z: 695.9 (M + H)+ |
| 5 | MS (ESI+) m/z: 698.5 (M + H)+ |
| 6 | MS (ESI+) m/z: 708.9 (M + H)+ |
| 7 | MS (ESI+) m/z: 722.8 (M + H)+ |
| 8 | MS (ESI+) m/z: 752.8 (M + H)+ |
| 9 | MS (ESI+) m/z: 655.7 (M + H)+ |
| 10 | MS (ESI+) m/z: 712.1 (M + H)+ |
| 11 | MS (ESI+) m/z: 655.9 (M + H)+<br>Elemental analysis value as $C_{32}H_{39}Cl_2F_3N_8O_4 + 0.8H_2O$<br>Calculated (%) C: 51.80 H: 5.52 N: 15.10<br>Found (%) C: 51.83 H: 5.50 N:14.90 |
| 12 | MS (ESI+) m/z: 673.3 (M + H)+ |
| 13 | MS (ESI+) m/z: 684.4 (M + H)+<br>Elemental analysis value as $C_{33}H_{42}Cl_2F_3N_9O_4 + 2.1H_2O$<br>Calculated (%) C: 49.90 H: 5.86 N: 15.87<br>Found (%) C: 49.79 H: 6.06 N: 15.49 |
| 14 | MS (ESI+) m/z: 722.9 (M + H)+<br>Elemental analysis value as $C_{37}H_{45}F_3N_9NaO_3 + 3H_2O$<br>Calculated (%) C: 55.70 H: 6.44 N: 15.80<br>Found (%) C: 55.92 H: 6.82 N: 15.53 |
| 15 | MS (ESI+) m/z: 726.0 (M + H)+<br>Elemental analysis value as $C_{36}H_{42}F_3N_8NaO_5 + 4H_2O$<br>Calculated (%) C: 52.81 H: 6.16 N:13.69<br>Found (%) C: 52.93 H: 5.76 N: 13.70 |
| 16 | MS (ESI+) m/z: 723.0 (M + H)+<br>Elemental analysis value as $C_{32}H_{45}F_3N_9NaO_3 + 3H_2O$<br>Calculated (%) C: 55.70 H: 6.44 N: 15.80<br>Found (%) C: 55.33 H: 6.29 N: 15.65 |

TABLE 100

| Ex | Data |
|---|---|
| 17 | MS (ESI+) m/z: 656.7 (M + H)+ |
| 18 | MS (ESI+) m/z: 653.9 (M + H)+ |
| 19 | MS (ESI+) m/z: 657.3 (M + H)+<br>Elemental analysis value as $C_{33}H_{36}F_4N_6O_4 \cdot 3HCl + 1.2H_2O$<br>Calculated (%) C: 50.32 H: 5.30 N: 10.67<br>Found (%) C: 50.37 H: 5.49 N: 10.56 |
| 20 | MS (ESI+) m/z: 709.0 (M + H)+<br>Elemental analysis value as $C_{36}H_{43}F_3N_9NaO_3 + 3.9H_2O$<br>Calculated (%) C: 54.05 H: 6.40 N: 15.76<br>Found (%) C: 53.95 H: 6.15 N: 15.54 |
| 21 | MS (ESI+) m/z: 614.8 (M + H)+ |
| 22 | MS (ESI+) m/z: 698.0 (M + H)+<br>Elemental analysis value as $C_{35}H_{39}F_4N_8NaO_3 + 3.8H_2O$<br>Calculated (%) C: 53.40 H: 5.97 N: 14.24<br>Found (%) C: 53.14 H: 5.66 N: 14.09 |
| 23 | MS (ESI+) m/z: 652.7 (M + H)+ |
| 24 | MS (ESI+) m/z: 651.3 (M + H)+ |
| 25 | MS (ESI+) m/z: 756.7 (M + H)+ |
| 26 | MS (ESI+) m/z: 640.3 (M + H)+ |

TABLE 100-continued

| Ex | Data |
|---|---|
| 27 | MS (ESI+) m/z: 655.3 (M + H)+ |
| 28 | MS (ESI+) m/z: 654.7 (M + H)+ |
| 29 | MS (ESI+) m/z: 669.4 (M + H)+ |
| 30 | MS (ESI+) m/z: 626.3 (M + H)+ |
| 31 | MS (ESI+) m/z: 663.3 (M + H)+ |
| 32 | MS (ESI+) m/z: 640.8 (M + H)+ |
| 33 | MS (ESI+) m/z: 664.8 (M + H)+ |
| 34 | MS (ESI+) m/z: 594.5 (M + H)+ |
| 35 | MS (ESI+) m/z: 655.3 (M + H)+ |
| 36 | MS (ESI+) m/z: 657.3 (M + H)+ |
| 37 | MS (ESI+) m/z: 643.8 (M + H)+ |
| 38 | MS (ESI+) m/z: 646.7 (M + H)+ |

TABLE 101

| Ex | Data |
|---|---|
| 39 | MS (ESI+) m/z: 642.8 (M+H)+ |
| 40 | MS (ESI+) m/z: 669.9 (M+H)+ |
| 41 | MS (ESI+) m/z: 624.8 (M+H)+ |
| 42 | MS (ESI+) m/z: 655.8 (M+H)+ |
| 43 | MS (ESI+) m/z: 656.3 (M+H)+ |
| 44 | MS (ESI+) m/z: 671.3 (M+H)+ |
| 45 | MS (ESI+) m/z: 684.8 (M+H)+ |
| 46 | MS (ESI+) m/z: 657.9 (M+H)+ |
| 47 | MS (ESI+) m/z: 671.6 (M+H)+ |
| 48 | MS (ESI+) m/z: 671.9 (M+H)+ |
| 49 | MS (ESI+) m/z: 657.8 (M+H)+ |
| 50 | MS (ESI+) m/z: 656.4 (M+H)+ |
| 51 | MS (ESI+) m/z: 685.3 (M+H)+ |
| 52 | MS (ESI+) m/z: 655.4 (M+H)+ |
| 53 | MS (ESI+) m/z: 656.9 (M+H)+ |
| 54 | MS (ESI+) m/z: 645.9 (M+H)+ |
| 55 | MS (ESI+) m/z: 694.9 (M+H)+ |
| 56 | MS (ESI+) m/z: 698.9 (M+H)+ |
| 57 | MS (ESI+) m/z: 685.4 (M+H)+ |
| 58 | MS (ESI+) m/z: 715.5 (M+H)+ |
| 59 | MS (ESI+) m/z: 695.4 (M+H)+ |
| 60 | MS (ESI+) m/z: 708.9 (M+H)+ |
| 61 | MS (ESI+) m/z: 685.9 (M+H)+ |
| 62 | MS (ESI+) m/z: 637.9 (M+H)+ |
| 63 | MS (ESI+) m/z: 663.9 (M+H)+ |
| 64 | MS (ESI+) m/z: 691.9 (M+H)+ |
| 65 | MS (ESI+) m/z: 667.9 (M+H)+ |
| 66 | MS (ESI+) m/z: 649.9 (M+H)+ |
| 67 | MS (ESI+) m/z: 663.9 (M+H)+ |
| 68 | MS (ESI+) m/z: 685.9 (M+H)+ |

TABLE 102

| Ex | Data |
|---|---|
| 69 | MS (ESI+) m/z: 651.9 (M + H)+ |
| 70 | MS (ESI+) m/z: 669.9 (M + H)+ |
| 71 | MS (ESI+) m/z: 643.9 (M + H)+ |
| 72 | MS (ESI+) m/z: 639.9 (M + H)+ |
| 73 | MS (ESI+) m/z: 668.8 (M + H)+ |
| 74 | MS (ESI+) m/z: 685.8 (M + H)+ |
| 75 | MS (ESI+) m/z: 683.8 (M + H)+ |
| 76 | MS (ESI+) m/z: 681.8 (M + H)+ |
| 77 | MS (ESI+) m/z: 651.8 (M + H)+ |
| 78 | MS (ESI+) m/z: 665.8 (M + H)+ |
| 79 | MS (ESI+) m/z: 679.8 (M + H)+ |
| 80 | MS (ESI+) m/z: 683.8 (M + H)+ |
| 81 | MS (ESI+) m/z: 677.9 (M + H)+ |
| 82 | MS (ESI+) m/z: 681.6 (M + H)+ |
| 83 | MS (ESI+) m/z: 693.8 (M + H)+ |
| 84 | MS (ESI+) m/z: 671.8 (M + H)+ |
| 85 | MS (ESI+) m/z: 667.8 (M + H)+ |
| 86 | MS (ESI+) m/z: 753.2 (M + H)+ |
| 87 | MS (ESI+) m/z: 653.9 (M + H)+ |
| 88 | MS (ESI+) m/z: 671.6 (M + H)+ |
| 89 | MS (ESI+) m/z: 698.9 (M + H)+ |

TABLE 102-continued

| Ex | Data |
|---|---|
|  | Elemental analysis value as $C_{34}H_{44}Cl_2F_3N_9O_4 + 3.5H_2O$<br>Calculated (%) C: 48.98 H: 6.17 N: 15.12<br>Found (%) C: 48.74 H: 5.86 N: 14.94 |
| 90 | MS(ESI+)m/z 671.3 (M + H)+<br>Elemental analysis value as $C_{33}H_{42}Cl_3F_4N_8O_3 + 0.5H_2O$<br>Calculated (%) C: 50.23 H: 5.37 N: 14.20<br>Found (%) C: 49.98 H: 5.72 N: 13.94 |

TABLE 103

| Ex | Data |
|---|---|
| 91 | MS (ESI+) m/z: 668.9 (M + H)+<br>Elemental analysis value as $C_{33}H_{39}F_3N_9NaO_3 + 3.5H_2O$<br>Calculated (%) C: 52.65 H: 6.16 N: 16.75<br>Found (%) C: 52.60 H: 6.18 N:16.54 |
| 92 | MS (ESI+) m/z: 667.0 (M + H)+ |
| 93 | MS (ESI+) m/z: 683.0 (M + H)+ |
| 94 | MS (ESI+) m/z: 669.9 (M + H)+ |
| 95 | MS (ESI+) m/z: 699.9 (M + H)+ |
| 96 | MS (ESI+) m/z: 722.9 (M + H)+ |
| 97 | MS (ESI+) m/z: 694.9 (M + H)+ |
| 98 | MS (ESI+) m/z: 669.9 (M + H)+<br>Elemental analysis value as $C_{35}H_{42}Cl_2F_4N_6O_3 + 0.5H_2O$<br>Calculated (%) C: 56.00 H: 5.77 N: 11.20<br>Found (%) C: 55.92 H: 5.57 N: 11.15 |
| 99 | MS (ESI+) m/z: 672.9 (M + H)+ |
| 100 | MS (ESI+) m/z: 682.9 (M + H)+ |
| 101 | MS (ESI+) m/z: 671.9 (M + H)+ |
| 102 | MS (ESI+) m/z: 693.0 (M + H)+ |
| 103 | MS (ESI+) m/z: 720.9 (M + H)+ |
| 104 | MS (ESI+) m/z: 709.0 (M + H)+ |
| 105 | MS (ESI+) m/z: 736.9 (M + H)+ |
| 106 | MS (ESI+) m/z: 723.9 (M + H)+ |
| 107 | MS (ESI+) m/z: 670.3 (M + H)+ |
| 108 | MS (ESI+) m/z: 659.9 (M + H)+ |
| 109 | MS (ESI+) m/z: 671.9 (M + H)+ |
| 110 | MS (ESI+) m/z: 672.9 (M + H)+ |
| 111 | MS (ESI+) m/z: 736.9 (M + H)+ |
| 112 | MS (ESI+) m/z: 707.9 (M + H)+ |
| 113 | MS (ESI+) m/z: 713.0 (M + H)+ |
| 114 | MS (ESI+) m/z: 695.0 (M + H)+ |

TABLE 104

| Ex | Data |
|---|---|
| 115 | MS (ESI+) m/z: 698.9 (M + H)+<br>Elemental analysis value as $C_{34}H_{42}F_3N_8NaO_4 + 2.5H_2O$<br>Calculated (%) C: 53.40 H: 6.06 N: 16.48<br>Found (%) C: 53.34 H: 6.30 N:16.33 |
| 116 | MS (ESI+) m/z: 673.9 (M + H)+<br>Elemental analysis value as $C_{32}H_{38}F_3N_8NaO_5 + 3.5H_2O$<br>Calculated (%) C: 50.72 H: 5.99 N: 14.79<br>Found (%) C: 50.72 H: 5.85 N: 14.65 |
| 117 | MS (ESI+) m/z: 685.9 (M + H)+ |
| 118 | MS (ESI+) m/z: 727.0 (M + H)+ |
| 119 | MS (ESI+) m/z: 714.0 (M + H)+<br>Elemental analysis value as $C_{36}H_{43}F_4N_8NaO_3 + 4.5H_2O$<br>Calculated (%) C: 53.00 H: 6.42 N: 13.74<br>Found (%) C: 52.66 H: 6.27 N: 13.64 |
| 120 | MS (ESI+) m/z: 701.0 (M + H)+ |
| 121 | MS (ESI+) m/z: 749.9 (M + H)+ |
| 122 | MS (ESI+) m/z: 699.9 (M + H)+ |
| 123 | MS (ESI+) m/z: 708.9 (M + H)+<br>Elemental analysis value as $C_{36}H_{43}F_3N_9NaO_3 + 2.8H_2O$<br>Calculated (%) C: 55.42 H: 6.28 N: 16.16<br>Found (%) C: 55.41 H: 6.59 N: 16.17 |
| 124 | MS (ESI+) m/z: 659.9 (M + H)+<br>Elemental analysis value as $C_{32}H_{32}F_4N_8NaO_3 + 5H_2O$<br>Calculated (%) C: 49.87 H: 6.15 N: 14.54<br>Found (%) C: 49.52 H: 5.76 N: 14.43 |

TABLE 104-continued

| Ex | Data |
|---|---|
| 125 | MS (ESI+) m/z: 682.0 (M + H)+ |
| 126 | MS (ESI+) m/z: 699.0 (M + H)+ |
| 127 | MS (ESI+) m/z: 687.0 (M + H)+ |
| 128 | MS (ESI+) m/z: 695.0 (M + H)+ |
| 129 | MS (ESI+) m/z: 683.0 (M + H)+ |
| 130 | MS (ESI+) m/z: 699.0 (M + H)+ |

TABLE 105

| Ex | Data |
|---|---|
| 131 | MS (ESI+) m/z: 695.0 (M + H)+ |
| 132 | MS (ESI+) m/z: 687.0 (M + H)+ |
| 133 | MS (ESI+) m/z: 683.0 (M + H)+ |
| 134 | MS (ESI+) m/z: 672.4 (M + H)+<br>Elemental analysis value as $C_{32}H_{39}F_3N_9NaO_4 + 4.5H_2O$<br>Calculated (%) C: 49.61 H: 6.25 N: 16.27<br>Found (%) C: 49.52 H: 5.89 N: 16.28 |
| 135 | MS (ESI+) m/z: 713.0 (M + H)+ |
| 136 | MS (ESI+) m/z: 712.0 (M + H)+ |
| 137 | MS (ESI+) m/z: 722.0 (M + H)+ |
| 138 | MS (ESI+) m/z: 744.5 (M + H)+<br>Elemental analysis value as $C_{34}H_{39}F_3N_9NaO_5S + 3H_2O$<br>Calculated (%) C: 49.81 H: 5.53 N: 15.38<br>Found (%) C: 49.66 H: 5.39 N: 15.30 |
| 139 | MS (ESI+) m/z: 673.0 (M + H)+ |
| 140 | MS (ESI+) m/z: 645.9 (M + H)+ |
| 141 | MS (ESI+) m/z: 657.9 (M + H)+ |
| 142 | MS (ESI+) m/z: 671.9 (M + H)+ |
| 143 | MS (ESI+) m/z: 709.0 (M + H)+ |
| 144 | MS (ESI+) m/z: 727.0 (M + H)+ |
| 145 | MS (ESI+) m/z: 724.0 (M + H)+ |
| 146 | MS (ESI+) m/z: 648.9 (M + H)+ |
| 147 | MS (ESI+) m/z: 713.0 (M + H)+ |
| 148 | MS (ESI+) m/z: 699.0 (M + H)+ |
| 149 | MS (ESI+) m/z: 709.8 (M + H)+ |
| 150 | MS (ESI+) m/z: 709.8 (M + H)+ |
| 151 | MS (ESI+) m/z: 736.0 (M + H)+ |
| 152 | MS (ESI+) m/z: 700.0 (M + H)+ |
| 153 | MS (ESI+) m/z: 677.9 (M + H)+ |
| 154 | MS (ESI+) m/z: 712.9 (M + H)+ |

TABLE 106

| Ex | Data |
|---|---|
| 155 | MS (ESI+) m/z: 712.8 (M + H)+ |
| 156 | MS (ESI+) m/z: 708.9 (M + H)+ |
| 157 | MS (ESI+) m/z: 664.8 (M + H)+ |
| 158 | MS (ESI+) m/z: 662.8 (M + H)+ |
| 159 | MS (ESI+) m/z: 695.8 (M + H)+ |
| 160 | MS (ESI+) m/z: 708.9 (M + H)+ |
| 161 | MS (ESI+) m/z: 735.8 (M + H)+ |
| 162 | MS (ESI+) m/z: 722.8 (M + H)+ |
| 163 | MS (ESI+) m/z: 707.9 (M + H)+<br>Elemental analysis value as $C_{37}H_{44}F_3N_8NaO_3 + 3.4H_2O$<br>Calculated (%) C: 56.25 H: 6.48 N: 14.18<br>Found (%) C: 56.10 H: 6.10 N: 13.96 |
| 164 | MS (ESI+) m/z: 708.8 (M + H)+ |
| 165 | MS (ESI+) m/z: 712.9 (M + H)+ |
| 166 | MS (ESI+) m/z: 726.9 (M + H)+ |
| 167 | MS (ESI+) m/z: 736.8 (M + H)+ |
| 168 | MS (ESI+) m/z: 737.8 (M + H)+ |
| 169 | MS (ESI+) m/z: 722.9 (M + H)+ |
| 170 | MS (ESI+) m/z: 725.9 (M + H)+ |
| 171 | MS (ESI+) m/z: 679.8 (M + H)+ |
| 172 | MS (ESI+) m/z: 711.8 (M + H)+ |
| 173 | MS (ESI+) m/z: 701.7 (M + H)+ |
| 174 | MS (ESI+) m/z: 683.6 (M + H)+ |
| 175 | MS (ESI+) m/z: 693.9 (M + H)+ |
| 176 | MS (ESI+) m/z: 670.5 (M + H)+ |
| 177 | MS (ESI+) m/z: 727.5 (M + H)+ |
| 178 | MS (ESI+) m/z: 707.5 (M + H)+ |
| 179 | MS (ESI+) m/z: 733.5 (M + H)+ |

TABLE 106-continued

| Ex | Data |
|---|---|
| 180 | MS (ESI+) m/z: 641.3 (M + H)+ |
| 181 | MS (ESI+) m/z: 649.9 (M + H)+ |

TABLE 107

| Ex | Data |
|---|---|
| 182 | MS (ESI+) m/z: 690.9 (M + H)+ |
| 183 | MS (ESI+) m/z: 668.9 (M + H)+ |
| 184 | MS (ESI+) m/z: 637.9 (M + H)+ |
| 185 | MS (ESI+) m/z: 641.9 (M + H)+ |
| 186 | MS (ESI+) m/z: 654.3 (M + H)+ |
| 187 | MS (ESI+) m/z: 671.3 (M + H)+ |
| 188 | MS (ESI+) m/z: 645.5 (M + H)+ |
| 189 | MS (ESI+) m/z: 684.9 (M + H)+ |
| 190 | MS (ESI+) m/z: 694.9 (M + H)+ |
| 191 | MS (ESI+) m/z: 693.0 (M + H)+<br>Elemental analysis value as $C_{37}H_{44}F_3N_7O_3 \cdot 2HCl + 2.6H_2O$<br>Calculated (%) C: 54.67 H: 6.36 N: 12.08<br>Found (%) C: 54.77 H: 6.47 N: 11.96 |
| 192 | MS (ESI+) m/z: 711.0 (M + H)+<br>Elemental analysis value as $C_{37}H_{46}F_3N_7O_4 \cdot 2HCl + 2.7H_2O$<br>Calculated (%) C: 53.45 H: 6.47 N: 11.79<br>Found (%) C: 53.48 H: 6.40 N: 11.74 |
| 193 | MS (ESI+) m/z: 707.0 (M + H)+<br>Elemental analysis value as $C_{38}H_{46}F_3N_7O_3 \cdot 2HCl + 2.5H_2O$<br>Calculated (%) C: 55.40 H: 6.49 N: 11.90<br>Found (%) C: 55.34 H: 6.34 N: 11.79 |
| 194 | MS (ESI+) m/z: 722.0 (M + H)+ |
| 195 | MS (ESI+) m/z: 680.9 (M + H)+<br>Elemental analysis value as $C_{34}H_{39}F_3N_9NaO_3 + 2.3H_2O$<br>Calculated (%) C: 54.95 H: 5.91 N: 16.96<br>Found (%) C: 55.29 H: 6.27 N: 16.82 |
| 196 | MS (ESI+) m/z: 695.0 (M + H)+<br>Elemental analysis value as $C_{35}H_{42}F_3N_9NaO_3 + 2.6H_2O$<br>Calculated (%) C: 55.13 H: 6.11 N: 16.53<br>Found (%) C: 55.42 H: 6.41 N: 16.32 |

TABLE 108

| Ex | Data |
|---|---|
| 197 | MS (ESI+) m/z: 694.9 (M + H)+ |
| 198 | MS (ESI+) m/z: 709.0 (M + H)+<br>Elemental analysis value as $C_{36}H_{43}F_3N_9NaO_3 + 4.1H_2O$<br>Calculated (%) C: 53.80 H: 6.42 N: 15.69<br>Found (%) C: 53.50 H: 6.03 N: 15.47 |
| 199 | MS (ESI+) m/z: 680.9 (M + H)+<br>Elemental analysis value as $C_{34}H_{39}F_3N_9NaO_3 + 3.6H_2O$<br>Calculated (%) C: 53.27 H: 6.08 N: 16.45<br>Found (%) C: 53.08 H: 5.82 N: 16.20 |
| 200 | MS (ESI+) m/z: 680.9 (M + H)+<br>Elemental analysis value as $C_{34}H_{39}F_3N_9NaO_3 + 4.1H_2O$<br>Calculated (%) C: 52.65 H: 6.13 N: 16.25<br>Found (%) C: 52.31 H: 5.80 N: 16.09 |
| 201 | MS (ESI+) m/z: 712.0 (M + H)+<br>Elemental analysis value as $C_{36}H_{42}F_4N_8NaO_3 + 4.2H_2O$<br>Calculated (%) C: 53.49 H: 6.16 N: 13.86<br>Found (%) C: 53.25 H: 5.89 N: 13.70 |
| 202 | MS (ESI+) m/z: 684.4 (M + H)+<br>Elemental analysis value as $C_{33}H_{39}F_3N_9NaO_4 + 5H_2O$<br>Calculated (%) C: 49.81 H: 6.21 N: 15.84<br>Found (%) C: 49.96 H: 5.82 N: 15.92 |
| 203 | MS (ESI+) m/z: 709.0 (M + H)+<br>Elemental analysis value as $C_{36}H_{43}F_3N_9NaO_3 + 3.6H_2O$<br>Calculated (%) C: 54.29 H: 6.12 N: 15.80<br>Found (%) C: 54.41 H: 6.37 N: 15.86 |
| 204 | MS (ESI+) m/z: 666.8 (M + H)+ |
| 205 | MS (ESI+) m/z: 677.9 (M + H)+ |
| 206 | MS (ESI+) m/z: 720.9 (M + H)+<br>Elemental analysis value as $C_{39}H_{42}F_3N_2NaO_3 + 3.7H_2O$<br>Calculated (%) C: 57.94 H: 6.78 N: 12.13<br>Found (%) C: 57.95 H: 6.74 N: 12.00 |

TABLE 109

| Ex | Data |
|---|---|
| 207 | MS (ESI+) m/z: 724.9 (M + H)+<br>Elemental analysis value as $C_{37}H_{45}F_3N_2NaO_3 + 4H_2O$<br>Calculated (%) C: 56.70 H: 6.54 N: 12.07<br>Found (%) C: 56.41 H: 6.78 N:12.45 |
| 208 | MS (ESI+) m/z: 725.8 (M + H)+<br>Elemental analysis value as $C_{37}H_{43}F_4N_8NaO_3 + 3.5H_2O$<br>Calculated (%) C: 54.88 H: 6.22 N: 13.84<br>Found (%) C: 54.80 H: 6.06 N: 13.68 |
| 209 | MS (ESI+) m/z: 667.9 (M + H)+ |
| 210 | MS (ESI+) m/z: 681.9 (M + H)+ |
| 211 | MS (ESI+) m/z: 743.9 (M + H)+ |
| 212 | MS (ESI+) m/z: 654.4 (M + H)+ |
| 213 | MS (ESI+) m/z: 669.3 (M + H)+ |

Biological test examples of the compounds of the present invention are described below.

Pharmacological activity of each compound was evaluated in the following tests. Each compound may be referred to as "test compound" in the following descriptions.

Test Example 1: Evaluation of M3 PAM Activity

CHO-K1 cells in which human muscarinic M3 receptor gene (GenBank registered number: NM_000740.2) was transducted to express M3 receptor stably (hereinafter also referred to as "M3R expressing cells") were subcultured in a growth medium at 37° C., 5% $CO_2$. For growth medium, alpha Modified Eagle Minimum Essential Medium (α-MEM, D8042, Sigma) containing final concentration of 10% inactivated fetal bovine serum (Cat. No. 172012, Sigma), final concentration of 2 mM GlutaMAX® (Cat. No. 35050, GIBCO), final concentration of 20 U/mL of penicillin and final concentration of 20 μg/mL of streptomycin (penicillin-streptomycin mixed solution, Cat. No. 26253-84, NACALAI TESQUE, INC.), and final concentration of 0.2 mg/mL G418 (Cat. No. 16513-26, NACALAI TESQUE, INC.) was used.

On the day before measurement of intracellular $Ca^{2+}$ concentration, the M3R expressing cells were suspended in the growth medium and seeded at 40,000 cells/well on a 96-well black plate with clear bottom (Cat. No. 215006, Porvair Sciences). The M3R expressing cells seeded on the 96-well plate were cultured at 37° C., 5% $CO_2$.

Intracellular $Ca^{2+}$ concentration in the M3R expressing cells was measured using a calcium assay kit (Screen Quest® Fluo-8 Medium Removal Calcium Assay Kit, Cat. No. 36309, AAT Bioquest) according to the attached instructions. On the day of the measurement, the growth medium was removed, and 100 μL/well of loading buffer was added to the 96-well plate. After culturing at 37° C., 5% $CO_2$ for 30 minutes, the plate was left at room temperature for 30 minutes, whereby the M3R expressing cells were loaded with visible light-excited calcium indicator (Fluo-8®, AAT Bioquest). A buffer containing the calcium indicator was used as loading buffer. The buffer used was Hanks' Balanced Salt Solution (HBSS buffer) (pH 7.4) containing final concentration of 20 mM HEPES (Cat. No. 340-01371, Dojindo Molecular Technologies, Inc.) and final concentration of 2.5 mM probenecid (165-15472, Wako Pure Chemical Corporation). Hanks' Balanced Salt Solution was prepared by 10-fold dilution of 10×HBSS (Cat. No. 14065-056, GIBCO) with ultrapure water.

Then, the 96-well plate was placed in fluorescence screening system (FLIPR TETRA®, Molecular Devices) and fluorescence intensity, which depends on the intracellular $Ca^{2+}$ concentration induced by a test compound, was measured. In the measurement of fluorescence intensity, the excitation wavelength was in the range of 470-495 nm and the fluorescence wavelength was in the range of 515-575 nm.

The test compound in a vehicle or a vehicle alone was added to the 96-well plate, and fluorescence intensity was measured for 2 minutes. HBSS buffer was used as a vehicle. The test compound was dissolved in dimethyl sulfoxide and added to the buffer. The final concentration of dimethyl sulfoxide was 2.5%. The final concentration of the test compound was varied within the range of 0-30 μM. Then, $EC_{20}$ (20% Effective Concentration) of acetylcholine which results in about 20% of maximum activity was added, and fluorescence intensity was measured for 1 minute. The $EC_{20}$ was about 10-30 nM.

The fluorescence intensity Lb, where HBSS buffer alone instead of the same containing a test compound and final concentration of 100 μM acetylcholine were added, was defined as 100%. The fluorescence intensity La, where HBSS buffer alone instead of the same containing a test compound was added in presence of $EC_{20}$ acetylcholine, was defined as 0%. In addition, a fluorescence intensity was defined as Lc where a test compound was added. The enhancement ratio Gr (unit: %) of fluorescence intensity induced by a test compound was calculated according to the following equation (1). Based on the enhancement ratio Gr, M3 PAM activities of test compounds were evaluated.

$$Gr = 100 \times (Lc - La)/(Lb - La) \quad (1)$$

Based on the enhancement ratio Gr for each concentration of the test compound, $EC_{50}$ (50% Effective Concentration) of the enhancement ratio Gr was estimated from the logistic equation, using statistics program (SASsystem, SAS Institute Japan). The results of the tests are shown in Tables 110 to 115. A lower $EC_{50}$ of the enhancement ratio Gr was considered as corresponding to a higher M3 PAM activity.

TABLE 110

| Test Compound (Example No.) | $EC_{50}$ (nM) |
| --- | --- |
| 1 | 2.14 |
| 2 | 2.59 |
| 3 | 3.04 |
| 4 | 0.288 |
| 5 | 2.83 |
| 6 | 1.40 |
| 7 | 0.923 |
| 8 | 4.92 |
| 9 | 3.06 |
| 10 | 4.58 |
| 11 | 2.66 |
| 12 | 2.86 |
| 13 | 0.500 |
| 14 | 2.17 |
| 15 | 0.557 |
| 16 | 2.07 |
| 17 | 4.58 |
| 18 | 5.24 |
| 19 | 4.74 |
| 20 | 2.33 |
| 21 | 3.67 |
| 22 | 1.39 |
| 23 | 5.73 |
| 24 | 7.42 |
| 25 | 3.48 |
| 26 | 0.566 |
| 27 | 1.52 |
| 28 | 9.98 |
| 29 | 3.01 |
| 30 | 2.39 |
| 31 | 1.85 |
| 32 | 6.67 |
| 33 | 5.23 |
| 34 | 9.42 |
| 35 | 1.46 |
| 36 | 1.24 |
| 37 | 0.930 |
| 38 | 0.690 |
| 39 | 1.00 |
| 40 | 1.03 |

TABLE 111

| Test Compound (Example No.) | $EC_{50}$ (nM) |
| --- | --- |
| 41 | 4.99 |
| 42 | 0.949 |
| 43 | 1.70 |
| 44 | 2.64 |
| 45 | 8.13 |
| 46 | 4.40 |
| 47 | 2.25 |
| 48 | 4.86 |
| 49 | 1.44 |
| 50 | 1.54 |
| 51 | 0.538 |
| 52 | 1.42 |
| 53 | 2.97 |
| 54 | 5.36 |
| 55 | 0.425 |
| 56 | 1.02 |
| 57 | 1.11 |
| 58 | 2.54 |
| 59 | 0.498 |
| 60 | 0.414 |
| 61 | 3.35 |
| 62 | 4.22 |
| 63 | 3.45 |
| 64 | 3.63 |
| 65 | 2.86 |
| 66 | 3.17 |
| 67 | 2.81 |
| 68 | 1.96 |
| 69 | 2.10 |
| 70 | 1.68 |
| 71 | 1.89 |
| 72 | 1.27 |
| 73 | 6.36 |
| 74 | 5.58 |
| 75 | 7.23 |
| 76 | 8.63 |
| 77 | 4.86 |
| 78 | 2.43 |
| 79 | 4.33 |
| 80 | 4.18 |

TABLE 112

| Test Compound (Example No.) | $EC_{50}$ (nM) |
| --- | --- |
| 81 | 4.68 |
| 82 | 9.98 |

TABLE 112-continued

| Test Compound (Example No.) | EC$_{50}$ (nM) |
|---|---|
| 83 | 7.91 |
| 84 | 4.82 |
| 85 | 7.00 |
| 86 | 1.55 |
| 87 | 4.27 |
| 88 | 2.00 |
| 89 | 0.879 |
| 90 | 2.05 |
| 91 | 0.279 |
| 92 | 0.552 |
| 93 | 0.596 |
| 94 | 0.409 |
| 95 | 0.266 |
| 96 | 0.466 |
| 97 | 0.283 |
| 98 | 1.45 |
| 99 | 0.415 |
| 100 | 0.379 |
| 101 | 2.70 |
| 102 | 0.581 |
| 103 | 0.582 |
| 104 | 0.605 |
| 105 | 0.935 |
| 106 | 0.140 |
| 107 | 0.489 |
| 108 | 1.04 |
| 109 | 1.59 |
| 110 | 0.761 |
| 111 | 1.93 |
| 112 | 6.51 |
| 113 | 0.444 |
| 114 | 1.48 |
| 115 | 2.46 |
| 116 | 0.417 |
| 117 | 2.67 |
| 118 | 0.871 |
| 119 | 2.08 |
| 120 | 0.558 |

TABLE 113

| Test Compound (Example No.) | EC$_{50}$ (nM) |
|---|---|
| 121 | 1.98 |
| 122 | 0.585 |
| 123 | 0.784 |
| 124 | 2.25 |
| 125 | 0.695 |
| 126 | 1.99 |
| 127 | 4.23 |
| 128 | 1.58 |
| 129 | 2.52 |
| 130 | 1.57 |
| 131 | 1.37 |
| 132 | 1.31 |
| 133 | 1.14 |
| 134 | 0.503 |
| 135 | 0.391 |
| 136 | 1.92 |
| 137 | 1.98 |
| 138 | 0.548 |
| 139 | 0.248 |
| 140 | 1.61 |
| 141 | 2.00 |
| 142 | 3.63 |
| 143 | 0.784 |
| 144 | 1.38 |
| 145 | 3.14 |
| 146 | 4.77 |
| 147 | 0.331 |
| 148 | 0.648 |
| 149 | 0.310 |
| 150 | 1.21 |
| 151 | 6.81 |
| 152 | 1.43 |
| 153 | 4.87 |
| 154 | 2.86 |
| 155 | 0.768 |
| 156 | 0.376 |
| 157 | 2.78 |
| 158 | 9.08 |
| 159 | 1.12 |
| 160 | 4.93 |

TABLE 114

| Test Compound (Example No.) | EC$_{50}$ (nM) | Test Compound (Example No.) | EC$_{50}$ (nM) |
|---|---|---|---|
| 161 | 1.48 | 181 | 2.43 |
| 162 | 2.77 | 182 | 1.57 |
| 163 | 3.55 | 183 | 1.61 |
| 164 | 4.22 | 184 | 2.35 |
| 165 | 1.73 | 185 | 2.26 |
| 166 | 1.11 | 186 | 9.64 |
| 167 | 2.64 | 187 | 4.96 |
| 168 | 4.72 | 188 | 3.62 |
| 169 | 5.25 | 189 | 1.49 |
| 170 | 2.10 | 190 | 0.168 |
| 171 | 6.39 | 191 | 0.269 |
| 172 | 4.52 | 192 | 0.912 |
| 173 | 3.78 | 193 | 0.826 |
| 174 | 3.41 | 194 | 0.703 |
| 175 | 0.617 | 195 | 0.422 |
| 176 | 3.09 | 196 | 0.563 |
| 177 | 1.68 | 197 | 1.06 |
| 178 | 1.75 | 198 | 0.820 |
| 179 | 0.761 | 199 | 0.966 |
| 180 | 0.381 | 200 | 0.694 |

TABLE 115

| Test Compound (Example No.) | EC$_{50}$ (nM) |
|---|---|
| 201 | 5.26 |
| 202 | 1.57 |
| 203 | 1.13 |
| 204 | 9.56 |
| 205 | 9.98 |
| 206 | 2.66 |
| 207 | 4.14 |
| 208 | 9.35 |
| 209 | 4.65 |
| 210 | 2.19 |
| 211 | 3.64 |
| 212 | 0.846 |
| 213 | 4.74 |

As shown in Tables 110 to 115, all of the test compounds were found to have a high M3 PAM activity.

In the absence of acetylcholine, an addition of a test compound alone did not increase fluorescence intensity. This showed that the test compounds do not have M3 receptor agonist activity.

Test Example 2: Effect on the Increase in Intravesical Pressure Induced by Electrical Stimulation of the Pelvic Nerve in Anesthetized Rats For evaluation of in vivo effect on neurogenic bladder contraction, effects of the test compounds on the increase in intravesical pressure induced by electrical stimulation of the pelvic nerve in rats were determined according to the following method.

SD female rats (Japan SLC, Inc.) were anesthetized by subcutaneous administration of 1200 mg/kg of urethane (Wako Pure Chemical Corporation), and the lower abdomens of the rats were incised in the midline. After the ureters were ligated and cut at locations proximal to the bladder, a cannula (PE-60, BECTON DICKINSON) for cystometry was inserted into the bladder through the external urethral orifice and fixed with sutures. After injecting saline (about 200 μL) via the cannula inserted into the bladder, the other end of the cannula was connected to a pressure transducer to measure intravesical pressure.

The pelvic nerve near the urinary bladder of the rat was gently separated and dissected under stereomicroscope observation and attached to an electrode for nerve stimulation (K2-14015M-PT, BrainScience idea. Co., Ltd.). The peritoneal cavity of the rat was filled with liquid paraffin (26114-75, NACALAI TESQUE, INC.). After the postoperative rest period, an electrical stimulator (SEN-7203, NIHON KOHDEN CORPORATION) was used to stimulate the pelvic nerve to induce increase in intravesical pressure. The stimulation frequency was 8 Hz, the pulse width was 0.3 ms, and the stimulation time was 10 seconds. The voltage of the electrical stimulator was adjusted so that the increase in intravesical pressure was about 50-70% of that at stimulation with 10 V.

The electric stimulation was repeated with an interval of 10 minutes. After the increase of intravesical pressure induced by electric stimulation was stabilized three times or more, a test compound (dosage 0.3 mg/kg), distigmine bromide (dosage 0.03, 0.1 mg/kg) or a vehicle was intravenously administered at 1.0 mL/kg via the catheter placed into femoral vein. The effect of the test compound on increase of intravesical pressure was measured for 1 hour. Saline was used as a vehicle, and the test compound was dissolved in dimethyl sulfoxide before adding to the vehicle. The final concentration of dimethyl sulfoxide was 10%.

The response data (intravesical pressure) were recorded on a personal computer via data collection and analysis system (PowerLab®, ADInstruments) and analyzed using analysis software (LabChart®, ADInstruments). For each electric stimulation, AUC of increase of intravesical pressure (area under the curve of transition of intravesical pressure) was calculated, and percentage change Rc (unit: %) compared to the value (AUC) before the administration of the test compound was calculated according to the following equation (2). In the equation (2), Ab is AUC before administering a test compound, and Aa is AUC after administering a test compound. In addition, the maximum effect observed during 1 hour after administering the test compound (maximum percentage change Rc) was defined as the effect of the test compound. The higher percentage change Rc, the higher effect on enhancement of bladder contraction force and increase of intravesical pressure. The result of the test is shown in Table 116.

$$Rc = 100 \times (Aa - Ab)/Ab \quad (2)$$

TABLE 116

| Test Compound (Example No.) | Percentage Change (%) |
|---|---|
| 1 | 325.6 |
| 2 | 330.7 |

TABLE 116-continued

| Test Compound (Example No.) | Percentage Change (%) |
|---|---|
| 3 | 311.0 |
| 4 | 122.8 |
| 6 | 570.8 |
| 7 | 608.5 |
| 8 | 374.0 |
| 10 | 82.6 |
| 11 | 270.4 |
| 14 | 400.0 |
| 15 | 275.9 |
| 16 | 182.5 |
| 20 | 249.3 |
| 37 | 91.2 |
| 38 | 98.1 |
| 42 | 119.1 |
| 68 | 133.1 |

All of the test compounds showed an enhancement effect on bladder contractility. While distigmine bromide showed enhancement of bladder contractility, a nicotinic side effect (fasciculation) was observed at 0.1 mg/kg.

Also, the compounds evaluated in this test did not induce increase of intravesical pressure under the condition without electrical stimulation to rat. This confirmed that a test compound alone did not induce a rise in intravesical pressure.

From the above, it was found that the test compounds in Table 116, when used alone, do not induce bladder contraction, but have an effect of enhancing bladder contraction induced by electrical stimulation of the pelvic nerve.

As described above, the test compounds were found to have in vitro M3 PAM activities. Also, the test compounds were found to enhance increase of intravesical pressure depending on nerve stimulus.

Further, while the test compounds alone did not have agonist activities against M3 receptor, they have an effect of bladder contraction enhancement depending on nerve stimulus. This enables the test compounds having M3 PAM activity to enhance signal level of M3 receptor under more physiological conditions, and they are expected to be therapeutically promising for diseases in which M3 receptor is involved. In addition, the test compounds may avoid a cholinergic side effect (cholinergic crisis) which has been reported on well-known medicaments (for example, distigmine bromide), and thus, the compounds may be therapeutic agents with excellent safety.

Test Example 3: Effect in Rat Lumbar Spinal Canal Stenosis Model 8 weeks-aged SD female rats (CLEA Japan, Inc.) are anesthetized with an intraperitoneal injection of a mixed anesthesia of 40 mg/kg ketamine (Ketalar®, DAIICHI SANKYO COMPANY, LIMITED) and 5 mg/kg xylazine (Selactar®, Bayer Yakuhin, Ltd). Under the anesthesia, the back of the rat is incised to expose the fifth and sixth lumbar arches.

The 5th lumbar arch is drilled to make a hole (about 1.5 mm of diameter), and a piece of silicone rubber (KOKUGO Co., Ltd.) is inserted into the epidural space between the 5th and 6th lumbar vertebrae to compress cauda equina nerve of the rat. The rat subjected to the compression of cauda equina nerve may be referred to as "operated rat" hereinafter. The piece is formed into a shape having 3.5 mm of length, 5.0 mm of width, and 0.5 mm of thickness. After inserting the piece, the incision is closed by suturing the incision. Subsequently, antibiotics (viccillin for injection, 100 mg per a rat, Meiji Seika Co., Ltd.) are administered systemically to the operated rat.

After two weeks from the surgery, a certain amount of injectable water (hereinafter referred to as "water") was administered orally to the operated rats. Subsequently, the operated rats are taken in a metabolism cage (Natsume Seisakusho Co., Ltd), and its urination within 6 hours after the start of water loading is determined. One hour before the water loading, a test compound or distigmine bromide in 0.5% aqueous methylcellulose (vehicle) or a vehicle alone is administered orally to the operated rats. The amount of urination is determined using the electronic balance (GX-200, A&D Company, Limited), and the data are recorded on a personal computer via data collection and analysis system (PowerLab®, ADInstruments) and analyzed using the analysis software (LabChart®, ADInstruments). The metabolism cage has 230 mm of width, 220 mm of length, and 150 mm of height.

The total amount of urination in 6 hours after water loading is evaluated. Further, the operated rats are taken out from the metabolism cage 6 hours after the start of water loading. The lower abdomens of the operated rats are pushed with finger to make urination to measure residual urine.

As described in Test Example 1 and Test Example 2, since a compound of the present invention has M3 PAM activity, and is effective to in in vivo models, it can be useful as a preventive or therapeutic agent for underactive bladder, hypotonic bladder, acontractile bladder, detrusor underactivity, and voiding or storage dysfunction in neurogenic bladder.

Formulation Example 1

Tablet (Oral)
In 80 mg tablet of Formulation 1:

| Compound of Example 1 | 5.0 mg |
| Corn starch | 46.6 mg |
| Crystalline cellulose | 24.0 mg |
| Methylcellulose | 4.0 mg |
| Magnesium stearate | 0.4 mg |

According to a conventional method, a mixed powder of the components is compressed to form an oral tablet.

INDUSTRIAL APPLICABILITY

Since a compound of the present invention or a pharmaceutically acceptable salt thereof has M3 PAM activity, it can be useful as a preventive or therapeutic agent for voiding and/or storage disorders in bladder/urethral diseases, glaucoma, or diabetes, in which M3 receptor is involved.

The invention claimed is:
1. An azabenzimidazole compound of the formula [1]:

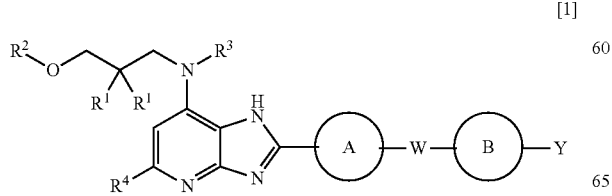

wherein:
$R^1$ is a hydrogen atom or alkyl, or two $R^1$ are taken together with adjacent carbon atom to form a 3- to 7-membered cycloalkyl or an oxygen-containing non-aromatic heterocycle;
$R^2$ is a hydrogen atom, alkyl, cycloalkyl, alkyl substituted with cycloalkyl, or alkoxyalkyl;
$R^3$ is a hydrogen atom, alkyl, or alkoxyalkyl;
$R^4$ is pyridyl optionally substituted with one or two groups selected from the group consisting of alkyl, trihaloalkyl, alkoxy, cyano and cycloalkyl, or phenyl optionally substituted with 1 to 3 groups selected from the group consisting of trihaloalkyl, halogen, alkoxy and cycloalkyl;
A is a group of the formula A-1, A-2, A-3, A-4, or A-5:

wherein the bond on the left side of each group is attached to the 2-position of the azabenzimidazole in the formula [1], and the bond on the right side is attached to W in the formula [1], and R" is a group selected from a hydrogen atom, halogen, alkyl, alkoxy or nitro;
W is a bond, or a group of the formula W-1, W-2, or W-3:

wherein $R^{21}$ is a hydrogen atom or alkyl;

B is a group of the formula B-1, B-2, B-3, or B-4:

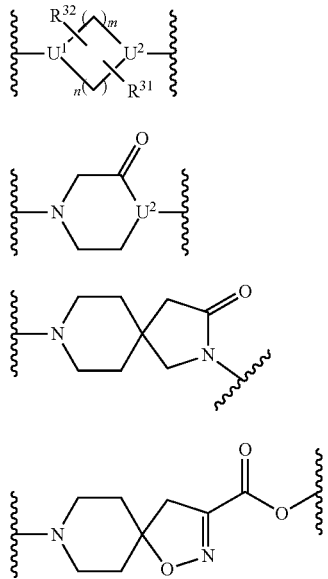

wherein
- the bond on the left side of each group is attached to W in the formula [1],
- the bond on the right side is attached to Y in the formula [1],
- $U^1$ is a nitrogen atom or $CR^{41}$, and $U^2$ is a nitrogen atom or $CR^{42}$, and $R^{41}$ and $R^{42}$ are independently a hydrogen atom, alkyl, halogen or a hydroxyl group, m and n are independently 1, 2 or 3, and $R^{31}$ and $R^{32}$ are independently a hydrogen atom, alkyl, halogen or alkoxyalkyl, or $R^{31}$ and $R^{32}$ are taken together with adjacent carbon atoms to form an alkylene bridge, provided that $R^{31}$ and $R^{32}$ substitute at any substitutable position other than $U^1$ and $U^2$;
- Y is a hydrogen atom, or a group of any one of the formula Y-1 to Y-4 and Y-11 to Y-16:

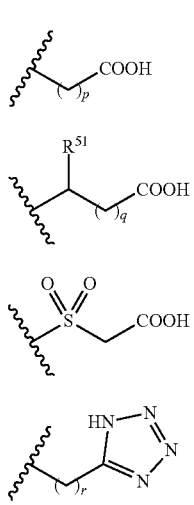

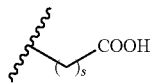

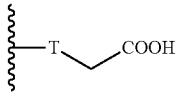

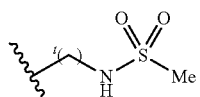

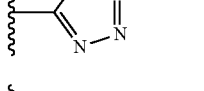

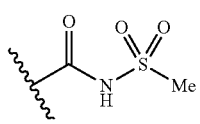

wherein
$R^{51}$ is alkyl; p is 1, 2, or 3; q is 0, 1, or 2; r is 1, 2, or 3; T is O, S, $SO_2$, or $NR^{61}$ wherein
$R^{61}$ is a hydrogen atom or alkyl; s is 0, 1, 2, or 3; and t is 0 or 1, with the proviso that
(a) when W is a bond,
- if B is B-1 or B-2 and $U^2$ is a nitrogen atom, then Y is Y-1, Y-2, Y-3, or Y-4,
- if B is B-1 or B-2 and $U^2$ is $CR^{42}$ wherein $R^{42}$ is as defined above, then $U^1$ is a nitrogen atom and Y is Y-11, Y-12, Y-13, Y-14, Y-15, or Y-16, and
- if B is B-3 or B-4, then Y is a hydrogen atom;

(b) when W is W-1,
- if B is B-1, $U^1$ is a nitrogen atom, and $U^2$ is a nitrogen atom, then Y is Y-1, Y-2, Y-3, or Y-4, and
- if B is B-1, $U^1$ is a nitrogen atom, and $U^2$ is $CR^{42}$ wherein $R^{42}$ is as defined above, then Y is Y-11, Y-12, Y-13, Y-14, Y-15, or Y-16;

(c) when W is W-2,
- if B is B-1 or B-2, $U^1$ is a nitrogen atom, and $U^2$ is a nitrogen atom, then Y is Y-1, Y-2, Y-3, or Y-4,
- if B is B-1 or B-2, $U^1$ is a nitrogen atom, and $U^2$ is $CR^{42}$ wherein $R^{42}$ is as defined above, then Y is Y-11, Y-12, Y-13, Y-14, Y-15, or Y-16, and
- if B is B-3 or B-4, then Y is a hydrogen atom; and (d) when W is W-3,
- if B is B-1, $U^1$ is $CR^{41}$ wherein $R^{41}$ is as defined above, and $U^2$ is a nitrogen atom, then Y is Y-1, Y-2, Y-3, or Y-4, or a pharmaceutically acceptable salt thereof, or a solvate thereof.

2. The azabenzimidazole compound according to claim 1, or a pharmaceutically acceptable salt thereof, or a solvate thereof, wherein W is a bond.

3. The azabenzimidazole compound according to claim 1, or a pharmaceutically acceptable salt thereof, or a solvate thereof, wherein
(1) B is B-1 or B-2, $U^2$ is a nitrogen atom, and Y is Y-1, Y-2 or Y-3;
(2) B is B-1 or B-2, $U^2$ is $CR^{42}$, and Y is Y-11, Y-12 or Y-15; or
(3) B is B-4 and Y is a hydrogen atom.

4. The azabenzimidazole compound according to claim 3, or a pharmaceutically acceptable salt thereof, or a solvate thereof, wherein $R^4$ is pyridyl substituted with a group selected from the group consisting of alkyl, trihaloalkyl, alkoxy, cyano and cycloalkyl, and with trihaloalkyl.

5. The azabenzimidazole compound according to claim 4, or a pharmaceutically acceptable salt thereof, or a solvate thereof, wherein A is A-4.

6. The azabenzimidazole compound according to claim 1, wherein the compound is any one of the following (1) to (213), or a pharmaceutically acceptable salt thereof, or a solvate thereof:

(1) 1-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylic acid, (2) 1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid, (3) 1-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)piperidine-4-carboxylic acid, (4) {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid, (5) 3-[4-(5-{5-[2-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid, (6) 3-[4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperazin-1-yl]propaonic acid, (7) 3-[(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propaonic acid, (8) 3-[(2S)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propaonic acid, (9) 1-(5-{5-[2-ethoxy-6-(trifluoromethyl)pyridin-4-yl]-7-({[1-(methoxymethyl)cyclopentyl]methyl}amino)-1H-imidazo[4,5-b]pyridin-2-yl}pyrazin-2-yl)piperidine-4-carboxylic acid,

(10) [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenoxy)piperidin-1-yl]acetic acid,

(11) 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid,

(12) 3-[4-fluoro-4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperidine-1-yl]propaonic acid,

(13) 3-[4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propaonic acid,

(14) 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propaonic acid,

(15) {[(1R,3r,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid,

(16) 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propaonic acid,

(17) [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidin-1-yl]acetic acid,

(18) 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}phenyl)piperidine-4-carboxylic acid,

(19) [4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)-4-hydroxypiperidin-1-yl]acetic acid,

(20) 3-[(3R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid,

(21) 1-(4-{5-[3-fluoro-5-(trifluoromethyl)phenyl]-7-[(3-methoxy-2,2-dimethylpropyl)(methyl)amino]-1H-imidazo[4,5-b]pyridin-2-yl}phenyl)piperidine-4-carboxylic acid,

(22) [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]acetic acid,

(23) 5-[3-fluoro-5-(trifluoromethyl)phenyl]-N-{[1-(methoxymethyl)cyclobutyl]methyl}-N-methyl-2-{5-[4-(1H-tetrazol-5-yl)piperidine-1-yl]pyrazin-2-yl}-1H-imidazo[4,5-b]pyridin-7-amine,

(24) 8-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-2,8-diazaspiro[4.5]decan-3-one,

(25) 1-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-N-(methanesulfonyl)piperidine-4-carboxamide,

(26) [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidin-1-yl]acetic acid, (27)₂—[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]propaonic acid,

(28) 1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperidine-4-carboxylic acid,

(29) {4-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)ethyl]piperazin-1-yl}acetic acid,

(30) 4-hydroxy-1-(5-{7-[{[1-(methoxymethyl)cyclobutyl]methyl}(methyl)amino]-5-[3-(trifluoromethyl)phenyl]-1H-imidazo[4,5-b]pyridin-2-yl}pyrazin-2-yl)piperidine-4-carboxylic acid,

(31) 8-(4-{7-[{[1-(methoxymethyl)cyclobutyl]methyl}(methyl)amino]-5-[3-(trifluoromethyl)phenyl]-1H-imidazo[4,5-b]pyridin-2-yl}phenyl)-1-oxa-2,8-diazaspiro[4.5]dec-2-ene-3-carboxylic acid,

(32) 1-(5-{7-[{[1-(methoxymethyl)cyclobutyl]methyl}(methyl)amino]-5-[4-methoxy-3-(trifluoromethyl)phenyl]-1H-imidazo[4,5-b]pyridin-2-yl}pyrazin-2-yl)piperidine-4-carboxylic acid,

(33) 8-(4-{7-[{[1-(methoxymethyl)cyclobutyl]methyl}(methyl)amino]-5-[5-(trifluoromethyl)pyridin-3-yl]-1H-imidazo[4,5-b]pyridin-2-yl}phenyl)-1-oxa-2,8-diazaspiro[4.5]dec-2-ene-3-carboxylic acid,

(34) 1-(4-{7-[{[1-(methoxymethyl)cyclobutyl]methyl}(methyl)amino]-5-[3-(trifluoromethyl)phenyl]-1H-imidazo[4,5-b]pyridin-2-yl}phenyl)pyrrolidine-3-carboxylic acid,

(35) {4-[(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)methyl]piperazin-1-yl}acetic acid,

(36) 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]propaonic acid,

(37) [4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]acetic acid,

(38) 4-fluoro-1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-carboxylic acid,

(39) [4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)piperazin-1-yl]acetic acid,

(40) N-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidine-4-yl]-N-methylglycine,

(41) [4-(4-{7-[{[1-(methoxymethyl)cyclobutyl]methyl}(methyl)amino]-5-[5-(trifluoromethyl)pyridin-3-yl]-1H-imidazo[4,5-b]pyridin-2-yl}phenyl)piperazin-1-yl]acetic acid,

(42) 1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid,

(43) [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)-4-hydroxypiperidine-1-yl]acetic acid,

(44) 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-oxopiperazin-1-yl]propaonic acid,

(45) 3-[4-(5-{5-[2-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propaonic acid,

(46) [4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-1,4-diazepan-1-yl]acetic acid,

(47) 3-[(2S)-4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid,

(48) 4-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoic acid,

(49) N-[1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-yl]glycine,

(50) {[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidine-4-yl]oxy}acetic acid,

(51) {[1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-yl]oxy}acetic acid,

(52) N-[1-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidine-4-yl]glycine,

(53) [4-(6-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-3-yl)-1,4-diazepan-1-yl]acetic acid,

(54) [4-(5-{5-[3-fluoro-5-(trifluoromethyl)phenyl]-7-[(3-methoxy-2,2-dimethylpropyl)(methyl)amino]-1H-imidazo[4,5-b]pyridin-2-yl}pyrazin-2-yl)-1,4-diazepan-1-yl]acetic acid,

(55) [4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-1,4-diazepan-1-yl]acetic acid,

(56) 3-[(2S)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid,

(57) 3-[4-(5-{7-[{[1-(ethoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propaonic acid,

(58) 3-[4-(5-{5-[3-fluoro-5-(trifluoromethyl)phenyl]-7-[({1-[(2-methoxyethoxy)methyl]cyclopentyl}methyl)(methyl)amino]-1H-imidazo[4,5-b]pyridin-2-yl}pyrazin-2-yl)piperazin-1-yl]propaonic acid,

(59) {[1-(5-{5-[6-cyclopropyl-5-(trifluoromethyl)pyridin-3-yl]-7-[{[1-(methoxymethyl)cyclopentyl]methyl}

(methyl)amino]-1H-imidazo[4,5-b]pyridin-2-yl}pyrazin-2-yl)piperidine-4-yl]oxy}acetic acid,
(60) 3-[(2S)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid,
(61) 1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid,
(62) 1-(4-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperidine-4-carboxylic acid,
(63) 1-(4-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperidine-4-carboxylic acid,
(64) 1-(4-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid,
(65) 1-(4-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid,
(66) 1-(4-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}phenyl)piperidine-4-carboxylic acid,
(67) 1-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid,
(68) 1-(4-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluorophenyl)piperidine-4-carboxylic acid,
(69) 1-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid,
(70) 1-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid,
(71) 1-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidine-4-carboxylic acid,
(72) 1-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylic acid,
(73) 1-(5-{5-[3-ethoxy-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-carboxylic acid,
(74) 1-(4-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}-3-fluorophenyl)piperidine-4-carboxylic acid,
(75) 1-(5-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid,
(76) 1-(4-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylic acid,
(77) 1-(5-{5-[5-cyclopropyl-6-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid,
(78) 1-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid,
(79) 1-(5-{5-[5-cyclopropyl-6-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid,
(80) 1-(5-{5-[6-ethoxy-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid,
(81) 1-(4-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}phenyl)piperidine-4-carboxylic acid,
(82) 1-(4-{7-[{[1-(ethoxymethyl)cyclopentyl]methyl}(methyl)amino]-5-[2-ethoxy-6-(trifluoromethyl)pyridin-4-yl]-1H-imidazo[4,5-b]pyridin-2-yl}phenyl)piperidine-4-carboxylic acid,
(83) 1-(5-{5-[6-cyclopropyl-5-(trifluoromethyl)pyridin-3-yl]-7-[{[1-(ethoxymethyl)cyclopentyl]methyl}(ethyl)amino]-1H-imidazo[4,5-b]pyridin-2-yl}pyrazin-2-yl)piperidine-4-carboxylic acid,
(84) 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-fluorophenyl)piperidine-4-carboxylic acid,
(85) 1-(4-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}-3-methylphenyl)piperidine-4-carboxylic acid,
(86) 3-[(2S)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-2-(methoxymethyl)piperazin-1-yl]propaonic acid,
(87) 1-(5-{7-[{[1-(methoxymethyl)cyclobutyl]methyl}(methyl)amino]-5-[6-propyl-5-(trifluoromethyl)pyridin-3-yl]-1H-imidazo[4,5-b]pyridin-2-yl}pyrazin-2-yl)piperidine-4-carboxylic acid,
(88) 3-[4-(5-{5-[3-fluoro-5-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid,
(89) 3-[4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid,
(90) 3-[4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid,
(91) 3-[4-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propaonic acid,

(92) 3-[4-(4-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propaonic acid,

(93) 3-[(2S)-4-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propaonic acid,

(94) {[1-(5-{5-[6-cyclopropyl-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidine-4-yl]oxy}acetic acid,

(95) {[1-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid,

(96) 3-[4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid,

(97) 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid,

(98) 3-[4-(4-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}phenyl)piperazin-1-yl]propaonic acid,

(99) 3-[4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperazin-1-yl]propaonic acid, (100) 3-[(2S)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propaonic acid, (101) 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperazin-1-yl]butanoic acid, (102) 3-[4-(4-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperazin-1-yl]propaonic acid, (103) 3-[4-(4-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}phenyl)piperazin-1-yl]propaonic acid, (104) 3-[(2S)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid, (105) 3-[(2S)-4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid, (106) [1-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid, (107) 3-[4-(4-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}phenyl)piperazin-1-yl]propaonic acid, (108) 3-[(2S)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-2-methylpiperazin-1-yl]propaonic acid, (109) 3-[(2S)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid, (110) {[1-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid, (111) 3-[(3R)-4-(5-{5-[5,6-bis(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid, (112) 2,2-difluoro-3-{[1-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyrazin-2-yl)piperidine-4-yl]amino}propaonic acid, (113) {[(3S,4R)-1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-fluoropiperidine-4-yl]amino}acetic acid, (114) 3-[4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperazin-1-yl]butanoic acid, (115) 3-[(3R)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propaonic acid, (116) {[1-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)piperidine-4-yl]oxy}acetic acid, (117) 3-[(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid, (118) {[(3S,4R)-1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-fluoropiperidine-4-yl](methyl)amino}acetic acid, (119) 3-[4-(5-{7-[{[1-(butoxymethyl)cyclopentyl]methyl}(methyl)amino]-5-[3-fluoro-5-(trifluoromethyl)phenyl]-1H-imidazo[4,5-b]pyridin-2-yl}pyrazin-2-yl)piperazin-1-yl]propaonic acid, (120) 3-[(2R,6S)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2,6-dimethylpiperazin-1-yl]propaonic acid, (121) 3-[(2R,6S)-4-(5-{5-[3,5-bis(trifluoromethyl)phenyl]-7-[{[1-(methoxymethyl)cyclopentyl]methyl}(methyl)amino]-1H-imidazo[4,5-b]pyridin-2-yl}pyrazin-2-yl)-2,6-dimethylpiperazin-1-yl]propaonic acid, (122) {[1-(5-{5-[2-ethoxy-6-(trifluoromethyl)pyridin-4-yl]-7-[{[1-(methoxymethyl)cyclopentyl]methyl}

(methyl)amino]-1H-imidazo[4,5-b]pyridin-2-yl}pyrazin-2-yl)piperidine-4-yl]oxy}acetic acid,
(123) 3-[(2R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid,
(124) 3-[(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]propaonic acid,
(125) {[1-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-yl]oxy}acetic acid,
(126) 3-[(3R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propaonic acid,
(127) 3-[(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propaonic acid,
(128) 3-[(3R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propaonic acid,
(129) 3-[(3R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]propaonic acid,
(130) 3-[(2R)-4-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid,
(131) 3-[(2R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid,
(132) 3-[(2R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propaonic acid,
(133) 3-[(2R)-4-(5-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-2-methylpiperazin-1-yl]propaonic acid,
(134) [(3R)-4-(5-{5-[6-ethoxy-5-(trifluoromethyl)pyridin-3-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetic acid,
(135) 3-[(2R,6S)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2,6-dimethylpiperazin-1-yl]propaonic acid,
(136) {[(1R,3r,5S)-8-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-8-azabicyclo[3.2.1]octan-3-yl]oxy}acetic acid,
(137) {[(1R,3r,5S)-8-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid,
(138) [4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperazin-1-sulfonyl]acetic acid,
(139) [(3R)-4-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)-3-methylpiperazin-1-yl]acetic acid,
(140) [(3R)-4-(5-{5-[4-fluoro-3-(trifluoromethyl)phenyl]-7-[(3-methoxy-2,2-dimethylpropyl)(methyl)amino]-1H-imidazo[4,5-b]pyridin-2-yl}pyrazin-2-yl)-3-methylpiperazin-1-yl]acetic acid,
(141) [(3R)-4-(5-{5-[4-fluoro-3-(trifluoromethyl)phenyl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetic acid,
(142) [(3R)-4-(5-{5-[4-fluoro-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetic acid,
(143) 3-[(2R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid,
(144) 3-[(2R,6S)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,6-dimethylpiperazin-1-yl]propaonic acid,
(145) {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3,3-dimethylpiperidine-4-yl]oxy}acetic acid,
(146) 1-(4-{5-[6-cyano-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperidine-4-carboxylic acid,
(147) 3-[(2R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid,
(148) [(3R)-4-(5-{5-[6-ethoxy-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]acetic acid,
(149) {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperidine-4-yl]oxy}acetic acid,
(150) {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-4-methylpiperidine-4-yl]oxy}acetic acid,
(151) {[(1R,3r,5S)-8-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxy}acetic acid, (152) {[1-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-4-methylpiperidine-4-yl]oxy}acetic acid,
(153) 1-(4-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)piperidine-4-carboxylic acid,
(154) 3-[(3R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid,
(155) 3-[(2R)-4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2-methylpiperazin-1-yl]propaonic acid,
(156) 3-[4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)piperazin-1-yl]propaonic acid,
(157) 1-(5-{5-[4-cyclopropyl-3-(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperidine-4-carboxylic acid,
(158) 1-(4-{5-[4-cyclopropyl-3-(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylic acid,
(159) {[1-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid,
(160) 3-[(3R)-4-(5-{5-[5-cyclopropyl-6-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid,
(161) {[(1R,3s,5S)-8-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-8-azabicyclo[3.2.1]octan-3-yl]oxy}acetic acid,
(162) 3-[4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propaonic acid,
(163) 3-[(3R)-4-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propaonic acid,
(164) [(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetic acid,
(165) [(3R)-4-(5-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetic acid,
(166) 3-[4-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-2,2-dimethylpiperazin-1-yl]propaonic acid,
(167) 3-[(2R,6S)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-2,6-dimethylpiperazin-1-yl]propaonic acid,
(168) {[1-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3,3-dimethylpiperidine-4-yl]oxy}acetic acid,
(169) 3-[(3R)-4-(5-{5-[6-cyclopropyl-5-(trifluoromethyl)pyridin-3-yl]-7-(ethyl{[1-(methoxymethyl)cyclopentyl]methyl}amino)-1H-imidazo[4,5-b]pyridin-2-yl}pyrazin-2-yl)-3-methylpiperazin-1-yl]propaonic acid,
(170) {[(1R,3s,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid,
(171) 1-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperidine-4-carboxylic acid,
(172) {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-yl]sulfanil}acetic acid,
(173) {[1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-yl]sulfanil}acetic acid,
(174) [4-(4-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}phenoxy)piperidine-1-yl]acetic acid,
(175) [4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidine-1-yl]acetic acid,
(176) 3-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenoxy)piperidine-1-yl]propaonic acid,
(177) [4-(3-chloro-4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidine-1-yl]acetic acid,
(178) 3-[4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)piperidine-1-yl]propaonic acid,
(179) 3-[(1R,3s,5S)-3-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenoxy)-8-azabicyclo[3.2.1]octan-8-yl]propaonic acid,
(180) [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperazin-1-yl]acetic acid,
(181) 1-(4-{5-[6-cyclopropyl-5-(trifluoromethyl)pyridin-3-yl]-7-[{[1-(methoxymethyl)cyclobutyl]methyl}

(methyl)amino]-1H-imidazo[4,5-b]pyridin-2-yl}phenyl)piperidine-4-carboxylic acid, (182) 1-(4-{5-[3,5-bis(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylic acid, (183) 1-(4-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}phenyl)piperidine-4-carboxylic acid, (184) 1-(4-{5-[2-cyclopropyl-6-(trifluoromethyl)pyridin-4-yl]-7-[(3-methoxy-2,2-dimethylpropyl)(methyl)amino]-1H-imidazo[4,5-b]pyridin-2-yl}phenyl)piperidine-4-carboxylic acid, (185) 1-(4-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}phenyl)piperidine-4-carboxylic acid, (186) {1-[(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)methyl]piperidine-4-yl}acetic acid, (187) 3-[4-(5-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}pyridin-2-yl)-4-hydroxypiperidine-1-yl]propaonic acid, (188) 3-[4-(5-{5-[3-fluoro-5-(trifluoromethyl)phenyl]-7-[(3-methoxy-2,2-dimethylpropyl)(methyl)amino]-1H-imidazo[4,5-b]pyridin-2-yl}pyrazin-2-yl)piperazin-1-yl]propaonic acid, (189) 3-[4-(6-{5-[3-fluoro-5-(trifluoromethyl)phenyl]-7-[{[1-(methoxymethyl)cyclohexyl]methyl}(methyl)amino]-1H-imidazo[4,5-b]pyridin-2-yl}pyridin-3-yl)piperazin-1-yl]propaonic acid, (190) 3-[4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid, (191) 3-[4-(4-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}phenyl)piperazin-1-yl]propaonic acid, (192) 3-[4-(4-{5-[6-ethoxy-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperazin-1-yl]propaonic acid, (193) 3-[4-(4-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperazin-1-yl]propaonic acid, (194) 3-[4-(5-{5-[3,5-bis(trifluoromethyl)phenyl]-7-[{[1-(methoxymethyl)cyclopentyl]methyl}(methyl)amino]-1H-imidazo[4,5-b]pyridin-2-yl}pyrazin-2-yl)piperazin-1-yl]propaonic acid, (195) 3-[4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)piperazin-1-yl]propaonic acid, (196) 3-[(2S)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-2-methylpiperazin-1-yl]propaonic acid, (197) 3-[(3S)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]propaonic acid, (198) [(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]acetic acid, (199) [(3R)-4-(5-{5-[2-cyclopropyl-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetic acid, (200) [(3R)-4-(5-{5-[6-cyclopropyl-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetic acid, (201) 3-[4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)piperazin-1-yl]propaonic acid, (202) [(3R)-4-(5-{5-[6-ethoxy-5-(trifluoromethyl)pyridin-3-yl]-7-[{[1-(methoxymethyl)cyclobutyl]methyl}(methyl)amino]-1H-imidazo[4,5-b]pyridin-2-yl}pyrazin-2-yl)-3-methylpiperazin-1-yl]acetic acid, (203) [(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]acetic acid, (204) 1-(4-{5-[4-ethoxy-3-(trifluoromethyl)phenyl]-7-[{[1-(methoxymethyl)cyclopentyl]methyl}(methyl)amino]-1H-imidazo[4,5-b]pyridin-2-yl}phenyl)piperidine-4-carboxylic acid, (205) 1-(4-{5-[5-cyclopropyl-6-(trifluoromethyl)pyridin-3-yl]-7-[{[1-(methoxymethyl)cyclohexyl]methyl}(methyl)amino]-1H-imidazo[4,5-b]pyridin-2-yl}phenyl)piperidine-4-carboxylic acid, (206) 3-[(3R)-4-(4-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}phenyl)-3-methylpiperazin-1-yl]propaonic acid, (207) 3-[(3R)-4-(4-{5-[2-ethoxy-6-(trifluoromethyl)pyridin-4-yl]-7-[{[1-(methoxymethyl)cyclohexyl]methyl}(methyl)amino]-1H-imidazo[4,5-b]pyridin-2-yl}phenyl)-3-methylpiperazin-1-yl]propaonic acid, (208) 3-[(3R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}-3-fluoropyridin-2-yl)-3-methylpiperazin-1-yl]propaonic acid, (209) 5-[3-fluoro-5-(trifluoromethyl)phenyl]-N-{[1-(methoxymethyl)cyclobutyl]methyl}-N-methyl-2-(5-{4-[(1H-tetrazol-5-yl)methyl]piperazin-1-yl}pyrazin-2-yl)-1H-imidazo[4,5-b]pyridin-7-amine, (210) 5-[3-fluoro-5-(trifluoromethyl)phenyl]-N-{[1-(methoxymethyl)cyclobutyl]methyl}-N-methyl-2-(5-{4-[2-(1H-tetrazol-5-yl)ethyl]piperazin-1-yl}pyrazin-2-yl)-1H-imidazo[4,5-b]pyridin-7-amine, (211) N-{2-[4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)piperazin-1-yl]ethyl}sulfonate amide, (212) 3-[4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}phenyl)piperidine-1-yl]propanoic acid, and (213) [4-(4-{5-[3-fluoro-5-(trifluoromethyl)phenyl]-7-[{[1-(methoxymethyl)cyclobutyl]methyl}(methyl)amino]-1H-imidazo[4,5-b]pyridin-2-yl}benzoyl)piperazin-1-yl]acetic acid.

7. A pharmaceutical composition comprising the azabenzimidazole compound according to claim 1 or a pharmaceutically acceptable salt thereof, or a solvate thereof, as an active ingredient.

8. An M3 PAM, which is the azabenzimidazole compound according to claim 1 or a pharmaceutically acceptable salt thereof, or a solvate thereof, acting as an active ingredient.

9. A therapeutic agent for voiding and/or storage disorders in bladder/urethral disease, glaucoma or diabetes in which an M3 receptor is involved, the therapeutic agent being the azabenzimidazole compound according to claim 1 or a pharmaceutically acceptable salt thereof, or a solvate thereof, acting as an active ingredient.

10. The therapeutic agent according to claim 6, wherein the voiding and/or storage disorders in bladder/urethral disease in which the M3 receptor is involved is due to underactive bladder, hypotonic bladder, acontractile bladder, detrusor underactivity, neurogenic bladder, urethral relaxation failure, or detrusor-external urethral sphincter dyssynergia.

11. The azabenzimidazole compound according to claim 1, wherein the compound is 1-(5-{5-[2-ethoxy-6-(trifluoromethyl)pyridin-4-yl]-7-[(3-methoxy-2,2-dimethylpropyl)(methyl)amino]-1H-imidazo[4,5-b]pyridin-2-yl}pyrazin-2-yl)piperidine-4-carboxylic acid, or a pharmaceutically acceptable salt thereof, or a solvate thereof.

12. The azabenzimidazole compound according to claim 1, wherein the compound is 1-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-carboxylic acid, or a pharmaceutically acceptable salt thereof, or a solvate thereof.

13. The azabenzimidazole compound according to claim 1, wherein the compound is 1-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)piperidine-4-carboxylic acid, or a pharmaceutically acceptable salt thereof, or a solvate thereof.

14. The azabenzimidazole compound according to claim 1, wherein the compound is {[1-(5-{5-[2-cyclopropyl-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)piperidine-4-yl]oxy}acetic acid, or a pharmaceutically acceptable salt thereof, or a solvate thereof.

15. The azabenzimidazole compound according to claim 1, wherein the compound is 3-[4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)piperazin-1-yl]propanoic acid, or a pharmaceutically acceptable salt thereof, or a solvate thereof.

16. The azabenzimidazole compound according to claim 1, wherein the compound is 3-[(3R)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoic acid, or a pharmaceutically acceptable salt thereof, or a solvate thereof.

17. The azabenzimidazole compound according to claim 1, wherein the compound is 3-[(2S)-4-(5-{5-[6-cyclopropyl-5-(trifluoromethyl)pyridin-3-yl]-7-[{[1-(methoxymethyl)cyclohexyl]methyl}(methyl)amino]-1H-imidazo[4,5-b]pyridin-2-yl}pyrazin-2-yl)-2-(methoxymethyl)piperazin-1-yl]propanoic acid, or a pharmaceutically acceptable salt thereof, or a solvate thereof.

18. The azabenzimidazole compound according to claim 1, wherein the compound is 1-(5-{5-[2-ethoxy-6-(trifluoromethyl)pyridin-4-yl]-7-[{[1-(methoxymethyl)cyclobutyl]methyl}(methyl)amino]-1H-imidazo[4,5-b]pyridin-2-yl}pyrazin-2-yl)piperidine-4-carboxylic acid, or a pharmaceutically acceptable salt thereof, or a solvate thereof.

19. The azabenzimidazole compound according to claim 1, wherein the compound is 3-[(3R)-4-(5-{5-[6-cyclopropyl-5-(trifluoromethyl)pyridin-3-yl]-7-[{[1-(ethoxymethyl)cyclopentyl]methyl}(methyl)amino]-1H-imidazo[4,5-b]pyridin-2-yl}pyrazin-2-yl)-3-methylpiperazin-1-yl]propanoic acid, or a pharmaceutically acceptable salt thereof, or a solvate thereof.

20. The azabenzimidazole compound according to claim 1, wherein the compound is {[(1R,3R,5S)-8-(5-{5-[2-ethoxy-6-(trifluoromethyl)pyridin-4-yl]-7-[{[1-(methoxymethyl)cyclopentyl]methyl}(methyl)amino]-1H-imidazo[4,5-b]pyridin-2-yl}pyrazin-2-yl)-8-azabicyclo[3.2.1]octan-3-yl]oxy}acetic acid, or a pharmaceutically acceptable salt thereof, or a solvate thereof.

21. The azabenzimidazole compound according to claim 1, wherein the compound is 3-[(3R)-4-(5-{5-[2-cyclopropyl-6-(trifluoromethyl)pyridin-4-yl]-7-[{[1-(methoxymethyl)cyclohexyl]methyl}(methyl)amino]-1H-imidazo[4,5-b]pyridin-2-yl}pyrazin-2-yl)-3-methylpiperazin-1-yl]propanoic acid, or a pharmaceutically acceptable salt thereof, or a solvate thereof.

22. The azabenzimidazole compound according to claim 1, wherein the compound is 3-[(3R)-4-(5-{5-[6-cyclopropyl-5-(trifluoromethyl)pyridin-3-yl]-7-[{[1-(methoxymethyl)cyclopentyl]methyl}(methyl)amino]-1H-imidazo[4,5-b]pyridin-2-yl}pyrazin-2-yl)-3-methylpiperazin-1-yl]propanoic acid, or a pharmaceutically acceptable salt thereof, or a solvate thereof.

* * * * *